(12) United States Patent
Ghidini et al.

(10) Patent No.: US 10,280,193 B2
(45) Date of Patent: *May 7, 2019

(54) ISOXAZOLIDINE DERIVATIVES

(71) Applicant: CHIESI FARMACEUTICI S.p.A., Parma (IT)

(72) Inventors: Eleonora Ghidini, Parma (IT); Andrea Rizzi, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/807,066

(22) Filed: Nov. 8, 2017

(65) Prior Publication Data

US 2018/0066010 A1 Mar. 8, 2018

Related U.S. Application Data

(60) Division of application No. 14/537,184, filed on Nov. 10, 2014, now Pat. No. 9,845,337, which is a continuation of application No. 13/421,150, filed on Mar. 15, 2012, now abandoned.

(30) Foreign Application Priority Data

Mar. 15, 2011 (EP) .................................... 11158230

(51) Int. Cl.
*A61K 31/58* (2006.01)
*A61K 45/06* (2006.01)
*C07J 71/00* (2006.01)

(52) U.S. Cl.
CPC ........... *C07J 71/0068* (2013.01); *A61K 31/58* (2013.01); *A61K 45/06* (2013.01)

(58) Field of Classification Search
CPC ....... C07J 71/0068; A61K 31/58; A61K 45/06
See application file for complete search history.

(56) References Cited

U.S. PATENT DOCUMENTS

| 3,631,033 | A | 12/1971 | Nathansohn et al. |
| 8,710,037 | B2 | 4/2014 | Ghidini et al. |
| 8,835,412 | B2 | 9/2014 | Ghidini et al. |
| 2011/0065678 | A1 | 3/2011 | Armani et al. |
| 2011/0201580 | A1 | 8/2011 | Ghidini et al. |
| 2014/0069419 | A1 | 3/2014 | Ghidini |

FOREIGN PATENT DOCUMENTS

| WO | 2006/005611 | 1/2006 |
| WO | 2011/029547 | 3/2011 |

OTHER PUBLICATIONS

European Search Report in Application No. 11158230.0, dated Aug. 29, 2011.
Green M. J. et al. "J. Med. Chem.", vol. 25, No. 12, (1982), pp. 1492-1495.
Angell R. M. et al., J. Chem. Soc., Perkin Trans. 1, (2002), pp. 831-839, XP-002656701.
Procopiou P.A. et al., "J. Med. Chem.", vol. 44, No. 4, (2001), pp. 602-612.

*Primary Examiner* — Barbara P Badio
(74) *Attorney, Agent, or Firm* — Oblon, McClelland, Maier & Neustadt, L.L.P.

(57) ABSTRACT

Anti-inflammatory and antiallergic compounds of the glucocorticosteroid series, according to formula (I) according to formula (I) defined herein are useful for treating diseases of the respiratory tract characterized by airway obstruction.

10 Claims, No Drawings

ISOXAZOLIDINE DERIVATIVES

CROSS REFERENCES TO RELATED APPLICATIONS

This application claims priority to European Patent Application No. 11158230.0 filed on Mar. 15, 2011, which is incorporated herein by reference in its entirety.

BACKGROUND OF THE INVENTION

Field of the Invention

The present invention relates to novel anti-inflammatory and antiallergic compounds of the glucocorticosteroid series, methods of preparing such a compound, pharmaceutical compositions which contain such a compound them, combinations which contain such a compound, and therapeutic uses of such a compound. The present invention also relates to methods of treating and/or preventing certain diseases and conditions by administering such a compound. More particularly, the invention relates to glucocorticosteroids that are isoxazolidine derivatives.

Discussion of the Background

Corticosteroids are potent anti-inflammatory agents, able to decrease the number, activity and movement of inflammatory cells. They are commonly used to treat a wide range of chronic and acute inflammatory conditions including asthma, chronic obstructive pulmonary disease (COPD), allergic rhinitis, rheumatoid arthritis, inflammatory bowel disease and autoimmune diseases. Corticosteroids mediate their effects through the glucocorticoid receptor (GR). The binding of corticosteroids to GR induces its nuclear translocation which, in turn, affects a number of downstream pathways via DNA-binding-dependent (e.g. transactivation) and -independent (e.g. transespression) mechanisms.

Corticosteroids for treating chronic inflammatory conditions in the lung such as asthma and COPD are currently administered through inhalation. One of the advantages of employing inhaled corticosteroids (ICS) is the possibility of delivering the drug directly at site of action, limiting systemic side-effects, thus resulting in a more rapid clinical response and a higher therapeutic ratio.

Although ICS treatment can afford important benefits, especially in asthma it is important to minimize ICS systemic exposure which leads to the occurrence and severity of unwanted side effects that may be associated with chronic administration. Moreover, the limited duration of action of ICS currently available in the clinical practice contributes to suboptimal management of the disease. While the inhaler technology is the key point to target the lung, the modulation of the substituents on the corticosteroids molecular scaffold is important for the optimization of pharmacokinetic and pharmacodynamic properties in order to decrease oral bioavailability, confine pharmacological activity only in the lung (prodrugs and soft drugs) and increase systemic clearance. Moreover, long lasting ICS activity in the lung is highly desirable as once daily administration of ICS would allow the reduction of the frequency of administration and, thus, substantially improve patient compliance and, as a result, disease management and control. In sum, there is a pressing medical need for developing ICS with improved pharmacokinetic and pharmacodynamic characteristics.

Glucocorticoids isoxazolidine derivatives are for instance described in WO 2006/005611, GB 1578446 and in "Synthesis and topical anti-inflammatory activity of some steroidal [16α,17α-d] isoxazolidines" (*J. Med. Chem.*, 25, 1492-1495, 1982), all of which are incorporated herein by reference in their entireties. Some glucocorticoid isoxazolidine derivatives are also described in the co-pending patent application WO 2011/029547, which is incorporated herein by reference in its entirety.

Thus, there remains a need for ICS with improved pharmacokinetic and pharmacodynamic characteristics.

SUMMARY OF THE INVENTION

Accordingly, it is one object of the present invention to provide novel anti-inflammatory and antiallergic compounds.

It is another object of the present invention to provide novel anti-inflammatory and antiallergic compounds, with improved pharmacokinetic and pharmacodynamic characteristics.

It is another object of the present invention to provide novel anti-inflammatory and antiallergic compounds of the glucocorticosteroid series.

It is another object of the present invention to provide novel methods of preparing such a compound.

It is another object of the present invention to provide novel pharmaceutical compositions which contain such a compound.

It is another object of the present invention to provide novel combinations of such a compound and another active agent.

It is another object of the present invention to provide novel therapeutic uses of such a compound.

It is another object of the present invention to provide novel methods of treating and/or preventing certain diseases and conditions by administering such a compound.

These and other objects, which will become apparent during the following detailed description, have been achieved by the inventors' discovery that compounds of formula (I), described below, exhibit improved developability, and pharmacokinetic and pharmacodynamic characteristics, such as low systemic exposure, great selectivity, potency or duration of action.

Thus, the present invention provides anti-inflammatory and antiallergic compounds of the glucocorticosteroid series of formula (I).

In another embodiment, the present invention provides to processes for preparing a compound of formula (I).

In another embodiment, the present invention provides pharmaceutical compositions which contain a compound of formula (I).

In another embodiment, the present invention provides combinations of a compound of formula (I) with other pharmaceutical active ingredients for the treatment of respiratory disorders, among which beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (FINE) inhibitors, phosphodiesterase 4 (PDE4) inhibitors, leukotriene modulators, non-steroidal anti-inflammatory agents (NSAIDs) and mucus regulators.

In another embodiment, the present invention provides methods of treating and/or preventing certain diseases by administering a compound of formula (I).

Surprisingly, it has been found that the compounds of the present invention show improved developability, pharmacokinetic or pharmacodynamic characteristics, such as low systemic exposure, great selectivity, potency or duration of action.

DETAILED DESCRIPTION OF THE PREFERRED EMBODIMENTS

In particular, the invention is directed to compounds of general formula (I):

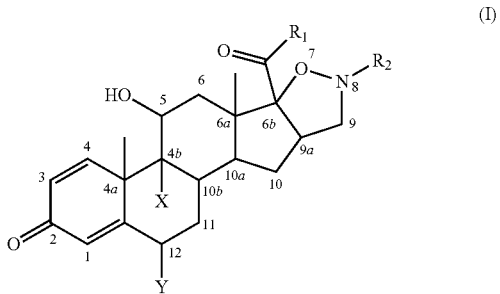

wherein
$R_1$ is —$(CH_2)_n$—Z—$(CH_2)_{n'}$—$R_3$ wherein n and n' are each independently 0, 1 or 2;
Z is a single bond or is selected from —S—, —O— and —OC($R_4R_5$)—;
$R_3$ is selected from the group consisting of:
  H, halogen, CN, OH, $CONH_2$, $(C_1-C_6)$alkyl, $(C_2-C_4)$ alkenyl, $(C_1-C_6)$haloalkyl, $(C_2-C_4)$alkynyl and $(C_1-C_6)$ alkylsulfonyl, and $(C_1-C_6)$alkylcarbonyl;
  $NR_4R_5$, wherein $R_4$ and $R_5$ are independently selected from the group consisting of $(C_1-C_6)$alkyl and $(C_1-C_6)$ alkoxy;
  $(C_3-C_8)$cycloalkyl, $(C_3-C_8)$heterocycloalkyl, aryl and heteroaryl, each of which is optionally substituted by one or more halogen atoms or oxo groups or CN groups; and
$R_2$ is selected from the group consisting of:
  linear or branched $(C_1-C_8)$alkyl, $(C_1-C_6)$alkoxy, $(C_1-C_6)$ haloalkyl, optionally substituted by one or more CN groups or halogen atoms;
  —$(CH_2)_mR_6$, wherein $R_6$ is selected from the group consisting of $(C_3-C_8)$cycloalkyl, $(C_3-C_8)$heterocycloalkyl, aryl, $(C_1-C_6)$arylalkyl, aryloxy, arylthio, and heteroaryl, each of which optionally substituted by one or more substituents selected from the group consisting of oxo, OH, halogen, CN, $NH_2$, $CONH_2$, $NO_2$, NHC(O)H, linear or branched $(C_1-C_6)$alkyl, linear or branched $(C_1-C_6)$haloalkyl, linear or branched $(C_1-C_6)$ alkoxy, linear or branched $(C_1-C_6)$haloalkoxy, $(C_1-C_6)$ hydroxyalkoxy, $(C_1-C_6)$haloalkoxy, $(C_1-C_6)$alkoxycarbonyl, $(C_1-C_6)$alkylcarboxyl, $(C_1-C_6)$alkylsulfonyl and $(C_1-C_6)$alkylsulfanyl, $(C_1-C_6)$alkyloxysulfonyl, $(C_1-C_6)$haloalkylsulfonyloxy, aminosulfonyl, $(C_3-C_8)$cycloalkyl, $(C_3-C_6)$heterocycloalkyl, and heteroaryl wherein m is 0 or an integer from 1 to 3 and
X and Y are independently H or halogen and
pharmaceutically acceptable salts thereof,
with the proviso that when $R_1$ is a group —$CH_2OH$ and $R_2$ is $(C_1-C_6)$alkyl or $(C_3-C_8)$cycloalkyl, then X and Y are fluorine atoms.

In the present description, unless otherwise provided, the term "halogen" includes fluorine, chlorine, bromine and iodine atoms.

The expressions "linear" and "straight" have the same meaning.

The term "$(C_1-C_6)$alkyl", "$(C_1-C_8)$alkyl" or "$(C_1-C_{15})$ alkyl" refers to straight or branched chain alkyl groups wherein the number of carbon atoms is from 1 to 6, 1 to 8 or 1 to 15 respectively. Examples of said groups are methyl, ethyl, n-propyl, isopropyl, n-butyl, isobutyl, sec-butyl, tert-butyl, pentyl, hexyl, eptyl, octyl, ethyl-butyl, propyl-butyl, methyl-butyl, ethyl-methyl-propyl, hexadecyl and the like.

The expression "$(C_2-C_6)$alkenyl" refers to straight or branched carbon chains with one or more double bonds, wherein the number of carbon atoms is from 2 to 6. Examples of said groups include ethenyl, propenyl, butenyl, pentenyl, hexenyl and the like.

The expression "$(C_2-C_6)$alkynyl" refers to straight or branched carbon chains with one or more triple bonds, wherein the number of carbon atoms is from 1 to 6. Examples of said groups comprise ethynyl, propynyl, butynyl, pentynyl, hexynyl and the like.

The expression "$(C_1-C_6)$alkylcarboxyl" refers to alkyl-COO groups.

The term "$(C_1-C_6)$alkoxy" refers to alkyl-oxy (e.g. alkoxy) groups, being the alkyl portion as above defined. Examples of said groups may thus comprise methoxy, ethoxy, n-propoxy, isopropoxy, n-butoxy, isobutoxy, sec-butoxy, tert-butoxy, pentoxy, hexoxy and the like.

The expressions "$(C_1-C_6)$alkoxycarbonyl" and "$(C_1-C_6)$ hydroxyalkoxy" refer respectively to alkoxy-O— and (OH) alkoxy-groups.

The expressions "$(C_1-C_6)$haloalkyl" and "$(C_1-C_6)$haloalkoxy" refer to the above "$(C_1-C_6)$alkyl" and "$(C_1-C_6)$ alkoxy" groups wherein one or more hydrogen atoms are replaced by one or more halogen atoms, which can be the same or different from each other.

Examples of said $(C_1-C_6)$haloalkyl and $(C_1-C_6)$haloalkoxy groups may thus include halogenated, poly-halogenated and fully halogenated alkyl and alkoxy groups wherein all of the hydrogen atoms are replaced by halogen atoms, e.g. trifluoromethyl or trifluoromethoxyl groups.

The expression "$(C_3-C_8)$cycloalkyl" refers to mono or bi-cycloaliphatic hydrocarbon groups with from 3 to 8 carbon atoms. Examples include cyclopropyl, cyclobutyl, cyclopentyl, cyclohexyl, cycloheptyl, bicyclo[2.2.1]hept-2-yl and the like.

The expression "$(C_3-C_8)$heterocycloalkyl" refers to $(C_3-C_8)$cycloalkyl groups, in which at least one ring carbon atom is replaced by a heteroatom or heteroaromatic group (e.g. N, NH, S or O).

The expression "aryl" refers to mono or bi- or tri-cyclic ring systems which have 6 to 20 ring atoms, preferably from 6 to 15 and wherein at least one ring is aromatic.

The expression "$(C_1-C_6)$arylalkyl" refers to $(C_1-C_6)$alkyl groups further substituted by aryl.

The expressions "aryloxy" and "arylthio" refer respectively to aryl-oxy- and aryl-S— groups, with the aryl portion as above defined.

The expressions "$(C_1-C_6)$alkylsulfanyl" and "$(C_1-C_6)$ alkylsulfonyl" refer respectively to alkyl-S— and alkyl-$SO_2$— groups.

The term "$(C_1-C_6)$haloalkylsulfonyloxy" refers to haloalkyl-$SO_2(O)$— groups.

The expression "aminosulfonyl" refers to $NH_2S(O_2)$—.

The expression "heteroaryl" refers to mono, bi- or tri-cyclic ring systems with 5 to 20 ring atoms, preferably from 5 to 15, in which at least one ring is aromatic and in which at least one carbon ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoazolyl), oxazole (ozazolyl), isothiazole (isothiazolyl), thiazole (thiazolyl), pyridine (pyidinyl), imidazolidine (imidazolidinyl), furan (furanyl) radicals and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoqinolinyl), indole (indolyl), isoindole (isoindolyl), benzothiophene (benzothiophenyl), dihydrobenzo dioxin, dihydrobenzo dioxepine, thiazole, benzo oxazine radicals and the like.

Examples of suitable aryl or heteroaryl tricyclic systems include fluorene radicals as well as benzocondensed derivatives of the aforementioned heteroaryl bicyclic systems.

The expressions "linear" and "straight" have the same meaning.

It will be apparent to those skilled in the art that compounds of general formula (I) contain asymmetric centers at least at the positions 4a, 4b, 5, 6a, 6b, 9a, 10a, 10b and therefore may exist as many optical stereoisomers and mixtures thereof. Therefore the invention is also directed to all of these forms and mixtures thereof.

Preferred compounds are those of general formula (I) wherein the stereochemistry of stereogenic carbon atoms is as reported in formula (I') below, absolute configuration is assigned on the basis of Cahn-Ingold-Prelog nomenclature based on groups' priorities In a preferred embodiment, in the compounds of the invention at least one of X and Y is a halogen atom, m is zero and $R_6$ is optionally substituted aryl, $(C_3-C_8)$cycloalkyl or heteroaryl. In a more preferred embodiment, both X and Y are independently halogen atoms and m is zero and $R_6$ is optionally substituted aryl, $(C_3-C_8)$cycloalkyl or heteroaryl. In a still more preferred embodiment, both X and Y are fluorine and m is zero and $R_6$ is optionally substituted aryl, $(C_3-C_8)$cycloalkyl or heteroaryl.

In a preferred embodiment, in the compounds of the invention m is zero, $R_6$ is optionally substituted aryl, $(C_3-C_8)$cycloalkyl or heteroaryl, $R_1$ is —$(CH_2)_n$—Z—$(CH_2)_{n'}$—$R_3$, wherein n is 1, Z is a single bond, n' is 0 and $R_3$ is —OH; or $R_1$ is —$(CH_2)_n$—Z—$(CH_2)_{n'}$—$R_3$, wherein n is 0, Z is —S—, n' is 1, and $R_3$ is an halogen atom; or $R_1$ is —$(CH_2)_n$—Z—$(CH_2)_{n'}$—$R_3$, wherein n is 0, Z is a bond, n' is 1, and $R_3$ is selected from the group consisting of an halogen atom, CN, $CONH_2$, $(C_1-C_6)$haloalkyl, and $(C_1-C_6)$alkylcarbonyl. In a more preferred embodiment, $R_1$ is —$(CH_2)_n$—Z—$(CH_2)_{n'}$—$R_3$, wherein n is 0, Z is —S—, n' is 1, and $R_3$ is an halogen atom, or $R_1$ is —$(CH_2)_n$—Z—$(CH_2)_{n'}$—$R_3$, wherein n is 0, Z is a bond, n' is 1 and $R_3$ is an halogen atom.

In a preferred embodiment, in the compounds of the invention, $R_1$ is selected from the group consisting of methyl, hydroxy, hydroxymethyl, N-methoxy-N-methylamino, N-methyl-N-cyanomethyl, chloromethyl, fluoromethyl, fluoromethoxy, fluoroethoxy, chloromethoxy, cyanomethyl, methylsulfanyl, methylsulfanylmethyl, cyclopropylmethoxy, fluoroethylsulfanyl, trifluoroethylsulfanyl, cyclobutylsulfanyl, cyanomethoxy and a group of formula (h), (h'), (h'''), (i), (i'), (l), (l'), (l'') or (l''') below

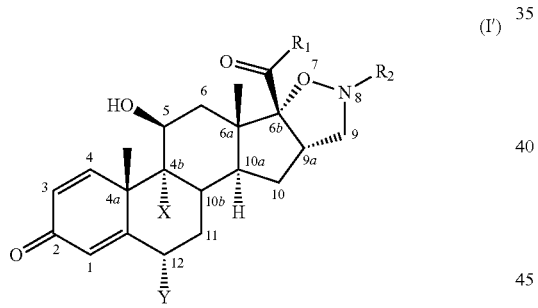
(I')

and wherein the meanings of $R_1$ and $R_2$ are as defined above.

In one preferred embodiment, for compounds of formula (I'), absolute configuration at asymmetric center 4a is (S), at 4b is (R), at 5 is (S), at 6a is (S), at 6b is (R), at 9a is (S), at 10a is (S), at 10b is (S) and at 12 is (S).

Compounds of general formula (I) may form acid addition salts, particularly with pharmaceutically acceptable acids. Pharmaceutically acceptable acid addition salts of the compounds of formula (I), thus encompassing also those of formula (I'), include those of inorganic acids, for example hydrohalogen acids such as hydrofluoric, hydrochloric, hydrobromic or hydroiodic; nitric, sulfuric, phosphoric; and organic acids, for example aliphatic monocarboxylic acids such as formic, acetic, trifluoroacetic and propionic; aliphatic hydroxyl acids such as lactic, citric, tartaric or malic; dicarboxylic acids such as maleic, fumaric, oxalic or succinic; aromatic carboxylic acids such as benzoic; aromatic hydroxyl acids and sulfonic acids. These salts may be prepared from compounds of formula (I) or (I') by known salt-forming procedures.

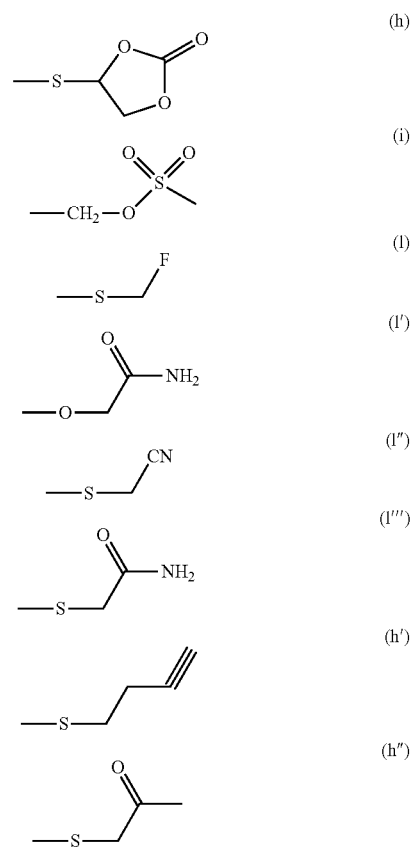

-continued

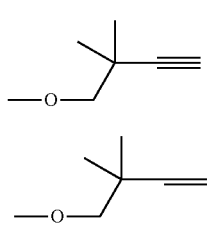

(h''')

(i')

In a preferred embodiment, in the compounds of the invention, R₂ is selected from the group consisting of cyclohexyl, ethyl-butyl, phenyl-propyl, phenoxy-ethyl, amino-carbonyl-phenyl, amino-sulfonyl-phenyl, bromo-phenyl, cyano-phenyl, cyclopropyl-phenyl, methoxy-benzyl, propyl-butyl, methyl-butyl, tert-butyl-benzyl, methyl-benzyl, dichloro-phenyl, chloro-furan-2-yl-methyl, chloro-thiophen-2-yl-methyl, phenylsulfanyl-ethyl, cyclohexyl, cyclopentylmethyl, ethyl-2-methyl-propyl, 4-chloro-3-trifluoromethyl-phenyl, 4-chloro-3-methyl-phenyl, trifluoro-propyl, 3,3-dimethyl-butyl, fluoro-benzyl, thiophen-2-ylm-ethyl, furan-2-ylmethyl, ethyl-methyl-propyl, ethyl-butyl, methoxy-carbonyl-phenyl, methoxy-carbonyl-benzyl, cyclohexylmethyl, cyclohexylphenyl, methylsulfanyl-benzyl, methylsulfanylthiophenyl, sec-butyl, cyclopentylm-ethyl, tert-butoxy-benzyl, tert-butoxy-carbonyl-benzyl, pyridin, thiazol-4-yl, thiazol-2-yl-methyl, oxazol-2-yl, imidazol-1-yl-ethyl, cyclohexyl-ethyl, pyridin-3-yl-propyl, furan-3-yl, 1H-indol-3-ylmethyl, 1-methyl-1H-indol-3-ylm-ethyl, quinolin-7-ylmethyl, benzothiazol-2-ylmethyl, bicyclo[2.2.1]hept-2-yl, propylbenzyl, quinolin-5-ylmethyl, benzofuran-3-yl, benzo[1,3]dioxol-5-yl, methyl-1H-indol-2-yl, methyl-1H-indol-3-ylmethyl, methyl-sulfonyl-phenyl, methyl-1H-imidazol-4-ylmethyl, 1H-imidazol-2-ylmethyl, chloro-phenyl, tolyl, chloro-benzyl, hydroxy-benzyl, thio-phen-2-ylmethyl, furan-2-ylmethyl, methyl-benzyl, methoxy-benzyl, butoxy-benzyl, cyclopentylmethyl, chloro-thiophen-2-ylmethyl, methyl-thiophen-2-yl-methyl, bicycloheptyl, imidazolylethyl, 4-piperidin-4yl-methyl-phenyl and a group of formula (t), (t'), (t'') or (t''') below

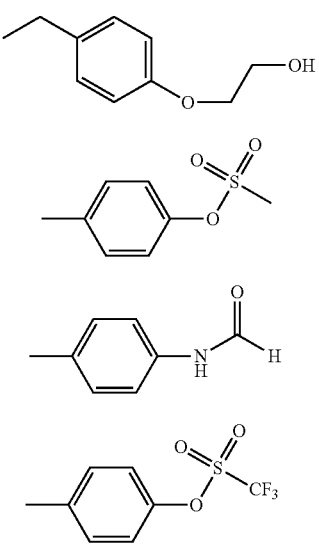

(t)

(t')

(t'')

(t''')

Preferred compounds of general formula (I) or (I') have the formula (IA), wherein X and Y are fluorine, n is 0 or 1, n' is 0 or 1; Z is a single bond, or is selected from —S—, —O— and —OC(R₄R₅); R₃ is selected from the groups consisting of H, halogen, —OH, —CN, —CONH₂, —NR₄R₅, (C₁-C₆)alkylsulfonyl, (C₁-C₆)alkylcarbonyl, an optionally substituted monocyclic (C₃-C₈)heterocycloalkyl, (C₁-C6) alkyl, (C₂-C₄)alkenyl, and (C₂-C₄)alkynyl; and the groups R₂, R₄, R₅ are as above defined for compounds of formula (I).

Other preferred compounds of general formula (I) or (I') have formula (IB), wherein X and Y are fluorine, R₁ is —(CH₂)ₙ—Z—(CH₂)ₙ'—R₃, wherein n is 1, Z is a single bond, n' is 0 and R₃ is —OH; and the group R₂ is as above defined for compounds of formula (I).

Preferred compounds of general formula (I) or (I') have formula (IC), wherein X and Y are fluorine, m is zero and R₆ is an optionally substituted aryl or heteroaryl, such that R₂ represents an optionally substituted aryl or heteroaryl; and R₁ is as above defined for compounds of formula (I).

In a preferred embodiment, in the compounds of formula (IC), R₂ is optionally substituted phenyl.

In another preferred embodiment, in the compounds of formula (IC), R₂ is an optionally substituted heteroaryl.

According to analogous procedures and methods described in the present application, the following compounds of formula (IC) may be obtained:

(4aS,4bR,5S,6aS,6bR,9aS,10aS,10bS,12S)-4b,12-difluoro-5-hydroxy-4a,6a-dimethyl-2-oxo-8-pyridin-3-yl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-thiazol-4-yl-2,4a,4b,5,6,6a,8,9,9a,10,10a,10,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-8-oxazol-2-yl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-8-furan-3-yl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Benzofuran-3-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Benzo[1,3]dioxol-5-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5     S,6aS,6bR,9aS,10aS,10bS,12S)-4b,12-Difluoro-5-hydroxy-4a,6a-dimethyl-8-(1-methyl-1H-indol-2-yl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10a8,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradeca-hydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-p-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-8-(4-methoxy-phenyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-o-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(3-Chloro-phenyl)-4b,12-difluoro-5-hydroxy-4a,6a-dimethyl-2-oxo-2,4a,4b,5,6,6a,8,9,9a,10,10a,10b,11,12-tetradeca-hydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-m-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-8-(3-methoxy-phenyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester.

In a preferred embodiment, the invention is directed to compounds of general formula (ID)

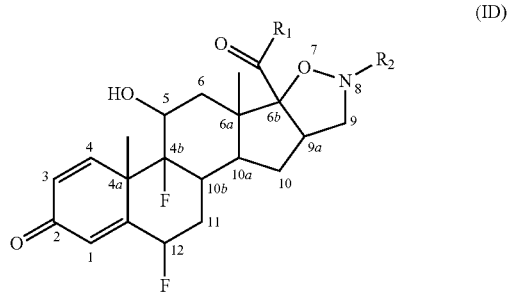

(ID)

wherein
R₁ is —(CH₂)$_n$—Z—(CH₂)$_{n'}$—R₃ wherein n and n' are each independently 0, 1 or 2;
Z is a single bond or is selected from —S— and —O—;
R₃ is selected from the group consisting of:
  H, halogen, CN, CONH₂, OH, straight or branched (C₁-C₁₅)alkyl, (C₁-C₆)haloalkyl and (C₁-C₆)alkylsulfonyl;
  NR₄R₅, wherein R₄ and R₅ are independently selected from the group consisting of (C₁-C₆)alkyl and (C₁-C₆)alkoxy;
  (C₃-C₈)cycloalkyl, (C₃-C₈)heterocycloalkyl, aryl, and heteroaryl, each of which is optionally substituted by one or more halogen atoms or oxo groups;
R₂ is selected from the group consisting of:
  straight or branched (C₁-C₈)alkyl;
  (CH₂)$_m$R₆, wherein R₆ is (C₃-C₈)cycloalkyl, wherein m is 0 or an integer from 1 to 3 and
and pharmaceutically acceptable salts thereof.

Examples of Compounds of Formula (ID) Include:
(4aS,4bR,5S,6aS,6bR,9aS,10aS,10bS,12S)-8-cyclopentyl-methyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-cyclohexyl-4b,12-difluoro-5-hydroxy-6b-(2-hydroxy-acetyl)-4a,6a-dimethyl-4a,4b,5,6,6a,6b,8,9,9a,10,10a,10b,11,12-tetra-decahydro-7-oxa-8-aza-pentaleno[2,1-a]phenanthren-2-one;

(4aS,4bR,5S,6aS,6bR,9aS,10aS,10bS,12S)-8-cyclohexyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester.

According to analogous procedures and methods described in the present application, the following compounds of formula (ID) may be obtained:
(4aS,4bR,5S,6aS,6bR,9aS,10aS,10bS,12S)-8-(2-cyclo-hexyl-ethyl)-4b,12-difluoro-5-hydroxy-4a,6a-dimethyl-2-oxo-2,4a,4b,5,6,6a,8,9,9a,10,10a,10b,11,12-tetradeca-hydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-bicyclo[2.2.1]hept-2-yl-4b,12-difluoro-5-hydroxy-4a,6a-dimethyl-2-oxo-2,4a,4b,5,6,6a,8,9,9a,10,10a,10b,11,12-tetradeca-hydro-7-oxa-8-aza-pentaleno[2,1-a]phenanthrene-6b-carbothioic acid S-fluoromethyl ester.

In a further preferred embodiment, the invention is directed to compounds of general formula (IE)

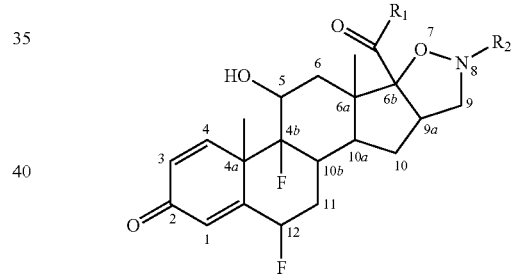

(IE)

wherein
R₁ is —(CH₂)$_n$—Z—(CH₂)$_{n'}$—R₃ wherein n and n' are each independently 0, 1 or 2;
Z is a single bond or is selected from —S— and —O—;
R₃ is selected from the group consisting of:
  H, halogen, CN, OH, (C₁-C₆)alkyl, (C₁-C₆)haloalkyl, and (C₁-C₆)alkylsulfonyl;
  NR₄R₅, wherein R₄ and R₅ are independently selected from the group consisting of (C₁-C₆)alkyl and (C₁-C₆) alkoxy;
  (C₁-C₆)alkyl; and
  (C₃-C₈)cycloalkyl, (C₃-C₈)heterocycloalkyl, aryl, and heteroaryl, each of which is optionally substituted by one or more halogen atoms or oxo groups;
R₂ is linear or branched (C₁-C₈)alkyl and
and pharmaceutically acceptable salts thereof.

Examples of Compounds of Formula (IE) Include:
(4aS,4bR,5S,6aS,6bR,9aS,10aS,10bS,12S)-8-(2-Ethyl-bu-tyl)-4b,12-difluoro-6b-(2-fluoro-acetyl)-5-hydroxy-4a,6a-dimethyl-4a,4b,5,6,6a,6b,8,9,9a,10,10a,10b,11,12-tet-radecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(1-propyl-butyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-4a,6a-dimethyl-8-(3-methyl-butyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(3-methyl-butyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-4a,6a-dimethyl-2-oxo-8-(1-propyl-butyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(1-propyl-butyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(3-methyl-butyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6bR,9aS,10aS,10bS,12S)-8-(1-Ethyl-2-methyl-propyl)-4b,12-difluoro-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-4a,6a-dimethyl-8-(3-methyl-butyl)-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-Difluoro-5-hydroxy-4a,6a-dimethyl-2-oxo-8-(1-propyl-butyl)-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-8-(2-Ethyl-butyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-8-(1-Ethyl-2-methyl-propyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-Difluoro-5-hydroxy-4a,6a-dimethyl-8-(3-methyl-butyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid 5-fluoromethyl ester;

(4aS,4bR,5S,6aS,6bR,9aS,10aS,10bS,12S)-4b,12-Difluoro-5-hydroxy-4a,6a-dimethyl-2-oxo-8-(1-propyl-butyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(2-Ethyl-butyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6bR,9aS,10aS,10bS,12S)-8-((S)-1-Ethyl-2-methyl-propyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester.

According to analogous procedures and methods described in the present application, the following compounds of the invention of formula (IE) may be obtained:

(4aS,4bR,5S,6aS,6bR,9aS,10aS,10bS,12S)-8-(1-Ethyl-2-methyl-propyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester.

In a preferred embodiment, the invention is directed to compounds of general formula (IF)

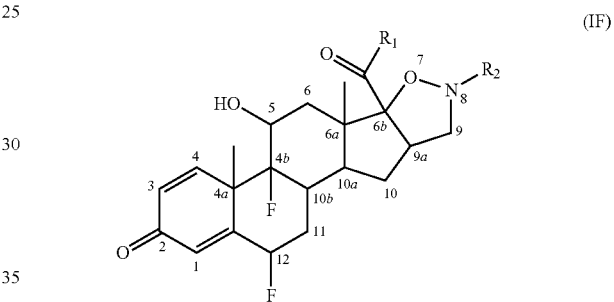

wherein $R_1$ is —$(CH_2)_n$—Z—$(CH_2)_{n'}$—$R_3$ wherein n is 1 and n' is zero;

Z is a single bond;

$R_3$ is a fluorine atom;

$R_2$ is selected from the group consisting of:

linear or branched $(C_1-C_8)$alkyl, $(C_1-C_6)$alkoxy, $(C_1-C_6)$haloalkyl, optionally substituted by one or more CN groups;

—$(CH_2)_m R_6$, wherein $R_6$ is selected from the group consisting of $(C_3-C_8)$cycloalkyl, $(C_3-C_8)$heterocloalkyl, aryl, aryloxy, arylthio, and heteroaryl, each of which optionally substituted by one or more substituents selected from the group consisting of oxo, OH, halogen, CN, $NH_2$, $NO_2$, linear or branched $(C_1-C_6)$alkyl, $(C_1-C_6)$alkoxy, aryl, $(C_1-C_6)$hydroxyalkoxy, $(C_1-C_6)$haloalkoxy, straight or branched $(C_1-C_6)$alkoxycarbonyl, $(C_1-C_6)$alkylcarboxyl, arylthio, and $(C_1-C_6)$alkylsulfanyl, wherein m is 0 or an integer from 1 to 3;

with the proviso that $R_2$ is not 4-chloro-benzyl;

and pharmaceutically acceptable salts thereof.

In particular, the invention is directed to compounds of general formula (IG)

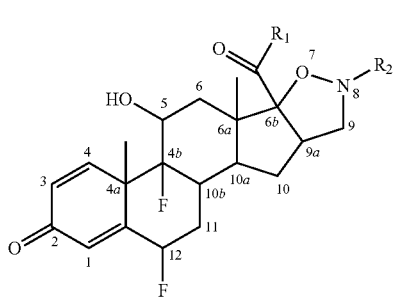

(IG)

wherein $R_1$ is —$(CH_2)_n$—Z—$(CH_2)_{n'}$—$R_3$ wherein n is 1 and n' is zero;

Z is a single bond;

$R_3$ is a fluorine atom;

$R_2$ is selected from the group consisting of:

linear or branched $(C_1-C_8)$alkyl;

—$(CH_2)_mR_6$, wherein $R_6$ is selected from the group consisting of $(C_3-C_8)$cycloalkyl, aryl, and heteroaryl, each of which optionally substituted by one or more substituents selected from the group consisting of halogen, linear or branched $(C_1-C_6)$alkyl, $(C_1-C_6)$alkoxy, $(C_1-C_6)$alkoxycarbonyl, and $(C_1-C_6)$alkylsulfanyl wherein m is 0 or an integer from 1 to 3;

with the proviso that $R_2$ is not 4-chloro-benzyl;

and pharmaceutically acceptable salts thereof.

In a preferred embodiment, in the compounds of formula (IG), $R_2$ is $(C_1-C_8)$alkyl or —$(CH_2)_mR_6$, where m is 1 and $R_6$ is optionally substituted heteroaryl.

Other compounds of formula (IG) which were obtained with analogous procedures to those described in the examples, are the following:

(4aS,4bR,5S,6aS,6bR,9aS,10aS,10bS,12S)-4b,12-difluoro-6b-(2-fluoro-acetyl)-5-hydroxy-4a,6a-dimethyl-8-(4-methyl-benzyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(2-Ethyl-butyl)-4b,12-difluoro-6b-(2-fluoro-acetyl)-5-hydroxy-4a,6a-dimethyl 4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-6b-(2-fluoro-acetyl)-5-hydroxy-4a,6a-dimethyl-8-phenyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-Chloro-phenyl)-4b,12-difluoro-6b-(2-fluoro-acetyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one.

In a preferred embodiment, the invention is directed to compounds of general formula (IH)

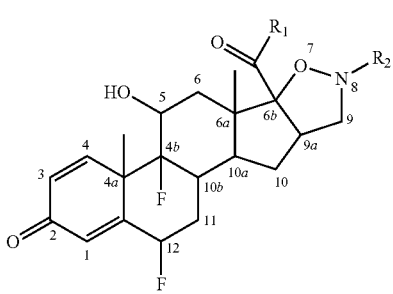

(IH)

wherein $R_1$ is —$(CH_2)_n$—Z—$(CH_2)_{n'}$—$R_3$ wherein n is zero and n' is 1;

Z is —S—;

$R_3$ is a fluorine atom;

$R_2$ is selected from the group consisting of:

linear or branched $(C_1-C_8)$alkyl, $(C_1-C_6)$alkoxy, $(C_1-C_6)$haloalkyl, optionally substituted by one or more CN groups or halogen atoms;

—$(CH_2)_mR_6$, wherein $R_6$ is selected from the group consisting of $(C_3-C_8)$cycloalkyl, $(C_3-C_8)$heterocycloalkyl, aryl, aryloxy, arylthio, and heteroaryl, each of which optionally substituted by one or more substituents selected from the group consisting of oxo, OH, halogen, CN, $NH_2$, $NO_2$, linear or branched $(C_1-C_6)$alkyl, linear or branched $(C_1-C_6)$haloalkyl, linear or branched $(C_1-C_6)$alkoxy, aryl, $(C_1-C_6)$hydroxyalkoxy, $(C_1-C_6)$haloalkoxy, $(C_1-C_6)$alkoxycarbonyl, $(C_1-C_6)$alkylcarboxyl, arylthio, and $(C_1-C_6)$alkylsulfanyl, wherein m is 0 or an integer from 1 to 3;

with the proviso that $R_2$ is neither 4-chloro-benzyl nor propyl-benzene;

and pharmaceutically acceptable salts thereof.

In particular, the invention is directed to compounds of general formula (IL)

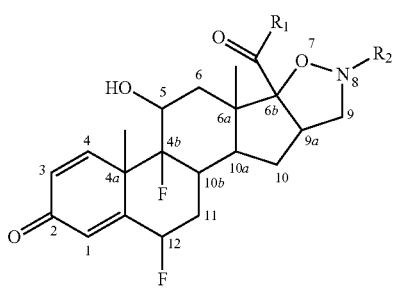

(IL)

wherein $R_1$ is —$(CH_2)_n$—Z—$(CH_2)_{n'}$—$R_3$ wherein n is zero and n' is 1;

Z is —S—;

$R_3$ is a fluorine atom;

$R_2$ is selected from the group consisting of:

linear or branched $(C_1-C_8)$alkyl optionally substituted by one or more halogen atoms;

—$(CH_2)_mR_6$, wherein $R_6$ is selected from the group consisting of $(C_3-C_8)$cycloalkyl, aryl, aryloxy, arylthio, and heteroaryl, each of which optionally substituted by one or more substituents selected from the group consisting of halogen, linear or branched $(C_1-C_6)$alkyl, linear or branched ($C_1$-$C_6$)haloalkyl, linear or branched ($C_1$-$C_6$)alkoxy, ($C_1$-$C_6$)alkoxycarbonyl, and ($C_1$-$C_6$)alkylsulfanyl wherein m is 0 or an integer from 1 to 3;
with the proviso that $R_2$ is neither 4-chloro-benzyl nor propyl-benzene;
and pharmaceutically acceptable salts thereof.

In a preferred embodiment, in the compounds of formula (IL), $R_2$ is —($CH_2$)$_m$$R_6$, m is 1 and $R_6$ is optionally substituted aryl or heteroaryl.

Other compounds which were obtained with analogous procedures to those described in the examples, are the following:

(4aS,4bR,5S,6aS,6bR,9aS,10aS,10bS,12S)-4b,12-Difluoro-5-hydroxy-4a,6a-dimethyl-2-oxo-8-(5-methyl-thiophen-2-yl-methyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-8-(4-methoxy-benzyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-8-(3-methyl-butyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Cyclopentyl-methyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(4-propyl-benzyl)-2,4a,4b,5,6,6a,8,9,9a,10,10a,10b,11,12-tetradecahydro-7-oxa-8-aza-pentaleno[2,1-a]phenanthrene-6b-carbothioic acid 5-fluoromethyl ester;

(4aS,4bR,5S,6bR,9aS,10aS,10bS,12S)-4b,12-Difluoro-5-hydroxy-4a,6a-dimethyl-8-(3-methyl-benzyl)-2-oxo-2,4a,4b,5,6,6a,8,9,9a,10,10a,10b,11,12-tetradecahydro-7-oxa-8-aza-pentaleno[2,1-a]henanthrene-6b-carbothioic acid S—((S)-fluoromethyl) ester;

(4aS,4bR,5S,6aS,6bR,9aS,10aS,10bS,12S)-4b,12-Difluoro-5-hydroxy-4a,6a-dimethyl-2-oxo-8-(5-chloro-thiophen-2-yl-methyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-8-(4-methyl-benzyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(4-tert-Butyl-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(2-phenylsulfanyl-ethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(1-propyl-butyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(2-phenoxy-ethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5 S,6aS,6bR,9aS,10aS,10bS,12S)-4b,12-Difluoro-5-hydroxy-4a,6a-dimethyl-2-oxo-8-(5-chloro-furan-2-yl-methyl-)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Cyclohexyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(5-methyl-thiophen-2-yl-methyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-8-(4-methoxy-benzyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-8-(3-methyl-butyl)-2-oxo-2,4a,4b,5,6,6a,8,9,9a,10,10a,10 b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Cyclopentyl-methyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(4-propyl-benzyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6bR,9aS,10aS,10bS,12S)-4b,12-Difluoro-5-hydroxy-4a,6a-dimethyl-8-(3-methyl-benzyl)-2-oxo-2,4a,4b,5,6,6a,8,9,9a,10,10a,10b,11,12-tetradecahydro-7-oxa-8-aza-pentaleno[2,1-a]henanthrene-6b-carbothioic acid S—((S)-fluoromethyl) ester;

(4aS,4bR,5S,6aS,6bR,9aS,10aS,10bS,12S)-4b,12-Difluoro-5-hydroxy-4a,6a-dimethyl-2-oxo-8-(5-chloro-thiophen-2-yl-methyl-)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-8-(4-methyl-benzyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(4-tert-Butyl-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(2-phenylsulfanyl-ethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(1-propyl-butyl)-2, 4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(2-phenoxy-ethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(5-chloro-furan-2-yl-methyl-)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Cyclohexyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(2-Ethyl-butyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(4-tert-Butoxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(4-Butoxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-8-(5-methyl-furan-2-ylmethyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-(5-methylsulfanyl-thiophen-2-ylmethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6bR,9aS,10aS,10bS,12S)-8-((S)-1-Ethyl-2-methyl-propyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(3,3,3-trifluoro-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Cyclopropylmethyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(2-Cyclohexyl-ethyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Bicyclo[2.2.1]hept-2-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6bR,9aS,10aS,10bS,12S)-4b,12-Difluoro-5-hydroxy-4a,6a-dimethyl-8-((S)-1-methyl-1H-indol-3-yl-methyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-m-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-o-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-p-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(3-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6bR,9aS,10aS,10bS,12S)-4b,12-Difluoro-8-(4-fluoro-phenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioicacid S—((S)-fluoromethyl) ester;

(4aS,4bR,5S,6aS,6bR,9aS,10aS,10bS,12S)-4b,12-Difluoro-5-hydroxy-4a,6a-dimethyl-2-oxo-8-pyridin-3-yl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6bR,9aS,10aS,10bS,12S)-4b,12-Difluoro-8-(3-fluoro-phenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioicacid S—((S)-fluoromethyl) ester;

(4aS,4bR,5S,6aS,6bR,9aS,10aS,10bS,12S)-4b,12-Difluoro-5-hydroxy-4a,6a-dimethyl-2-oxo-8-(4-trifluoromethyl-phenyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester.

According to analogous procedures and methods described in the present application, the following compounds may be obtained:

(4aS,4bR,5S,6aS,6bR,9aS,10aS,10bS,12S)-8-(1-ethyl-2-methyl-propyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-propyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-pyridin-3-yl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-thiazol-4-yl-2,4a,4b, 5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-8-oxazol-2-yl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-thiazol-2-ylmethyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-8-(2-imidazol-1-yl-ethyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(2-Cyclohexyl-ethyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(3-pyridin-3-yl-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-8-furan-3-yl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-8-(1H-indol-3-ylmethyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-quinolin-7-ylmethyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Benzothiazol-2-ylmethyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Bicyclo[2.2.1]hept-2-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-quinolin-5-ylmethyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-quinolin-2-ylmethyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Benzofuran-3-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-Benzo[1,3]dioxol-5-yl-4b,12-difluoro-5-hydroxy-4a,6a-dimethyl-2-oxo-2,4a,4b,5,6,6a,8,9,9a,10,10a,10,11,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-8-(1-methyl-1H-indol-2-yl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(1-methyl-1H-indol-3-ylmethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-(1-methyl-1H-imidazol-4-ylmethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-8-(1H-imidazol-2-ylmethyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(4-Chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-p-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-8-(4-methoxy-phenyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-Difluoro-5-hydroxy-4a,6a-dimethyl-2-oxo-8-o-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(3-chlorophenyl)-4b,12-difluoro-5-hydroxy-4a,6a-dimethyl-2-oxo-2,4a,4b,5,6,6a,8,9,9a,10,10a, 10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-m-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-8-(3-methoxy-phenyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester.

Other compounds which were obtained with analogous procedures to those described in the examples, are the following:

(4aS,4bR,5S,6aS,6bR,9aS,10aS,10bS,12S)-4b,12-Difluoro-5-hydroxy-6b-(2-hydroxy-acetyl)-4a,6a-dimethyl-8-(1-propyl-butyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-tert-Butyl-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(4-propyl-benzyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-Cyclohexyl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(3-methyl-butyl)-4a,4b,5,6,6a,6b,8,9,9a,10,10a,10b,11,12-tetradecahydro-7-oxa-8-aza-pentaleno[2,1-a]phenanthren-2-one.

In a preferred embodiment, the invention is directed to compounds of general formula (IM)

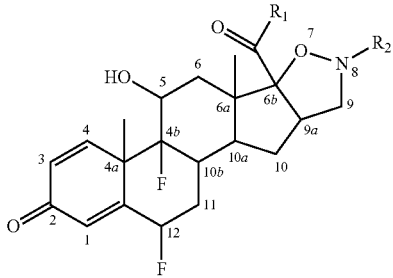

(IM)

wherein
$R_1$ is —$(CH_2)_n$—Z—$(CH_2)_{n'}$—$R_3$ wherein n is zero and n' is 1;
Z is a single bond;
$R_3$ is —OH;
$R_2$ is selected from the group consisting of:
linear or branched ($C_1$-$C_8$)alkyl;
—$(CH_2)_m R_6$, wherein $R_6$ is selected from the group consisting of ($C_3$-$C_8$)cycloalkyl, wherein m is 0 or an integer from 1 to 3 and
and pharmaceutically acceptable salts thereof.

In a preferred embodiment, the invention is directed to compounds of general formula (IN)

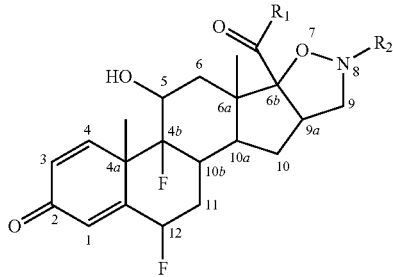

(IN)

wherein
$R_1$ is —$(CH_2)_n$—Z—$(CH_2)_{n'}$—$R_3$ wherein n is zero and n' is 1;
Z is a single bond;
$R_3$ is —OH;
$R_2$ is —$(CH_2)_m R_6$, wherein $R_6$ is aryl optionally substituted by one or more substituents selected from the group consisting of halogen, CN, $CONH_2$, NHC(O)H, linear or branched ($C_1$-$C_6$)alkyl, ($C_1$-$C_6$)alkylsulfonyl, linear or branched ($C_1$-$C_6$)haloalkyl, linear or branched ($C_1$-$C_6$)haloalkoxy, ($C_1$-$C_6$)alkoxycarbonyl, ($C_1$-$C_6$)alkoxysulfonyl, ($C_1$-$C_6$)haloalkylsulfonyloxy, ($C_3$-$C_8$)cycloalkyl, ($C_3$-$C_6$)heterocycloalkyl, aminosulfonyl, and heteroaryl and m is 0
and pharmaceutically acceptable salts thereof.

Other compounds which were obtained with analogous procedures to those described in the examples, are the following:

(4aS,4bR,5S,6aS,6bR,9aS,10aS,10bS,12S)-4b,12-Difluoro-5-hydroxy-6b-(2-hydroxy-acetyl)-4a,6a-dimethyl-8-(1-propyl-butyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-Cyclohexyl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(3-methyl-butyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-p-tolyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-m-tolyl-4a,4b,5,6,6a,6b,8,9,9a,10,10a,10b,11,12-tetradecahydro-7-oxa-8-aza-pentaleno[2,1-aphenanthren-2-one;

(4aS,4bR,5S,6bR,9aS,10aS,10bS,12S)-4b,12-Difluoro-8-(4-fluoro-phenyl)-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(3-Chloro-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(4-trifluoromethyl-phenyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6bR,9aS,10aS,10bS,12S)-4b,12-Difluoro-8-(3-fluoro-phenyl)-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-o-tolyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6bR,9aS,10aS,10bS,12S)-8-(4-Chloro-3-methyl-phenyl)-4b,12-difluoro-5-hydroxy-6b-((S)-2-hydroxy-acetyl)-4a,6a-dimethyl-4a,4b,5,6,6a,6b,8,9,9a,10, 10a,10b,11,12-tetradecahydro-7-oxa-8-aza-pentaleno[2, 1-a]phenanthren-2-one;

(4aS,4bR,5S,6aS,6bR,9aS,10aS,10bS,12S)-8-(4-Chloro-3-trifluoromethyl-phenyl)-4b,12-difluoro-5-hydroxy-6b-(2-hydroxy-acetyl)-4a,6a-dimethyl-4a,4b,5,6,6a,6b,8,9,9a, 10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(3,4-Dichloro-phenyl)-4b,12-difluoro-5-hydroxy-6b-(2-hydroxy-acetyl)-4a,6a-dimethyl-4a,4b,5,6,6a,6b,8,9,9a,10, 10a,10b,11,12-tetradecahydro-7-oxa-8-aza-pentaleno[2, 1-a]phenanthren-2-one;

(4aS,4bR,5S,6aS,6bR,9aS,10aS,10bS,12S)-8-(4-Bromo-phenyl)-4b,12-difluoro-5-hydroxy-6b-(2-hydroxy-acetyl)-4a,6a-dimethyl-4a,4b,5,6,6a,6b,8,9,9a,10,10a, 10b,11,12-tetradecahydro-7-oxa-8-aza-pentaleno[2,1-a] phenanthren-2-one;

4-[(4aS,4bR,5S,6aS,6bR,9aS,10aS,10bS)-4b-Fluoro-5-hydroxy-6b-(2-hydroxy-acetyl)-4a,6a-dimethyl-2-oxo-2,4a, 4b,5,6,6a,6b,9,9a,10,10a,10b,11,12-tetradecahydro-7-oxa-8-aza-pentaleno[2,1-a]phenanthren-8-yl]-benzonitrile;

4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzamide;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(4-trifluoromethoxy-phenyl)-4a,4b,5,6,6a,6b,8,9,9a,10,10a, 10b,11,12-tetradecahydro-7-oxa-8-aza-pentaleno[2,1-a] phenanthren-2-one;

Methanesulfonic acid 4-[(4aS,4bR,5S,6aS,6bR,9aS,10aS, 10bS,12S)-4b,12-difluoro-5-hydroxy-6b-(2-hydroxy-acetyl)-4a,6a-dimethyl-2-oxo-2,4a,4b,5,6,6a,6b,9,9a,10, 10a,10b,11,12-tetradecahydro-7-oxa-8-aza-pentaleno[2, 1-a]phenanthren-8-yl]-phenyl ester;

(4aS,4bR,5S,6aS,6bR,9aS,10aS,10bS,12S)-8-(4-Cyclo-hexyl-phenyl)-4b,12-difluoro-5-hydroxy-6b-(2-hydroxy-acetyl)-4a,6a-dimethyl-4a,4b,5,6,6a,6b,8,9,9a,10,10a, 10b,11,12-tetradecahydro-7-oxa-8-aza-pentaleno[2,1-a] phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(4-thiophen-2-yl-phenyl) 4a,4b,5,6,6a,6b,8,9,9a,10,10a,10b, 11,12-tetradecahydro-7-oxa-8-aza-pentaleno[2,1-a] phenanthren-2-one;

4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzoic acid methyl ester;

(4aS,4bR,5S,6aS,6bR,9aS,10aS,10bS,12S)-4b,12-Difluoro-5-hydroxy-6b-(2-hydroxy-acetyl)-8-(4-methanesulfonyl-phenyl)-4a,6a-dimethyl-4a,4b,5,6,6a,6b,8,9,9a,10,10a, 10b,11,12-tetradecahydro-7-oxa-8-aza-pentaleno[2,1-a] phenanthren-2-one;

3-[(4aS,4bR,5S,6aS,6bR,9aS,10aS,10bS,12S)-4 b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradeca-hydro-7-oxa-8-aza-pentaleno[2,1-a]phenanthren-8-yl]-benzonitrile;

4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradeca-hydro-7-oxa-8-aza-pentaleno[2,1-a]phenanthren-8-yl]-benzene sulfonamide;

(4aS,4bR,5 S,6aS,6bR,9aS,10aS,10bS,12S)-8-(4-Cyclopro-pyl-phenyl)-4b,12-difluoro-5-hydroxy-6b-(2-hydroxy-acetyl)-4a,6a-dimethyl-4a,4b,5,6,6a,6b,8,9,9a,10,10a, 10b,11,12-tetradecahydro-7-oxa-8-aza-pentaleno[2,1-a] phenanthren-2-one;

(4aS,4bR,5S,6aS,6bR,9aS,10aS,10bS,12S)-8-(4-tert-Butyl-phenyl)-4b,12-difluoro-5-hydroxy-6b-(2-hydroxy-acetyl)-4a,6a-dimethyl-4a,4b,5,6,6a,6b,8,9,9a,10,10a, 10b,11,12-tetradecahydro-7-oxa-8-aza-pentaleno[2,1-a] phenanthren-2-one;

N-{4-[(4aS,4bR,5S,6a8,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-phenyl}-formamide;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(3-trifluoromethyl-phenyl)-4a,4b,5,6,6a,6b,8,9,9a,10,10a, 10b,11,12-tetradecahydro-7-oxa-8-aza-pentaleno[2,1-a] phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(3-trifluoromethoxy-phenyl)-4a,4b,5,6,6a,6b,8,9,9a,10,10a, 10b,11,12-tetradecahydro-7-oxa-8-aza-pentaleno[2,1-a] phenanthren-2-one;

(4aS,4bR,5S,6aS,6bR,9aS,10aS,10bS,12S)-8-(3-Bromo-phenyl)-4b,12-difluoro-5-hydroxy-6b-(2-hydroxy-acetyl)-4a,6a-dimethyl-4a,4b,5,6,6a,6b,8,9,9a,10,10a, 10b,11,12-tetradecahydro-7-oxa-8-aza-pentaleno[2,1-a] phenanthren-2-one;

(4aS,4bR,5S,6aS,6bR,9aS,10aS,10bS,12S)-8-Benzothiazol-6-yl-4b,12-difluoro-5-hydroxy-6b-(2-hydroxy-acetyl)-4a, 6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-8-(4-hydroxy-phenyl-trifluoromethansulfonate)-4a,6a-dimethyl-4a,4b,5,6,6a, 6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(3-Cyclopro-pyl-phenyl)-4b,12-difluoro-5-hydroxy-6b-(2-hydroxy-acetyl)-4a,6a-dimethyl-4a,4b,5,6,6a,6b,8,9,9a,10,10a, 10b,11,12-tetradecahydro-7-oxa-8-aza-pentaleno[2,1-a] phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-(4-piperidin-4-ylmethyl-phenyl)-4a,4b,5,6,6a,6b,8,9,9a,10, 10a,10b,11,12-tetradecahydro-7-oxa-8-aza-pentaleno[2, 1-a]phenanthren-2-one.

In a preferred embodiment, the invention is directed to compounds of general formula (IN')

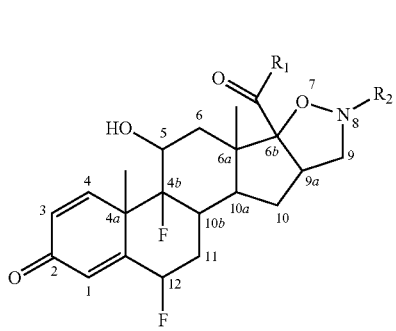

(IN')

wherein
R$_1$ is —(CH$_2$)$_n$—Z—(CH$_2$)$_{n'}$—R$_3$ wherein n is zero and n' is 1;
Z is a single bond;
R$_3$ is —OH;
R$_2$ is —(CH$_2$)$_m$R$_6$, wherein R$_6$ is heteroaryl and m is 0 and pharmaceutically acceptable salts thereof.

Other compounds which were obtained with analogous procedures to those described in the examples, are the following:

(4aS,4bR,5S,6aS,6bR,9aS,10aS,10bS,12S)-4b,12-Difluoro-5-hydroxy-6b-(2-hydroxy-acetyl)-4a,6a-dimethyl-8-quinolin-6-yl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-Difluoro-5-hydroxy-6b-(2-hydroxy-acetyl)-4a,6a-dimethyl-8-pyridin-3-yl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-Benzothiazol-6-yl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one.

It is to be understood that the present invention covers all combinations of particular and preferred groups and embodiments described hereinabove.

Hereinafter, compounds of formula (I), (I'), (IA), (IB), (IC), (ID), (IF), (IG), (IH), (IL), (IM), (IN), and (IN') and their pharmaceutically acceptable salts and solvates are referred to as "compounds of the invention".

Examples of preferred compounds of the invention are:

| Compound | Chemical Name |
| --- | --- |
| 10 | (4aS,4bR,5S,6aS,6bR,9aS,10aS,10bS,12S)-8-(3,3-dimethyl-butyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 11 | (4aS,4bR,5S,6aS,6bR,9aS,10aS,10bS,12S)-4b,12-difluoro-8-(4-fluoro-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 12 | (4aS,4bR,5S,6aS,6bR,9aS,10aS,10bS,12S)-4b,12-difluoro-5-hydroxy-6b-(2-hydroxy-acetyl)-4a,6a-dimethyl-8-thiophen-2-ylmethyl-4a,4b,5,6,6a,6b,8,9,9a,10,10a,10b,11,12-tetradecahydro-7-oxa-8-aza-pentaleno[2,1-a]phenanthren-2-one |
| 13 | (4aS,4bR,5S,6aS,6bR,9aS,10aS,10bS,12S)-4b,12-difluoro-8-furan-2-ylmethyl-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 14 | (4aS,4bR,5S,6aS,6bR,9aS,10aS,10bS,12S)-8-(2-ethyl-butyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 15 | 3-[(4aS,4bR,5S,6aS,6bR,9aS,10aS,10bS,12S)-4b,12-difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-ylmethyl]-benzoic acid methyl ester |
| 16 | (4aS,4bR,5S,6aS,6bR,9aS,10aS,10bS,12S)-8-cyclohexylmethyl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 17 | (4aS,4bR,5S,6aS,6bR,9aS,10aS,10bS,12S)-4b,12-difluoro-5-hydroxy-6b-(2-hydroxy-acetyl)-4a,6a-dimethyl-8-(4-methylsulfanyl-benzyl)-4a,4b,5,6,6a,6b,8,9,9a,10,10a,10b,11,12-tetradecahydro-7-oxa-8-aza-pentaleno[2,1-a]phenanthren-2-one |
| 18 | (4aS,4bR,5S,6aS,6bR,9aS,10aS,10bS,12S)-8-((R,S)-sec-butyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 19 | (4aS,4bR,5S,6aS,6bR,9aS,10aS,10bS,12S)-8-cyclopentylmethyl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 20 | 4-[(4aS,4bR,5S,6aS,6bR,9aS,10aS,10bS,12S)-4b,12-difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-ylmethyl]-benzoic acid tert-butyl ester |
| 21 | (4aS,4bR,5S,6aS,6bR,9aS,10aS,10bS,12S)-8-(4-chloro-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |

-continued

| Compound | Chemical Name |
|---|---|
| 23 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(1-propyl-butyl)-4a,4b,5,6,6a,6b,8,9,9a,10,10a,10b,11,12-tetradecahydro-7-oxa-8-aza-pentaleno[2,1-a]phenanthren-2-one |
| 24 | (4aS,4bR,5S,6aS,6bR,9aS,10aS,10bS,12S)-8-(4-tert-Butyl-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 25 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-propyl-benzyl)-4a,4b,5,6,6a,6b,8,9,9a,10,10a,10b,11,12-tetradecahydro-7-oxa-8-aza-pentaleno[2,1-a]phenanthren-2-one |
| 26 | (4aS,4bR,5S,6aS,6bR,9aS,10aS,10bS,12S)-8-Cyclohexyl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 27 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(3-methyl-butyl)-4a,4b,5,6,6a,6b,8,9,9a,10,10a,10b,11,12-tetradecahydro-7-oxa-8-aza-pentaleno[2,1-a]phenanthren-2-one |
| 28 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(5-methylsulfanyl-thiophen-2-ylmethyl)-4a,4b,5,6,6a,6b,8,9,9a,10,10a,10b,11,12-tetradecahydro-7-oxa-8-aza-pentaleno[2,1-a]phenanthren-2-one |
| 29 | (4aS,4bR,5S,6bR,9aS,10aS,10bS,12S)-8-(1-Ethyl-2-methyl-propyl)-4b,12-difluoro-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 30 | (4aS,4bR,5S,6aS,6bR,9aS,10aS,10bS,12S)-8-(4-Butoxy-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 31 | (4aS,4bR,5S,6aS,6bR,9aS,10aS,10bS,12S)-8-(2-Cyclohexyl-ethyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 32 | (4aS,4bR,5S,6aS,6bR,9aS,10aS,10bS,12S)-4b,12-Difluoro-5-hydroxy-6b-((S)-2-hydroxy-acetyl)-4a,6a-dimethyl-8-(1-methyl-1H-indol-3-ylmethyl)-4a,4b,5,6,6a,6b,8,9,9a,10,10a,10b,11,12-tetradecahydro-7-oxa-8-aza-pentaleno[2,1-a]phenanthren-2-one |
| 33 | (4aS,4bR,5S,6aS,6bR,9aS,10aS,10bS,12S)-8-Bicyclo[2.2.1]hept-2-yl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 34 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(3-pyridin-3-yl-propyl)-4a,4b,5,6,6a,6b,8,9,9a,10,10a,10b,11,12-tetradecahydro-7-oxa-8-aza-pentaleno[2,1-a]phenanthren-2-one |
| 35 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(3,3,3-trifluoro-propyl)-4a,4b,5,6,6a,6b,8,9,9a,10,10a,10b,11,12-tetradecahydro-7-oxa-8-aza-pentaleno[2,1-a]phenanthren-2-one |
| 36 | (4aS,4bR,5S,6aS,6bR,9aS,10aS,10bS,12S)-4b,12-Difluoro-5-hydroxy-6b-(2-hydroxy-acetyl)-8-(2-imidazol-1-yl-ethyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 37 | (4aS,5S,6aS,6bR,9aS,10aS,10bS,12S)-4b-(R)-Fluoro-12-fluoro-5-hydroxy-6b-(2-hydroxy-acetyl)-4a,6a-dimethyl-8-quinolin-5-ylmethyl-4a,4b,5,6,6a,6b,8,9,9a,10,10a,10b,11,12-tetradecahydro-7-oxa-8-aza-pentaleno[2,1-a]phenanthren-2-one |
| 38 | (4aS,4bR,5S,6aS,6bR,9aS,10aS,10bS,12S)-4b,12-Difluoro-5-hydroxy-6b-(2-hydroxy-acetyl)-4a,6a-dimethyl-8-thiazol-2-ylmethyl-4a,4b,5,6,6a,6b,8,9,9a,10,10a,10b,11,12-tetradecahydro-7-oxa-8-aza-pentaleno[2,1-a]phenanthren-2-one |
| 39 | Methanesulfonic acid 2-[(4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 40 | (4aS,4bR,5S,6aS,6bR,9aS,10aS,10bS,12S)-6b-acetyl-8-(4-chloro-benzyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 41 | (4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |

-continued

| Compound | Chemical Name |
|---|---|
| 42 | (4aS,4bR,5S,6aS,6bR,9aS,10aS,10bS,12S)-8-(3,3-dimethyl-butyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 43 | (4aS,4bR,5S,6aS,6bR,9aS,10aS,10bS,12S)-4b,12-difluoro-8-(4-fluoro-benzyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 44 | (4aS,4bR,5S,6aS,6bR,9aS,10aS,10bS,12S)-4b,12-difluoro-5-hydroxy-4a,6a-dimethyl-2-oxo-8-thiophen-2-ylmethyl-2,4a,4b,5,6,6a,8,9,9a,10,10a,10b,11,12-tetradecahydro-7-oxa-8-aza-pentaleno[2,1-a]phenanthrene-6b-carboxylic acid |
| 45 | (4aS,4bR,5S,6aS,6bR,9aS,10aS,10bS,12S)-4b,12-difluoro-8-furan-2-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 46 | (4aS,4bR,5S,6aS,6bR,9aS,10aS,10bS,12S)-4b,12-Difluoro-5-hydroxy-4a,6a-dimethyl-8-(5-methyl-thiophen-2-ylmethyl)-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 47 | (4aS,4bR,5S,6aS,6bR,9aS,10aS,10bS,12S)-4b,12-Difluoro-5-hydroxy-8-(4-methoxy-benzyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 48 | (4aS,4bR,5S,6aS,6bR,9aS,10aS,10bS,12S)-4b,12-Difluoro-5-hydroxy-4a,6a-dimethyl-8-(3-methyl-butyl)-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 49 | (4aS,4bR,5S,6aS,6bR,9aS,10aS,10bS,12S)-8-Cyclopentylmethyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 50 | (4aS,4bR,5S,6aS,6bR,9aS,10aS,10bS,12S)-4b,12-Difluoro-5-hydroxy-4a,6a-dimethyl-2-oxo-8-(4-propyl-benzyl)-2,4a,4b,5,6,6a,8,9,9a,10,10a,10b,11,12-tetradecahydro-7-oxa-8-aza-pentaleno[2,1-a]phenanthrene-6b-carboxylic acid |
| 51 | (4aS,4bR,5S,6aS,6bR,9aS,10aS,10bS,12S)-4b,12-Difluoro-5-hydroxy-4a,6a-dimethyl-8-(3-methyl-benzyl)-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 52 | (4aS,4bR,5S,6aS,6bR,9aS,10aS,10bS,12S)-8-(5-Chloro-thiophen-2-ylmethyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 53 | (4aS,4bR,5S,6aS,6bR,9aS,10aS,10bS,12S)-4b,12-Difluoro-5-hydroxy-4a,6a-dimethyl-8-(4-methyl-benzyl)-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 54 | (4aS,4bR,5S,6aS,6bR,9aS,10aS,10bS,12S)-8-(4-tert-Butyl-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 55 | (4aS,4bR,5S,6aS,6bR,9aS,10aS,10bS,12S)-4b,12-Difluoro-5-hydroxy-4a,6a-dimethyl-2-oxo-8-(2-phenylsulfanyl-ethyl)-2,4a,4b,5,6,6a,8,9,9a,10,10a,10b,11,12-tetradecahydro-7-oxa-8-aza-pentaleno[2,1-a]phenanthrene-6b-carboxylic acid |
| 56 | (4aS,4bR,5S,6aS,6bR,9aS,10aS,10bS,12S)-4b,12-Difluoro-5-hydroxy-4a,6a-dimethyl-2-oxo-8-(1-propyl-butyl)-2,4a,4b,5,6,6a,8,9,9a,10,10a,10b,11,12-tetradecahydro-7-oxa-8-aza-pentaleno[2,1-a]phenanthrene-6b-carboxylic acid |
| 57 | (4aS,4bR,5S,6aS,6bR,9aS,10aS,10bS,12S)-4b,12-Difluoro-5-hydroxy-4a,6a-dimethyl-2-oxo-8-(2-phenoxy-ethyl)-2,4a,4b,5,6,6a,8,9,9a,10,10a,10b,11,12-tetradecahydro-7-oxa-8-aza-pentaleno[2,1-a]phenanthrene-6b-carboxylic acid |
| 58 | (4aS,4bR,5S,6aS,6bR,9aS,10aS,10bS,12S)-8-(5-Chloro-furan-2-ylmethyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 59 | (4aS,4bR,5S,6aS,6bR,9aS,10aS,10bS,12S)-8-Cyclohexyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 60 | (4aS,4bR,5S,6aS,6bR,9aS,10aS,10bS,12S)-8-(2-Ethyl-butyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |

| Compound | Chemical Name |
|---|---|
| 61 | (4aS,4bR,5S,6aS,6bR,9aS,10aS,10bS,12S)-8-(4-tert-Butoxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 62 | (4aS,4bR,5S,6aS,6bR,9aS,10aS,10bS,12S)-8-(4-Butoxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 63 | (4aS,4bR,5S,6aS,6bR,9aS,10aS,10bS,12S)-4b,12-Difluoro-5-hydroxy-4a,6a-dimethyl-8-(5-methyl-furan-2-ylmethyl)-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 64 | (4aS,4bR,5S,6aS,6bR,9aS,10aS,10bS,12S)-4b,12-Difluoro-5-hydroxy-4a,6a-dimethyl-8-(5-methylsulfanyl-thiophen-2-ylmethyl)-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 65 | (4aS,4bR,5S,6aS,6bR,9aS,10aS,10bS,12S)-8-(1-Ethyl-2-methyl-propyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 66 | (4aS,4bR,5S,6aS,6bR,9aS,10aS,10bS,12S)-4b,12-Difluoro-5-hydroxy-4a,6a-dimethyl-2-oxo-8-(3,3,3-trifluoro-propyl)-2,4a,4b,5,6,6a,8,9,9a,10,10a,10b,11,12-tetradecahydro-7-oxa-8-aza-pentaleno[2,1-a]phenanthrene-6b-carboxylic acid |
| 67 | (4aS,4bR,5S,6aS,6bR,9aS,10aS,10bS,12S)-8-Cyclopropylmethyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 68 | (4aS,4bR,5S,6aS,6bR,9aS,10aS,10bS,12S)-8-(2-Cyclohexyl-ethyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 69 | (4aS,4bR,5S,6aS,6bR,9aS,10aS,10bS,12S)-8-Bicyclo[2.2.1]hept-2-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 70 | (4aS,4bR,5S,6aS,6bR,9aS,10aS,10bS,12S)-4b,12-Difluoro-5-hydroxy-4a,6a-dimethyl-8-(1-methyl-1H-indol-3-ylmethyl)-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 71 | (4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-oxo-[1,3]dioxolan-4-yl) ester |
| 72 | (4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid methoxy-methyl-amide |
| 73 | (4aS,4bR,5S,6aS,6bR,9aS,10aS,10bS,12S)-4b,12-difluoro-5-hydroxy-4a,6a-dimethyl-2-oxo-8-thiophen-2-ylmethyl-2,4a,4b,5,6,6a,8,9,9a,10,10a,10b,11,12-tetradecahydro-7-oxa-8-aza-pentaleno[2,1-a]phenanthrene-6b-carboxylic acid fluoromethyl ester |
| 74 | (4aS,4bR,5S,6aS,6bR,9aS,10aS,10bS,12S)-4b,12-difluoro-8-(4-fluoro-benzyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid fluoromethyl ester |
| 75 | (4aS,4bR,5S,6aS,6bR,9aS,10aS,10bS,12S)-4b,12-difluoro-8-(4-fluoro-benzyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl ester |
| 76 | (4aS,4bR,5S,6aS,6bR,9aS,10aS,10bS,12S)-4b,12-difluoro-5-hydroxy-4a,6a-dimethyl-2-oxo-8-thiophen-2-ylmethyl-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl ester |
| 77 | (4aS,4bR,5S,6aS,6bR,9aS,10aS,10bS,12S)-4b,12-difluoro-8-furan-2-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 78 | (4aS,4bR,5S,6aS,6bR,9aS,10aS,10bS,12S)-4b,12-difluoro-8-(4-fluoro-benzyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |

| Compound | Chemical Name |
|---|---|
| 79 | (4aS,4bR,5S,6aS,6bR,9aS,10aS,10bS,12S)-4b,12-difluoro-5-hydroxy-4a,6a-dimethyl-2-oxo-8-thiophen-2-ylmethyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 80 | (4aS,4bR,5S,6aS,6bR,9aS,10aS,10bS,12S)-8-(3,3-dimethyl-butyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 81 | (4aS,4bR,5S,6aS,6bR,9aS,10aS,10bS,12S)-4b,12-Difluoro-5-hydroxy-4a,6a-dimethyl-2-oxo-8-(5-methyl-thiophen-2-yl-methyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 82 | (4aS,4bR,5S,6aS,6bR,9aS,10aS,10bS,12S)-4b,12-Difluoro-5-hydroxy-8-(4-methoxy-benzyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 83 | (4aS,4bR,5S,6aS,6bR,9aS,10aS,10bS,12S)-4b,12-Difluoro-5-hydroxy-4a,6a-dimethyl-8-(3-methyl-butyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 84 | (4aS,4bR,5S,6aS,6bR,9aS,10aS,10bS,12S)-8-Cyclopentylmethyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 85 | (4aS,4bR,5S,6aS,6bR,9aS,10aS,10bS,12S)-4b,12-Difluoro-5-hydroxy-4a,6a-dimethyl-2-oxo-8-(4-propyl-benzyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 86 | (4aS,4bR,5S,6bR,9aS,10aS,10bS,12S)-4b,12-Difluoro-5-hydroxy-4a,6a-dimethyl-8-(3-methyl-benzyl)-2-oxo-2,4a,4b,5,6,6a,8,9,9a,10,10a,10b,11,12-tetradecahydro-7-oxa-8-aza-pentaleno[2,1-a]henanthrene-6b-carbothioic acid S-((S)-fluoromethyl) ester |
| 87 | (4aS,4bR,5S,6aS,6bR,9aS,10aS,10bS,12S)-4b,12-Difluoro-5-hydroxy-4a,6a-dimethyl-2-oxo-8-(5-chloro-thiophen-2-yl-methyl-)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 88 | (4aS,4bR,5S,6aS,6bR,9aS,10aS,10bS,12S)-4b,12-Difluoro-5-hydroxy-4a,6a-dimethyl-8-(4-methyl-benzyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 89 | (4aS,4bR,5S,6aS,6bR,9aS,10aS,10bS,12S)-8-(4-tert-Butyl-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 90 | (4aS,4bR,5S,6aS,6bR,9aS,10aS,10bS,12S)-4b,12-Difluoro-5-hydroxy-4a,6a-dimethyl-2-oxo-8-(2-phenylsulfanyl-ethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 91 | (4aS,4bR,5S,6aS,6bR,9aS,10aS,10bS,12S)-4b,12-Difluoro-5-hydroxy-4a,6a-dimethyl-2-oxo-8-(1-propyl-butyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 92 | (4aS,4bR,5S,6aS,6bR,9aS,10aS,10bS,12S)-4b,12-Difluoro-5-hydroxy-4a,6a-dimethyl-2-oxo-8-(2-phenoxy-ethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 93 | (4aS,4bR,5S,6aS,6bR,9aS,10aS,10bS,12S)-4b,12-Difluoro-5-hydroxy-4a,6a-dimethyl-2-oxo-8-(5-chloro-furan-2-yl-methyl-)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 94 | (4aS,4bR,5S,6aS,6bR,9aS,10aS,10bS,12S)-8-Cyclohexyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 95 | (4aS,4bR,5S,6aS,6bR,9aS,10aS,10bS,12S)-8-(2-Ethyl-butyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 96 | (4aS,4bR,5S,6aS,6bR,9aS,10aS,10bS,12S)-8-(4-tert-Butoxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 97 | (4aS,4bR,5S,6aS,6bR,9aS,10aS,10bS,12S)-8-(4-Butoxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |

-continued

| Compound | Chemical Name |
|---|---|
| 98 | (4aS,4bR,5S,6aS,6bR,9aS,10aS,10bS,12S)-4b,12-Difluoro-5-hydroxy-4a,6a-dimethyl-8-(5-methyl-furan-2-ylmethyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 99 | (4aS,4bR,5S,6aS,6bR,9aS,10aS,10bS,12S)-4b,12-Difluoro-5-hydroxy-4a,6a-dimethyl-2-oxo-(5-methylsulfanyl-thiophen-2-ylmethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 100 | (4aS,4bR,5S,6bR,9aS,10aS,10bS,12S)-8-((S)-1-Ethyl-2-methyl-propyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 101 | (4aS,4bR,5S,6aS,6bR,9aS,10aS,10bS,12S)-4b,12-Difluoro-5-hydroxy-4a,6a-dimethyl-2-oxo-8-(3,3,3-trifluoro-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 102 | (4aS,4bR,5S,6aS,6bR,9aS,10aS,10bS,12S)-8-Cyclopropylmethyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 103 | (4aS,4bR,5S,6aS,6bR,9aS,10aS,10bS,12S)-8-(2-Cyclohexyl-ethyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 104 | (4aS,4bR,5S,6aS,6bR,9aS,10aS,10bS,12S)-8-Bicyclo[2.2.1]hept-2-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 105 | (4aS,4bR,5S,6aS,6bR,9aS,10aS,10bS,12S)-4b,12-Difluoro-5-hydroxy-4a,6a-dimethyl-8-((S)-1-methyl-1H-indol-3-yl-methyl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 107 | (4aS,4bR,5S,6aS,6bR,9aS,10aS,10bS,12S)-4b,12-difluoro-6b-(2-fluoro-acetyl)-5-hydroxy-4a,6a-dimethyl-8-(4-methyl-benzyl)-4a,4b,5,6,6a,6b,8,9,9a,10,10a,10b,11,12-tetradecahydro-7-oxa-8-aza-pentaleno[2,1-a]phenanthren-2-one |
| 108 | (4aS,4bR,5S,6aS,6bR,9aS,10aS,10bS,12S)-4b,12-Difluoro-6b-(2-fluoro-acetyl)-5-hydroxy-4a,6a-dimethyl-8-thiophen-2-ylmethyl-4a,4b,5,6,6a,6b,8,9,9a,10,10a,10b,11,12-tetradecahydro-7-oxa-8-aza-pentaleno[2,1-a]phenanthren-2-one |
| 109 | (4aS,4bR,5S,6aS,6bR,9aS,10aS,10bS,12S)-4b,12-difluoro-6b-(2-fluoro-acetyl)-8-(4-fluoro-benzyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 110 | (4aS,4bR,5S,6aS,6bR,9aS,10aS,10bS,12S)-4b,12-difluoro-6b-(2-fluoro-acetyl)-8-furan-2-ylmethyl-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 111 | (4aS,4bR,5S,6aS,6bR,9aS,10aS,10bS,12S)-4b,12-difluoro-6b-(2-fluoro-acetyl)-5-hydroxy-8-(4-methoxy-benzyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 112 | (4aS,4bR,5S,6aS,6bR,9aS,10aS,10bS,12S)-8-cyclopentylmethyl-4b,12-difluoro-6b-(2-fluoro-acetyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 113 | (4aS,4bR,5S,6aS,6bR,9aS,10aS,10bS,12S)-8-(3,3-dimethyl-butyl)-4b,12-difluoro-6b-(2-fluoro-acetyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 114 | (4aS,4bR,5S,6aS,6bR,9aS,10aS,10bS,12S)-8-(5-chloro-thiophen-2-ylmethyl)-4b,12-difluoro-6b-(2-fluoro-acetyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 116 | (4aS,4bR,5S,6aS,6bR,9aS,10aS,10bS,12S)-4b,12-difluoro-5-hydroxy-6b-(2-hydroxy-acetyl)-8-[4-(2-hydroxy-ethoxy)-benzyl]-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 122 | (4aS,4bR,5S,6aS,6bR,9aS,10aS,10bS,12S)-4b,12-difluoro-5-hydroxy-6b-(2-hydroxy-acetyl)-4a,6a-dimethyl-8-phenyl-4a,4b,5,6,6a,6b,8,9,9a,10,10a,10b,11,12-tetradecahydro-7-oxa-8-aza-pentaleno[2,1-a]phenanthren-2-one |
| 123 | (4aS,4bR,5S,6aS,6bR,9aS,10aS,10bS,12S)-8-(4-chloro-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |

-continued

| Compound | Chemical Name |
|---|---|
| 124 | (4aS,4bR,5S,6aS,6bR,9aS,10aS,10bS,12S)-4b,12-Difluoro-5-hydroxy-6b-(2-hydroxy-acetyl)-4a,6a-dimethyl-8-p-tolyl-4a,4b,5,6,6a,6b,8,9,9a,10,10a,10b,11,12-tetradecahydro-7-oxa-8-aza-pentaleno[2,1-a]phenanthren-2-one |
| 125 | (4aS,4bR,5S,6aS,6bR,9aS,10aS,10bS,12S)-4b,12-Difluoro-5-hydroxy-6b-(2-hydroxy-acetyl)-4a,6a-dimethyl-8-quinolin-6-yl-4a,4b,5,6,6a,6b,8,9,9a,10,10a,10b,11,12-tetradecahydro-7-oxa-8-aza-pentaleno[2,1-a]phenanthren-2-one |
| 126 | (4aS,4bR,5S,6aS,6bR,9aS,10aS,10bS,12S)-4b,12-Difluoro-5-hydroxy-6b-(2-hydroxy-acetyl)-4a,6a-dimethyl-8-pyridin-3-yl-4a,4b,5,6,6a,6b,8,9,9a,10,10a,10b,11,12-tetradecahydro-7-oxa-8-aza-pentaleno[2,1-a]phenanthren-2-one |
| 127 | (4aS,4bR,5S,6aS,6bR,9aS,10aS,10bS,12S)-4b,12-Difluoro-5-hydroxy-6b-(2-hydroxy-acetyl)-4a,6a-dimethyl-8-m-tolyl-4a,4b,5,6,6a,6b,8,9,9a,10,10a,10b,11,12-tetradecahydro-7-oxa-8-aza-pentaleno[2,1-aphenanthren-2-one |
| 128 | (4aS,4bR,5S,6bR,9aS,10aS,10bS,12S)-4b,12-Difluoro-8-(4-fluoro-phenyl)-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 129 | (4aS,4bR,5S,6aS,6bR,9aS,10aS,10bS,12S)-8-(3-Chloro-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 130 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-trifluoromethyl-phenyl)-4a,4b,5,6,6a,6b,8,9,9a,10,10a,10b,11,12-tetradecahydro-7-oxa-8-aza-pentaleno[2,1-a]phenanthren-2-one |
| 131 | (4aS,4bR,5S,6bR,9aS,10aS,10bS,12S)-4b,12-Difluoro-8-(3-fluoro-phenyl)-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 132 | (4aS,4bR,5S,6aS,6bR,9aS,10aS,10bS,12S)-4b,12-Difluoro-5-hydroxy-6b-(2-hydroxy-acetyl)-4a,6a-dimethyl-8-o-tolyl-4a,4b,5,6,6a,6b,8,9,9a,10,10a,10b,11,12-tetradecahydro-7-oxa-8-aza-pentaleno[2,1-a]phenanthren-2-one |
| 133 | (4aS,4bR,5S,6bR,9aS,10aS,10bS,12S)-8-(4-Chloro-3-methyl-phenyl)-4b,12-difluoro-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 134 | (4aS,4bR,5S,6aS,6bR,9aS,10aS,10bS,12S)-8-(4-Chloro-3-trifluoromethyl-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 135 | (4aS,4bR,5S,6aS,6bR,9aS,10aS,10bS,12S)-8-(3,4-Dichloro-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 136 | (4aS,4bR,5S,6aS,6bR,9aS,10aS,10bS,12S)-8-(4-Bromo-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 137 | 4-[(4aS,4bR,5S,6aS,6bR,9aS,10aS,10bS)-4b-Fluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzonitrile |
| 138 | 4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzamide |
| 139 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-trifluoromethoxy-phenyl)-4a,4b,5,6,6a,6b,8,9,9a,10,10a,10b,11,12-tetradecahydro-7-oxa-8-aza-pentaleno[2,1-a]phenanthren-2-one |
| 140 | Methanesulfonic acid 4-[(4aS,4bR,5S,6aS,6bR,9aS,10aS,10bS,12S)-4b,12-difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-phenyl ester |
| 141 | (4aS,4bR,5S,6aS,6bR,9aS,10aS,10bS,12S)-8-(4-Cyclohexyl-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 142 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-thiophen-2-yl-phenyl) 4a,4b,5,6,6a,6b,8,9,9a,10,10a,10b,11,12-tetradecahydro-7-oxa-8-aza-pentaleno[2,1-a]phenanthren-2-one |

-continued

| Compound | Chemical Name |
|---|---|
| 143 | 4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzoic acid methyl ester |
| 144 | (4aS,4bR,5S,6aS,6bR,9aS,10aS,10bS,12S)-4b,12-Difluoro-5-hydroxy-6b-(2-hydroxy-acetyl)-8-(4-methanesulfonyl-phenyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 145 | 3-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzonitrile |
| 146 | 4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzene sulfonamide |
| 147 | (4aS,4bR,5S,6aS,6bR,9aS,10aS,10bS,12S)-8-(4-Cyclopropyl-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 148 | (4aS,4bR,5S,6aS,6bR,9aS,10aS,10bS,12S)-8-(4-tert-Butyl-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 149 | N-{4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-phenyl}-formamide |
| 150 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(3-trifluoromethyl-phenyl)-4a,4b,5,6,6a,6b,8,9,9a,10,10a,10b,11,12-tetradecahydro-7-oxa-8-aza-pentaleno[2,1-a]phenanthren-2-one |
| 151 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(3-trifluoromethoxy-phenyl)-4a,4b,5,6,6a,6b,8,9,9a,10,10a,10b,11,12-tetradecahydro-7-oxa-8-aza-pentaleno[2,1-a]phenanthren-2-one |
| 152 | (4aS,4bR,5S,6aS,6bR,9aS,10aS,10bS,12S)-8-(3-Bromo-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 153 | (4aS,4bR,5S,6aS,6bR,9aS,10aS,10bS,12S)-8-Benzothiazol-6-yl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 154 | (4aS,4bR,5S,6aS,6bR,9aS,10aS,10bS,12S)-4b,12-Difluoro-5-hydroxy-6b-(2-hydroxy-acetyl)-8-(4-hydroxy-phenyltrifluoromethansulfonate)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 155 | (4aS,4bR,5S,6aS,6bR,9aS,10aS,10bS,12S)-8-(3-Cyclopropyl-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 156 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-piperidin-4-ylmethyl-phenyl)-4a,4b,5,6,6a,6b,8,9,9a,10,10a,10b,11,12-tetradecahydro-7-oxa-8-aza-pentaleno[2,1-a]phenanthren-2-one |
| 158 | (4aS,4bR,5S,6aS,6bR,9aS,10aS,10bS,12S)-4b,12-Difluoro-5-hydroxy-4a,6a-dimethyl-2-oxo-8-phenyl-2,4a,4b,5,6,6a,8,9,9a,10,10a,10b,11,12-tetradecahydro-7-oxa-8-aza-pentaleno[2,1-a]phenanthrene-6b-carboxylic acid |
| 159 | (4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 160 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 161 | (4aS,4bR,5S,6aS,6bR,9aS,10aS,10bS,12S)-4b,12-Difluoro-5-hydroxy-4a,6a-dimethyl-2-oxo-8-m-tolyl-2,4a,4b,5,6,6a,8,9,9a,10,10a,10b,11,12-tetradecahydro-7-oxa-8-aza-pentaleno[2,1-a]phenanthrene-6b-carboxylic acid |
| 162 | (4aS,4bR,5S,6aS,6bR,9aS,10aS,10bS,12S)-4b,12-Difluoro-5-hydroxy-4a,6a-dimethyl-2-oxo-8-o-tolyl-2,4a,4b,5,6,6a,8,9,9a,10,10a,10b,11,12-tetradecahydro-7-oxa-8-aza-pentaleno[2,1-a]phenanthrene-6b-carboxylic acid |

| Compound | Chemical Name |
|---|---|
| 163 | (4aS,4bR,5S,6aS,6bR,9aS,10aS,10bS,12S)-4b,12-Difluoro-5-hydroxy-4a,6a-dimethyl-2-oxo-8-p-tolyl-2,4a,4b,5,6,6a,8,9,9a,10,10a,10b,11,12-tetradecahydro-7-oxa-8-aza-pentaleno[2,1-a]phenanthrene-6b-carboxylic acid |
| 164 | (4aS,4bR,5S,6aS,6bR,9aS,10aS,10bS,12S)-8-(3-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 165 | (4aS,4bR,5S,6aS,6bR,9aS,10aS,10bS,12S)-4b,12-Difluoro-8-(4-fluoro-phenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 166 | (4aS,4bR,5S,6aS,6bR,9aS,10aS,10bS,12S)-4b,12-Difluoro-5-hydroxy-4a,6a-dimethyl-2-oxo-8-pyridin-3-yl-2,4a,4b,5,6,6a,8,9,9a,10,10a,10b,11,12-tetradecahydro-7-oxa-8-aza-pentaleno[2,1-a]phenanthrene-6b-carboxylic acid |
| 167 | (4aS,4bR,5S,6aS,6bR,9aS,10aS,10bS,12S)-4b,12-Difluoro-8-(3-fluoro-phenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 168 | (4aS,4bR,5S,6aS,6bR,9aS,10aS,10bS,12S)-4b,12-Difluoro-5-hydroxy-4a,6a-dimethyl-2-oxo-8-(4-trifluoromethyl-phenyl)-2,4a,4b,5,6,6a,8,9,9a,10,10a,10b,11,12-tetradecahydro-7-oxa-8-aza-pentaleno[2,1-a]phenanthrene-6b-carboxylic acid |
| 169 | (4aS,4bR,5S,6aS,6bR,9aS,10aS,10bS,12S)-4b,12-difluoro-5-hydroxy-4a,6a-dimethyl-2-oxo-8-phenyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 170 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 171 | (4aS,4bR,5S,6aS,6bR,9aS,10aS,10bS,12S)-4b,12-Difluoro-5-hydroxy-4a,6a-dimethyl-2-oxo-8-m-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 172 | (4aS,4bR,5S,6aS,6bR,9aS,10aS,10bS,12S)-4b,12-Difluoro-5-hydroxy-4a,6a-dimethyl-2-oxo-8-o-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 173 | (4aS,4bR,5S,6aS,6bR,9aS,10aS,10bS,12S)-4b,12-Difluoro-5-hydroxy-4a,6a-dimethyl-2-oxo-8-p-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 174 | (4aS,4bR,5S,6aS,6bR,9aS,10aS,10bS,12S)-8-(3-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 175 | (4aS,4bR,5S,6bR,9aS,10aS,10bS,12S)-4b,12-Difluoro-8-(4-fluoro-phenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioicacid S-((S)-fluoromethyl) ester |
| 176 | (4aS,4bR,5S,6aS,6bR,9aS,10aS,10bS,12S)-4b,12-Difluoro-5-hydroxy-4a,6a-dimethyl-2-oxo-8-pyridin-3-yl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 177 | (4aS,4bR,5S,6bR,9aS,10aS,10bS,12S)-4b,12-Difluoro-8-(3-fluoro-phenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioicacid S-((S)-fluoromethyl) ester |
| 178 | (4aS,4bR,5S,6aS,6bR,9aS,10aS,10bS,12S)-4b,12-Difluoro-5-hydroxy-4a,6a-dimethyl-2-oxo-8-(4-trifluoromethyl-phenyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 179 | (4aS,4bR,5S,6aS,6bR,9aS,10aS,10bS,12S)-4b,12-Difluoro-6b-(2-fluoro-acetyl)-5-hydroxy-4a,6a-dimethyl-8-phenyl-4a,4b,5,6,6a,6b,8,9,9a,10,10a,10b,11,12-tetradecahydro-7-oxa-8-aza-pentaleno[2,1-a]phenanthren-2-one |
| 180 | (4aS,4bR,5S,6aS,6bR,9aS,10aS,10bS,12S)-8-(4-Chloro-phenyl)-4b,12-difluoro-6b-(2-fluoro-acetyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |

-continued

| Compound | Chemical Name |
|---|---|
| 181 | Methanesulfonic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 182 | (4aS,4bR,5S,6aS,6bR,9aS,10aS,10bS,12S)-6b-(2-Chloro-acetyl)-8-(4-chloro-phenyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 183 | (4aS,4bR,5S,6aS,6bR,9aS,10aS,10bS,12S)-8-(4-Chloro-phenyl)-4b,12-difluoro-5-hydroxy-4a,6a-dimethyl-6b-(2-methylsulfanyl-acetyl)-4a,4b,5,6,6a,6b,8,9,9a,10,10a,10b,11,12-tetradecahydro-7-oxa-8-aza-pentaleno[2,1-a]phenanthren-2-one |
| 184 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid chloromethyl thioester |
| 185 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyclopropylmethyl ester |
| 186 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl ester |
| 187 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid carbamoylmethyl ester |
| 188 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid 2,2,2-trifluoro-ethyl ester |
| 189 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid 2-fluoro-ethyl ester |
| 190 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-cyanomethyl ester |
| 191 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-fluoro-ethyl) ester |
| 192 | 4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2,2,2-trifluoro-ethyl) ester |
| 193 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-carbamoylmethyl ester |
| 194 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-prop-2-ynyl ester |
| 195 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-cyclobutyl ester |
| 196 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothoic acid S-(2-oxo-propyl) ester |
| 197 | 4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid methyl ester |

| Compound | Chemical Name |
|---|---|
| 198 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl-methyl-amide |
| 199 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-methyl ester |
| 201 | (4aS,4bR,5S,6aS,6bR,9aS,10aS,10bS,12S)-6b-Acetyl-8-(4-chloro-phenyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 202 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid 1,1-dimethyl-prop-2-ynyl ester |
| 203 | (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid 1,1-dimethyl-allyl ester |

Other preferred compounds of general formula (I), which were obtained with analogous procedures to those described in the examples, are the following:

| Chemical name |
|---|
| (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carboxylic acid dimethylamide |
| (4aS,4bR,5S,6aS,6bR,9aS,10aS,10bS,12S)-8-(3,3-Dimethyl-butyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl ester |
| (4aS,4bR,5S,6aS,6bR,9aS,10aS,10bS,12S)-8-(2-Ethyl-butyl)-4b,12-difluoro-6b-(2-fluoro-acetyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl ester |

According to analogous procedures and methods described in the present application, preferred compounds of the invention from the list below reported, may be obtained:

| Chemical name |
|---|
| (4aS,4bR,5S,6aS,6bR,9aS,10aS,10bS,12S)-4b,12-Difluoro-5-hydroxy-4a,6a-dimethyl-2-oxo-8-propyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-pyridin-3-yl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-thiazol-4-yl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-8-oxazol-2-yl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-thiazol-2-ylmethyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-8-(2-imidazol-1-yl-ethyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-(3-pyridin-3-yl-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |

| Chemical name |
| --- |
| (4aS,4bR,5S,6aS,6bR,9aS,10aS,10bS,12S)-4b,12-Difluoro-8-furan-3-yl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-8-(1H-indol-3-ylmethyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-quinolin-7-ylmethyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-8-Benzothiazol-2-ylmethyl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-quinolin-5-ylmethyl-2,4a,4b,5,6,6a,8,9,9a,10,10a,10b,11,12-tetradecahydro-7-oxa-8-aza-pentaleno[2,1-a]6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-quinolin-2-ylmethyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-8-Benzofuran-3-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-8-Benzo[1,3]dioxol-5-yl-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-8-(1-methyl-1H-indol-2-yl)-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-(1-methyl-1H-indol-3-ylmethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-(1-methyl-1H-imidazol-4-ylmethyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-8-(1H-imidazol-2-ylmethyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-p-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-8-(4-methoxy-phenyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-4a,6a-dimethyl-2-oxo-8-o-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| (4aS,4bR,5S,6aS,6bR,9aS,10aS,10bS,12S)-4b,12-Difluoro-5-hydroxy-8-(3-methoxy-phenyl)-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |

The present invention also provides pharmaceutical compositions comprising a compound of the invention, either as such or as pharmaceutically acceptable salt, and one or more pharmaceutically acceptable carriers and/or excipients.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The present invention also provides combinations of a compound of the invention, either as such or as pharmaceutically acceptable salt, with a β2-agonist selected from the group consisting of carmoterol, GSK-642444, indacaterol, milveterol, arformoterol, formoterol, salbutamol, levalbuterol, terbutaline, AZD-3199, BI-1744-CL, LAS-100977, bambuterol, isoproterenol, procaterol, clenbuterol, reproterol, fenoterol, and ASF-1020 and salts thereof.

The present invention also provides combinations of a compound of the invention, either as such or as pharmaceutically acceptable salt, with an antimuscarinic agent selected from the group consisting of aclidinium, tiotropium, ipratropium, trospium, glycopyrronium, and oxitropium salts.

The present invention also provides combinations of a compound of the invention, either as such or as pharmaceutically acceptable salt, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the invention, either as such or as pharmaceutically acceptable salt, with a P38 MAP kinase inhibitor selected from the group consisting of semapimod, talmapimod, pirfenidone, PH-797804, GSK-725, minokine, and losmapimod and salts thereof.

In a preferred embodiment, the present invention provides combinations of a compound of the invention with an IKK2 inhibitor.

The invention also provides combinations of a compound of the invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of the invention, either as such or as pharmaceutically acceptable salt, with a leukotriene modulator selected from the group consisting of montelukast, zafirlukast, and pranlukast.

The invention also provides combinations of a compound of the invention, either as such or as pharmaceutically acceptable salt, with a NSAID selected from the group consisting of ibuprofen, and ketoprofen.

The invention also provides combinations of a compound of the invention, either as such or as pharmaceutically acceptable salt, with a mucus regulator selected from the group consisting of INS-37217, diquafosol, sibenadet, CS-003, talnetant, DNK-333, MSI-1956, and gefitinib.

The present invention also provides a compound of the invention for use as a medicament.

The invention also relates to the use of a compound of the invention to decrease the number, activity and movement of the inflammatory cells in vitro and/or in vivo.

The present invention is also directed to compounds of the invention for use in the prevention or treatment of any disease wherein the decrease in the number, activity, and movement of inflammatory cells is involved.

In a further aspect the present invention provides the use of compounds of the invention for the prevention and/or treatment of any disease wherein the decrease in the number, activity, and movement of inflammatory cells is involved.

In particular, compounds of the invention, either alone or combined with one or more active ingredients, may be administered for the prevention and/or treatment of a disease of the respiratory tract characterized by airway obstruction such as asthma and COPD.

In a further aspect the present invention provides the use of compounds of the invention for the preparation of a medicament for the prevention and/or treatment of any disease wherein the decrease in the number, activity, and movement of inflammatory cells is involved.

Moreover the present invention provides a method for prevention and/or treatment of any disease wherein the decrease in the number, activity, and movement of inflammatory cells is involved, said method comprising administering to a patient in need of such treatment a therapeutically effective amount of a compound of the invention.

The present invention also provides pharmaceutical preparations of compounds of the invention suitable for administration by inhalation, by injection, orally or intranasally.

Inhalable preparations include inhalable powders, propellant-containing metering aerosols or propellant-free inhalable formulations.

The invention is also directed to a device which may be a single- or multi-dose dry powder inhaler, a metered dose inhaler or a nebulizer, in particular a soft mist nebulizer comprising a compound of the invention.

The invention is also directed to a kit comprising the pharmaceutical compositions of compounds of the invention alone or in combination with or in admixture with one or more pharmaceutically acceptable carriers and/or excipients and a device which may be a single- or multi-dose dry powder inhaler, a metered dose inhaler or a nebulizer.

The compounds of the present invention may be prepared according to a variety of synthetic steps which are carried out according to conventional methods and techniques or which are hereinbelow described.

In one aspect, the present invention provides processes for the preparation of compounds of the invention and intermediates thereof.

The present invention is also directed to a process for the preparation of a compound of general formula (I'), wherein $R_1=(CH_2)_n—Z—(CH_2)_{n'}—R_3$, n and n'=0, Z and $R_3$ are as defined above, which comprises the conversion of the hydroxyl group of 2-hydroxy acetyl moiety at position 6b of compounds of general formula (VI) into a leaving group (LG) of compounds of general formula (XI)

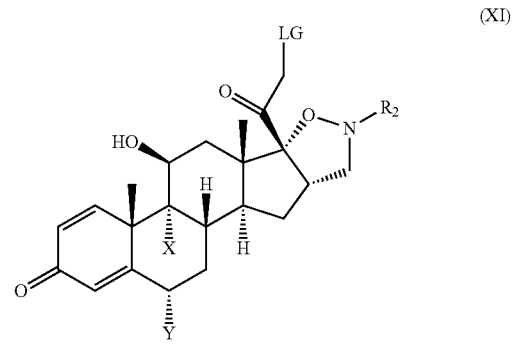

wherein the LG may be displaced by a nucleophile or wherein, after introduction of the LG on the C21 hydroxy moiety, an oxidoreduction reaction can be performed, to afford the corresponding methyl ketone.

The present invention is also directed to a process for the preparation of compounds of general formula (I'), wherein $R_1=(CH_2)_n—Z—(CH_2)_{n'}—R_3$, n and n'=0, Z and $R_3$ are as defined above, which comprises:

the reaction of a compound of formula (VI) to obtain a compound of general formula (XII)

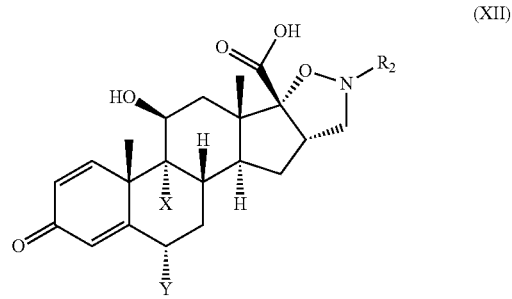

the treatment of compound of formula (XII) with one or more equivalents of an acid activating agent and then with a nucleophile.

The present invention is also directed to a process for the preparation of compounds of general formula (I') wherein $R_1=(CH_2)_n-Z-(CH_2)_{n'}-R_3$ wherein n=n'=0, Z=S and $R_3$ is as defined above, which comprises:

the reaction of compounds of formula (VI) under oxidizing conditions to obtain the intermediates of general formula (XII)

its conversion into compounds of general formula (XIII)

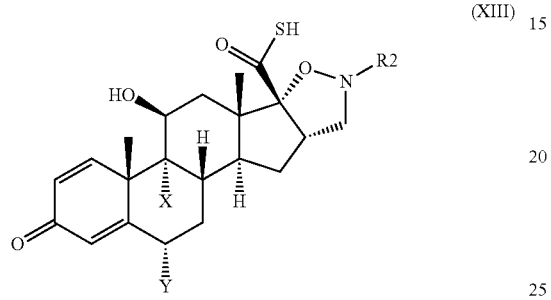
(XIII)

the alkylation of compound of formula (XIII).

The present invention is also directed to a process for the preparation of compounds of general formula (VI)

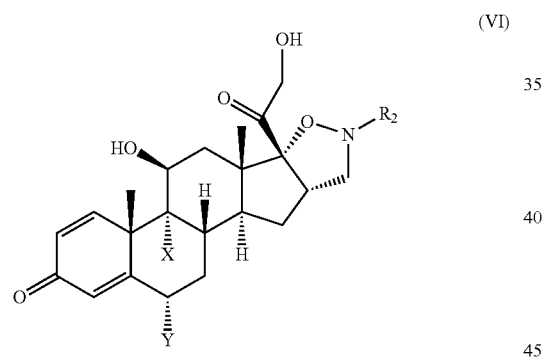
(VI)

which comprises:
the reaction of a compound of general formula (IV)

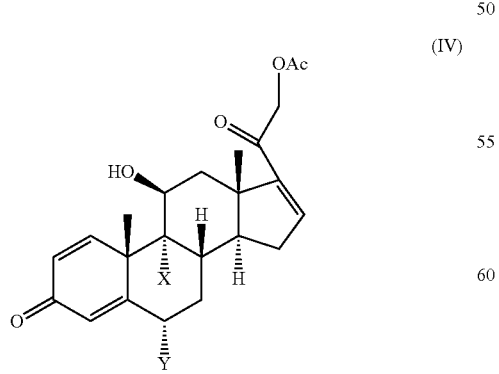
(IV)

with N-tetrahydropyranyl hydroxylamine (HO—NH-THP), to prepare a compound of formula (V)

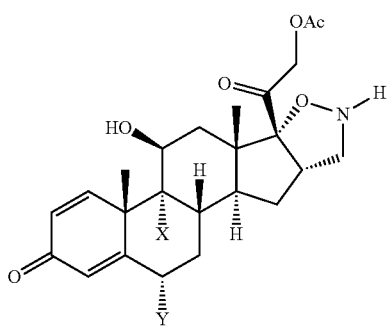
(V)

the optional further functionalization of compound of formula (V) and the deprotection.

The present invention is also directed to a process for the preparation of a compound of general formula (VI), which comprises:

the reaction of a compound of formula (VII)

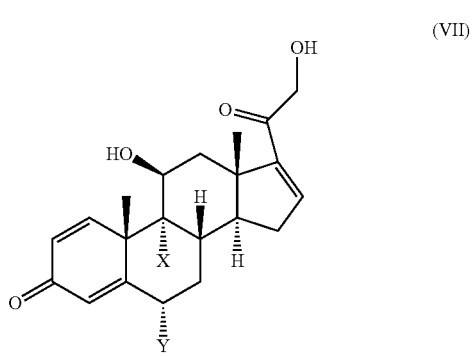
(VII)

with a compound of formula (X)

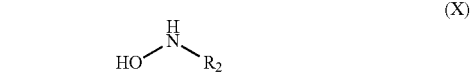
(X)

The present invention is also directed to a process for the preparation of a compound of general formula (VI), which comprises:

reacting a compound of formula (VII) with N-tetrahydropyranyl hydroxylamine (HO—NH-THP) to obtain compound of formula (VIII)

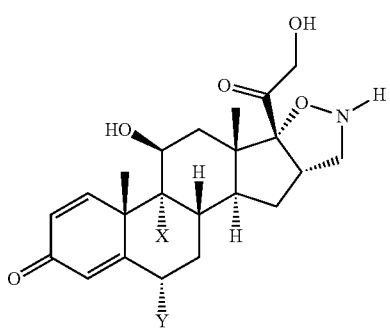

(VIII)

protecting s compound of formula (VIII) to obtain compound of formula (IX)

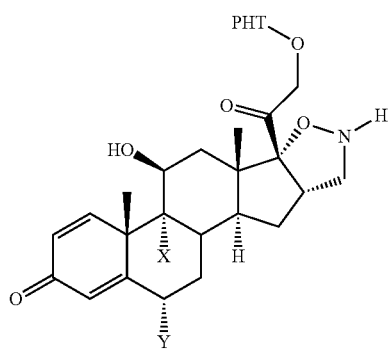

(IX)

optional further functionalization of a compound of formula (IX) and
deprotection.

The present invention is also directed to a process for the preparation of compounds of general formula (I'), wherein $R_1=(CH_2)_n-Z-(CH_2)_{n'}-R_3$, n and n'=0, Z=O and $R_3$=Ac, which comprises the reaction of the intermediates of general formula (IV) with hydroxylamines of formula (X).

The present invention is also directed to a process for the reparation of compounds of general formula (I'), wherein $R_1=(CH_2)_n-Z-(CH_2)_{n'}-R_3$, n=0, n'=1, $R_3$=F, which comprises
reaction of compound (VII) with mesyl chloride and DIPEA in dry acetonitrile;
in situ addition of tetra-n-butylammonium fluoride (TBAF) and KI and
cycloaddition reaction of the obtained intermediate (XV)

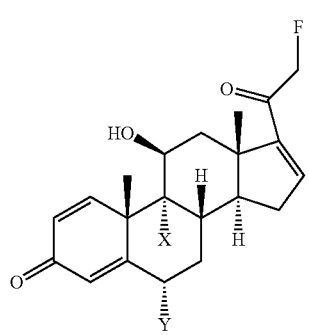

(XV)

with HO—NH-THP.

The present invention is also directed to a process for the preparation of compounds of general formula (I') wherein $R_1=-(CH_2)_n-Z-(CH_2)_{n'}-R_3$ wherein n=1, n'=0, Z=O, $R_3$=H and X=Cl as reported in scheme, by reacting the compounds of formula (I') wherein n=1, n'=0, Z=O, $R_3$=Ac and X=H with methanesulfonyl chloride in the presence of a base to obtain compounds of formula (XIV)

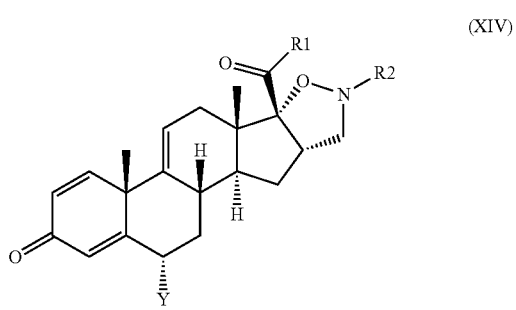

(XIV)

which is reacted with a chlorinating agent and, after hydrolysis of the acetyl ester by treatment of a base, affords the aforementioned compounds of general formula (I').

In preferred embodiment of the invention, all the processes herein described are performed with compounds and intermediates where X and Y are fluorine.

From all of the above, it is clear to the person skilled in the art that by selecting the starting material with a proper stereochemical configuration, any of the possible stereoisomers of formula (I) can be obtained.

Some of the processes used for the preparation of the compounds of formula (I'), as described in Scheme 1, may also be applied to compounds of formula (I)

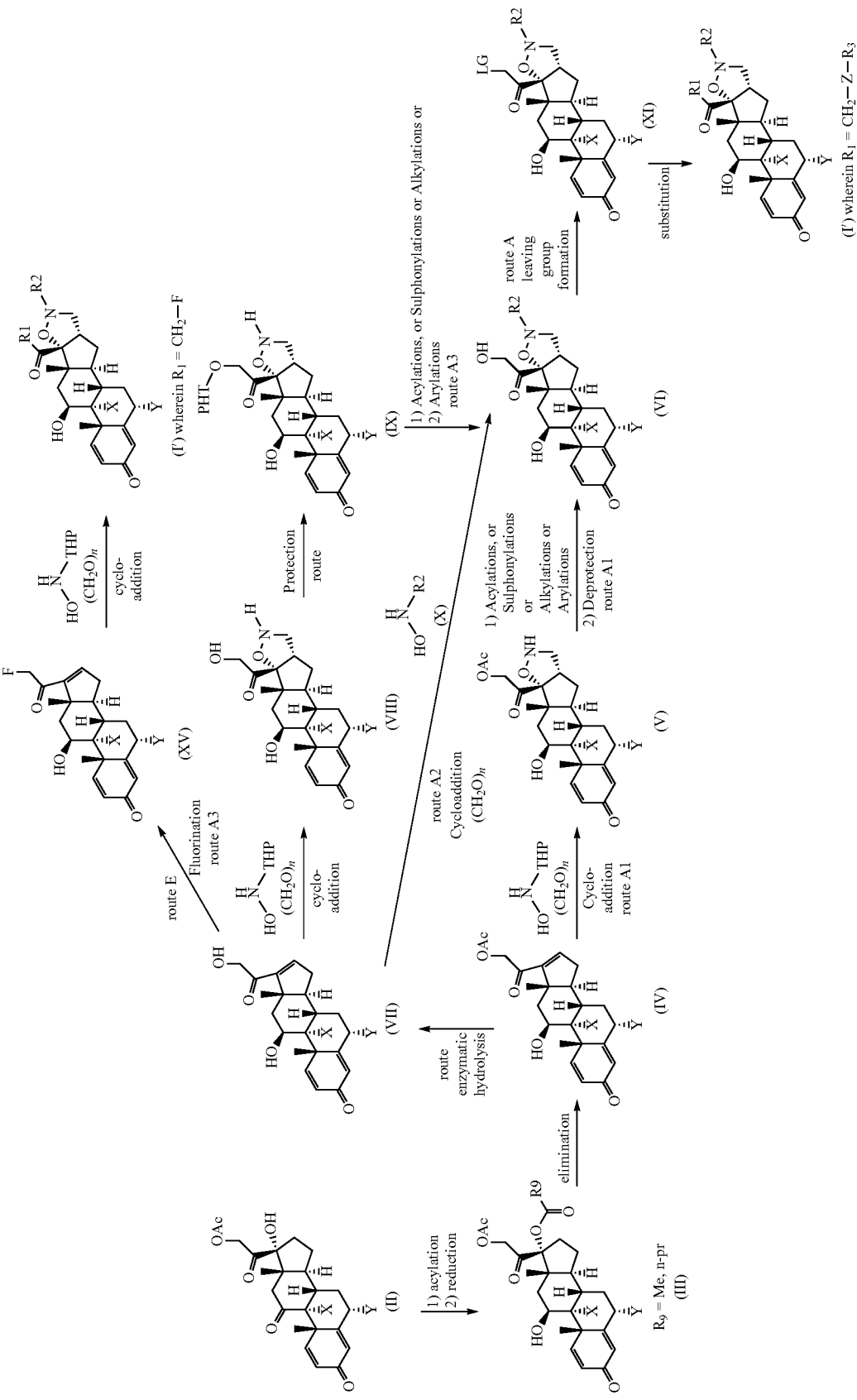

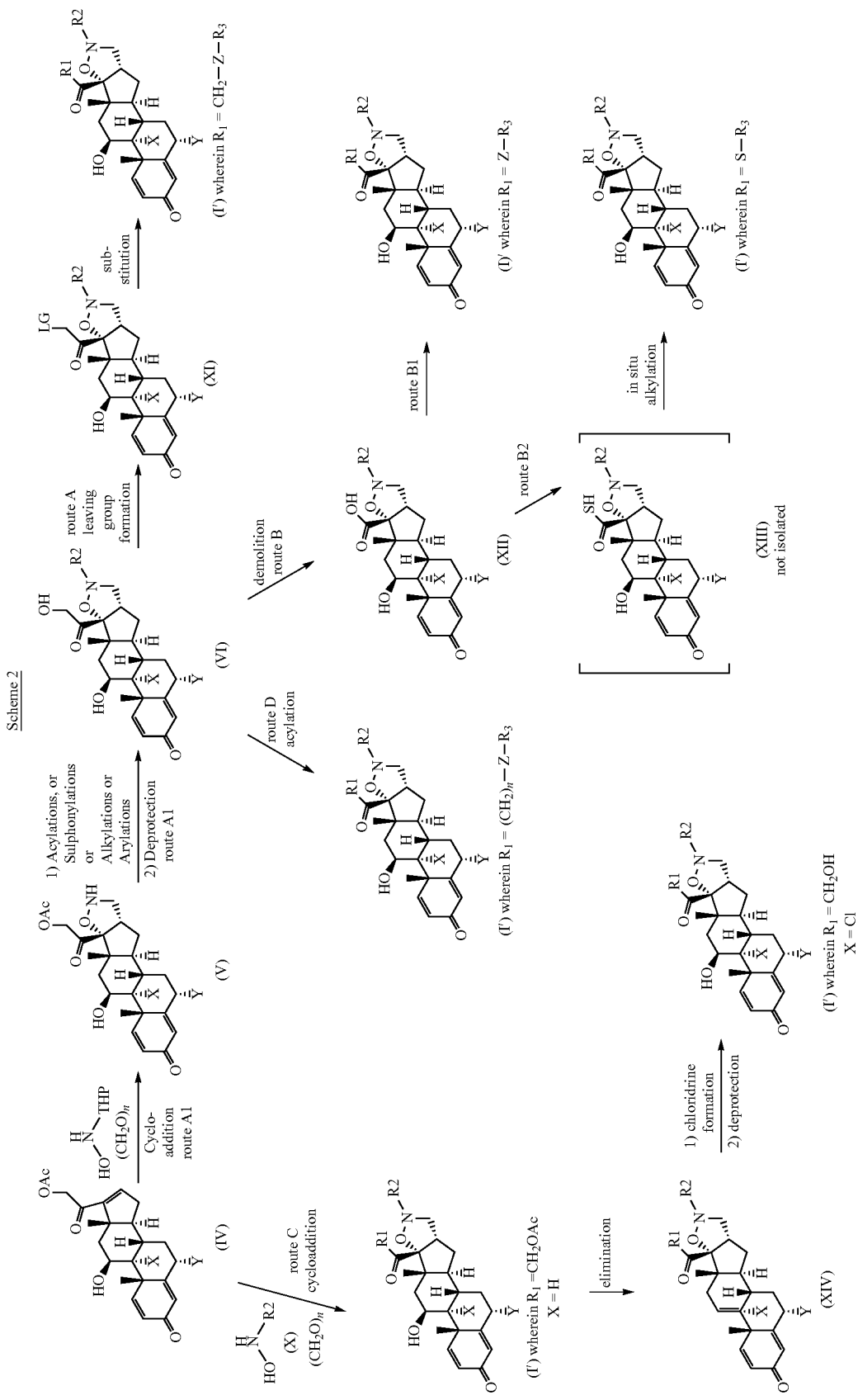

Procedure for the Preparation of the Compounds of the Invention

According to particular embodiments, the compounds of the invention may be prepared according to different routes described in scheme 1, depending on the nature of the substituents $R_1$ and $R_2$.

Route A1—the reaction of compounds of general formula (IV) with N-tetrahydropyranyl hydroxylamine (HO—NH-THP), to prepare a compound of formula (V), can be conveniently conducted in a protic solvent such as EtOH at a temperature ranging from 80 to 100° C. The THP protecting group is directly cleaved in the reaction conditions.

These compounds may be further functionalized with alkyl halides, acyl halides, isocyanates, carbamoyl chlorides or sulphonyl chlorides using method readily apparent for those skilled in the art (*J. Med. Chem.*, 379-388, 1995; *J. C. S. Chem. Comm.*, 256-257, 1985, which are both incorporated herein by reference in their entireties), to give compounds of general formula (VI). These reactions are usually carried out in a solvent such as dichloromethane (DCM) or tetrahydrofuran (THF) and proceed at a temperature range from room temperature (RT) to reflux. A base such as triethylamine or diisopropylethylamine may be required to promote the reaction. The reaction with aryl halides may be performed under the known copper catalyzed N-arylation of isoxazolidine (*Bioorg. Med. Chem. Lett.*, 2834, 2005, which is incorporated herein by reference in its entirety). The acetyl ester may be easily hydrolyzed using standard conditions for the deacetylation of alcohols, treating for example the compound with a base such as sodium or potassium hydroxide or potassium carbonate in a suitable solvent (e.g. methanol or ethanol). This reaction usually proceeds at RT over a period of 1 to 5 hours leading to compounds of general formula (VI).

Compounds of general formula (IV) may be conveniently prepared according to standard procedures reported in the literature. For instance they may be prepared by treatment of compounds of general formula (III) with a base such as potassium acetate. This reaction is usually performed in a suitable polar solvent such as dimethylformamide (DMF) and typically proceeds at a temperature range from 80 to 110° C., over a period of 0.5 to 4 hours.

Compounds of formula (III) may be readily prepared from known compounds by methods well known to those skilled in the art, starting from compounds of general formula (II) (*J. Med. Chem.*, 1982, 25, 1492-1495, which is incorporated herein by reference in its entirety).

Route A2—alternatively, the compounds of general formula (VI) may be prepared starting from the reaction of a compound of formula (VII) with a compound of formula (X) in the presence of paraformaldehyde, using known procedures for the isoxazolidine formation, by cycloaddition of nitrones (*J. Med. Chem.*, 25, 1492-1495, 1982, which is incorporated herein by reference in its entirety). The reaction is conveniently carried out in a protogenic solvent, such as ethanol, at temperatures ranging from 80 to 100° C. Hydroxyl amine of formula (X) are either commercially available or may be easily prepared using procedures well known for those skilled in the art, for example by reducing an oxime with a reducing agent, such as borane pyridine complex (*J. Med. Chem.*, 40, 1955-1968, 1997, which is incorporated herein by reference in its entirety) or by reaction of O-tetrahydropyranyl hydroxylamine with a suitable alkylating agent such as alkyl halides (*Chem. Pharm. Bull.*, 46, 966-972, 1998, which is incorporated herein by reference in its entirety).

The compounds of formula (VII) may be prepared hydrolyzing the compounds of formula (IV). This reaction is preferably carried out by subjecting compounds (IV) to the action of an enzyme, such as immobilized Lipase from *Candida Antarctica* (Sigma Aldrich) (*Tetrahedron*, 50, 13165-13172, 1994, which is incorporated herein by reference in its entirety).

Route A3—compounds of general formula (VIII) may be prepared starting from the reaction of a compound of formula (VII) with HO—NH-THP. This reaction may be conveniently conducted in dioxane or in a protic solvent such as EtOH at a temperature ranging from 80 to 100° C. The THP protecting group is directly cleaved in the reaction conditions. The obtained (VIII) can be conveniently and selectively protected by treatment with dihydropyran in a suitable solvent such as DCM or THF, at temperature from 0° C. to RT, to obtain compound of formula (IX). The reaction is complete in time ranging from 0.5 to 3 hours. Compounds of formula (IX) may be further functionalized with alkyl halides, acyl halides, isocyanates, carbamoyl chlorides or sulphonyl chlorides as described in Route A1. The THP protecting group can be easily removed by treating the protected intermediate with HCl in a suitable solvent, such as THF or dioxane. This reaction usually proceeds at RT over a period of 1 to 15 hours leading to compounds of general formula (VI).

Route A—conversion of the hydroxyl group of 2-hydroxy acetyl moiety at position 6b of compounds of general formula (VI) into a leaving group (LG) of compounds of general formula (XI) can be carried out by treating compounds of formula (VI) with methanesulfonyl chloride or p-toluenesulphonyl chloride (March's, "Advanced Organic Chemistry", Wiley-Interscience, which is incorporated herein by reference in its entirety), in a suitable solvent, such as pyridine. This reaction is usually performed at RT over a period of 1 to 5 hours.

The LG of compounds of general formula (XI) may be easily displaced by nucleophiles such as halide anions, alcohols, thiols, thioacids, amines, amides and carbanions (*J. Org. Chem.*, 1042, 1999; *J. Steroid. Biochem.*, 13, 311-322, 1980, which are both incorporated herein by reference in their entireties), to obtain compounds of general formula (I) and (I') wherein $R_1$=$(CH_2)_n$—Z—$(CH_2)_{n'}$—$R_3$, n and n'=0, Z and $R_3$ are as defined above. The reaction is usually performed in a suitable solvent, such as DCM, THF or DMF, in a range of temperature from 0 to 80° C. over a period of 1 to 5 hours and may be promoted by a base such as sodium or potassium carbonate or sodium hydride. After introduction of the LG (for example mesylate) on the C21 hydroxy moiety, an oxidoreduction reaction can be performed, for example by means of an excess of sodium iodide, to afford the corresponding methyl ketone. The obtained product may be further functionalized modifying the moiety introduced by the described nucleophilic substitution reaction.

Route B—reaction of compounds of formula (VI) under well known oxidation conditions to obtain the intermediates of general formula (XII). This reaction is usually performed in open air at RT over a period of 12 to 48 hours, in a suitable solvent such as THF in the presence of aqueous solution of an inorganic base, such as sodium or potassium hydroxide.

Route B1—conversion of the intermediates of formula (XII) into compounds of general formula (I) and (I') wherein $R_1$=$(CH_2)_n$—Z—$(CH_2)_{n'}$—$R_3$, n and n'=0, Z and $R_3$ are as defined above, by treating the acid (XII) with one or more equivalents of an acid activating agent such as carbonyldiimidazole or HATU. The reaction is usually performed in a suitable polar solvent such as DMF, in a range of temperature from 0 to 80° C. over a period of 1 to 2 hours. The activated acid may be reacted with a nucleophile, such as alcohols, thiols, thioacids and amines. The reaction may be promoted by a base such as sodium or potassium carbonate, sodium hydride and proceeds at a temperature ranging from 0 to 20° C. over a period of 1 to 24 hours.

Alternatively, the intermediates of formula (XII) may be converted into the corresponding acyl chloride under well known conditions, using oxalyl chloride in a suitable solvent such as DCM. The activated intermediate may be reacted with a nucleophile such as alcohols, thiols, thioacids, amines and carbanions such as alkyl, aryl and heteroaryl cuprates or other metallorganic compounds reported in the literature, to be suitable for the conversion of acyl chlorides into the corresponding ketones.

Intermediates of formula (XII) may be also converted into compounds of general formula (I) and (I') wherein $R_1$=$(CH_2)_n$—Z—$(CH_2)_{n'}$—$R_3$, n and n'=0, Z=O and $R_3$ is as defined above, by treating the acid (XII) with a base such as potassium sodium or cesium carbonate and triethylamine, in a suitable solvent such as DMF or acetonitrile, at a temperature ranging from 0 to 20° C. Sometimes these alkylation reactions may be promoted by copper salts such as copper iodide, in the presence of KI. The obtained products may be further functionalized modifying the moiety introduced by the described nucleophilic substitution reaction.

Route B2—conversion of intermediates of formula (XII) into compounds of general formula (XIII), derived from reaction of acid (XII) with carbonyldiimidazole or HATU, followed by reaction with the sodium salt of thioacetic acid and/or anhydrous hydrogen sulphide. The reaction is usually performed adding the solution of the preformed salt in the reaction solvent to the solution of the activated acid at a temperature ranging from 0 to 20° C. or directly adding the solid sodium hydrogen sulphide anhydrous. The thioacid intermediate (XIII) readily formed is in situ reacted with an alkylating reagent, such as bromoalkanes, leading to thioesters of general formula (I) and (I') wherein $R_1$=$(CH_2)_n$—Z—$(CH_2)_{n'}$—$R_3$, n and n'=0, Z=S and $R_3$ is as defined above. The choice of suitable bromoalkane, such as bromochloromethane, may allow the preparation of compounds of formula (I) and (I') wherein $R_1$=$(CH_2)_n$—Z—$(CH_2)_{n'}$—$R_3$, n and n'=0, Z=S and $R_3$ is as defined above, that may be further modified. For example, the reaction of these compounds in which $R_3$ is chloromethyl with potassium iodide, followed by treatment with silver fluoride, may allow the preparation of compounds of formula (I) and (I') in which $R_3$=fluoromethyl. These reactions are well known to those skilled in the art (*J. Med. Chem.*, 37, 3717-3729, 1994, which is incorporated herein by reference in its entirety). Alternatively, the thioacid intermediate (XIII) may be in situ reacted with a DMF solution of bromofluoromethane affording smoothly compounds of formula (I) and (I') in which $R_3$=fluoromethyl.

Route C—reaction of the intermediates of general formula (IV) with hydroxylamines of formula (X) in the presence of paraformaldehyde using known procedures for the isoxazolidine formation by cycloaddition of nitrones. The reaction is conveniently performed in a protogenic solvent, such as ethanol. The reaction is conveniently carried out at high temperature, for example from 60 to 85° C. and leads to compounds of general formula (I) and (I') wherein $R_1$=—$(CH_2)_n$—Z—$(CH_2)_{n'}$—$R_3$, wherein n=1, n'=0, Z=O and $R_3$=Ac.

The intermediates of general formula (XIV) may be prepared by treating compounds of general formula (I) and (I') wherein $R_1$=—$(CH_2)_n$—Z—$(CH_2)_{n'}$—$R_3$, wherein n=1, n'=0, Z=O, $R_3$=Ac and X=H, with methanesulfonyl chloride in a suitable solvent, such as DMF, in the presence of a base, such as pyridine. The reaction proceeds at a temperature ranging from 80 to 100° C. over a period of 1 to 5 hours.

Reacting compounds of formula (XIV) under well known conditions for the preparation of chlorohydrine starting from the corresponding alkene, compounds of general formula (I') wherein $R_1$=$(CH^2)_n$—Z—$(CH_2)_{n'}$—R3 and wherein n=1, n'=0, Z=O, $R_3$=H and X=Cl, are obtained. The reaction involves the use of a chlorinating agent, such as N-chlorosuccinimide or dichloro-5,5-dimethylhydantoin, and is promoted by an acid such as perchloric acid. The reaction is usually carried out in a polar solvent such as THF, in a range of temperature from 0 to 20° C. over a period of 1 to 4 hours. The acetyl ester of compounds of formula (XIV) may be easily hydrolyzed using standard conditions for the deacetylation of alcohols, treating for example the compound with a base such as sodium or potassium carbonate in a solvent such as methanol or ethanol. This reaction usually proceeds at low temperature, ranging from 0 to 20° C., over a period of 0.5 to 2 hours.

Route D—reaction of the intermediates of general formula (VI) with acyl chlorides, using procedures well known for those skilled in the art. The reaction is conveniently performed in DCM as solvent in the presence of a base such as triethylamine, at room temperatures over a period of 20 to 50 hours. This procedure may allow the preparation of compounds of formula (I') wherein $R_1$=—$(CH_2)_n$—Z—$(CH_2)_{n'}$—$R_3$, n=1, n'=0, Z=O, and $R_3$ are as defined above.

Route E—reaction of compound (VII) with mesyl chloride and N,N-diisopropylethylamine (DIPEA) in dry acetonitrile. Then, the introduction of fluorine atom can be conveniently performed by in situ addition of tetra-n-butylammonium fluoride (TBAF) and KI and heating over a period of 8 to 20 hours. Cycloaddition reaction of the obtained intermediate (XV) with hydroxylamines of formula (X) in the presence of paraformaldehyde, under the known conditions described in Route C, lead to the formation of compounds of general formula (I'), wherein $R_1$=—$(CH_2)_n$—Z—$(CH_2)_{n'}$—$R_3$, n=0, n'=1, $R_3$=F, and $R_2$ is as defined above.

Hydroxylamines of formula (X) are either commercially available or may be prepared according to different synthetic routes, some of which are well known to those skilled in the art.

In one aspect of the present invention, synthetic routes for the preparation of Hydroxylamines of formula (X) are provided as described in Scheme 2.

Scheme 2

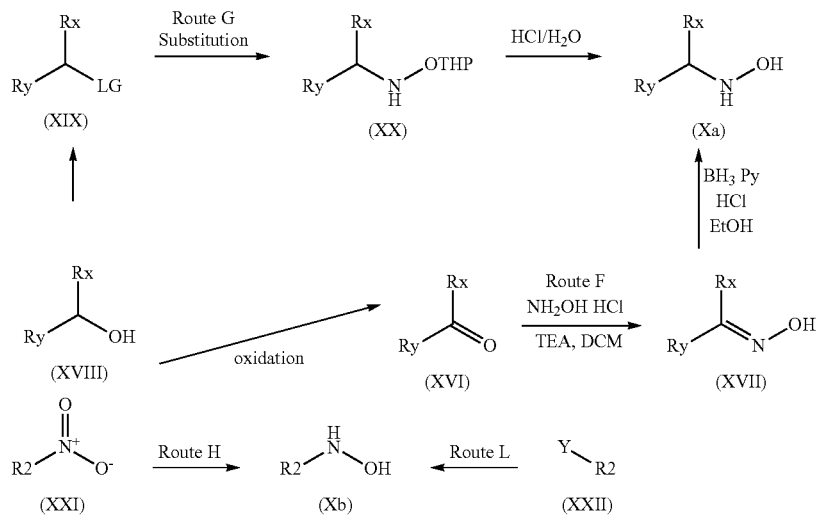

Route F—reaction of compounds of general formula (XVI) with hydroxylamine hydrochloride (NH₂OH HCl) in presence of triethyl amine, to prepare an oxime of formula (XVII) can be conveniently conducted in DCM as solvent at a temperature ranging from RT to 50° C.

These compounds [oximes of general formula (XVII)] may be reduced to hydroxylamines of general formula (Xa), wherein $R_x$ and $R_y$ may assume different meanings within the scope of the instant invention, with a reducing agent such as, for example, borane pyridine complex and HCl in polar protic solvents such as ethanol at RT (Tetrahedron, 1992, Vol. 47, N° 17, 3557-3570; J. Med. Chem., 1997, 40, 1955-1968, both of which are incorporated herein by reference in their entireties). Compounds of general formula (XVI) are commercially available or can be obtained by oxidation of compounds of general formula (XVIII) by well known procedures (for example Swern oxidation: J.A.C.S., 2005, 127, 29, 10396, which is incorporated herein by reference in its entirety).

Route G—Alternatively, the compounds of general formula (Xa) may be prepared by the reaction of an activated compound of general formula (XIX), where LG is a suitable leaving group, such as for example an halide (Cl, Br or I), a mesylate, a tosylate or another leaving group, with O-tetrahydropyranyl hydroxylamine (NH₂OTHP) to generate an intermediate of formula (XX), using well known procedures (J.A.C.S., 2000, 122, 18, 4522; Tetrahedron, 1999, 55, 41, 12069, both of which are incorporated herein by reference in their entireties), and subsequent deprotection of the THP protective group. The substitution reaction is conveniently carried out in DMF, ethanol or acetonitrile as solvents, in the presence of different kind of bases such as K₂CO₃ or DIPEA and at temperatures ranging from RT to 80° C. Compounds of general formula (XIX) may be commercially available or may be prepared starting from an alcohol of general formula (XVIII) and converting the hydroxyl group into the suitable leaving group by procedures well known to those skilled in the art. For example, mesylates can be conveniently obtained from alcohols (XVIII) with mesylchloride and TEA in DCM (Organic Letters, 2002, vol. 4, No 15, 2485, which is incorporated herein by reference in its entirety).

Route H—Hydroxylamines of general formula (Xb), wherein R2 is optionally substituted aryl or heteroaryl, may be prepared starting from the corresponding nitro-aryl or nitro-heteroaryl compounds. For example, nitro compounds (XXI) can be conveniently reduced to hydroxylamines (Synthetic Communications, 1997, Vol. 27, No 20, 3497-3504, which is incorporated herein by reference in its entirety) with BiCl₃ and KBH₄ in polar protic solvents, such as ethanol at RT. Alternatively, aryl or heteroaryl hydroxylamines (Xb) may be conveniently obtained by reduction of nitro compounds (XXI) with hydrazine in the presence of Raney nickel in an appropriate mixture of solvents, such as ethanol and dichloromethane (Synthesis, 1984, 11, 938-941, which is incorporated herein by reference in its entirety). It is necessary, in this procedure, to control the temperature between 0 and 10° C. Finally, another convenient reductive method to afford compounds of general formula (Xb), entails the reduction of compounds (XXI) with Zn and NH₄Cl (Tetrahedron Letters, 2005, Vol. 46, N° 35, 5913-5918; J. Org. Chem., 1982, 47, 7, 1171, both of which are incorporated herein by reference in their entireties), in different polar solvents such as acetone or ethanol.

Route L—Alternatively, aryl or heteroaryl hydroxylamines of general formula (Xb) as above defined, may be prepared by nucleophilic aromatic substitution from aryl or heteroaryl electron-poor chlorides or fluorides with hydroxylamine, using methods readily apparent for those skilled in the art. For example, reaction of a compound of general formula (XXII), wherein Y is a suitable leaving group such as chlorine or fluorine, with aqueous hydroxylamine in ethanol (J. Med. Chem., 2009, 52, 19, 5974, which is incorporated herein by reference in its entirety) may give hydroxylamines of general formula (Xb). The reaction is conducted at reflux in time ranging from 6 to 10 hours. Different methods (WO2006/74187; (2006); (A2) English, which is incorporated herein by reference in its entirety) entail reaction of the suitable aryl or heteroaryl electron-poor chlorides or fluorides with hydroxylamine hydrochloride in polar protic solvents, such as isopropanol. The reaction can be conveniently conducted under microwave heating at a temperature of 130° C., in time ranging from 15 to 25 hours.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Of course, the exact dosage will depend on the identity of the compound or salt being administered, the route of administration, the condition being treated, and the age, weight, and condition of the patient, and may be easily determined by a doctor treating the patient.

Preferably, the compounds of the invention alone or combined with other active ingredients may be administered for the prevention and/or treatment of any obstructive respiratory disease such as asthma, chronic bronchitis and chronic obstructive pulmonary disease (COPD).

However the compounds of the invention may be administered for the prevention and/or treatment of any disease wherein the decrease in the number, activity and movement of inflammatory cells is involved.

Examples of such diseases include: diseases involving inflammation such as asthma and other allergic disorders, COPD, acute rhinitis; reverse acute transplant rejection and acute exacerbations of selected autoimmune disorders, graft-versus-host disease in bone-marrow transplantation; autoimmune disorders such as rheumatoid and other arthritis; skin conditions such as systemic lupus erythematosus, systemic dermatomyositis, psoriasis; inflammatory bowel disease, inflammatory ophthalmic diseases, autoimmune hematologic disorders, and acute exacerbations of multiple sclerosis; kidney, liver, heart, and other organ transplantation; Behçet's acute ocular syndrome, endogenous uveitis, atopic dermatitis, inflammatory bowel disease, and nephrotic syndrome; Hodgkin's disease and non-Hodgkin's lymphoma, multiple myeloma and chronic lymphocytic leukemia (CLL); autoimmune hemolytic anemia and thrombocytopenia associated with CLL; leukemia, and malignant lymphoma.

Preferably the compounds of the invention may be administered for the prevention and/or treatment of respiratory diseases such as from mild to acute severe conditions of asthma and COPD.

Other features of the invention will become apparent in the course of the following descriptions of exemplary embodiments which are given for illustration of the invention and are not intended to be limiting thereof.

EXAMPLES

In the reported experimental procedures, the following abbreviations may be used: TEA=triethylamine; DCM=dichloromethane; RT=room temperature; AcOEt=ethyl acetate; DMF=N,N-dimethylformamide; DMSO=dimethylsulfoxide; HATU=O-(7-Azabenzotriazol-1-yl)-N,N,N',N'-tetramethyluronium hexafluorophosphate.

Example 1. Preparation of acetic acid (8S,9S,10R, 13S,14S,17R)-17-(2-acetoxy-acetyl)-10,13-dimethyl-3,11dioxo-6,7,8,9,10,11,12,13,14,15,16,17-dodecahydro-3H-cyclopenta[a]phenanthren-17-yl ester (intermediate 2)

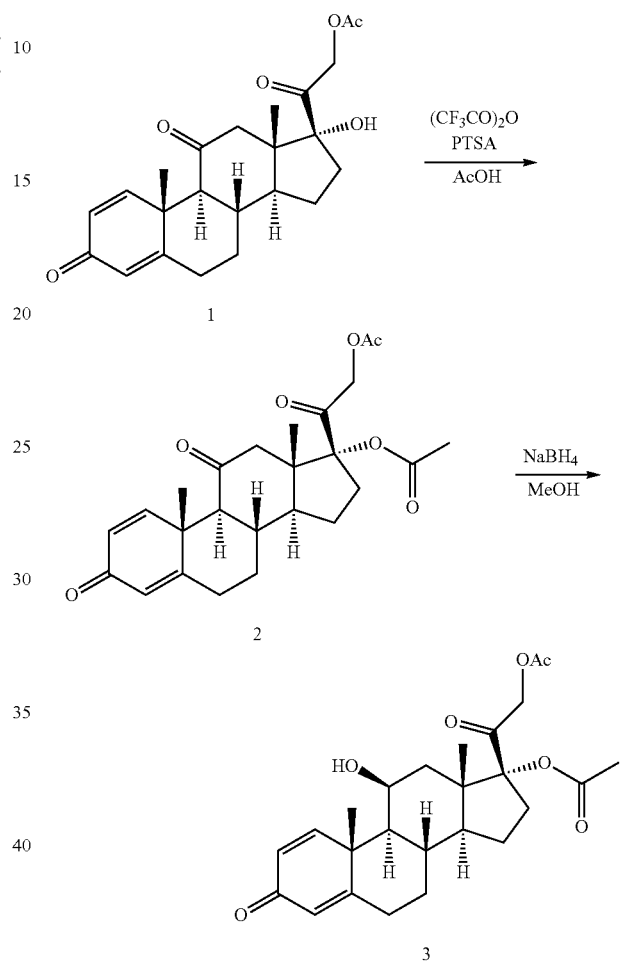

To a suspension of acetic acid 2-((10R,13S,17R)-17-hydroxy-10,13-dimethyl-3,11-dioxo-6,7,8,9,10,11,12,13,14,15,16,17-dodecahydro-3H-cyclopenta[a]phenanthren-17-yl)-2-oxo-ethyl ester (intermediate 1) (2 g, 4.99 mmol) and p-toluene sulphonic acid (PTSA) (200 mg, 1.051 mmol) in acetic acid (5 ml), at 0° C., trifluoroacetic anhydride (5 ml, 35.4 mmol) was slowly added over 10 minutes. After stirring at 0° C. for 20 minutes, the reaction mixture was stirred at RT for 3 hours.

The reaction mixture was poured in ice/water (130 ml), and the resulting mixture was extracted with DCM (2×100 ml) and AcOEt (2×100 ml). The combined organic extracts were dried over anhydrous $Na_2SO_4$ and concentrated. The crude product was purified by flash chromatography on silica gel, in gradient elution from DCM to DCM AcOEt 50:50 to give the title compound (2.64 g, quantitative yield).

LC-MS (ESI POS): 445.2 (MH+)

Preparation of acetic acid (8S,9S,10R,13S,14S,17R)-17-(2-acetoxy-acetyl)-11-hydroxy-10,13-dimethyl-3-oxo-6,7,8,9,10,11,12,13,14,15,16,17-dodecahydro-3H-cyclopenta[a]phenanthren-17-yl ester (intermediate 3)

To an ice cooled solution of intermediate 2 (2.64 g, 5.97 mmol) in THF (15 ml) and MeOH (15.00 ml), sodium borohydride (221 mg, 5.84 mmol) was added in portions over a period of 2.5 hours. The reaction mixture was poured in 1 N HCl and ice (150 ml). The formed precipitate was extracted with AcOEt (3×100 ml), and the combined organic layers were dried over anhydrous $Na_2SO_4$ and concentrated. The crude material was purified by flash chromatography on silica gel, in gradient elution from DCM to DCM/AcOEt 40:60 to afford the title compound (1.21 g, 45.6% yield).

$^1$H NMR (300 MHz, CHLOROFORM-d) ppm 7.28 (d, 1H), 6.30 (dd, 1H), 6.05 (t, 1H), 4.92 (d, 1H), 4.69 (d, 1H), 4.48-4.58 (m, 1H), 2.75-2.91 (m, 1H), 2.61 (m, 1H), 2.37 (ddd, 1H), 2.18-2.21 (m, 3H), 2.09-2.28 (m, 3H), 2.07 (s, 3H), 1.74-1.98 (m, 3H), 1.51-1.70 (m, 3H), 1.48 (s, 3H), 1.26-1.39 (m, 2H), 1.11-1.19 (m, 1H), 1.05 (s, 3H)

LC-MS (ESI POS): 445.2 (MH+)

Example 2. Preparation of acetic acid 2-((6S,8S,9R,10S,11S,13S,14S)-6,9-difluoro-11-hydroxy-10,13-dimethyl-3-oxo-6,7,8,9,10,11,12,13,14,15-decahydro-3H-cyclopenta[a]phenanthren-17-yl)-2-oxo-ethyl ester (intermediate 5)

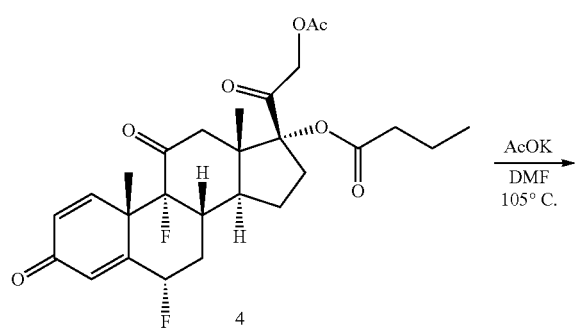

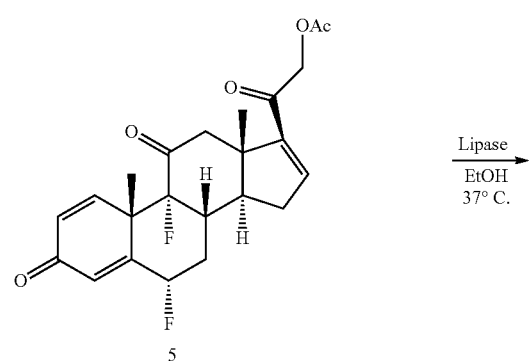

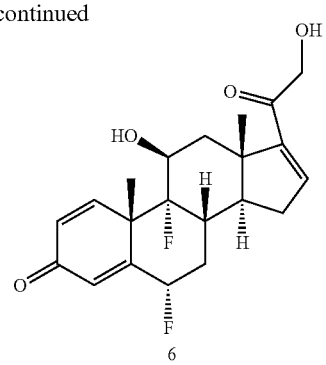

To a solution of butyric acid (9R,10S,11S,13S,17R)-17-(2-acetoxy-acetyl)-9-chloro-11-hydroxy-10,13-dimethyl-3-oxo-6,7,8,9,10,11,12,13,14,15,16,17-dodecahydro-3H-cyclopenta[a]phenanthren-17-yl ester (intermediate 4) (2.48 g, 4.88 mmol) in anhydrous DMF (60 ml), under nitrogen atmosphere, potassium acetate (3.83 g, 39.0 mmol) was added and the reaction mixture was stirred at 100° C. for 1.5 hours. The cooled reaction mixture was poured into ice and brine (200 ml), and the aqueous layer was extracted with AcOEt (3×150 ml). The combined organic extracts were washed with water and brine, dried over $Na_2SO_4$, and concentrated to afford 2.55 g of crude title compound which was used in the next step without further purification.

$^1$H NMR (300 MHz, DMSO-$d_6$): ppm 7.29 (dd, 1H), 6.99 (dd, 1H), 6.29 (dd, 1H), 5.98-6.15 (m, 1H), 5.68 (dddd, 1H), 5.56 (dd, 1H), 5.10 (d, 1H), 4.92 (d, 1H), 3.98-4.23 (m, 1H), 2.56-2.83 (m, 1H), 2.26-2.44 (m, 3H), 2.14-2.26 (m, 1H), 2.09 (s, 3H), 1.71-1.87 (m, 1H), 1.55-1.65 (m, 2H), 1.53 (s, 3H), 1.15 (s, 3H).

LC-MS (ESI POS): 421.97 (MH+)

Preparation of (6S,8S,9R,10S,11S,13S,14S)-6,9-difluoro-11-hydroxy-17-(2-hydroxy-acetyl)-10,13-dimethyl-6,7,8,9,10,11,12,13,14,15-decahydro-cyclopenta[a]phenanthren-3-one (intermediate 6)

To a solution of (intermediate 5) (2.55 g, 6.06 mmol) in ethanol (100 ml), *Candida Antarctica* Lipase (2 U/mg) (510 mg, 6.06 mmol) was added, and the reaction mixture was stirred at 37° C. overnight. The reaction mixture was filtered, washing with methanol, and the residue was purified by flash chromatography on silica gel, in gradient elution from DCM/AcOEt 90:10 to DCM/AcOEt 50:50, to afford 1.62 g of title compound (70.6% yield).

$^1$H NMR (300 MHz, DMSO-$d_6$): ppm 7.29 (dd, 1H), 6.87 (dd, 1H), 6.29 (dd, 1H), 6.09-6.17 (m, 1H), 5.67 (dddd, 1H), 5.53 (dd, 1H), 4.77 (t, 1H), 4.44 (dd, 1H), 4.26 (dd, 1H), 4.04-4.15 (m, 1H), 2.56-2.79 (m, 1H), 2.39 (dd, 1H), 2.25-2.35 (m, 2H), 2.09-2.25 (m, 1H), 1.76 (td, 1H), 1.55-1.66 (m, 2H), 1.53 (s, 3H), 1.17 (s, 3H).

LC-MS (ESI POS): 379.99 (MH+)

Intermediates 7 and 8 listed in Table 1 were prepared as previously described for intermediates 5 and 6, starting from intermediate 3.

TABLE 1

| Intermediate | Structure | Yield | Analytical |
|---|---|---|---|
| 7 | 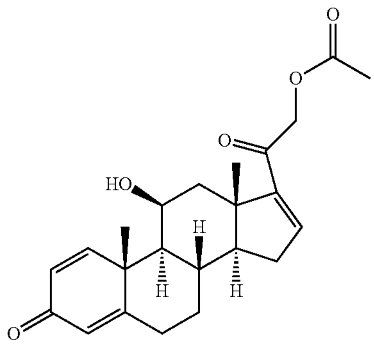 | 50% | LC-MS (ESI POS): 385.45 (MH+)<br>$^1$H NMR (300 MHz, CHLOROFORM-d) ppm<br>7.32 (d, 1 H), 6.74 (dd, 1 H), 6.29 (dd, 1 H), 6.03 (t, 1 H), 5.02 (d, 1 H), 4.88 (d, 1 H), 4.36-4.51 (m, 1 H), 2.55-2.73 (m, 1 H), 2.21-2.54 (m, 5 H), 2.19 (s, 3 H), 2.05-2.18 (m, 1 H), 1.66 (dd, 1 H), 1.51 (s, 3 H), 1.28 (s, 3 H), 1.04-1.44 (m, 4 H) |
| 8 | 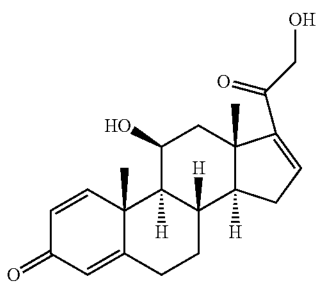 | 94% | LC-MS (ESI POS): 343.2 (MH+)<br>$^1$H NMR (300 MHz, DMSO-$d_6$) ppm 7.34 (d, 1 H), 6.83 (dd, 1 H), 6.16 (dd, 1 H), 5.92 (t, 1 H), 4.80 (d, 1 H), 4.74 (t, 1 H), 4.42 (dd, 1 H), 4.23 (dd, 1 H), 4.15-4.23 (m, 1 H), 2.53-2.67 (m, 1 H), 2.43 (dd, 1 H), 1.94-2.39 (m, 5 H), 1.42-1.48 (m, 1 H), 1.39 (dd, 1 H), 1.17 (s, 3 H), 0.74-1.33 (m, 5 H) |

Example 3. Preparation of (6S,8S,9R,10S,11S,13S, 14S)-17-(2-(tert-butyldimethylsilyloxy)acetyl)-6,9-difluoro-11-hydroxy-10,13-dimethyl-6,7,8,9,10,11, 12,13,14,15-decahydro-3H-cyclopenta[a] phenanthren-3-one (intermediate 9)

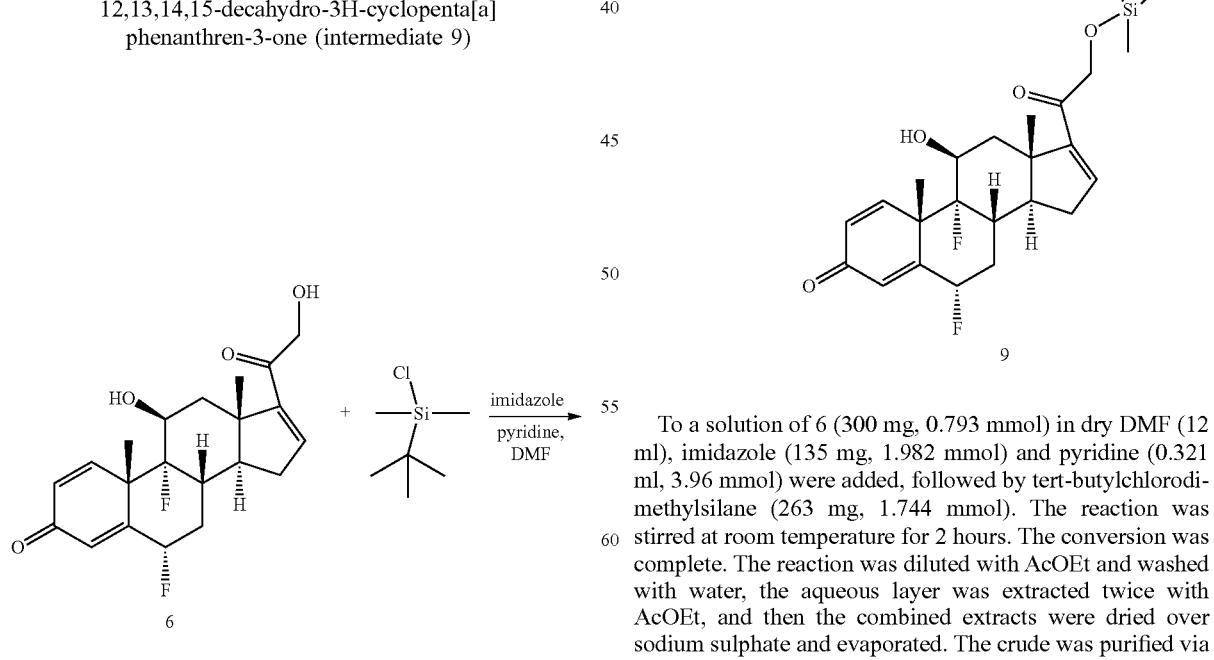

To a solution of 6 (300 mg, 0.793 mmol) in dry DMF (12 ml), imidazole (135 mg, 1.982 mmol) and pyridine (0.321 ml, 3.96 mmol) were added, followed by tert-butylchlorodimethylsilane (263 mg, 1.744 mmol). The reaction was stirred at room temperature for 2 hours. The conversion was complete. The reaction was diluted with AcOEt and washed with water, the aqueous layer was extracted twice with AcOEt, and then the combined extracts were dried over sodium sulphate and evaporated. The crude was purified via chromatographic column over silica gel (DCM, DCM/AcOEt 8:1) to give 365 mg (93% yield).

LC-MS (ESI POS): 493.1 (MH+)

Example 4. Preparation of (4aS,4bR,5S,6aS,6bR, 9aS,10aS,10bS,12S)-8-(3,3-dimethyl-butyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one (compound 10)

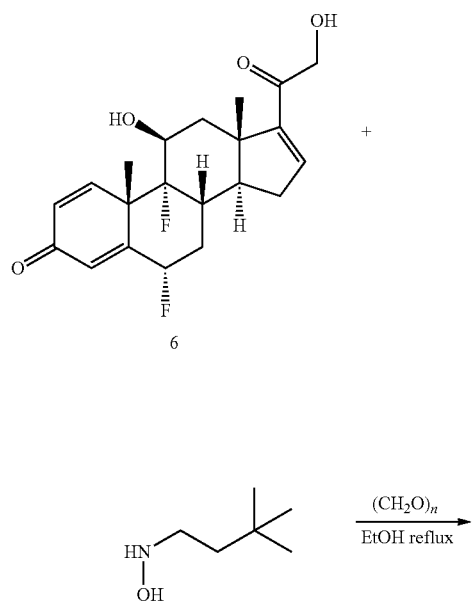

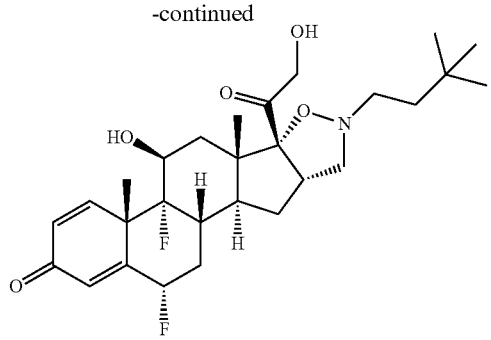

A mixture of 6 (1.3 g, 3.44 mmol), N-(3, 3-dimethylbutyl) hydroxylamine (826 mg, 7.05 mmol) and paraformaldehyde (0.650 g, 21.64 mmol) in ethanol (50 ml) was stirred at reflux overnight. The solvent was evaporated and the crude was purified by silica gel chromatography (DCM/MeOH 98:2) to give compound 9 (1.56 g, 3.07 mmol, 89% yield).

$^1$H NMR (300 MHz, DMSO-$d_6$) ppm 7.25 (dd, 1H) 6.29 (dd, 1H) 6.11 (s, 1H) 5.49-5.79 (m, 1H) 5.44 (d, 1H) 4.77 (t, 1H) 4.48 (dd, 1H) 4.12-4.24 (m, 1H) 4.12 (dd, 1H) 3.43-3.60 (m, 1H) 3.31-3.43 (m, 1H) 2.54-2.72 (m, 3H) 2.08-2.34 (m, 2H) 1.80-2.01 (m, 2H) 1.51-1.71 (m, 3H) 1.49 (s, 3H) 1.18-1.46 (m, 3H) 0.86 (s, 9H) 0.81 (s, 3H)

LC-MS (ESI POS): 508.26 MH+

$[\alpha]_D^{25}$=+131.4 (c 0.213; CHCl$_3$)

The compounds listed in Table 2 were prepared as previously described for compound 10, by cycloaddition of intermediate 6, 8 or 9 with suitable hydroxylamine or hydroxylamine hydrochloride. Final compounds were purified by silica gel column chromatography or preparative HPLC.

TABLE 2

| Compound | Structure | Yield | Analytical |
|---|---|---|---|
| 11 | 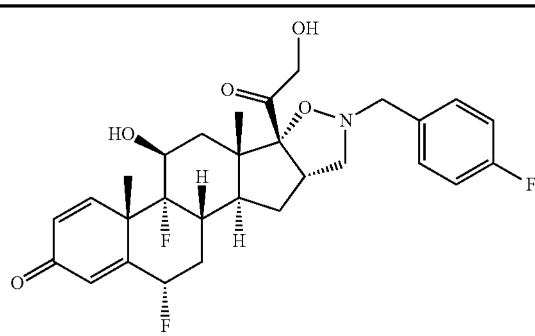 | 88% | LC-MS (ESI POS): 532.03 (MH+)<br>$[\alpha]_D^{25}$ = +175.3 (c = 0.22, CHCl$_3$)<br>$^1$H NMR (300 MHz, DMSO-$d_6$) ppm 7.28-7.37 (m, 2 H), 7.26 (dd, 1 H), 7.01-7.18 (m, 2 H), 6.30 (dd, 1 H), 6.12 (s, 1 H), 5.50-5.78 (m, 1 H), 5.43 (dd, 1 H), 4.57-4.77 (m, 1 H), 3.99-4.26 (m, 2 H), 3.89 (d, 1 H), 3.83-3.95 (m, 1 H), 3.75 (d, 1 H), 3.43-3.60 (m, 1 H), 3.34-3.43 (m, 1 H), 2.57-2.69 (m, 1 H), 2.04-2.36 (m, 3 H), 1.78-1.99 (m, 1 H), 1.52-1.72 (m, 3 H), 1.49 (s, 3 H), 1.38-1.48 (m, 1 H), 0.80 (s, 3 H) |
| 12 | 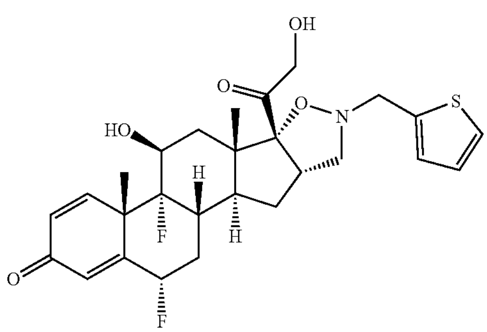 | 43% | LC-MS (ESI POS): 519.98 (MH+)<br>$[\alpha]_D^{25}$ = +129.9° (c = 0.63, CHCl$_3$)<br>$^1$H NMR (300 MHz, DMSO-$d_6$) ppm 7.40-7.47 (m, 1 H), 7.26 (dd, 1 H), 6.83-7.03 (m, 2 H), 6.30 (dd, 1 H), 6.12 (s, 1 H), 5.49-5.80 (m, 1 H), 5.45 (dd, 1 H), 4.72 (br. s., 1 H), 4.33 (dd, 1 H), 4.09-4.24 (m, 2 H), 3.88-4.07 (m, 2 H), 3.43-3.60 (m, 1 H), 3.34-3.43 (m, 1 H), 2.55-2.70 (m, 1 H), 2.04-2.39 (m, 3 H), 1.90-2.03 (m, 1 H), 1.51-1.71 (m, 3 H), 1.49 (s, 3 H), 1.37-1.47 (m, 1 H), 0.81 (s, 3 H) |

TABLE 2-continued

| Compound | Structure | Yield | Analytical |
|---|---|---|---|
| 13 | 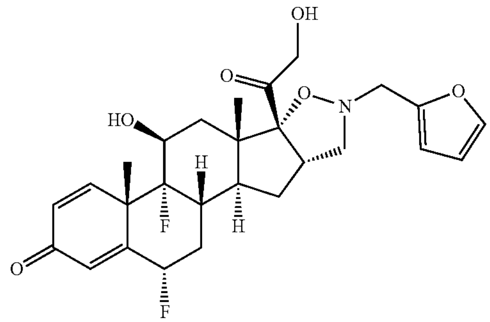 | 59% | LC-MS (ESI POS): 504.02 (MH+)<br>[α]$_D^{25}$ = +133.1° (c = 0.30, CHCl$_3$)<br>$^1$H NMR (300 MHz, DMSO-d$_6$) ppm 7.55 (dd, 1 H), 7.26 (dd, 1 H), 6.40 (dd, 1 H), 6.22-6.35 (m, 2 H), 6.12 (s, 1 H), 5.49-5.78 (m, 1 H), 5.43 (d, 1 H), 4.71 (s br, 1H), 4.27 (d, 1 H), 3.99 (d, 1 H), 3.92 (d, 1 H), 3.82 (d, 1 H), 3.35-3.54 (m, 3 H), 2.55-2.71 (m, 1 H), 2.01-2.31, (m, 3 H), 1.84-1.98 (m, 1 H),1.51-1.68 (m, 3 H), 1.49 (s, 3 H), 1.42 (dd, 1 H), 0.81 (s, 3 H) |
| 14 | 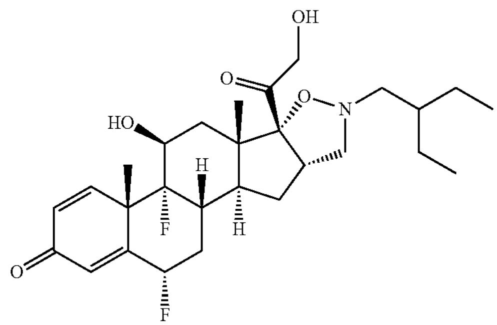 | 10% | LC-MS (ESI POS): 508.45 MH+<br>[α]$_D^{25}$ = +126.4 (c 0.135, CHCl$_3$)<br>$^1$H NMR (300 MHz, DMSO-d$_6$) ppm 7.25 (dd, 1 H), 6.29 (dd, 1 H), 6.11 (s, 1 H), 5.49-5.81 (m, 1 H), 5.44 (dd, 1 H), 4.81 (t, 1 H), 4.45 (dd, 1 H), 4.15-4.24 (m, 1 H), 4.12 (dd, 1 H), 3.42-3.60 (m, 1 H), 3.33-3.43 (m, 1 H), 2.55-2.70 (m, 1 H), 2.06-2.34 (m, 2 H), 1.83-2.06 (m, 2 H), 1.50-1.71 (m, 3 H), 1.49 (s, 3 H), 1.12-1.46 (m, 8 H), 0.62-0.92 (m, 9 H) |
| 15 | 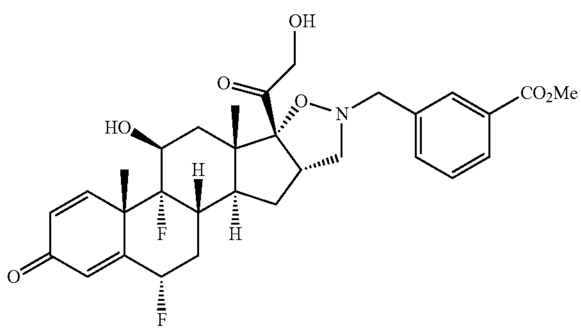 | 41% | LC-MS (ESI POS): 572.42 MH+<br>[α]$_D^{25}$ = +148.3 (c 0.2 MeOH)<br>$^1$H NMR (300 MHz, DMSO-d$_6$) ppm 7.90 (s, 1 H), 7.87 (dt, 1 H), 7.55 (dt, 1 H), 7.47 (t, 1 H), 7.26 (dd, 1 H), 6.30 (dd, 1 H), 6.13 (s, 1 H), 5.48-5.81 (m, 1 H), 5.43 (dd, 1 H), 4.67 (br. s., 1 H), 3.84-4.26 (m, 5 H), 3.83 (s, 3 H), 3.45-3.60 (m, 1 H), 3.34-3.45 (m, 1 H), 2.56-2.71 (m, 1 H), 2.05-2.36 (m, 3 H), 1.81-1.97 (m, 1 H), 1.51-1.70 (m, 3 H), 1.49 (s, 3 H), 1.36-1.46 (m, 1 H), 0.80 (s, 3 H) |
| 16 | 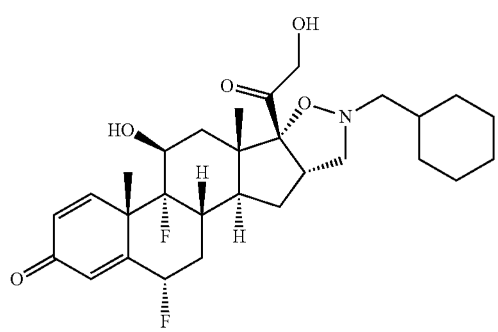 | 71% | LC-MS (ESI POS): 520.45 MH+<br>[α]$_D^{25}$ = +150.2 (c 0.2 MeOH)<br>$^1$H NMR (300 MHz, DMSO-d$_6$) ppm 7.25 (dd, 1 H), 6.29 (dd, 1 H), 6.11 (s, 1 H), 5.49-5.82 (m, 1 H), 5.44 (dd, 1 H), 4.80 (t, 1 H), 4.45 (dd, 1 H), 4.16-4.25 (m, 1 H), 4.12 (dd, 1 H), 3.40-3.56 (m, 1 H), 3.32-3.40 (m, 1 H), 2.56-2.71 (m, 1 H), 2.05-2.33 (m, 2 H), 1.85-2.05 (m, 2 H), 1.75 (dd, 1 H), 1.51-1.70 (m, 7 H), 1.49 (s, 3 H), 1.41 (dd, 1 H), 1.03-1.31 (m, 5 H), 0.83-1.00 (m, 3 H), 0.81 (s, 3 H) |

TABLE 2-continued

| Compound | Structure | Yield | Analytical |
|---|---|---|---|
| 17 | 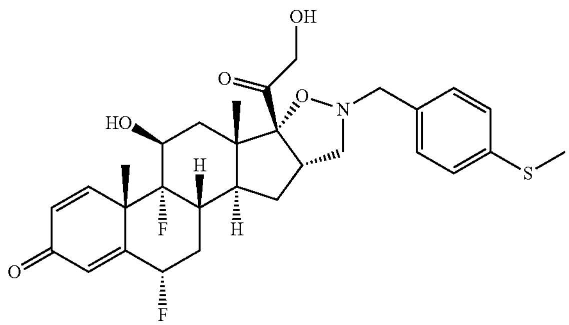 | 70% | LC-MS (ESI POS): 560.3 MH+<br>$[\alpha]_D^{25}$ = +203.5 (c 0.2 MeOH)<br>$^1$H NMR (300 MHz, DMSO-d$_6$) ppm 7.07-7.36 (m, 5 H), 6.30 (dd, 1 H), 6.12 (s, 1 H), 5.48-5.77 (m, 1 H), 5.43 (d, 1 H), 4.48-4.82 (m, 1 H), 4.02-4.29 (m, 2 H), 3.87-3.98 (m, 1 H), 3.86 (d, 1 H), 3.73 (d, 1 H), 3.32-3.54 (m, 2 H), 2.55-2.67 (m, 1 H), 2.45 (s, 3 H), 2.01-2.31 (m, 3 H), 1.91 (d, 1 H), 1.48 (s, 3 H), 1.33-1.73 (m, 4 H), 0.80 (s, 3 H) |
| 18 | 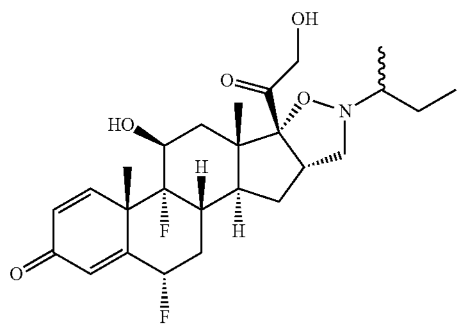 | 23% | LC-MS (ESI POS): 480.34 MH+<br>$[\alpha]_D^{25}$ = +84.1 (c 0.2 MeOH)<br>$^1$H NMR (300 MHz, DMSO-d$_6$) ppm 7.25 (dd, 1 H), 6.29 (dd, 1 H), 6.04-6.19 (m, 1 H), 5.49-5.77 (m, 1 H), 5.37-5.49 (m, 1 H), 4.47 (d, 1 H), 4.16-4.21 (m, 1 H), 4.12 (d, 1 H), 3.25-3.42 (m, 2 H), 2.57-2.68 (m, 1 H), 1.87-2.25 (m, 4 H), 1.50-1.69 (m, 3 H), 1.49 (s, 3 H), 1.22-1.47 (m, 4 H), 0.90 and 1.05 (d, 3 H), 0.76-0.87 (m, 6 H) |
| 19 | 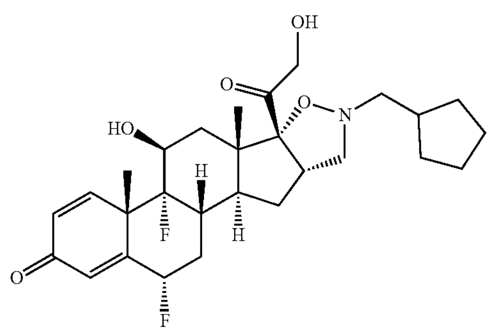 | 82% | LC-MS (ESI POS): 506.25 MH+<br>$[\alpha]_D^{25}$ = +151.5 (c 0.2 MeOH)<br>$^1$H NMR (300 MHz, DMSO-d$_6$) ppm 7.25 (dd, 1 H), 6.29 (dd, 1 H), 6.11 (s, 1 H), 5.48-5.75 (m, 1 H), 5.38-5.46 (m, 1 H), 4.71-4.86 (m, 1 H), 4.48 (dd, 1 H), 4.15-4.23 (m, 1 H), 4.11 (dd, 1 H), 3.42-3.58 (m, 1 H), 3.32-3.42 (m, 1 H), 2.57 (d, 2 H), 2.35-2.45 (m, 1 H), 1.86-2.19 (m, 6 H), 1.51-1.78 (m, 6 H), 1.49 (s, 3 H), 1.34-1.45 (m, 2 H), 1.03-1.22 (m, 3 H), 0.82 (s, 3 H) |
| 20 | 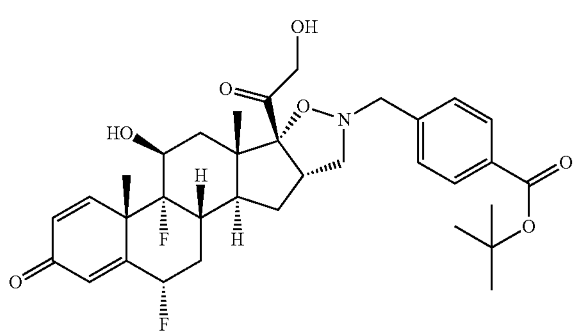 | 39% | LC-MS (ESI POS): 614.29 MH+<br>$[\alpha]_D^{25}$ = +208.5 (c 0.2 MeOH)<br>$^1$H NMR (300 MHz, DMSO-d$_6$) ppm 7.76-7.90 (m, 2 H), 7.32-7.48 (m, 2 H), 7.25 (dd, 1 H), 6.30 (dd, 1 H), 6.13 (s, 1 H), 5.48-5.82 (m, 1 H), 5.42 (dd, 1 H), 4.63-4.77 (m, 1 H), 4.10-4.22 (m, 1 H), 3.71-4.10 (m, 4 H), 3.46-3.62 (m, 1 H), 3.35-3.46 (m, 1 H), 2.57-2.70 (m, 1 H), 2.06-2.36 (m, 2 H), 1.79-1.96 (m, 1 H), 1.57-1.67 (m, 4 H), 1.54 (s, 9 H), 1.49 (s, 3 H), 1.36-1.51 (m, 1 H), 0.80 (s, 3 H) |

TABLE 2-continued

| Compound | Structure | Yield | Analytical |
|---|---|---|---|
| 21 | 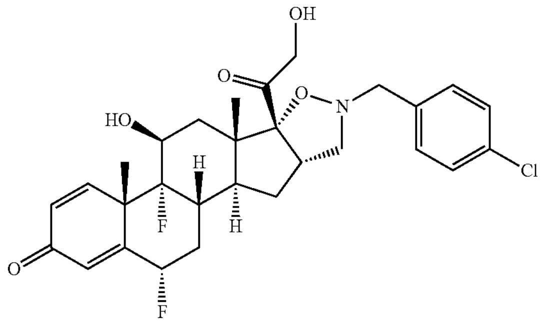 | 84% | LC-MS (ESI POS): 547.99 (MH+)<br>$^1$H NMR (300 MHz, DMSO-$d_6$) ppm 7.20-7.43 (m, 5 H), 6.30 (dd, 1 H), 6.12 (s, 1 H), 5.50-5.81 (m, 1 H), 5.43 (dd, 1 H), 4.54-4.78 (m, 1 H), 4.00-4.23 (m, 2 H), 3.81-3.97 (m, 2 H), 3.74 (d, 1 H), 3.33-3.59 (m, 2 H), 2.55-2.63 (m, 1 H), 2.01-2.35 (m, 3 H), 1.77-1.96 (m, 1 H), 1.51-1.69 (m, 3 H), 1.49 (s, 3 H), 1.35-1.46 (m, 1 H), 0.80 (s, 3 H) |
| 22 | 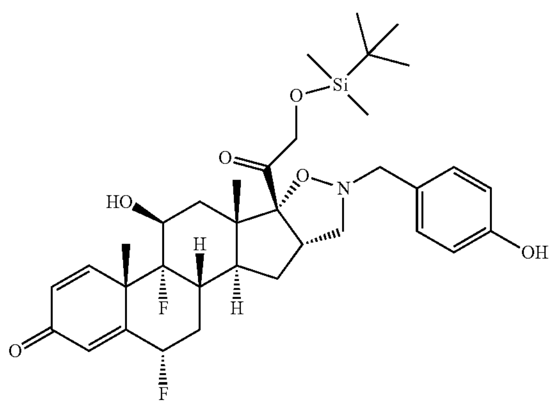 | 86% | LC-MS (ESI POS): 644.0 (MH+) |
| 23 | 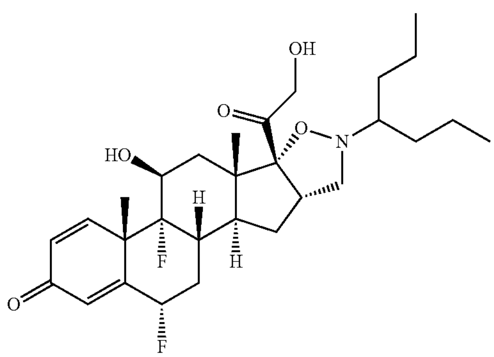 | 40% | LC-MS (ESI POS): 522.13 MH+<br>$[\alpha]_D^{25}$ = +133.6 (c 0.2 MeOH)<br>$^1$H NMR (300 MHz, DMSO-$d_6$) 7.26 (dd, 1 H), 6.29 (dd, 1 H), 6.07-6.17 (m, 1 H), 5.48-5.79 (m, 1 H), 5.43 (dd, 1 H), 4.79 (t, 1 H), 4.44 (dd, 1 H), 4.16-4.22 (m, 1 H), 4.12 (dd, 1 H), 3.31-3.49 (m, 2 H), 2.55-2.66 (m, 1 H), 2.41-2.47 (m, 1 H), 1.83-2.32 (m, 5 H), 1.50-1.70 (m, 3 H), 1.49 (s, 3 H), 1.11-1.46 (m, 8 H), 0.85 (t, 6 H), 0.81 (s, 3 H) |
| 24 | 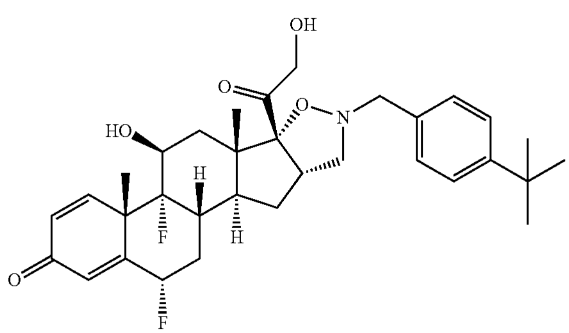 | 68% | LC-MS (ESI POS): 570.18 MH+<br>$[\alpha]_D^{25}$ = +122.4 (C 0.149, CHCl$_3$)<br>$^1$H NMR (300 MHz, DMSO-$d_6$) ppm 7.28-7.34 (m, 2 H), 7.26 (dd, 1 H), 7.15-7.22 (m, 2 H), 6.30 (dd, 1 H), 6.11 (s, 1 H), 5.48-5.79 (m, 1 H), 5.43 (dd, 1 H), 4.57-4.82 (m, 1 H), 4.29 (dd, 1 H), 4.11-4.22 (m, 1 H), 3.98 (dd, 1 H), 3.87 (d, 1 H), 3.79 (d, 1 H), 3.31-3.51 (m, 2 H), 2.55-2.68 (m, 1 H), 2.01-2.32 (m, 3 H), 1.82-1.98 (m, 1 H), 1.51-1.74 (m, 2 H), 1.48 (s, 3 H), 1.29-1.44 (m, 2 H), 1.25 (s, 9 H), 0.80 (s, 3 H) |

TABLE 2-continued

| Compound | Structure | Yield | Analytical |
|---|---|---|---|
| 25 | 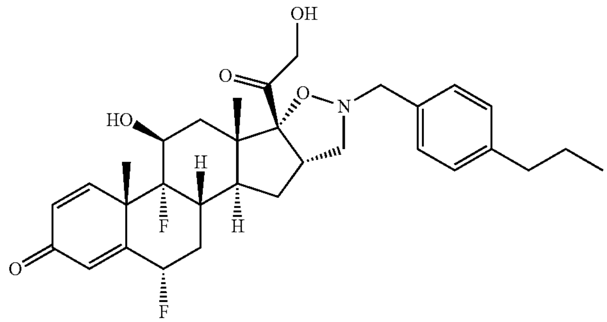 | 71% | LC-MS (ESI POS): 556.25 MH+<br>$[\alpha]_D^{25}$ = +151.3 (c 0.147, CHCl$_3$)<br>$^1$H NMR (300 MHz, DMSO-d$_6$) ppm 7.26 (dd, 1 H), 7.14-7.20 (m, 2 H), 7.06-7.14 (m, 2 H), 6.30 (dd, 1 H), 6.12 (s, 1 H), 5.49-5.77 (m, 1 H), 5.43 (dd, 1 H), 4.66 (br. s., 1 H), 4.08-4.31 (m, 2 H), 3.92 (d, 1 H), 3.85 (d, 1 H), 3.76 (d, 1 H), 3.33-3.51 (m, 2 H), 2.58-2.71 (m, 1 H), 2.44-2.48 (m, 2 H), 1.99-2.33 (m, 3 H), 1.80-1.98 (m, 1 H), 1.50-1.70 (m, 5 H), 1.47 (s, 3 H), 1.31-1.45 (m, 1 H), 0.87 (t, 3 H), 0.80 (s, 3 H) |
| 26 | 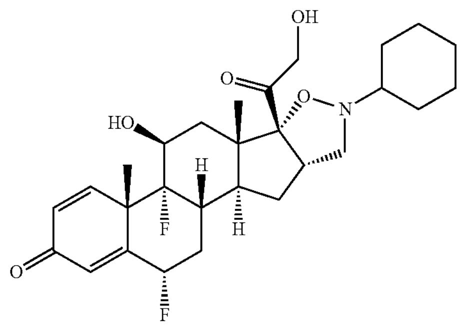 | 69% | LC-MS (ESI POS): 506.29 MH+<br>$[\alpha]_D^{25}$ = +97.8 (c 0.2 MeOH)<br>$^1$H NMR (300 MHz, DMSO-d$_6$) ppm 7.25 (dd, 1 H), 6.29 (dd, 1 H), 6.11 (s, 1 H), 5.49-5.74 (m, 1 H), 5.43 (dd, 1 H), 4.76 (t, 1 H), 4.49 (dd, 1 H), 4.13-4.22 (m, 1 H), 4.12 (dd, 1 H), 3.41-3.61 (m, 1 H), 3.31-3.41 (m, 1 H), 2.54-2.69 (m, 1 H), 2.31-2.44 (m, 1 H), 1.82-2.31 (m, 5 H), 1.50-1.76 (m, 6 H), 1.49 (s, 3 H), 1.35-1.46 (m, 1 H), 0.97-1.30 (m, 6 H), 0.81 (s, 3 H) |
| 27 | 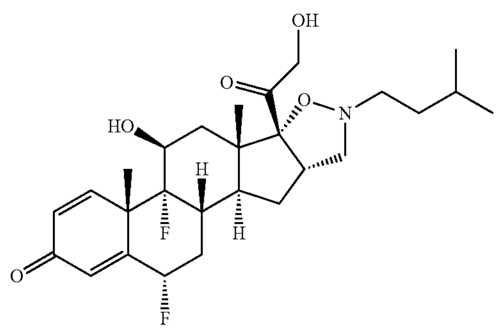 | 77% | LC-MS (ESI POS): 494.17 MH+<br>$[\alpha]_D^{25}$ = +242.2 (c 0.09, CHCl$_3$)<br>$^1$H NMR (300 MHz, DMSO-d$_6$) ppm 7.25 (dd, 1 H), 6.29 (dd, 1 H), 6.11 (s, 1 H), 5.48-5.80 (m, 1 H), 5.44 (d, 1 H), 4.78 (dd, 1 H), 4.47 (dd, 1 H), 4.11-4.22 (m, 1 H), 4.12 (dd, 1 H), 3.41-3.58 (m, 1 H), 3.32-3.42 (m, 1 H), 2.55-2.71 (m, 3 H), 2.03-2.37 (m, 2 H), 1.83-2.03 (m, 2 H), 1.50-1.72 (m, 4 H), 1.49 (s, 3 H), 1.27-1.46 (m, 3 H), 0.85 (d, 3 H), 0.85 (d, 3 H), 0.81 (s, 3 H) |
| 28 | 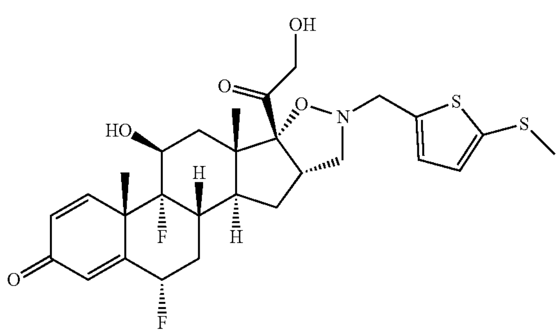 | 66% | LC-MS (ESI POS): 566.13 MH+<br>$[\alpha]_D^{25}$ = +140.2 (c 0.119, CHCl$_3$)<br>$^1$H NMR (300 MHz, DMSO-d$_6$) ppm 7.26 (dd, 1 H), 6.95 (d, 1 H), 6.85 (d, 1 H), 6.30 (dd, 1 H), 6.11 (s, 1 H), 5.48-5.79 (m, 1 H), 5.44 (dd, 1 H), 4.38 (d, 1 H), 4.08-4.25 (m, 2 H), 4.03 (d, 1 H), 3.95 (d, 1 H), 3.38-3.51 (m, 2 H), 2.56-2.68 (m, 1 H), 2.41 (s, 3 H), 2.03-2.32 (m, 3 H), 1.89-2.04 (m, 1 H), 1.51-1.71 (m, 4 H), 1.49 (s, 3 H), 1.34-1.45 (m, 1 H), 0.81 (s, 3 H) |

TABLE 2-continued

| Compound | Structure | Yield | Analytical |
|---|---|---|---|
| 29 | 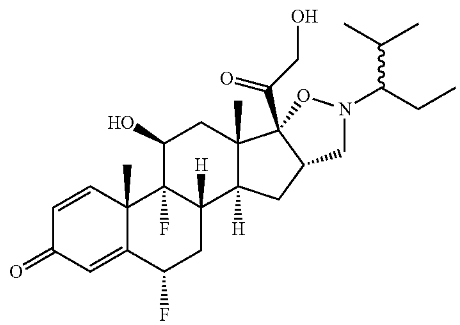 | 58% | LC-MS (ESI POS): 508.22 MH+<br>[α]$_D^{25}$ = +118.8 (c 0.26, MeOH)<br>$^1$H NMR (300 MHz, DMSO-d$_6$) ppm 7.25 (d, 1 H), 6.29 (dd, 1 H), 6.11 (s, 1 H), 5.46-5.81 (m, 1 H), 5.43 (d, 1 H), 4.81 and 4.83 (t, 1 H), 4.48 (dd, 1 H), 4.13-4.25 (m, 1 H), 4.10 and 4.13 (dd, 1 H), 3.31-3.53 (m, 2 H), 2.53-2.70 (m, 2 H), 2.27 (dt, 2 H), 2.02-2.21 (m, 3 H), 1.87-2.01 (m, 1 H), 1.68- 1.87 (m, 1 H), 1.53 (s, 3 H), 1.36-1.68 (m, 4 H), 0.88 and 0.95 (t, 3 H), 0.84 and 0.85 (d, 3 H), 0.82 (s, 3 H), 0.75 and 0.82 (d, 3 H) |
| 30 | 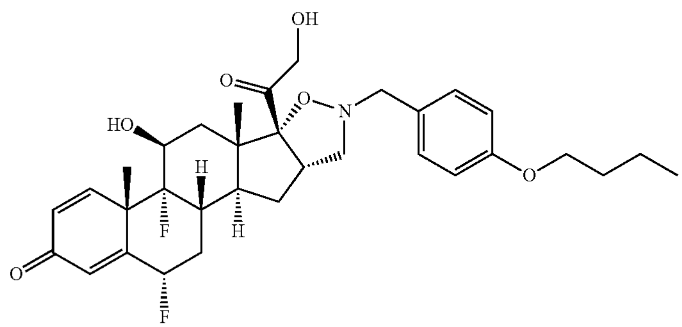 | 69% | LC-MS (ESI POS): 596.09 MH+<br>[α]$_D^{25}$ = +154.9 (c 0.2 MeOH)<br>$^1$H NMR (300 MHz, DMSO-d$_6$) ppm 7.26 (dd, 1 H), 7.16 (m, 2 H), 6.84 (m, 2 H), 6.30 (dd, 1 H), 6.12 (s, 1 H), 5.47-5.79 (m, 1 H), 5.42 (d, 1 H), 4.50-4.77 (m, 1 H), 4.05-4.26 (m, 2 H), 3.94 (m, 3 H), 3.59-3.86 (m, 2 H), 3.33-3.46 (m, 1 H), 1.98-2.31 (m, 3 H), 1.93 (d, 1 H), 1.51-1.79 (m, 5 H), 1.49 (s, 3 H), 1.36-1.47 (m, 3 H), 0.93 (t, 3 H), 0.80 (s, 3 H) |
| 31 | 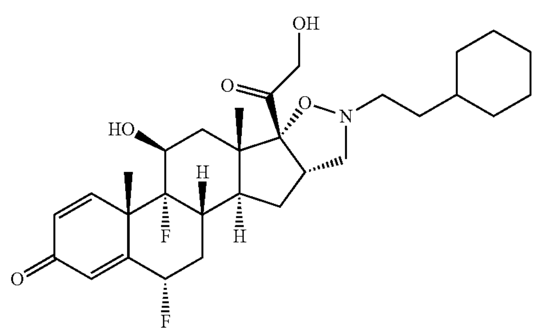 | 65% | LC-MS (ESI POS): 534.28 MH+<br>[α]$_D^{25}$ = +152.3 (c 0.23, MeOH)<br>$^1$H NMR (300 MHz, DMSO-d$_6$) ppm 7.25 (dd, 1 H), 6.29 (dd, 1 H), 6.11 (s, 1 H), 5.48-5.78 (m, 1 H), 5.44 (dd, 1 H), 4.78 (t, 1 H), 4.46 (dd, 1 H), 4.12-4.24 (m, 1 H), 4.12 (dd, 1 H), 3.42-3.57 (m, 1 H), 3.31-3.41 (m, 1 H), 2.56-2.74 (m, 3 H), 2.02-2.33 (m, 2 H), 1.83-1.97 (m, 2 H), 1.51-1.72 (m, 8 H), 1.49 (s, 3 H), 1.04-1.46 (m, 7 H), 0.83-0.97 (m, 2 H), 0.81 (s, 3 H) |
| 32 | 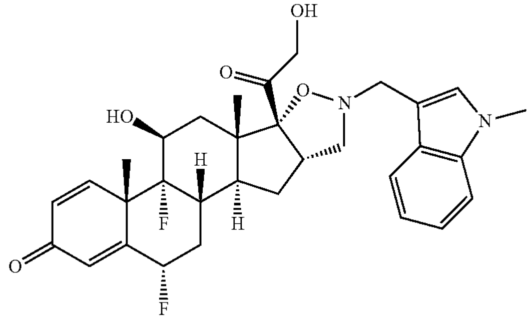 | 8% | LC-MS (ESI POS): 567.23 M+<br>[α]$_D^{25}$ = +110 (c 0.26, MeOH)<br>$^1$H NMR (300 MHz, DMSO-d$_6$) ppm 7.55 (d, 1 H), 7.38 (d, 1 H), 7.28 (dd, 1 H), 7.22 (s, 1 H), 7.13 (ddd, 1 H), 7.00 (ddd, 1 H), 6.32 (dd, 1 H), 6.14 (s, 1 H), 5.49-5.81 (m, 1 H), 5.45 (dd, 1 H), 4.65 (br. s., 1 H), 3.83-4.38 (m, 5 H), 3.72 (s, 3 H), 3.30-3.49 (m, 2 H), 2.55-2.69 (m, 1 H), 1.95-2.36 (m, 4 H), 1.52-1.71 (m, 3 H), 1.50 (s, 3 H), 1.41 (dd, 1 H), 0.82 (s, 3 H) |

TABLE 2-continued

| Compound | Structure | Yield | Analytical |
|---|---|---|---|
| 33 | 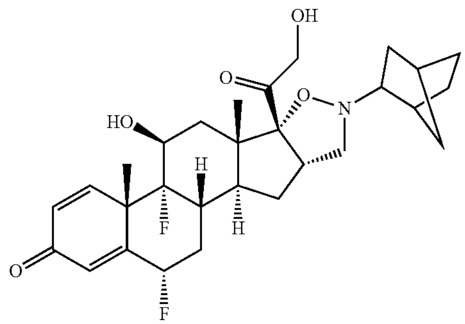 | 80% | LC-MS (ESI POS): 518.11 MH+<br>$[\alpha]_D^{25}$ = +108.5 (c 0.24, MeOH)<br>$^1$H NMR (300 MHz, DMSO-d$_6$) ppm 7.25 (d, 1 H), 6.29 (dt, 1 H), 6.11 (s, 1 H), 5.48-5.86 (m, 1 H), 5.43 (d, 1 H), 4.76 and 4.83 (t, 1 H), 4.30-4.67 (m, 1 H), 4.05-4.24 (m, 1 H), 4.08 (dd, 1 H), 3.35-3.60 (m, 2 H), 2.55-2.75 (m, 2 H), 2.18-2.37 (m, 1 H), 2.10 (br. s., 2 H), 1.81-2.05 (m, 2 H), 1.32-1.68 (m, 5 H), 1.48 (s, 3 H), 1.12-1.32 (m, 4 H), 0.93-1.12 (m, 3 H), 0.79 and 0.82 (s, 3 H), 0.58-0.90 and 0.84-0.96 (m, 1 H) |
| 34 | 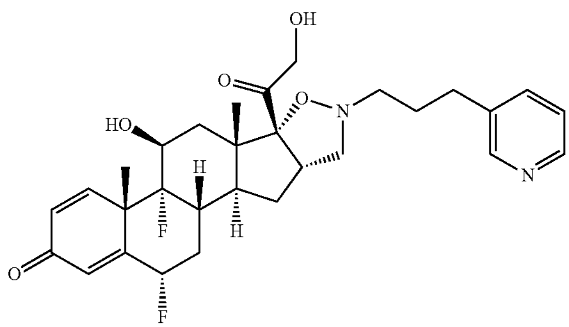 | 34% | LC-MS (ESI POS): 543.24 MH+<br>$[\alpha]_D^{25}$ = +136.9 (c 0.3, MeOH)<br>$^1$H NMR (300 MHz, DMSO-d$_6$) ppm 8.33-8.48 (m, 2 H), 7.60 (dt, 1 H), 7.29 (ddd, 1 H), 7.25 (dd, 1 H), 6.29 (dd, 1 H), 6.11 (s, 1 H), 5.49-5.80 (m, 1 H), 5.44 (dd, 1 H), 4.83 (t, 1 H), 4.51 (dd, 1 H), 4.14-4.23 (m, 1 H), 4.13 (dd, 1 H), 3.44-3.57 (m, 1 H), 3.33-3.44 (m, 1 H), 2.57-2.81 (m, 5 H), 2.06-2.33 (m, 2 H), 1.86-2.03 (m, 2 H), 1.69-1.85 (m, 2 H), 1.51-1.69 (m, 3 H), 1.49 (s, 3 H), 1.42 (dd, 1 H), 0.82 (s, 3 H) |
| 35 | 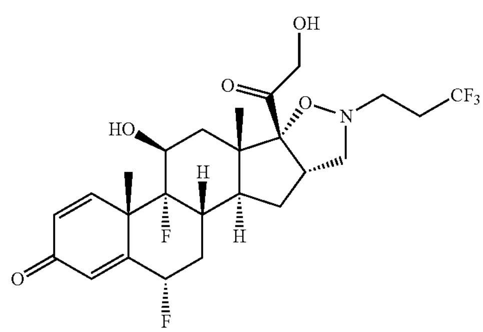 | 16% | LC-MS (ESI POS): 520.17 MH+<br>$[\alpha]_D^{25}$ = +123.8 (c 0.27, MeOH)<br>$^1$H NMR (300 MHz, DMSO-d$_6$) ppm 7.25 (dd, 1 H), 6.29 (dd, 1 H), 6.11 (s, 1 H), 5.50-5.80 (m, 1 H), 5.45 (dd, 1 H), 4.81 (t, 1 H), 4.43 (dd, 1 H), 4.14-4.24 (m, 1 H), 4.14 (dd, 1 H), 3.47-3.64 (m, 1 H), 3.33-3.47 (m, 1 H), 2.89-3.10 (m, 1 H), 2.76-2.89 (m, 1 H), 2.58-2.70 (m, 2 H), 2.38-2.46 (m, 1 H), 1.85-2.35 (m, 4 H), 1.53-1.72 (m, 3 H), 1.49 (s, 3 H), 1.43 (dd, 1 H), 0.82 (s, 3 H) |
| 36 | 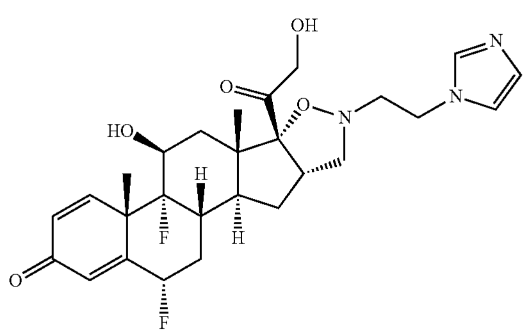 | 62% | LC-MS (ESI POS): 518.25 MH+<br>$[\alpha]_D^{25}$ = +122.2 (c 0.1435; MeOH)<br>$^1$H NMR (300 MHz, DMSO-d$_6$) ppm 7.57 (s, 1 H), 7.26 (dd, 1 H), 7.12 (t, 1 H), 6.83 (s, 1 H), 6.30 (dd, 1 H), 6.12 (s, 1 H), 5.50-5.83 (m, 1 H), 5.45 (dd, 1 H), 4.86 (t, 1 H), 4.45 (dd, 1 H), 4.01-4.24 (m, 4 H), 3.35-3.51 (m, 2 H), 3.03-3.21 (m, 1 H), 2.87-3.03 (m, 1 H), 2.58-2.71 (m, 1 H), 1.86-2.30 (m, 4 H), 1.52-1.76 (m, 3 H), 1.49 (s, 3 H), 1.42 (dd, 1 H), 0.82 (s, 3 H) |

TABLE 2-continued

| Compound | Structure | Yield | Analytical |
|---|---|---|---|
| 37 | 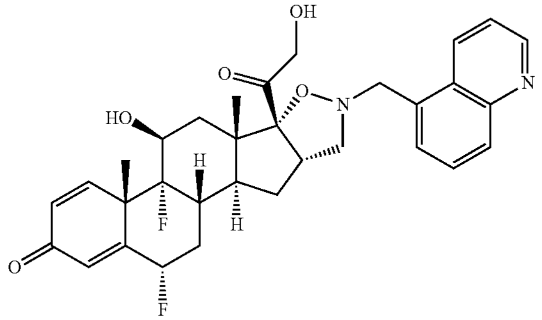 | 18% | LC-MS (ESI POS): 565.27 MB+<br>$[\alpha]_D^{25}$ = +193.2 (c 0.25, MeOH)<br>$^1$H NMR (300 MHz, DMSO-$d_6$) ppm 8.89 (dd, 1 H), 8.55 (dt, 1 H), 7.97 (d, 1 H), 7.70 (dd, 1 H), 7.54 (dd, 1 H), 7.49 (dd, 1 H), 7.27 (dd, 1 H), 6.32 (dd, 1 H), 6.14 (s, 1 H), 5.49-5.80 (m, 1 H), 5.42 (dd, 1 H), 4.53 (br. s., 1 H), 4.38 (d, 1 H), 4.29 (d, 1 H), 4.09-4.22 (m, 1 H), 3.66-3.91 (m, 2 H), 3.53 (br. s., 1 H), 3.37 (br. s., 1 H), 2.54-2.70 (m, 1 H), 2.15-2.35 (m, 3 H), 1.83-1.97 (m, 1 H), 1.52-1.72 (m, 3 H), 1.49 (s, 3 H), 1.39-1.46 (m, 1 H), 0.78 (s, 3 H) |
| 38 | 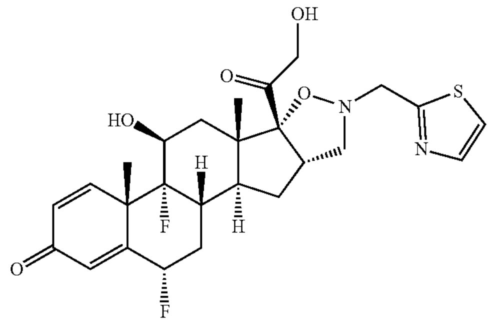 | 29% | LCMS (ESI POS): 521.22 MH+<br>$[\alpha]_D^{25}$ = +172.7 (c 0.33, MeOH)<br>$^1$H NMR (300 MHz, DMSO-$d_6$) ppm 7.73 (d, 1 H), 7.69 (d, 1 H), 7.26 (dd, 1 H), 6.30 (dd, 1 H), 6.12 (s, 1 H), 5.49-5.79 (m, 1 H), 5.44 (dd, 1 H), 4.81 (t, 1 H), 4.38 (dd, 1 H), 4.07-4.23 (m, 1 H), 4.06-4.39 (m, 2 H), 3.99 (dd, 1 H), 3.53-3.74 (m, 1 H), 3.41-3.53 (m, 1 H), 2.56-2.71 (m, 1 H), 2.07-2.36 (m, 3 H), 1.82-1.97 (m, 1 H), 1.51-1.69 (m, 3 H), 1.49 (s, 3 H), 1.38-1.47(m, 1 H), 0.81 (s, 3 H) |

Example 5. Preparation of Methanesulfonic acid 2-[(4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester (compound 39)

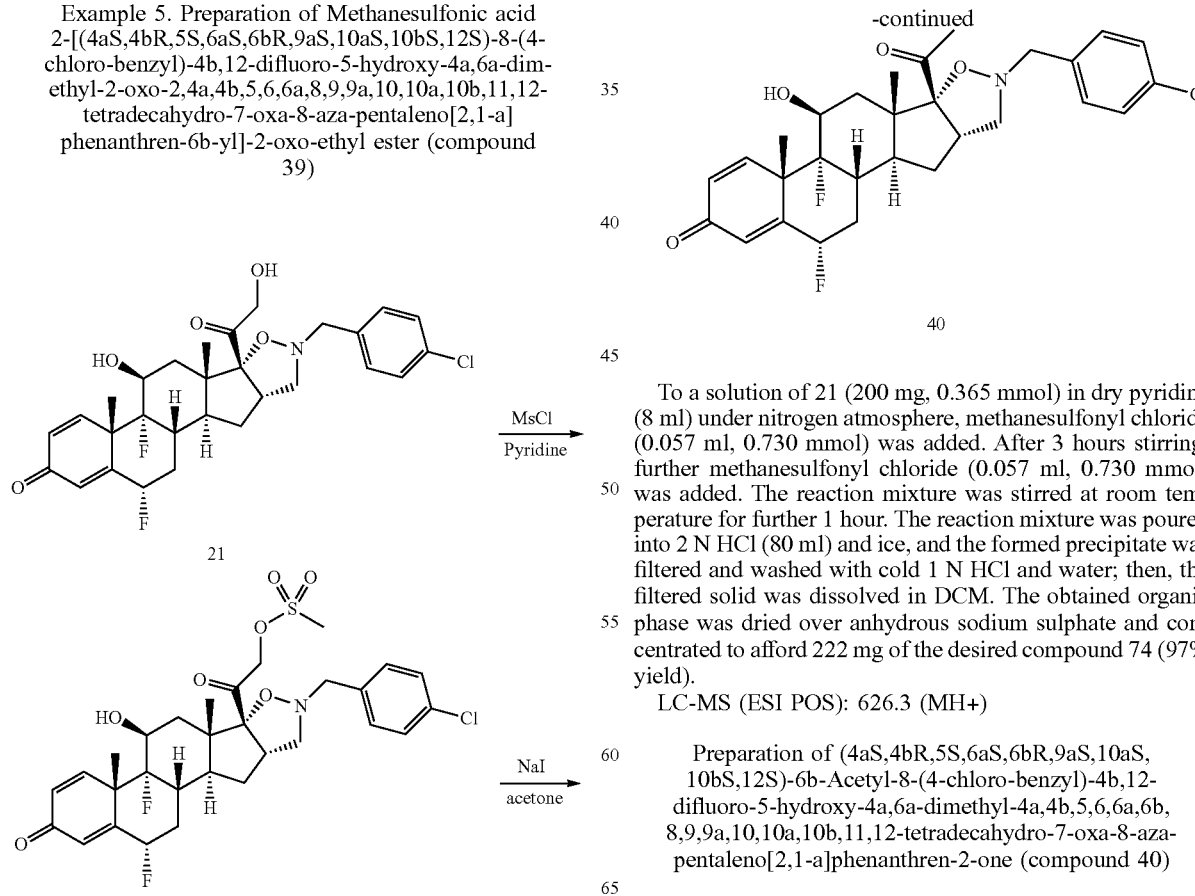

To a solution of 21 (200 mg, 0.365 mmol) in dry pyridine (8 ml) under nitrogen atmosphere, methanesulfonyl chloride (0.057 ml, 0.730 mmol) was added. After 3 hours stirring, further methanesulfonyl chloride (0.057 ml, 0.730 mmol) was added. The reaction mixture was stirred at room temperature for further 1 hour. The reaction mixture was poured into 2 N HCl (80 ml) and ice, and the formed precipitate was filtered and washed with cold 1 N HCl and water; then, the filtered solid was dissolved in DCM. The obtained organic phase was dried over anhydrous sodium sulphate and concentrated to afford 222 mg of the desired compound 74 (97% yield).

LC-MS (ESI POS): 626.3 (MH+)

Preparation of (4aS,4bR,5S,6aS,6bR,9aS,10aS,10bS,12S)-6b-Acetyl-8-(4-chloro-benzyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one (compound 40)

Compound 39 (308 mg, 0.492 mmol) was dissolved in acetone (12 ml), and sodium iodide (738 mg, 4.92 mmol)

was added. The reaction mixture was stirred at 65° C. overnight. The reaction mixture was diluted with AcOEt (80 ml), washed with sat Na$_2$S$_2$O$_3$ until disappearance of the iodine, then with sat NaHCO$_3$. The organic layer was dried over Na$_2$SO$_4$ and evaporated, to give 224 mg of crude material, which was purified by preparative HPLC, to afford 65 mg of pure compound 75 (25% yield).

$^1$H NMR (300 MHz, DMSO-d$_6$) ppm 7.33-7.42 (m, 2H), 7.28-7.33 (m, 2H), 7.26 (d, 1H), 6.30 (dd, 1H), 6.13 (s, 1H), 5.48-5.80 (m, 1H), 5.43 (br. s., 1H), 4.07-4.27 (m, 1H), 3.93 (d, 1H), 3.74 (d, 1H), 3.44-3.57 (m, 1H), 3.34-3.44 (m, 1H), 2.56-2.76 (m, 1H), 2.05-2.36 (m, 3H), 1.91-2.04 (m, 1H), 1.88 (s, 3H), 1.52-1.69 (m, 3H), 1.49 (s, 3H), 1.43 (dd, 1H), 0.79 (s, 3H)

LC-MS (ESI POS): 532.28 (MH+)

[α]$_D^{25}$=+285.8 (c 0.11, CHCl$_3$)

Example 6. Preparation of (4aS,4bR,5S,6aS,6bR, 9aS,10aS,10bS,12S)-8-(4-Chloro-benzyl)-4b,12-difluoro-5-hydroxy-4a,6a-dimethyl-2-oxo-2,4a,4b,5, 6,6a,8,9,9a,10,10a,10b,11,12-tetradecahydro-7-oxa-8-aza-pentaleno[2,1-a]phenanthrene-6b-carboxylic acid (compound 41)

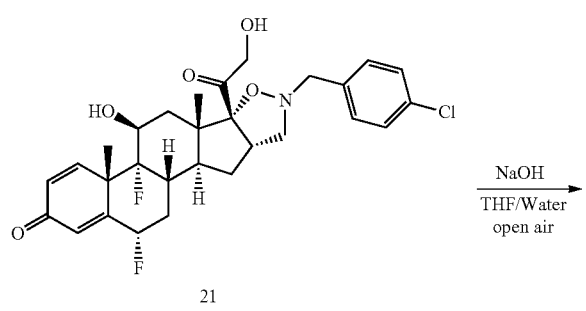

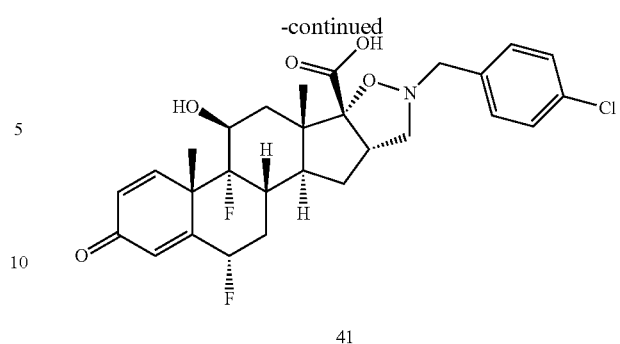

To a solution of compound 21 (1.55 g, 2.83 mmol) in tetrahydrofuran (60 ml) and water (30.0 ml) at 0° C., 6 N sodium hydroxide (1.414 ml, 8.49 mmol) was added dropwise, and the reaction mixture was stirred at 0° C. for 10 minutes and at room temperature for 56 hours. Tetrahydrofuran was evaporated, and the aqueous layer was acidified to pH 1 and extracted with AcOEt (100 ml×3). The combined organic extracts were washed with brine, dried (Na$_2$SO$_4$) and concentrated. The crude was purified by silica gel flash chromatography in DCM/AcOEt/HCO2H 60:39.5:0.5, to afford 1.11 g of pure compound (Rf=0.34 in DCM/AcOEt/HCO2H 50:49.5:0.5).

LC-MS (ESI POS): 534.2 (MH+)

Compounds listed in Table 3 were prepared as previously described for compound 41:

TABLE 3

| Compound | Structure | Yield | Analytical |
|---|---|---|---|
| 42 | 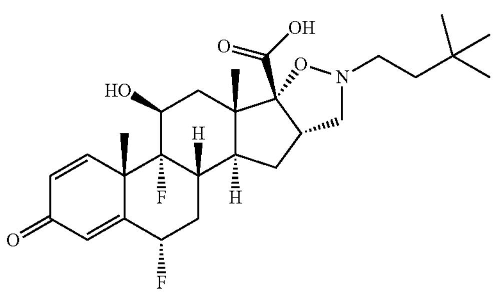 | 89% | LC_MS (ESI POS): 494.2 (MH+) |
| 43 | 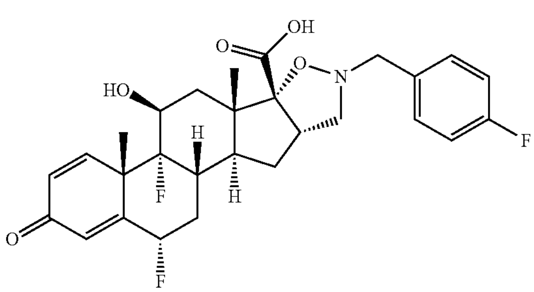 | 62% | LC_MS (ESI POS): 518.1 (MH+) |

TABLE 3-continued

| Compound | Structure | Yield | Analytical |
|---|---|---|---|
| 44 | 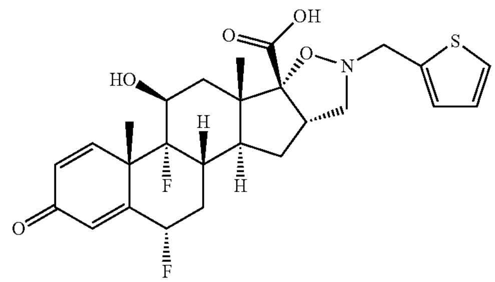 | 55% | LC_MS (ESI POS): 506.1 (MH+) |
| 45 | 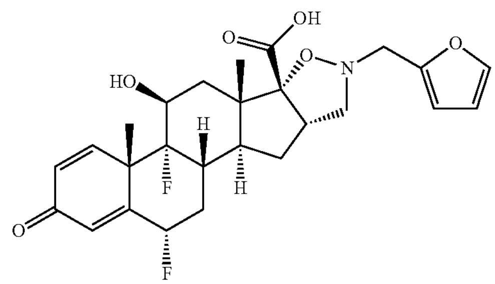 | 41% | LC_MS (ESI POS): 490.1 (MH+) |
| 46 | 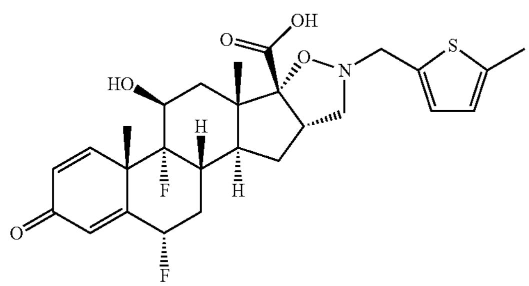 | 20% | LC_MS (ESI POS): 520.1 (MH+) |
| 47 | 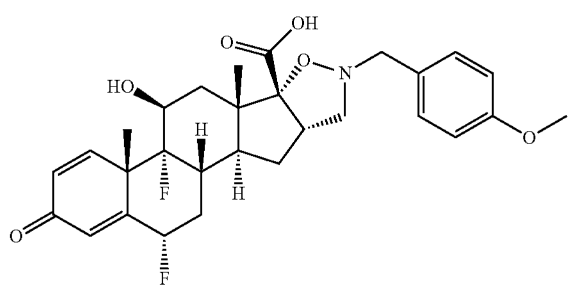 | 99% | LC_MS (ESI POS): 530.1 (MH+) |
| 48 | 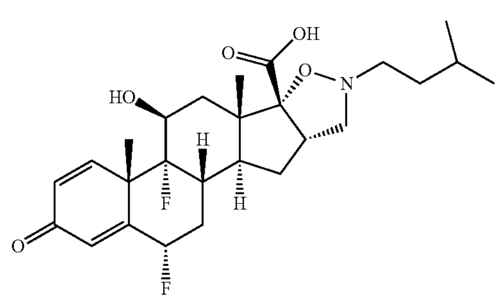 | 96% | LC_MS (ESI POS): 480.1 (MH+) |

TABLE 3-continued

| Compound | Structure | Yield | Analytical |
|---|---|---|---|
| 49 | 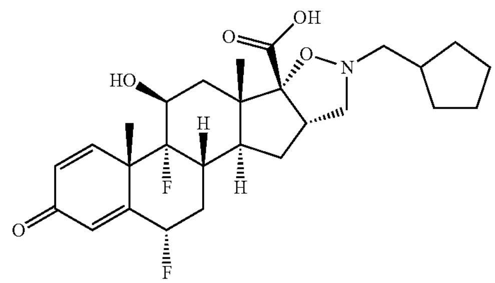 | 71% | LC_MS (ESI POS): 492.1 (MH+) |
| 50 | 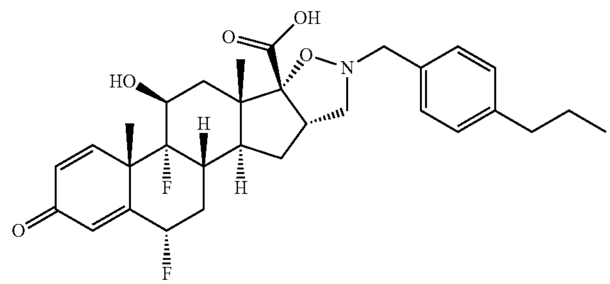 | 43% | LC_MS (ESI POS): 542.1 (MH+) |
| 51 | 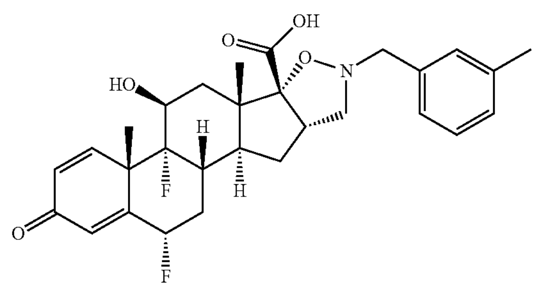 | 98% | LC_MS (ESI POS): 514.1 (MH+) |
| 52 | 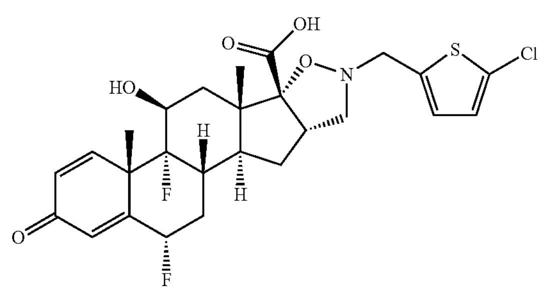 | 97% | LC_MS (ESI POS): 540.0 (MH+) |
| 53 | 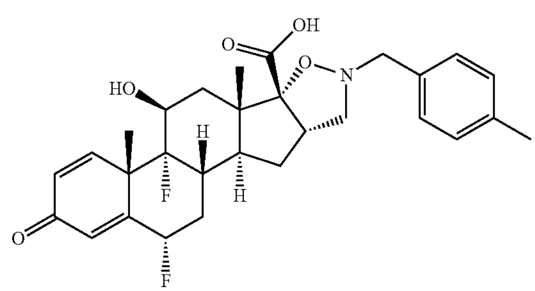 | 97% | LC_MS (ESI POS): 514.2 (MH+) |

TABLE 3-continued

| Compound | Structure | Yield | Analytical |
|---|---|---|---|
| 54 | 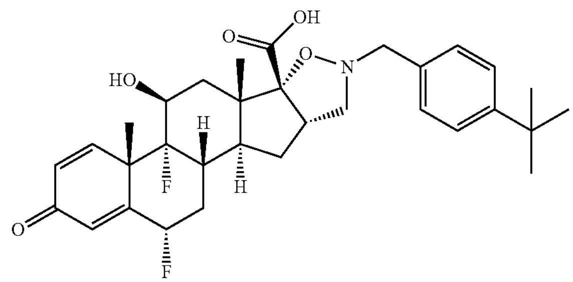 | 50% | LC_MS (ESI POS): 556.2 (MH+) |
| 55 | 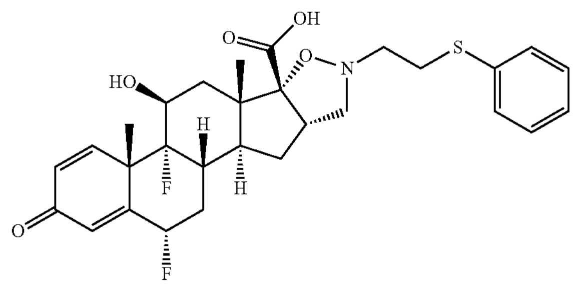 | 59% | LC_MS (ESI POS): 546.1 (MH+) |
| 56 | 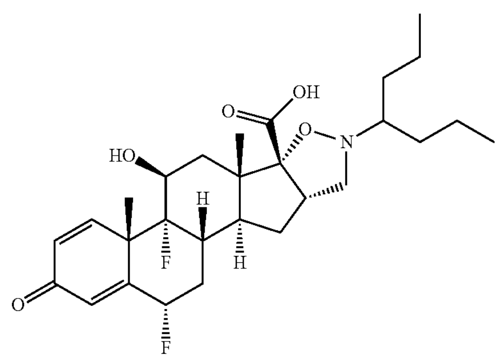 | 78% | LC_MS (ESI POS): 508.1 (MH+) |
| 57 | 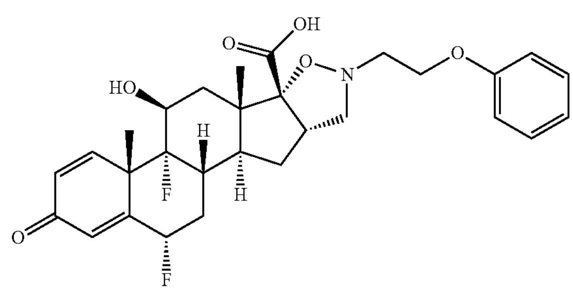 | 99% | LC_MS (ESI POS): 530.1 (MH+) |
| 58 | 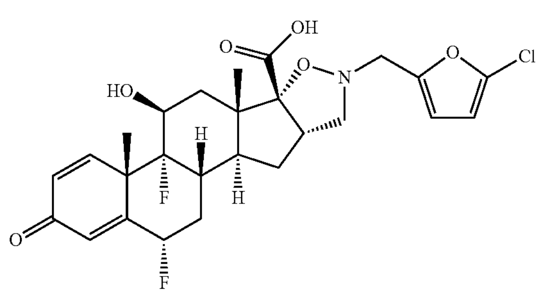 | 31% | LC_MS (ESI POS): 524.0 (MH+) |

TABLE 3-continued

| Compound | Structure | Yield | Analytical |
|---|---|---|---|
| 59 | 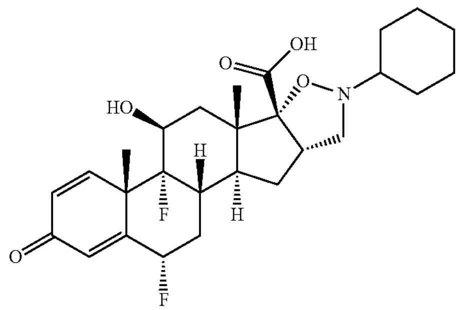 | 63% | LC_MS (ESI POS): 492.1 (MH+) |
| 60 | 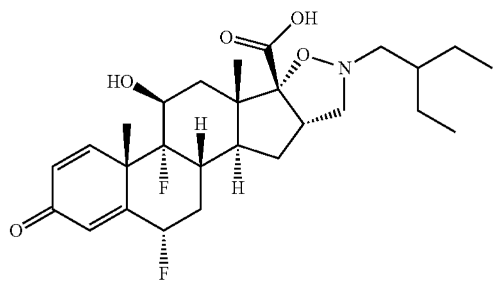 | 68% | LC_MS (ESI POS): 494.1 (MH+) |
| 61 | 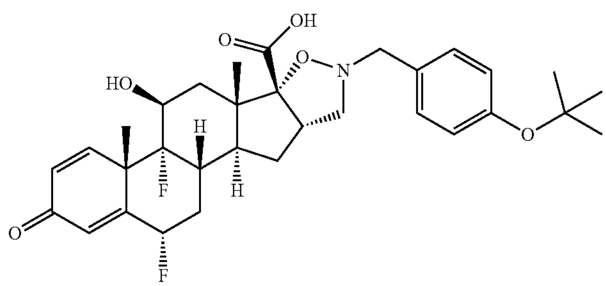 | 44% | LC_MS (ESI POS): 572.2 (MH+) |
| 62 | 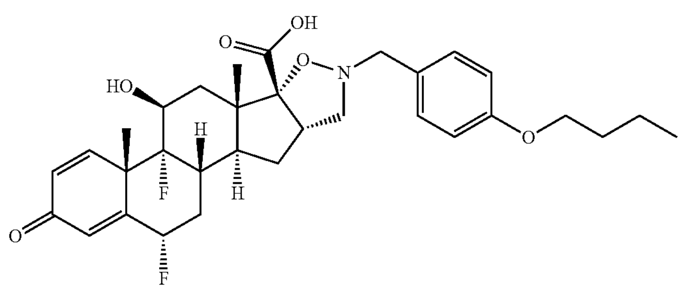 | 79% | LC_MS (ESI POS): 572.2 (MH+) |
| 63 | 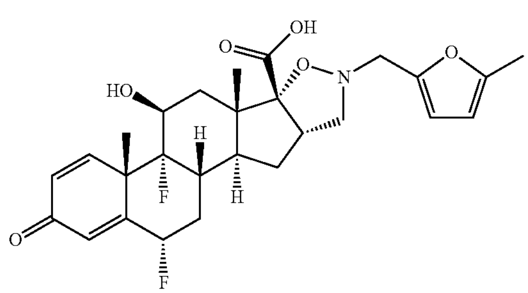 | 91% | LC_MS (ESI POS): 504.0 (MH+) |

TABLE 3-continued

| Compound | Structure | Yield | Analytical |
|---|---|---|---|
| 64 | 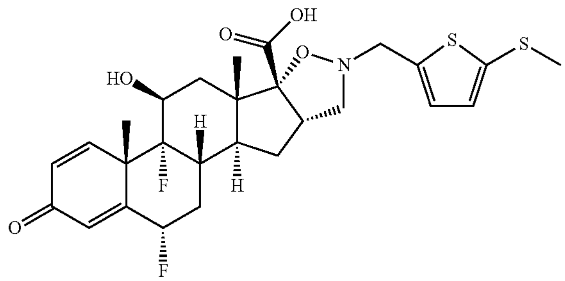 | 95% | LC_MS (ESI POS): 552.1 (MH+) |
| 65 | 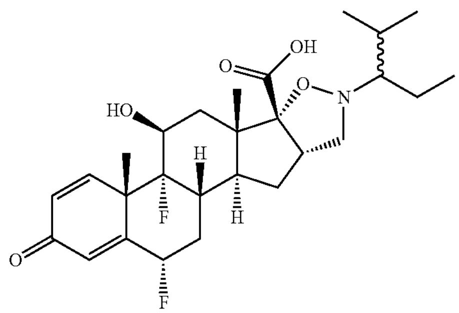 | 99% | LC_MS (ESI POS): 494.1 (MH+) |
| 66 | 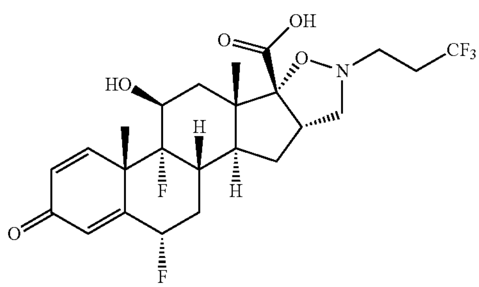 | 60% | LC_MS (ESI POS): 506.0 (MH+) |
| 67 | 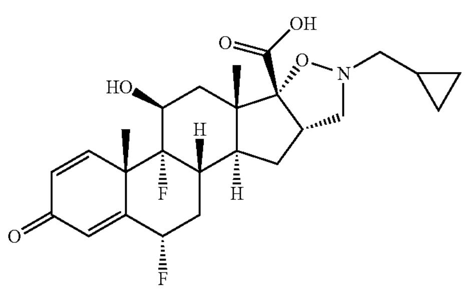 | 88% | LC_MS (ESI POS): 464.1 (MH+) |
| 68 | 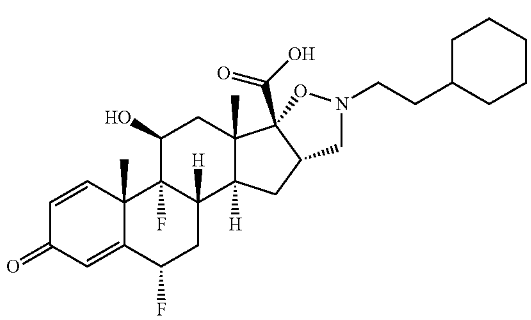 | 72% | LC_MS (ESI POS): 520.2 (MH+) |

TABLE 3-continued

| Compound | Structure | Yield | Analytical |
|---|---|---|---|
| 69 | 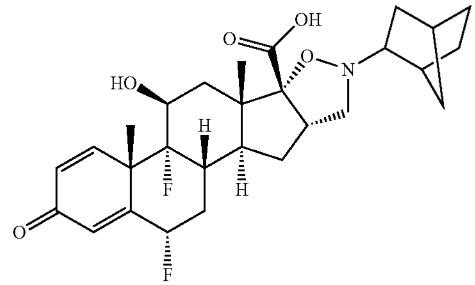 | 97% | LC_MS (ESI POS): 504.1 (MH+) |
| 70 | 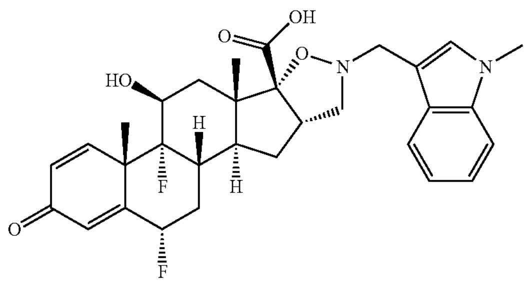 | 96% | LC_MS (ESI POS): 553.2 (MH+) |

Example 7. Preparation of (4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,1,12-tetradecahydro-7-oxa-8-aza-pentaleno[2,1-a]phenanthrene-6b-carbothioic acid S-(2-oxo-[1,3]dioxolan-4-yl) ester (compound 71)

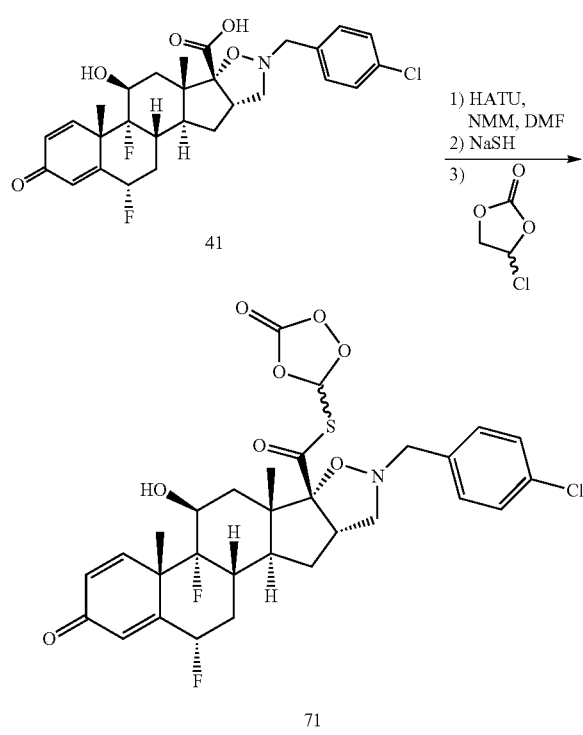

To a solution of compound 41 (300 mg, 0.562 mmol) in dry DMF (11.2 ml), kept under nitrogen, HATU (235 mg, 0.618 mmol) was added, followed by N-methylmorpholine (0.062 ml, 0.562 mmol). The reaction mixture was heated at 65° C. for 40 minutes, after which time conversion into the activate ester was complete. The mixture was cooled down to room temperature, and NaSH (94 mg, 1.685 mmol) was added portion wise. The solution, turned deep green, was stirred at room temperature for 20 minutes, then 4-chloro-1,3-dioxolan-2-one (206 mg, 1.685 mmol) was then added dropwise, followed by KI (46.6 mg, 0.281 mmol), and mixture stirred at room temperature overnight. AcOEt (70 ml) was added, and the mixture washed with brine; the aqueous layer was extracted with AcOEt (2×70 ml), and the combined organic extracts were washed with 1N HCl solution and brine. Organic phase was dried over $Na_2SO_4$ and evaporated, affording 940 mg of crude, which was purified via chromatographic column on silica gel in gradient elution from DCM/AcOEt 30:1 to DCM/AcOEt 5:1, to afford 320 mg of the desired compound. It was further purified via preparative HPLC (mobile phase: water/ACN without acidic additive) to afford 140 mg of a solid (39% yield). $^1$H-NMR analysis reveals the presence of the aldehyde arising from hydrolysis of the carbonate.

$^1$H NMR (300 MHz, DMSO-$d_6$) ppm 7.18-7.42 (m, 5H), 6.26-6.38 (m, 2H), 6.13 (s, 1H), 5.45-5.80 (m, 2H), 4.88 and 4.92 (t, 1H), 4.33 and 4.42 (dd, 1H), 4.09-4.24 (m, 1H), 3.99 and 4.02 (d, 1H), 3.84 and 3.85 (d, 1H), 3.45-3.60 (m, 1H), 3.34-3.45 (m, 1H), 2.56-2.70 (m, 1H), 1.97-2.34 (m, 4H), 1.52-1.91 (m, 4H), 1.48 and 1.49 (s, 3H), 0.90 and 0.92 (s, 3H)

LC-MS (ESI POS): 636.35 (MH+)

Example 8. Preparation of (4aS,4bR,5S,6aS,6bR, 9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid methoxy-methyl-amide (compound 72)

Example 9. Preparation of (4aS,4bR,5S,6aS,6bR, 9aS,10aS,10bS,12S)-4b,12-Difluoro-5-hydroxy-4a, 6a-dimethyl-2-oxo-8-thiophen-2-ylmethyl-2,4a,4b,5, 6,6a,8,9,9a,10,10a,10b,11,12-tetradecahydro-7-oxa-8-aza-pentaleno[2,1-a]phenanthrene-6b-carboxylic acid fluoromethyl ester (compound 73)

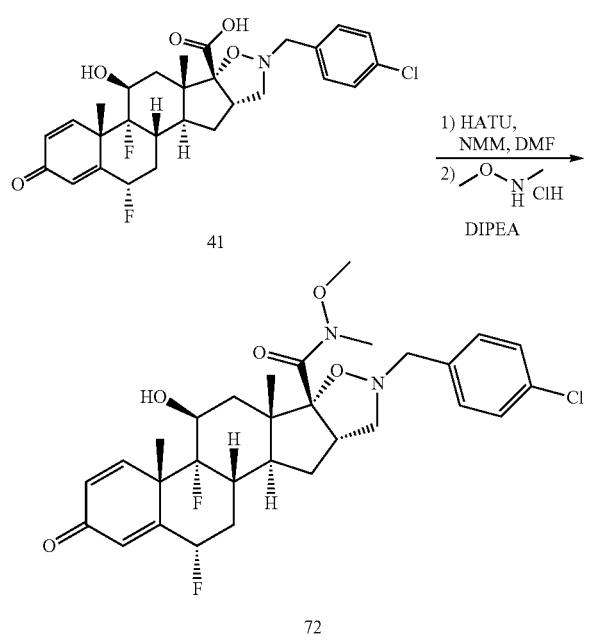

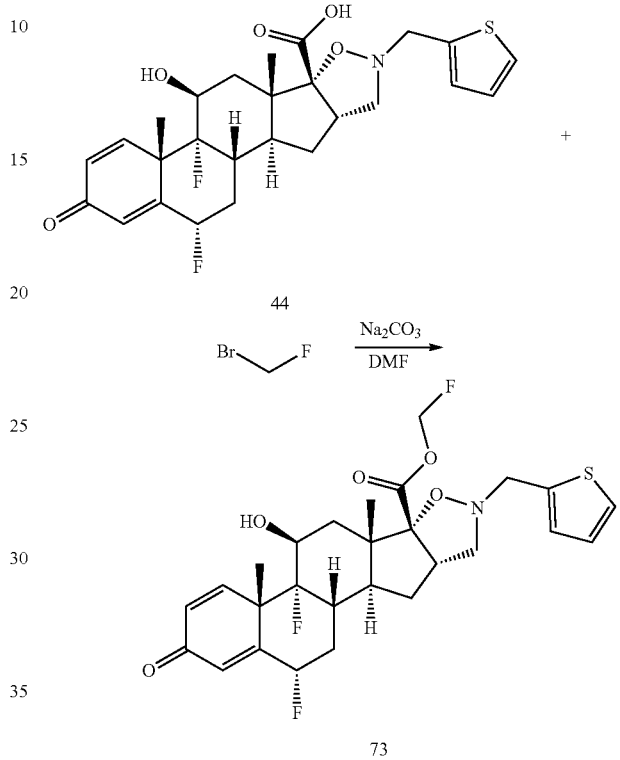

To a solution of compound 41 (300 mg, 0.562 mmol) in dry DMF (10.6 ml), kept under nitrogen atmosphere, HATU (235 mg, 0.618 mmol) is added, followed by N-methylmorpholine (0.062 ml, 0.562 mmol). The mixture is stirred at 70° C. for 40 minutes, after which time conversion into the activated ester is complete. The reaction is cooled down to room temperature and N, O-dimethyl hydroxylamine hydrochloride (164 mg, 1.685 mmol) is added, followed by TEA (0.313 ml, 2.247 mmol). The mixture is stirred at room temperature overnight. Further addition of N, O-dimethyl hydroxylamine hydrochloride (164 mg, 1.685 mmol) and TEA (0.313 ml, 2.247 mmol) is done, and mixture heated at 65° C. for 5 hours. Conversion is complete. The mixture is diluted with AcOEt (60 ml) and washed with brine (60 ml). Aqueous layer is extracted with AcOEt (2×60 ml), and then organic extracts are washed with 1N HCl solution, dried over $Na_2SO_4$ and evaporated. Crude (700 mg) is purified via preparative HPLC (neutral mobile phase), obtaining 96 mg of pure solid (30% yield).

$^1$H NMR (300 MHz, DMSO-$d_6$) ppm 7.27-7.39 (m, 4H), 7.24 (dd, 1H), 6.29 (dd, 1H), 6.12 (s, 1H), 5.46-5.75 (m, 1H), 5.36 (d, 1H), 4.02-4.21 (m, 1H), 3.72-3.97 (m, 3H), 3.38-3.63 (m, 1H), 3.29 (s, 3H), 2.98 (br. s., 3H), 2.56-2.66 (m, 1H), 2.03-2.34 (m, 3H), 1.69-2.01 (m, 2H), 1.51-1.68 (m, 2H), 1.49 (s, 3H), 1.31-1.46 (m, 1H), 0.87 (s, 3H)

LC-MS (ESI POS): 577.29 MH+

$[\alpha]_D^{25}$=+122.1 (c 0.134, CHCl$_3$)

To a solution of compound 44 (150 mg, 0.297 mmol) in dry DMF (3 ml) under nitrogen atmosphere, sodium carbonate (157 mg, 1.483 mmol) was added. After stirring at room temperature for 20 minutes, the mixture was cooled to 0° C. and bromofluoromethane (0.371 ml, 0.742 mmol) was added. The reaction mixture was stirred at 0° C. for 15 minutes and at RT for 1 hour; then, further 2 M solution of bromofluoromethane (0.371 ml, 0.742 mmol) in DMF was added, and the mixture was stirred at RT for 46 hours. The reaction mixture was poured into a cooled HCl solution (1 ml of 1 N HCl and 19 ml of water), and the aqueous phase was extracted with AcOEt (3×40 ml). The combined organic extracts were dried (Na2SO4) and concentrated. The crude material (162 mg) was purified by silica gel flash chromatography in gradient elution from DCM/AcOEt 97:3 to DCM/AcOEt 84:16 to afford 92 mg of pure compound (58% yield; Rf=0.39 in AcOEt/DCM 20:80).

$^1$H NMR (300 MHz, DMSO-$d_6$) ppm 7.39 (dd, 1H), 7.26 (dd, 1H), 6.76-7.02 (m, 2H), 6.30 (dd, 1H), 6.12 (s, 1H), 5.76 (dd, 1H), 5.89 (dd, 3H), 5.53-5.73 (m, 1H), 5.50 (d, 1H), 4.12-4.28 (m, 1H), 4.10 (br. s., 2H), 3.48-3.65 (m, 2H), 2.56-2.70 (m, 1H), 2.04-2.33 (m, 2H), 1.83-2.04 (m, 1H), 1.54-1.83 (m, 2H), 1.50 (s, 3H), 1.35-1.48 (m, 1H), 0.94 (s, 3H)

LC-MS (ESI POS): 538.28 MH+

$[\alpha]_D^{25}$=+46.49 (c 0.111; CHCl$_3$)

The compounds listed in Table 4 were prepared as previously described for compound 73 utilizing the suitable alkylating agent:

TABLE 4

| Compound | Structure | Yield | Analytical |
|---|---|---|---|
| 74 | 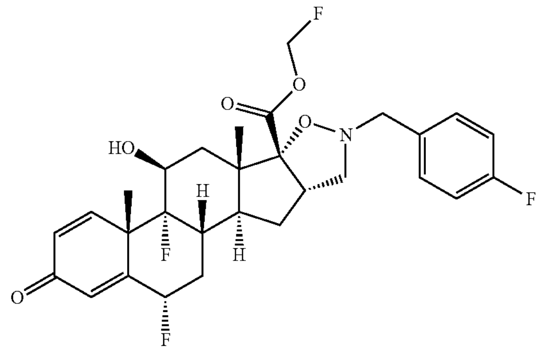 | 64% | LC-MS (ESI POS): 550.31 MH+<br>$[\alpha]_D^{25}$ = +222.5 (c 0.064; CHCl$_3$)<br>$^1$H NMR (300 MHz, DMSO-d$_6$) ppm<br>7.27-7.35 (m, 2 H), 7.25 (dd, 1 H),<br>6.98-7.16 (m, 2 H), 6.29 (dd, 1 H), 6.12<br>(s, 1 H), 5.86 (dd, 1 H), 5.80 (dd, 1 H),<br>5.52-5.76 (m, 1 H), 5.50 (dd, 1 H),<br>4.09-4.24 (m, 1 H), 3.92 (d, 1 H), 3.84<br>(d, 1 H), 3.42-3.69 (m, 2 H), 2.55-2.71<br>(m, 1 H), 2.05-2.36 (m, 2H),<br>1.77-1.92 (m, 1 H), 1.53-1.77<br>(m, 4 H), 1.49 (s, 3 H), 1.39-1.47<br>(m, 1 H), 0.94 (s, 3 H) |
| 75 | 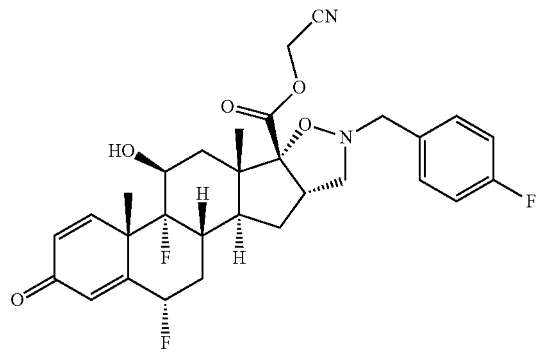 | 75% | LC-MS (ESI POS): 557.3 MH+<br>$[\alpha]_D^{25}$ = +112.3 (c 0.2 MeOH)<br>$^1$H NMR (300 MHz, DMSO-d$_6$) ppm<br>7.20-7.39 (m, 3 H), 7.09 (t, 2 H), 6.29<br>(dd, 1 H), 6.12 (s, 1 H), 5.54-5.79 (m,<br>1 H), 5.52 (d, 1 H), 5.11 (d, 1 H), 5.05<br>(d, 1 H), 4.08-4.22 (m, 1 H), 3.93 (d,<br>1 H), 3.82 (d, 1 H), 3.51-3.59 (m,<br>1 H), 2.53-2.63 (m, 1 H), 2.36-2.45<br>(m, 1 H), 2.22-2.36 (m, 2 H),<br>2.04-2.21 (m, 1 H), 1.59-1.91 (m,<br>3 H), 1.33-1.59 (m, 2 H), 1.49<br>(s, 3 H), 0.93 (s, 3 H) |
| 76 | 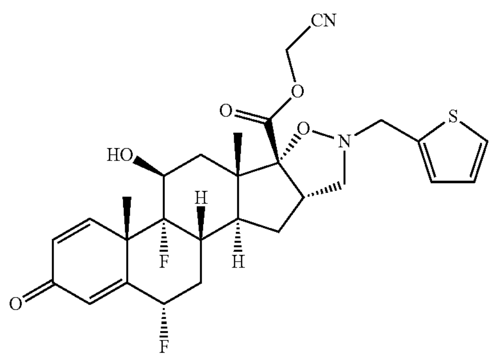 | 37% | LC-MS (ESI POS): 545.04 MH+<br>$[\alpha]_D^{25}$ = +74.80 (c 0.2 MeOH)<br>$^1$H NMR (300 MHz, DMSO-d$_6$) ppm<br>7.35-7.42 (m, 1 H), 7.26 (dd, 1 H),<br>6.84-6.99 (m, 2 H), 6.30 (dd, 1 H),<br>6.12 (s, 1 H), 5.55-5.80 (m, 1 H),<br>5.50-5.55 (m, 1 H), 5.06 (s, 2 H),<br>4.12-4.28 (m, 1 H), 3.93-4.12<br>(m, 2 H), 3.45-3.68 (m, 2 H),<br>2.55-2.63 (m, 1 H), 2.02-2.33<br>(m, 3 H), 1.81-2.02 (m, 1 H),<br>1.59-1.81 (m, 2 H), 1.49 (s, 3 H),<br>1.32-1.47 (m, 2 H), 0.93 (s, 3 H) |

Example 10. Preparation of (4aS,4bR,5S,6aS,6bR, 9aS,10aS,10bS,12S)-4b,12-Difluoro-8-furan-2-ylmethyl-5-hydroxy-4a,6a-dimethyl-2-oxo-2,4a,4b,5,6, 6a,8,9,9a,10,10a,10b,11,12-tetradecahydro-7-oxa-8-aza-pentaleno[2,1-a]phenanthrene-6b-carbothioic acid S-fluoromethyl ester (compound 77)

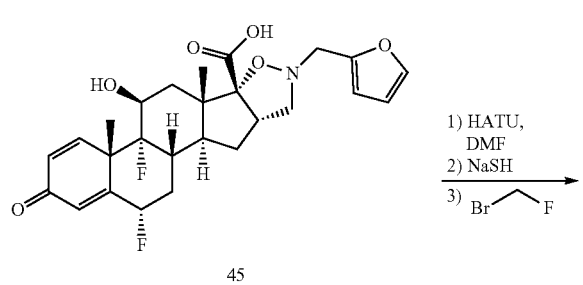

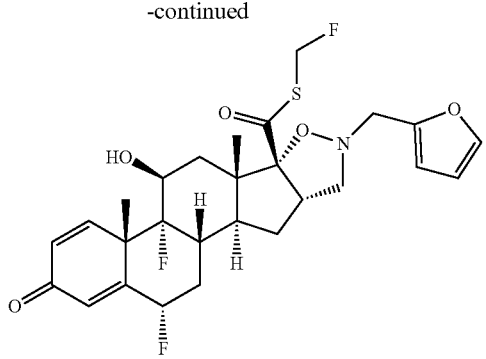

A mixture of compound 45 (453 mg, 0.925 mmol), HATU (387 mg, 1.018 mmol), and N-methylmorpholine (0.102 ml, 0.925 mmol) in dry DMF (15 ml) was stirred under nitrogen atmosphere at 70° C. for 1.5 hours, and LC-MS showed the formation of the desired activated ester (93% conversion). The solution was cooled to RT, and sodium hydrogen sulfide, anhydrous (156 mg, 2.78 mmol) was added. The mixture was stirred at RT for 25 minutes, then 2 M solution of bromofluoromethane (1.388 ml, 2.78 mmol) in DMF was added, and the mixture was stirred at Room Temperature for 2 hours. Further bromofluoromethane (0.463 ml, 0.925 mmol) was added, and the reaction mixture stirred at RT overnight.

The reaction mixture was diluted with AcOEt (130 ml), and the organic phase was washed with water and brine, dried ($Na_2SO_4$) and concentrated. The obtained crude mixture (561 mg) was purified by flash chromatography on silica gel in gradient elution from AcOEt/petroleum ether 5:95 to AcOEt/petroleum ether 30:70 and then with DCM to afford 184 mg of the title compound (37% yield; Rf=0.79 in AcOEt/DCM 30:70).

$^1$H NMR (300 MHz, DMSO-$d_6$) ppm 7.54 (dd, 1H), 7.25 (dd, 1H), 6.26-6.41 (m, 3H), 6.12 (s, 1H), 5.88 (dd, 1H), 5.78 (dd, 1H), 5.51-5.75 (m, 1H), 5.50 (dd, 1H), 4.10-4.26 (m, 1H), 3.95 (s, 2H), 3.42-3.55 (m, 1H), 3.33-3.42 (m, 1H), 2.56-2.69 (m, 1H), 2.02-2.37 (m, 3H), 1.90 (dt, 1H), 1.50-1.77 (m, 3H), 1.49 (s, 3H), 1.40-1.48 (m, 1H), 0.88 (s, 3H)

LC-MS (ESI POS): 538.4 (MH+)

$[\alpha]_D^{25}$=+112.4 (c 0.145; $CHCl_3$)

The compounds listed in Table 5 were prepared as previously described for compound 77, starting from the suitable acid derivative:

TABLE 5

| Compound | Structure | Yield | Analytical |
|---|---|---|---|
| 78 | 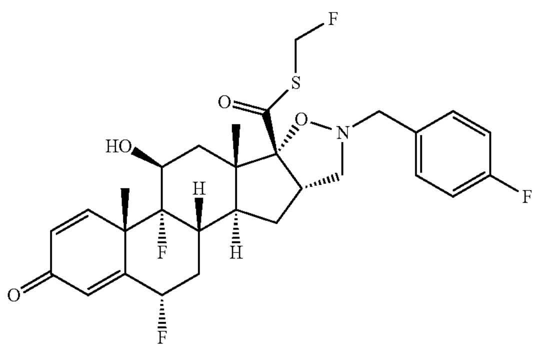 | 86% | LC-MS (ESI POS): 566.46 MH+<br>$[\alpha]_D^{25}$ = +163.3 (c 0.174, $CHCl_3$)<br>$^1$H NMR (300 MHz, DMSO-$d_6$) ppm 7.29-7.39 (m, 2 H), 7.24 (dd, 1 H), 7.04-7.16 (m, 2 H), 6.30 (dd, 1 H), 6.13 (s, 1 H), 5.86 (dd, 1 H), 5.76 (dd, 1 H), 5.52-5.74 (m, 1 H), 5.50 (dd, 1 H), 4.07-4.28 (m, 1 H), 3.95 (d, 1 H), 3.86 (d, 1 H), 3.46-3.61 (m, 1 H), 3.33-3.46 (m, 1 H), 2.56-2.76 (m, 1 H), 2.04-2.31 (m, 3 H), 1.78-1.95 (m, 1 H), 1.51-1.74 (m, 4 H), 1.49 (s, 3 H), 0.88 (s, 3 H) |
| 79 | 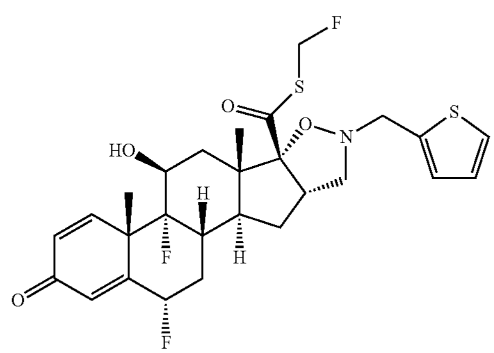 | 39% | LC-MS (ESI POS): 554.42 MH+<br>$[\alpha]_D^{25}$ = +123.9 (c 0.108, $CHCl_3$)<br>$^1$H NMR (300 MHz, DMSO-$d_6$) ppm 7.42 (dd, 1 H), 7.25 (dd, 1 H), 6.99 (dd, 1 H), 6.95 (dd, 1 H), 6.30 (dd, 1 H), 6.12 (s, 1 H), 5.88 (dd, 1 H), 5.78 (dd, 1 H), 5.53-5.76 (m, 1 H), 5.51 (dd, 1 H), 4.18-4.21 (m, 1 H), 4.19 (d, 1 H), 4.12 (d, 1 H), 3.44-3.58 (m, 1 H), 3.35-3.44 (m, 1 H), 2.58-2.75 (m, 1 H), 2.03-2.37 (m, 3 H), 1.86-2.03 (m, 1 H), 1.52-1.79 (m, 3 H), 1.49 (s, 3 H), 1.38-1.48 (m, 1 H), 0.89 (s, 3 H) |
| 80 | 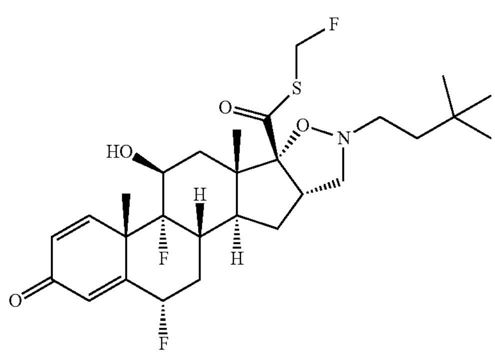 | 16% | LC-MS (ESI POS): 542.37 MH+<br>$[\alpha]_D^{25}$ = +134.9 (0.23, MeOH)<br>$^1$H NMR (300 MHz, DMSO-$d_6$) ppm 7.24 (d, 1 H), 6.29 (dd, 1 H), 6.12 (s, 1 H), 5.89 (dd, 1 H), 5.81 (dd, 1 H), 5.53-5.73 (m, 1 H), 5.50 (dd, 1 H), 4.07-4.24 (m, 1 H), 3.46-3.67 (m, 1 H), 3.32-3.45 (m, 1 H), 2.55-2.78 (m, 3 H), 1.95-2.33 (m, 3 H), 1.82-1.95 (m, 1 H), 1.51-1.80 (m, 4 H), 1.49 (s, 3 H), 1.29-1.47 (m, 2 H), 0.89 (s, 3 H), 0.86 (s, 9 H) |

TABLE 5-continued

| Compound | Structure | Yield | Analytical |
|---|---|---|---|
| 81 | 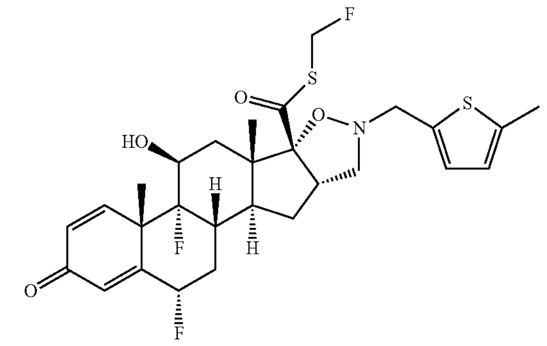 | 11% | LC-MS (ESI POS): 568.14 MH+<br>[α]$_D^{25}$ = +57.09 (c 0.27, DMF)<br>$^1$H NMR (300 MHz, DMSO-d$_6$) ppm 7.25 (dd, 1 H), 6.75 (d, 1 H), 6.61 (dq, 1 H), 6.30 (dd, 1 H), 6.09-6.14 (m, 1 H), 5.89 (dd, 1 H), 5.79 (dd, 1 H), 5.51-5.75 (m, 1 H), 5.49 (dd, 1 H), 4.14-4.26 (m, 1 H), 4.10 (d, 1 H), 4.04 (d, 1 H), 3.31-3.50 (m, 2 H), 2.56-2.70 (m, 1 H), 2.34 (d, 3 H), 2.02-2.30 (m, 3 H), 1.90-2.02 (m, 1 H), 1.72 (d, 1 H), 1.51-1.67 (m, 1 H), 1.49 (s, 3 H), 1.31-1.48 (m, 2 H), 0.89 (s, 3 H) |
| 82 | 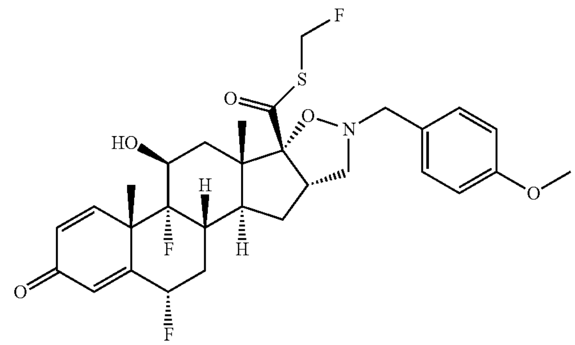 | 20% | LC-MS (ESI POS): 578.11 MH+<br>[α]$_D^{25}$ = +131.6 (c 0.25, CHCl$_3$)<br>$^1$H NMR (300 MHz, DMSO-d$_6$) ppm 7.25 (dd, 1 H), 7.14-7.22 (m, 2 H), 6.75-6.90 (m, 2 H), 6.30 (dd, 1 H), 6.12 (s, 1 H), 5.87 (dd, 1 H), 5.77 (dd, 1 H), 5.51-5.73 (m, 1 H), 5.49 (dd, 1 H), 4.08-4.28 (m, 1 H), 3.89 (d, 1 H), 3.83 (d, 1 H), 3.71 (s, 3 H), 3.39-3.52 (m, 1 H), 3.32-3.41 (m, 1 H), 2.55-2.71 (m, 1 H), 2.03-2.37 (m, 3 H), 1.82-1.97 (m, 1 H), 1.52-1.75 (m, 3 H), 1.49 (s, 3 H), 1.40-1.48 (m, 1 H), 0.88 (s, 3 H) |
| 83 | 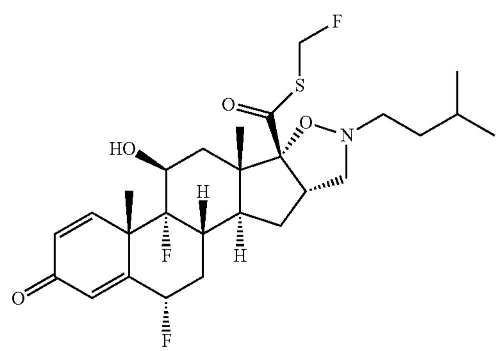 | 37% | LC-MS (ESI POS): 528.2 MH+<br>[α]$_D^{25}$ = +132.9 (c 0.1145 CHCl$_3$)<br>$^1$H NMR (300 MHz, DMSO-d$_6$) ppm 7.24 (dd, 1 H), 6.29 (dd, 1H), 6.08-6.18 (m, 1 H), 5.89 (dd, 1 H), 5.81 (dd, 1 H), 5.51-5.73 (m, 1 H), 5.49 (dd, 1 H), 4.05-4.26 (m, 1 H), 3.45-3.66 (m, 1 H), 3.31-3.45 (m, 1 H), 2.55-2.81 (m, 3 H), 2.19-2.36 (m, 1 H), 1.95-2.19 (m, 2 H), 1.79-1.93 (m, 1 H), 1.67-1.77 (m, 1 H), 1.51-1.67 (m, 3 H), 1.49 (s, 3 H), 1.43-1.48 (m, 1 H), 1.40 (q, 2 H), 0.89 (s, 3 H), 0.84 (d, 3 H), 0.84 (d, 3 H) |
| 84 | 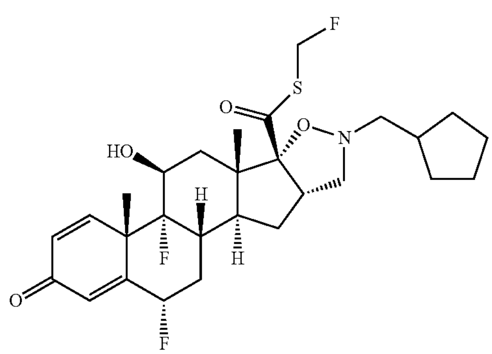 | 10% | LC-MS (ESI POS): 540.2 MH+<br>[α]$_D^{25}$ = +149.8 (C 0.145, CHCl$_3$)<br>$^1$H NMR (300 MHz, DMSO-d$_6$) ppm 7.24 (d, 1 H), 6.29 (dd, 1 H), 6.11 (s, 1 H), 5.89 (dd, 1 H), 5.82 (dd, 1 H), 5.55 (m, 1 H), 5.49 (dd, 1 H), 3.99-4.28 (m, 1 H), 3.44-3.65 (m, 1 H), 3.37 (m, 1 H), 2.56-2.70 (m, 1 H), 2.54-2.70 (m, 2 H), 2.19-2.34 (m, 1 H), 1.98-2.19 (m, 3 H), 1.82-1.98 (m, 1 H), 1.56-1.82 (m, 4 H), 1.37-1.56 (m, 6 H), 1.48 (s, 3 H), 0.98-1.24 (m, 2 H), 0.89 (s, 3 H) |

TABLE 5-continued

| Compound | Structure | Yield | Analytical |
|---|---|---|---|
| 85 | 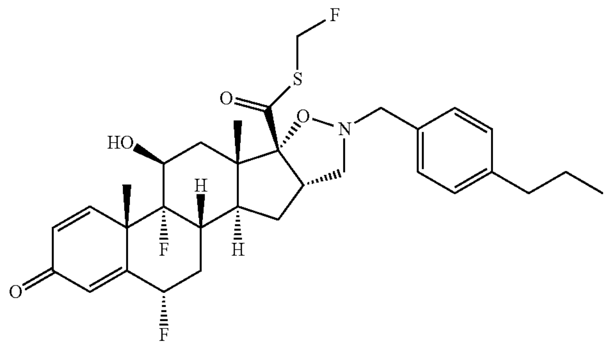 | 43% | LC-MS (ESI POS): 590.18 MH+<br>$[\alpha]_D^{25}$ = +84.95 (c 0.109, CHCl$_3$)<br>$^1$H NMR (300 MHz, DMSO-d$_6$) ppm 7.24 (dd, 1 H), 7.14-7.21 (m, 2 H), 7.05-7.14 (m, 2 H), 6.30 (dd, 1 H), 6.12 (s, 1 H), 5.88 (dd, 1 H), 5.77 (dd, 1 H), 5.50-5.74 (m, 1 H), 5.48 (dd, 1 H), 4.08-4.24 (m, 1 H), 3.90 (s, 2 H), 3.32-3.51 (m, 2 H), 2.55-2.71 (m, 1 H), 2.43-2.48 (m, 2 H), 2.01-2.33 (m, 3 H), 1.82-1.94 (m, 1 H), 1.69 (d, 1 H), 1.50-1.65 (m, 4 H), 1.48 (s, 3 H), 1.36-1.46 (m, 1 H), 0.88 (s, 3 H), 0.86 (t, 3 H) |
| 86 | 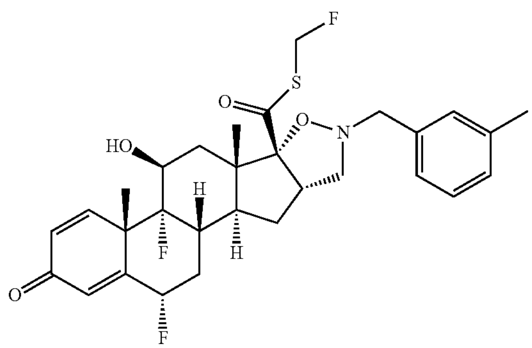 | 14% | LC-MS (ESI POS): 562.15 MH+<br>$[\alpha]_D^{25}$ = + 181.2 (c 0.37, DMF)<br>$^1$H NMR (300 MHz, DMSO-d$_6$) ppm 7.24 (dd, 1 H), 7.16 (t, 1 H), 7.11-7.15 (m, 1 H), 6.98-7.10 (m, 2 H), 6.30 (dd, 1 H), 6.13 (s, 1 H), 5.89 (dd, 1 H), 5.80 (dd, 1 H), 5.51-5.76 (m, 1 H), 5.49 (dd, 1 H), 4.07-4.28 (m, 1 H), 3.90 (s, 2 H), 3.42-3.54 (m, 1 H), 3.34-3.45 (m, 1 H), 2.56-2.71 (m, 1 H), 2.25 (s, 3 H), 2.02-2.24 (m, 3 H), 1.79-1.94 (m, 1 H), 1.51-1.73 (m, 4 H), 1.49 (s, 3 H), 0.89 (s, 3 H) |
| 87 | 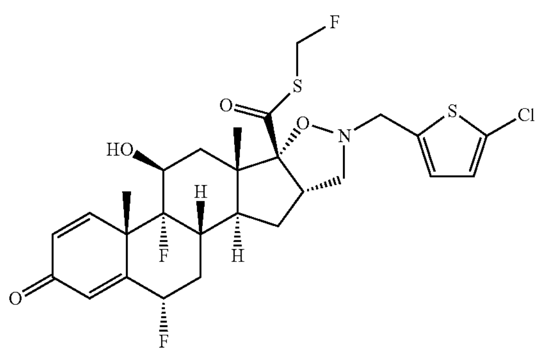 | 31% | LC-MS (ESI POS): 588.11 MH+<br>$[\alpha]_D^{25}$ = +155.6 (c 0.43, DMF)<br>$^1$H NMR (300 MHz, DMSO-d$_6$) ppm 7.25 (dd, 1 H), 6.94 (d, 1 H), 6.86 (d, 1 H), 6.30 (dd, 1 H), 6.12 (s, 1 H), 5.88 (dd, 1 H), 5.79 (dd, 1 H), 5.53-5.76 (m, 1 H), 5.51 (dd, 1 H), 4.16-4.25 (m, 1 H), 4.18 (d, 1 H), 4.02 (d, 1 H), 3.45-3.61 (m, 1 H), 3.35-3.46 (m, 1 H), 2.56-2.70 (m, 1 H), 2.05-2.31 (m, 3 H), 1.85-1.98 (m, 1 H), 1.68-1.78 (m, 1 H), 1.53-1.68 (m, 2 H), 1.49 (s, 3 H), 1.39-1.47 (m, 1 H), 0.89 (s, 3 H) |
| 88 | 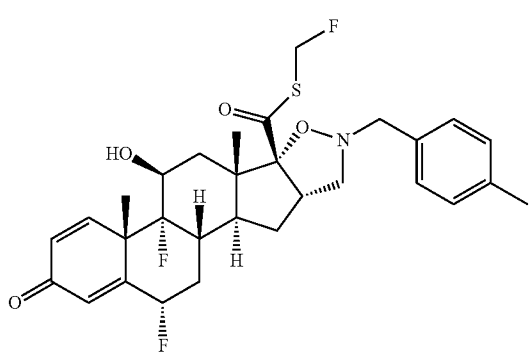 | 10% | LC-MS (ESI POS): 562.16 MH+<br>$[\alpha]_D^{25}$ = +145.2 (c 0.34, MeOH)<br>$^1$H NMR (300 MHz, DMSO-d$_6$) ppm 7.24 (dd, 1 H), 7.15-7.21 (m, 2 H), 7.02-7.13 (m, 2 H), 6.30 (dd, 1 H), 6.09-6.15 (m, 1 H), 5.88 (dd, 1 H), 5.78 (dd, 1 H), 5.51-5.76 (m, 1 H), 5.49 (dd, 1 H), 4.09-4.23 (m, 1 H), 3.91 (d, 1 H), 3.85 (d, 1 H), 3.41-3.54 (m, 1 H), 3.34-3.42 (m, 1 H), 2.55-2.70 (m, 1 H), 2.26 (s, 3 H), 2.01-2.25 (m, 3 H), 1.79-1.96 (m, 1 H), 1.49 (s, 3 H), 1.41-1.76 (m, 4 H), 0.88 (s, 3 H) |

TABLE 5-continued

| Compound | Structure | Yield | Analytical |
|---|---|---|---|
| 89 | 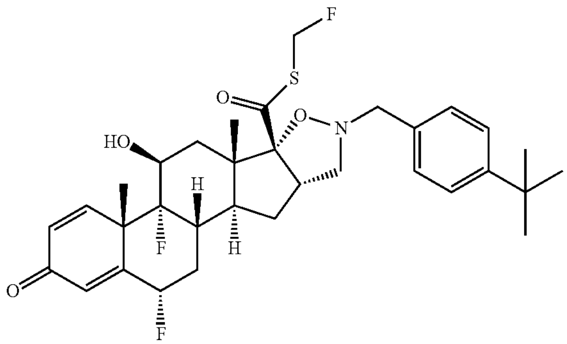 | 5% | LC-MS (ESI POS): 604.18 MH+<br>$[\alpha]_D^{25}$ = +94.6 (c 0.0905, CHCl$_3$)<br>$^1$H NMR (300 MHz, DMSO-d$_6$) ppm 7.27-7.35 (m, 2 H), 7.24 (d, 1 H), 7.16-7.22 (m, 2 H), 6.30 (dd, 1 H), 6.11 (s, 1 H), 5.90 (dd, 1 H), 5.79 (dd, 1 H), 5.52-5.69 (m, 1 H), 4.07-4.28 (m, 1 H), 3.93 (s, 2 H), 3.31-3.52 (m, 2 H), 2.54-2.70 (m, 1 H), 1.81-2.37 (m, 5 H), 1.69 (d, 1 H), 1.53-.65 (m, 1 H), 1.48 (s, 3 H), 1.34-1.46 (m, 2 H), 1.23 (s, 9 H), 0.88 (s, 3 H) |
| 90 | 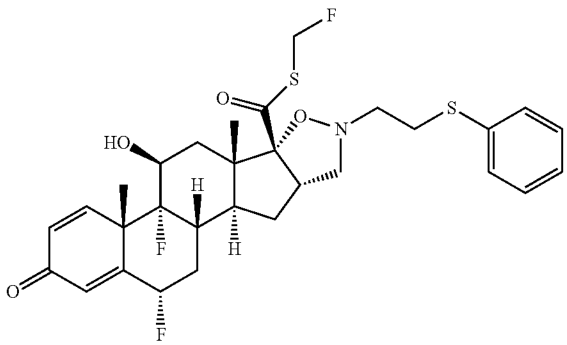 | 38% | LC-MS (ESI POS): 594.2 MH+<br>$[\alpha]_D^{25}$ = +80.97 (c 0.103, CHCl$_3$)<br>$^1$H NMR (300 MHz, DMSO-d$_6$) ppm 7.05-7.41 (m, 6 H), 6.30 (dd, 1 H), 6.11 (s, 1 H), 5.91 (dd, 1 H), 5.82 (dd, 1 H), 5.53-5.73 (m, 1 H), 5.52 (dd, 1 H), 4.01-4.36 (m, 1 H), 3.46-3.63 (m, 1 H), 3.33-3.46 (m, 1 H), 3.13-3.23 (m, 1 H), 3.03-3.13 (m, 1 H), 2.94-3.03 (m, 1 H), 2.80-2.94 (m, 1 H), 2.55-2.68 (m, 1 H), 2.01-2.36 (m, 3 H), 1.81-2.01 (m, 1 H), 1.53-1.81 (m, 3 H), 1.49 (s, 3 H), 1.38-1.48 (m, 1 H), 0.90 (s, 3 H) |
| 91 | 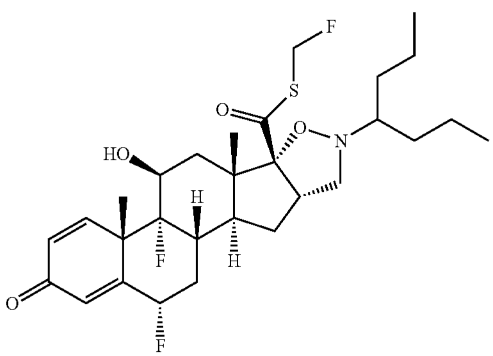 | 15% | LC-MS (ESI POS): 556.26 MH+<br>$[\alpha]_D^{25}$ = +137.9 (c 0.2 MeOH)<br>$^1$H NMR (300 MHz, DMSO-d$_6$) ppm 7.24 (dd, 1 H), 6.29 (dd, 1 H), 6.11 (s, 1 H), 5.90 (dd, 1 H), 5.81 (dd, 1 H), 5.51-5.71 (m, 1 H), 5.49 (dd, OH), 4.04-4.27 (m, 1 H), 3.42-3.59 (m, 1 H), 3.32-3.42 (m, 1 H), 2.56-2.70 (m, 2 H), 1.97-2.32 (m, 4 H), 1.82-1.96 (m, 1 H), 1.69-1.80 (m, 1 H), 1.51-1.69 (m, 3 H), 1.49 (s, 3 H), 1.13-1.47 (m, 8 H), 0.88 (s, 3 H), 0.85 (t, 3 H), 0.83 (t, 3 H) |
| 92 | 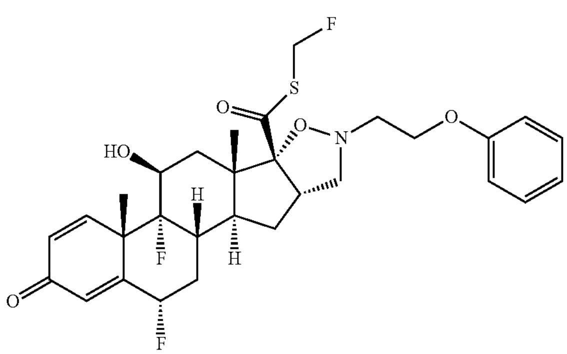 | 14% | LC-MS (ESI POS): 578.2 MH+<br>$[\alpha]_D^{25}$ = +131.1 (c 0.28, CHCl$_3$)<br>$^1$H NMR (300 MHz, DMSO-d$_6$) ppm 7.17-7.34 (m, 3 H), 6.82-7.01 (m, 3 H), 6.30 (dd, 1 H), 6.12 (s, 1 H), 5.86 (dd, 1 H), 5.73 (dd, 1 H), 5.53-5.74 (m, 1 H), 5.51 (dd, 1 H), 4.15-4.31 (m, 1 H), 4.14 (t, 2 H), 3.51-3.71 (m, 1 H), 3.33-3.51 (m, 1H), 3.13-3.24 (m, 1 H), 2.96-3.13 (m, 1 H), 2.55-2.76 (m, 1 H), 2.04-2.35 (m, 3 H), 1.82-1.97 (m, 1 H), 1.51-1.80 (m, 4 H), 1.49 (s, 3 H), 0.90 (s, 3 H) |

TABLE 5-continued

| Compound | Structure | Yield | Analytical |
|---|---|---|---|
| 93 | 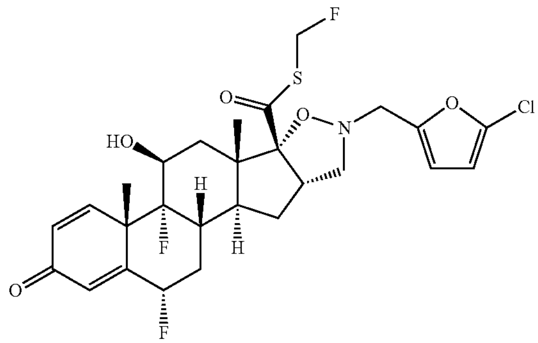 | 32% | LC-MS (ESI POS): 572.13 MH+<br>$[\alpha]_D^{25}$ = +148.7 (c 0.33, DMF)<br>$^1$H NMR (300 MHz, DMSO-d$_6$) ppm 7.24 (dd, 1 H), 6.42 (d, 1 H), 6.37 (d, 1 H), 6.30 (dd, 1 H), 6.12 (s, 1 H), 5.87 (dd, 1 H), 5.77 (dd, 1 H), 5.51-5.76 (m, 1 H), 5.49 (dd, 1 H), 4.07-4.27 (m, 1 H), 3.96 (d, 1 H), 3.86 (d, 1 H), 3.45-3.58 (m, 1 H), 3.34-3.45 (m, 1 H), 2.57-2.71 (m, 1 H), 1.98-2.32 (m, 3 H), 1.83-1.94 (m, 1 H), 1.49 (s, 3 H), 1.42-1.76 (m, 4 H), 0.88 (s, 3 H) |
| 94 | 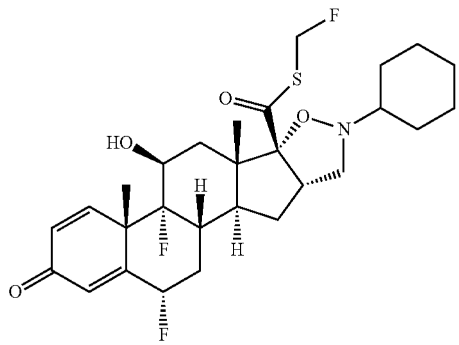 | 21% | LC-MS (ESI POS): 540.27 MH+<br>$[\alpha]_D^{25}$ = +126.8 (c 0.2 MeOH)<br>$^1$H NMR (300 MHz, DMSO-d$_6$) ppm 7.24 (dd, 1 H), 6.29 (dd, 1 H), 6.11 (s, 1 H), 5.89 (dd, 1 H), 5.79 (dd, 1 H), 5.51-5.75 (m, 1 H), 5.49 (dd, 1 H), 4.01-4.26 (m, 1 H), 3.43-3.64 (m, 1 H), 3.31-3.42 (m, 1 H), 2.55-2.71 (m, 2 H), 2.19-2.35 (m, 1 H), 1.95-2.19 (m, 3 H), 1.81-1.95 (m, 1 H), 1.52-1.78 (m, 7 H), 1.49 (s, 3 H), 1.40-1.48 (m, 1 H), 1.01-1.36 (m, 5 H), 0.89 (s, 3 H) |
| 95 | 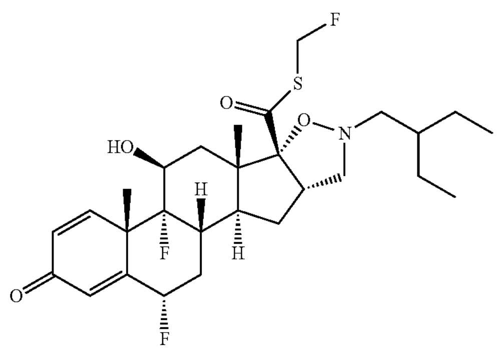 | 23% | LC-MS (ESI POS): 542.05 MH+<br>$[\alpha]_D^{25}$ = +167.0 (c 0.2, CHCl$_3$)<br>$^1$H NMR (300 MHz, DMSO-d$_6$) ppm 7.24 (dd, 1 H), 6.29 (dd, 1 H), 6.11 (s, 1 H), 5.89 (dd, 1 H), 5.82 (dd, 1 H), 5.50-5.72 (m, 1 H), 5.49 (dd, 1 H), 4.08-4.26 (m, 1 H), 3.43-3.59 (m, 1 H), 3.33-3.43 (m, 1 H), 2.61-2.70 (m, 1 H), 2.58 (t, 2 H), 1.98-2.36 (m, 3 H), 1.80-1.94 (m, 1 H), 1.51-1.77 (m, 5 H), 1.49 (s, 3 H), 1.39-1.48 (m, 1 H), 1.13-1.36 (m, 3 H), 0.89 (s, 3 H), 0.81 (t, 3 H), 0.78 (t, 3 H) |
| 96 | 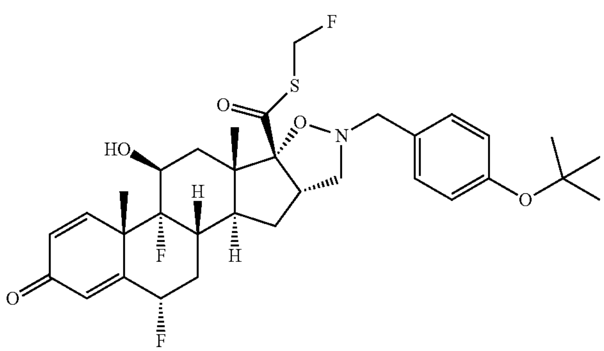 | 16% | LC-MS (ESI POS): 620.19 MH+<br>$[\alpha]_D^{25}$ = +128.8 (c 0.105, CHCl$_3$)<br>$^1$H NMR (300 MHz, DMSO-d$_6$) ppm 7.24 (dd, 1 H), 7.13-7.21 (m, 2 H), 6.81-6.90 (m, 2 H), 6.30 (dd, 1 H), 6.11 (s, 1 H), 5.86 (dd, 1 H), 5.75 (dd, 1 H), 5.49-5.75 (m, 1 H), 5.48 (dd, 1 H), 4.10-4.24 (m, 1 H), 3.94 (d, 1 H), 3.87 (d, 1 H), 3.31-3.50 (m, 2 H), 2.54-2.72 (m, 1 H), 1.95-2.32 (m, 3 H), 1.82-1.95 (m, 1 H), 1.51-1.75 (m, 3 H), 1.48 (s, 3 H), 1.34-1.46 (m, 1 H), 1.24 (s, 9 H), 0.88 (s, 3 H) |

TABLE 5-continued

| Compound | Structure | Yield | Analytical |
|---|---|---|---|
| 97 | 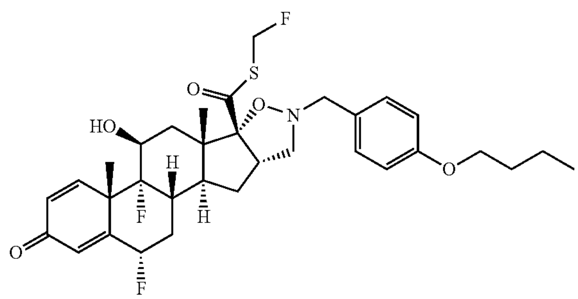 | 27% | LC-MS (ESI POS): 620.24 MH+<br>[α]$_D^{25}$ = +142.4 (c 0.2 MeOH)<br>$^1$H NMR (300 MHz, DMSO-d$_6$) ppm 7.25 (dd, 1 H), 7.12-7.21 (m, 2 H), 6.76-6.87 (m, 2 H), 6.30 (dd, 1 H), 6.12 (s, 1 H), 5.88 (dd, 1 H), 5.77 (dd, 1 H), 5.51-5.75 (m, 1 H), 5.49 (dd, 1 H), 4.09-4.26 (m, 1 H), 3.91 (t, 2 H), 3.89 (br. s., 1H), 3.83 (d, 1 H), 3.32-3.50 (m, 2 H), 2.56-2.71 (m, 1 H), 2.01-2.35 (m, 3 H), 1.81-1.98 (m, 1 H), 1.53-1.77 (m, 5 H), 1.49 (s, 3 H), 1.34-1.47 (m, 3 H), 0.93 (t, 3 H), 0.88 (s, 3 H) |
| 98 | 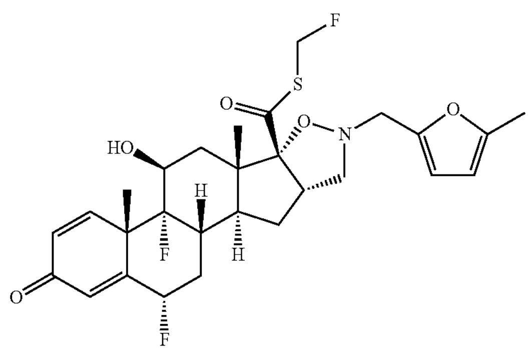 | 18% | LC-MS (ESI POS): 552.2 MH+<br>[α]$_D^{25}$ = +104.3 (c 0.6, CHCl$_3$)<br>$^1$H NMR (300 MHz, DMSO-d$_6$) ppm 7.25 (dd, 1 H), 6.30 (dd, 1 H), 6.18 (d, 1 H), 6.12 (s, 1 H), 5.96 (dq, 1 H), 5.88 (dd, 1 H), 5.79 (dd, 1 H), 5.51-5.76 (m, 1 H), 5.49 (dd, 1 H), 4.09-4.26 (m, 1 H), 3.92 (d, 1 H), 3.85 (d, 1 H), 3.40-3.52 (m, 1 H), 3.33-3.42 (m, 1 H), 2.57-2.70 (m, 1 H), 2.20-2.26 (m, 1 H), 2.18 (d, 3 H), 2.01-2.16 (m, 2 H), 1.83-1.96 (m, 1 H), 1.52-1.77 (m, 3 H), 1.49 (s, 3 H), 1.37-1.48 (m, 1 H), 0.88 (s, 3 H) |
| 99 | 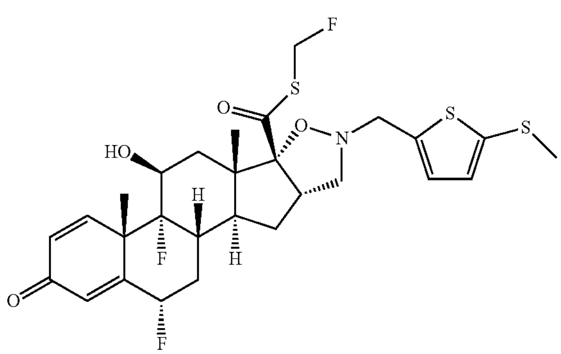 | 16% | LC-MS (ESI POS): 599.88 MH+<br>[α]$_D^{25}$ = +115.9 (c 0.162, CHCl$_3$)<br>$^1$H NMR (300 MHz, DMSO-d$_6$) ppm 7.25 (dd, 1 H), 6.95 (d, 1 H), 6.87 (d, 1 H), 6.30 (dd, 1 H), 6.11 (s, 1 H), 5.89 (dd, 1 H), 5.79 (dd, 1 H), 5.52-5.72 (m, 1 H), 5.50 (dd, 1 H), 4.19 (d, 1 H), 4.15-4.21 (m, 1 H), 4.08 (d, 1 H), 3.33-3.52 (m, 2 H), 2.54-2.70 (m, 1 H), 2.37 (s, 3 H), 2.04-2.30 (m, 3 H), 1.89-2.03 (m, 1 H), 1.68-1.79 (m, 1 H), 1.52-1.68 (m, 1 H), 1.49 (s, 3 H), 1.35-1.47 (m, 2 H), 0.89 (s, 3 H) |
| 100 | 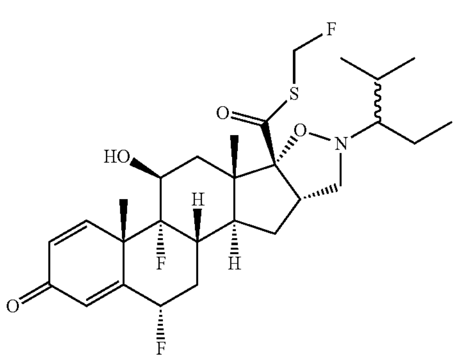 | 19% | LC-MS (ESI POS): 542.18 MH+<br>[α]$_D^{25}$ = +143.9 (c 0.25, MeOH)<br>$^1$H NMR (300 MHz, DMSO-d$_6$) ppm 7.24 (dd, 1 H), 6.29 (dd, 1 H), 6.11 (s, 1 H), 5.79-6.03 (m, 1 H), 5.71-5.94 (m, 1 H), 5.51-5.73 (m, 1 H), 5.49 (dd, 1 H), 4.18 (dd, 1 H), 3.51 (t, 1 H), 3.32-3.45 (m, 1 H), 2.58-2.70 (m, 1 H), 2.01-2.35 (m, 5 H), 1.83-2.01 (m, 1 H), 1.56-1.83 (m, 4 H), 1.49 (s, 3 H), 1.43-1.56 (m, 2 H), 0.97 (t, 3 H), 0.80-0.93 (m, 7 H), 0.75 (d, 2 H) |

TABLE 5-continued

| Compound | Structure | Yield | Analytical |
|---|---|---|---|
| 101 | 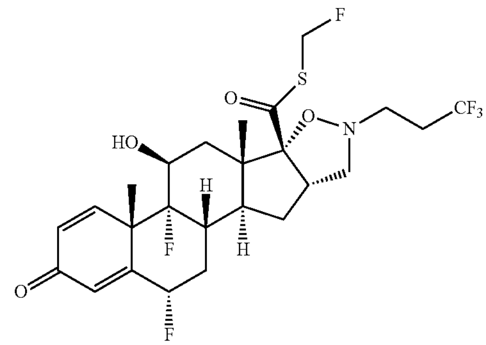 | 18% | LC-MS (ESI POS): 554.02 MH+<br>$[\alpha]_D^{25}$ = +129.0 (c 0.111, CHCl$_3$)<br>$^1$H NMR (300 MHz, DMSO-d$_6$) ppm 7.24 (dd, 1 H), 6.29 (dd, 1 H), 6.12 (s, 1 H), 5.90 (dd, 1 H), 5.82 (dd, 1 H), 5.56 (m, 1 H), 5.51 (m, 1 H), 3.98-4.30 (m, 1 H), 3.49-3.73 (m, 1 H), 3.34-3.47 (m, 1 H), 2.96-3.17 (m, 1 H), 2.76-2.93 (m, 1 H), 2.55-2.69 (m, 1 H), 2.21-2.32 (m, 2 H), 2.02-2.20 (m, 2 H), 1.89 (dt, 1 H), 1.54-1.80 (m, 4 H), 1.43-1.53 (m, 1 H), 1.49 (s, 3 H), 0.90 (s, 3 H) |
| 102 | 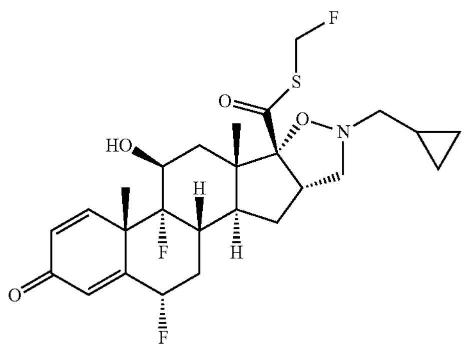 | 17% | LC-MS (ESI POS): 512.12 MH+<br>$[\alpha]_D^{25}$ = +129.6 (c 0.25, MeOH)<br>$^1$H NMR (300 MHz, DMSO-d$_6$) ppm 7.24 (d, 1 H), 6.29 (dd, 1 H), 6.11 (s, 1 H), 5.90 (dd, 1 H), 5.80 (dd, 1 H), 5.51-5.77 (m, 1 H), 5.49 (dd, 1 H), 4.16 (d, 1 H), 3.46-3.66 (m, 1 H), 3.31-3.46 (m, 1 H), 2.60-2.80 (m, 1 H), 2.60-2.75 (m, 1 H), 2.19-2.36 (m, 1 H), 2.01-2.19 (m, 2 H), 1.81-1.96 (m, 1 H), 1.55-1.81 (m, 2 H), 1.49 (s, 3 H), 1.34-1.55 (m, 2 H), 0.78-0.99 (m, 1 H), 0.90 (s, 3 H), 0.27-0.59 (m, 2 H), −0.06-0.27 (m, 2 H) |
| 103 | 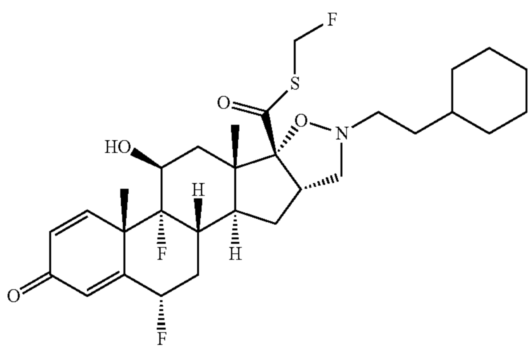 | 29% | LC-MS (ESI POS): 568.23 MH+<br>$[\alpha]_D^{25}$ = +172.6 (c 0.21, MeOH)<br>$^1$H NMR (300 MHz, DMSO-d$_6$) ppm 7.24 (dd, 1 H), 6.29 (dd, 1 H), 6.11 (s, 1 H), 5.89 (dd, 1 H), 5.81 (dd, 1 H), 5.51-5.71 (m, 1 H), 5.49 (dd, 1 H), 4.02-4.26 (m, 1 H), 3.45-3.66 (m, 1 H), 3.31-3.45 (m, 1 H), 2.55-2.82 (m, 3 H), 2.17-2.33 (m, 1 H), 1.95-2.17 (m, 2 H), 1.81-1.94 (m, 1 H), 1.52-1.78 (m, 8 H), 1.49 (s, 3 H), 1.26-1.47 (m, 4 H), 1.00-1.24 (m, 3 H), 0.89 (s, 3 H), 0.70-0.86 (m, 2 H) |
| 104 | 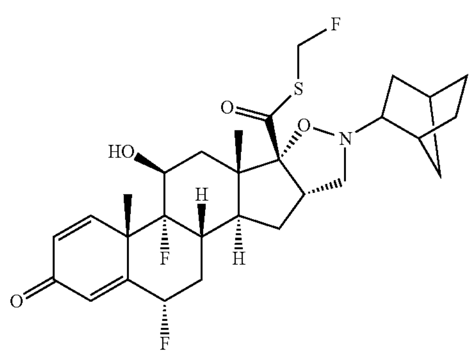 | 19% | LC-MS (ESI POS): 552.22 MH+<br>$[\alpha]_D^{25}$ = +150.4 (c 0.24, MeOH)<br>$^1$H NMR (300 MHz, DMSO-d$_6$) ppm 7.24 (d, 1 H), 6.29 (dd, 1 H), 6.11 (s, 1 H), 5.91 (dd, 1 H), 5.83 (dd, 1 H), 5.51-5.75 (m, 1 H), 5.50 (dd, 1 H), 3.51-3.69 (m, 1 H), 3.41 (q, 1 H), 2.54-2.87 (m, 2 H), 1.51-2.36 (m, 11 H), 1.49 (s, 3 H), 0.95-1.46 (m, 7 H), 0.87 (s, 3 H), 0.51-0.75 (m, 1 H) |

TABLE 5-continued

| Compound | Structure | Yield | Analytical |
|---|---|---|---|
| 105 | 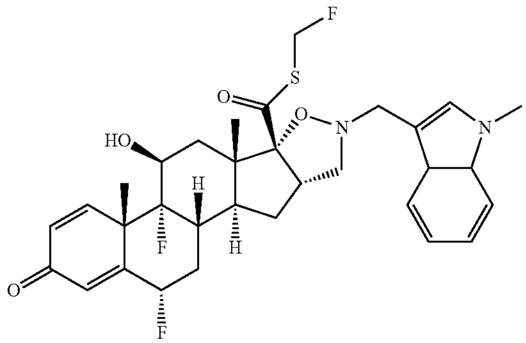 | 7% | LC-MS (ESI POS): 601.08 MH+<br>$[\alpha]_D^{25}$ = +76.63 (c 0.16 DMF)<br>$^1$H NMR (300 MHz, DMSO-$d_6$) ppm 7.55 (dt, 1 H), 7.37 (d, 1 H), 7.20-7.30 (m, 2 H), 7.12 (ddd, 1 H), 6.98 (ddd, 1 H), 6.32 (dd, 1 H), 6.13 (s, 1 H), 5.91 (dd, 1 H), 5.81 (dd, 1 H), 5.53-5.77 (m, 1 H), 5.51 (dd, 1 H), 4.10-4.38 (m, 2 H), 3.84-4.03 (m, 1 H), 3.71 (s, 3 H), 3.33-3.41 (m, 2 H), 2.55-2.68 (m, 1 H), 2.10-2.34 (m, 3 H), 1.92-2.03 (m, 1H), 1.53-1.86 (m, 3 H), 1.50 (s, 3 H), 1.38-1.48 (m, 1 H), 0.90 (s, 3 H) |

Example 11. Preparation of (6S,8S,9R,10S,11S,13S,14S)-6,9-difluoro-17-(2-fluoro-acetyl)-11-hydroxy-10,13-dimethyl-6,7,8,9,10,11,12,13,14,15-decahydro-cyclopenta[a]phenanthren-3-one (intermediate 106)

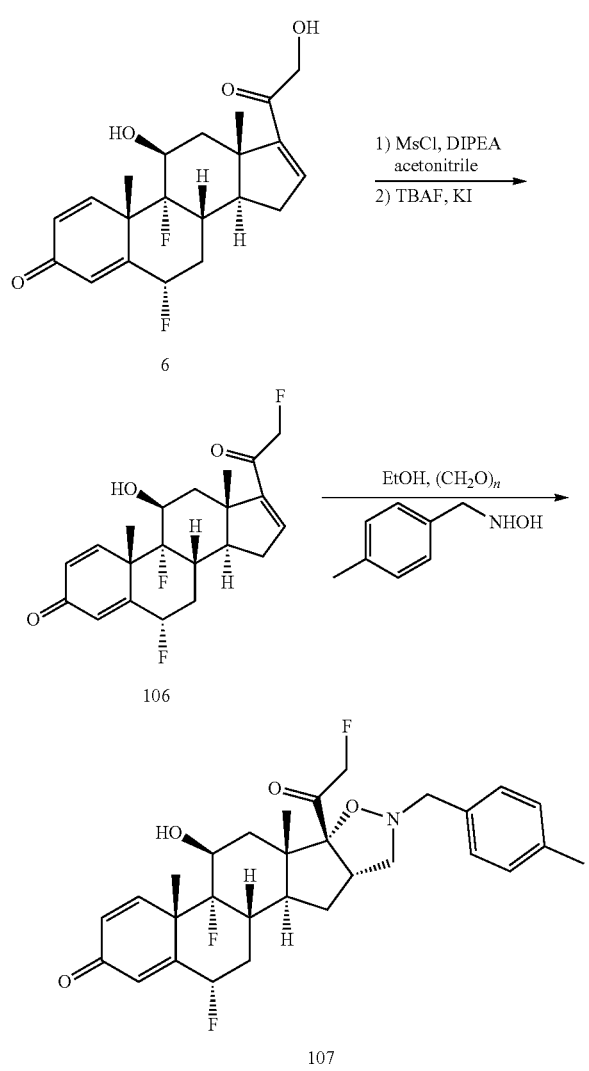

To a solution of compound 6 (0.5 g, 1.321 mmol) in dry acetonitrile (20 ml), under nitrogen atmosphere, DIPEA (0.396 ml, 2.246 mmol) and Ms-Cl (0.155 ml, 1.982 mmol) are added, and the reaction mixture is stirred at room temperature for 1 hour. Then, TBAF (2.64 ml, 2.64 mmol) 1 M in THF and potassium fluoride (0.077 g, 1.321 mmol) are added, and the mixture is heated at reflux overnight. The mixture was diluted with AcOEt, and the organic phase was washed with water, brine, dried (Na$_2$SO$_4$) and concentrated. The crude was purified by flash chromatography on silica gel, in gradient elution from petroleum ether/AcOEt 8:2 to AcOEt, to afford the title compound (98% yield).

LC-MS (ESI POS): 381.3 MH+

Preparation of (4aS,4bR,5S,6aS,6bR,9aS,10aS,10bS,12S)-4b,12-Difluoro-6b-(2-fluoro-acetyl)-5-hydroxy-4a,6a-dimethyl-8-(4-methyl-benzyl)-4a,4b,5,6,6a,6b,8,9,9a,10,10a,10b,11,12-tetradecahydro-7-oxa-8-aza-pentaleno[2,1-a]phenanthren-2-one (compound 107)

Compound 107 is obtained in 48% yield reacting intermediate 40 with N-(4-Methyl-benzyl)-hydroxylamine, as previously described for compound 10 (Example 4).

$^1$H NMR (300 MHz, DMSO-$d_6$) ppm 7.27 (dd, 1H), 7.03-7.22 (m, 4H), 6.30 (dd, 1H), 6.13 (s, 1H), 5.49-5.79 (m, 1H), 5.45 (d, 1H), 4.89 (d, 2H), 4.07-4.29 (m, 1H), 3.87 (d, 1H), 3.76 (d, 1H), 3.40-3.61 (m, 1H), 3.31-3.40 (m, 1H), 2.55-2.68 (m, 1H), 2.28 (s, 3H), 2.02-2.27 (m, 3H), 1.74-1.96 (m, 1H), 1.51-1.73 (m, 3H), 1.49 (s, 3H), 1.46 (dd, 1H), 0.84 (s, 3H)

LC-MS (ESI POS): 530.25 MH+

$[\alpha]_D^{25}$=+176.3 (c=0.1715, CHCl$_3$)

The compounds listed in Table 6 were prepared as previously described for compound 41 107, by cycloaddition of intermediate 106 with suitable hydroxylamine or hydroxylamine hydrochloride.

TABLE 6

| Compound | Structure | Yield | Analytical |
|---|---|---|---|
| 108 | 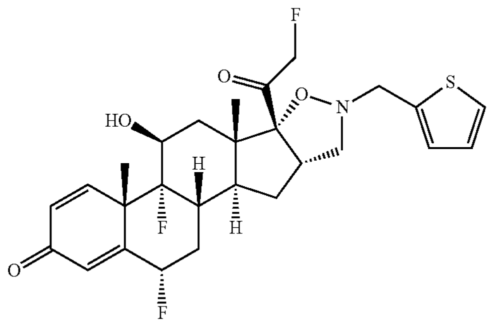 | 43% | LC-MS (ESI POS): 506.19 MH+<br>$[\alpha]_D^{25}$ = +180.8 (c 0.2 MeOH)<br>$^1$H NMR (300 MHz, DMSO-$d_6$) ppm 7.59 (dd, 1 H), 7.27 (dd, 1 H), 6.41 (dd, 1 H), 6.25-6.35 (m, 2 H), 6.12 (s, 1 H), 5.49-5.80 (m, 1 H), 5.46 (dd, 1 H), 5.00 (d, 2 H), 4.09-4.26 (m, 1 H), 3.98 (d, 1 H), 3.84 (d, 1 H), 3.41-3.61 (m, 1 H), 3.31-3.41 (m, 1 H), 2.56-2.70 (m, 1 H), 2.03-2.33 (m, 3 H), 1.79-1.96 (m, 1 H), 1.50-1.70 (m, 3 H), 1.49 (s, 3 H), 1.44 (dd, 1 H), 0.85 (s, 3 H) |
| 109 | 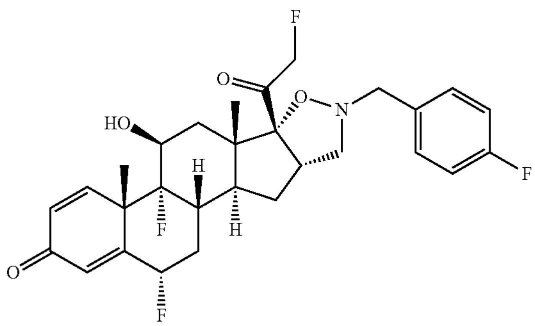 | 30% | LC-MS (ESI POS): 534.27 MH+<br>$[\alpha]_D^{25}$ = +157.4 (c 0.2 MeOH)<br>$^1$H NMR (300 MHz, DMSO-$d_6$) ppm 7.30-7.38 (m, 2 H), 7.27 (dd, 1 H), 7.07-7.21 (m, 2 H), 6.30 (dd, 1H), 6.13 (s, 1 H), 5.48-5.83 (m, 1 H), 5.45 (m, 1 H), 4.90 (dd, 1 H), 4.80 (dd, 1 H), 4.16 (m, 1 H), 3.93 (d, 1 H), 3.79 (d, 1 H), 3.44-3.60 (m, 1 H), 3.25-3.43 (m, 1 H), 2.56-2.70 (m, 1 H), 2.10-2.32 (m, 3 H), 1.79-1.97 (m, 1 H), 1.52-1.71 (m, 3 H), 1.49 (s, 3 H), 1.40-1.47 (m, 1 H), 0.84 (s, 3 H) |
| 110 | 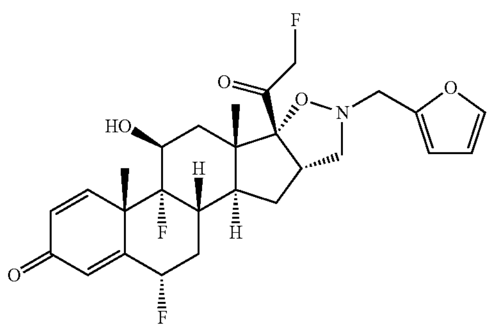 | 79% | LC-MS (ESI POS): 506.19 MH+<br>$[\alpha]_D^{25}$ = +180.8 (c 0.2 MeOH)<br>$^1$H NMR (300 MHz, DMSO-$d_6$) ppm 7.59 (dd, 1 H), 7.27 (dd, 1 H), 6.41 (dd, 1 H), 6.25-6.35 (m, 2 H), 6.12 (s, 1 H), 5.49-5.80 (m, 1 H), 5.46 (dd, 1 H), 5.00 (d, 2 H), 4.09-4.26 (m, 1 H), 3.98 (d, 1 H), 3.84 (d, 1 H), 3.41-3.61 (m, 1 H), 3.31-3.41 (m, 1 H), 2.56-2.70 (m, 1 H), 2.03-2.33 (m, 3 H), 1.79-1.96 (m, 1 H), 1.50-1.70 (m, 3 H), 1.49 (s, 3 H), 1.44 (dd, 1 H), 0.85 (s, 3 H) |
| 111 | 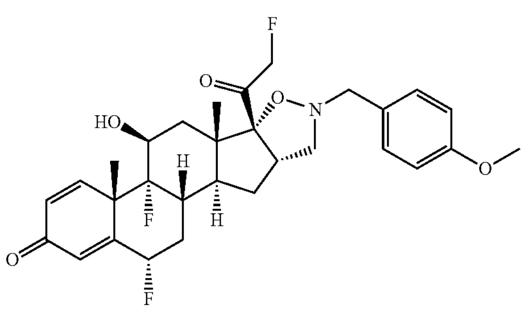 | 54% | LC-MS (ESI POS): 546.23 MH+<br>$[\alpha]_D^{25}$ = +189.2 (c 0.2 MeOH)<br>$^1$H NMR (300 MHz, DMSO-$d_6$) ppm 7.27 (dd, 1 H), 7.12-7.24 (m, 2 H), 6.79-6.94 (m, 2 H), 6.30 (dd, 1 H), 6.13 (s, 1 H), 5.50-5.79 (m, 1 H), 5.45 (dd, 1 H), 4.89 (d, 2 H), 4.12-4.25 (m, 1 H), 3.85 (d, 1 H), 3.73 (s, 3 H), 3.75 (d, 1 H), 3.39-3.54 (m, 1 H), 3.30-3.38 (m, 1 H), 2.55-2.68 (m, 1 H), 2.04-2.33 (m, 3 H), 1.80-1.96 (m, 1 H), 1.51-1.71 (m, 3 H), 1.49 (s, 3 H), 1.45 (dd, 1 H), 0.84 (s, 3 H) |

TABLE 6-continued

| Compound | Structure | Yield | Analytical |
|---|---|---|---|
| 112 | 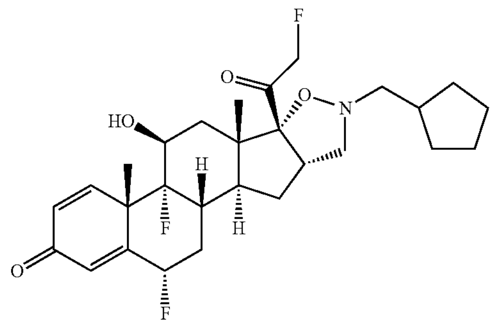 | 33% | LC-MS (ESI POS): 508.3 MH+<br>$[\alpha]_D^{25}$ = +147.6 (c 0.2 MeOH)<br>$^1$H NMR (300 MHz, DMSO-d$_6$) ppm 7.26 (dd, 1 H), 6.29 (dd, 1 H), 6.11 (s, 1 H), 5.49-5.82 (m, 1 H), 5.45 (dd, 1 H), 5.29 (dd, 1 H), 5.17 (dd, 1 H), 4.00-4.28 (m, 1 H), 3.53 (dt, 1 H), 3.31-3.43 (m, 1 H), 2.56-2.68 (m, 3 H), 1.83-2.43 (m, 6 H), 1.51-1.77 (m, 6 H), 1.49 (s, 3 H), 1.35-1.47 (m, 3 H), 1.06-1.29 (m, 2 H), 0.86 (s, 3 H) |
| 113 | 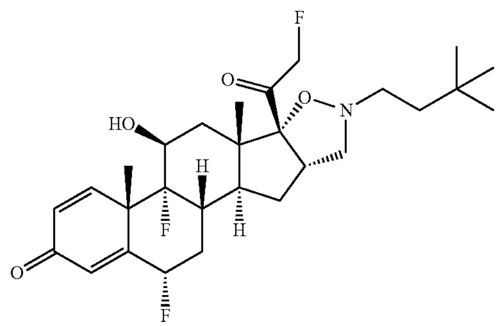 | 27% | LC-MS (ESI POS): 510.31 MH+<br>$[\alpha]_D^{25}$ = +118.3 (c 0.25, CHCl$_3$)<br>$^1$H NMR (300 MHz, DMSO-d$_6$) ppm 7.26 (dd, 1 H), 6.29 (dd, 1 H), 6.11 (s, 1 H), 5.49-5.79 (m, 1 H), 5.46 (d, 1 H), 5.30 (dd, 1 H), 5.17 (dd, 1 H), 4.04-4.29 (m, 1 H), 3.54 (t, 1 H), 3.31-3.40 (m, 1 H), 2.55-2.86 (m, 3 H), 2.06-2.34 (m, 2 H), 1.82-2.03 (m, 2 H), 1.52-1.75 (m, 2 H), 1.49 (s, 3 H), 1.39-1.48 (m, 3 H), 1.22-1.38 (m, 1 H), 0.86 (s, 9 H), 0.86 (s, 3 H) |
| 114 | 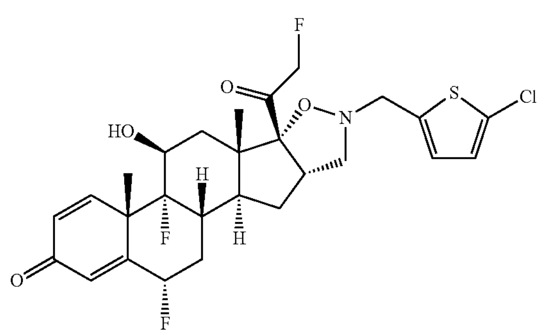 | 42% | LC-MS (ESI POS): 556.14 MH+<br>$[\alpha]_D^{25}$ = +185.0 (c 0.2 MeOH)<br>$^1$H NMR (300 MHz, DMSO-d$_6$) ppm 7.27 (dd, 1 H), 6.97 (d, 1 H), 6.87 (d, 1 H), 6.30 (dd, 1 H), 6.12 (s, 1 H), 5.50-5.79 (m, 1 H), 5.47 (d, 1 H), 5.15 (dd, 1 H), 5.04 (dd, 1 H), 4.15-4.21 (m, 1 H), 4.19 (d, 1 H), 3.96 (d, 1 H), 3.44-3.58 (m, 1 H), 3.31-3.44 (m, 1 H), 2.55-2.67 (m, 1 H), 2.05-2.25 (m, 3 H), 1.84-1.98 (m, 1 H), 1.63-1.73 (m, 1 H), 1.51-1.63 (m, 1 H), 1.49 (s, 3 H), 1.38-1.47 (m, 2 H), 0.85 (s, 3 H) |

Example 12. Preparation of (4aS,4bR,5S,6aS,6bR, 9aS,10aS,10bS,12S)-4b,12-Difluoro-5-hydroxy-6b-(2-tert-butyl-dimethyl-sililoxy-acetyl)-8-[4-(2-tert-butyl-dimethyl-sililoxy-ethoxy)-benzyl]-4a,6a-dimethyl-4a,4b,5,6,6a,6b,8,9,9a,10,10a,10b,11,12-tetradecahydro-7-oxa-8-aza-pentaleno[2,1-a]phenanthren-2-one (intermediate 115)

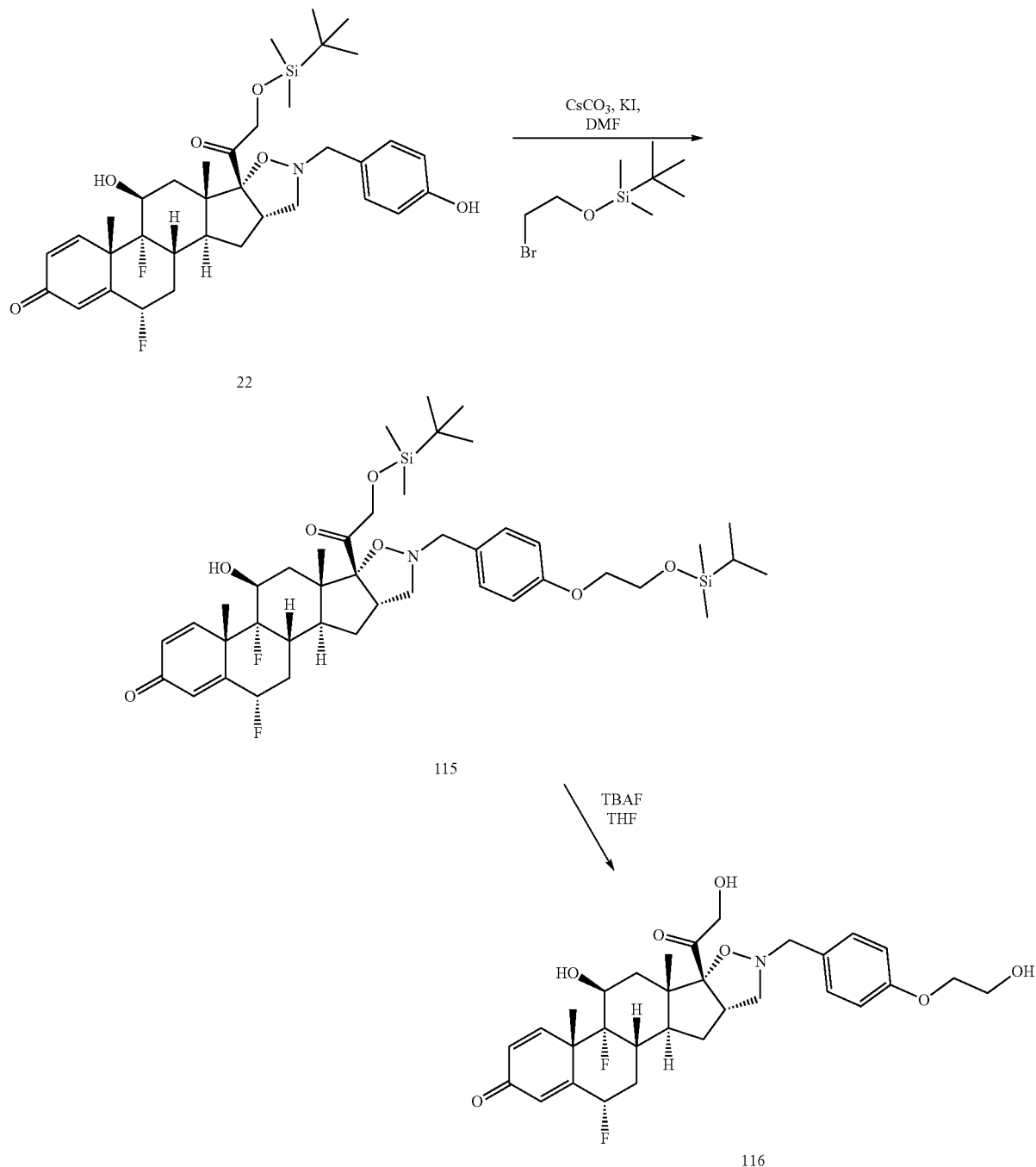

To a solution of compound 22 (200 mg, 0.311 mmol) in dry DMF (8 ml), under nitrogen atmosphere, cesium carbonate (223 mg, 0.683 mmol), (2-bromoethoxy)(tert-butyl)dimethylsilane (135 μl, 0.621 mmol) and potassium iodide (10 mg, 0.066 mmol) were added. The reaction mixture was heated at 50° C. overnight, and further cesium carbonate (0.056 g, 0.171 mmol) and (2-bromoethoxy)(tert-butyl)dimethylsilane (0.033 ml, 0.155 mmol) were added. The mixture was then further stirred at 50° C. for 8 hours. The reaction mixture was diluted with AcOEt, and the organic phase was washed with water, dried over $Na_2SO_4$ and concentrated. The residue was purified by flash chromatography on silica gel, in gradient elution from DCM to DCM/AcOEt 7:3 affording 256 mg, (92% yield).

LC-MS (ESI POS): 802.4 (MH+)

Preparation of (4aS,4bR,5S,6aS,6bR,9aS,10aS, 10bS,12S)-4b,12-Difluoro-5-hydroxy-6b-(2-hydroxy-acetyl)-8-[4-(2-hydroxy-ethoxy)-benzyl]-4a, 6a-dimethyl-4a,4b,5,6,6a,6b,8,9,9a,10,10a,10b,11, 12-tetradecahydro-7-oxa-8-aza-pentaleno[2,1-a] phenanthren-2-one (compound 116)

To a solution of compound 115 (0.256 g, 0.319 mmol) in dry THF (8 ml), at 0° C. under nitrogen atmosphere, tetrabutylammonium fluoride (0.670 ml, 0.670 mmol) was added, and the mixture was stirred at 0° C. for 1 hour and at room temperature for 1.5 hours. Solvent was evaporated, and the crude (535 mg) was purified by flash chromatography on silica gel, in gradient elution from DCM/AcOEt 9:1 to AcOEt/EtOH 9:1. Repurification of the obtained product by flash chromatography on silica gel, in gradient elution from DCM/AcOEt 6:4 to AcOEt/EtOH 97:3 afforded 46 mg of the title compound (25% yield).

¹H NMR (300 MHz, DMSO-d₆) ppm 7.26 (dd, 1H), 7.11-7.22 (m, 2H), 6.76-6.91 (m, 2H), 6.30 (dd, 1H), 6.13 (s, 1H), 5.50-5.74 (m, 1H), 5.43 (dd, 1H), 4.80 (t, 1H), 4.65 (s, 1H), 4.04-4.25 (m, 1H), 3.92-4.01 (m, 2H), 3.60-3.90 (m, 5H), 3.32-3.56 (m, 2H), 2.56-2.68 (m, 1H), 1.83-2.44 (m, 5H), 1.51-1.68 (m, 3H), 1.49 (s, 3H), 1.37-1.47 (m, 1H), 0.80 (s, 3H)

LC-MS (ESI POS): 574.39 (MH+)

$[\alpha]_D^{25}$=+155.8 (c 0.2 MeOH)

Example 13. Preparation of N-(4-chlorophenyl) hydroxylamine (intermediate 118)

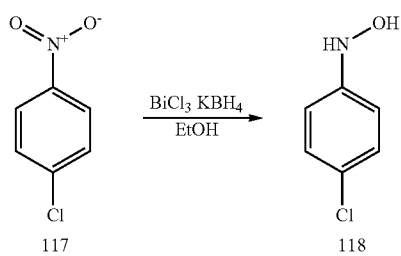

To a dispersion of 1-chloro-4-nitrobenzene 117 (1 g, 6.35 mmol) in absolute ethanol (32 ml) and water (10.24 ml), bismuth(III)chloride (0.400 g, 1.269 mmol) was added; then, potassium borohydride (0.514 g, 9.52 mmol) was added gradually with stirring in water bath, under nitrogen atmosphere. The mixture turned black and a black precipitate was formed. After 20 minutes stirring at RT, under nitrogen atmosphere, the mixture was acidified with 0.5 N HCl to pH 7 and immediately extracted with ethyl ether. The organic extracts were dried over Na₂SO₄ and concentrated to afford the desired hydroxylamine (959 mg), which was used as such without further purification.

LC-MS (ESI POS): 126.9 (MH+)

Example 14. Preparation of acetic acid 2-((6S,9R, 10S,11S,13S)-6,9-difluoro-11-hydroxy-10,13-dimethyl-3-oxo-6,7,8,9,10,11,12,13,14,15-decahydro-3H-cyclopenta[a]phenanthren-17-yl)-2-oxo-ethyl ester (intermediate 120)

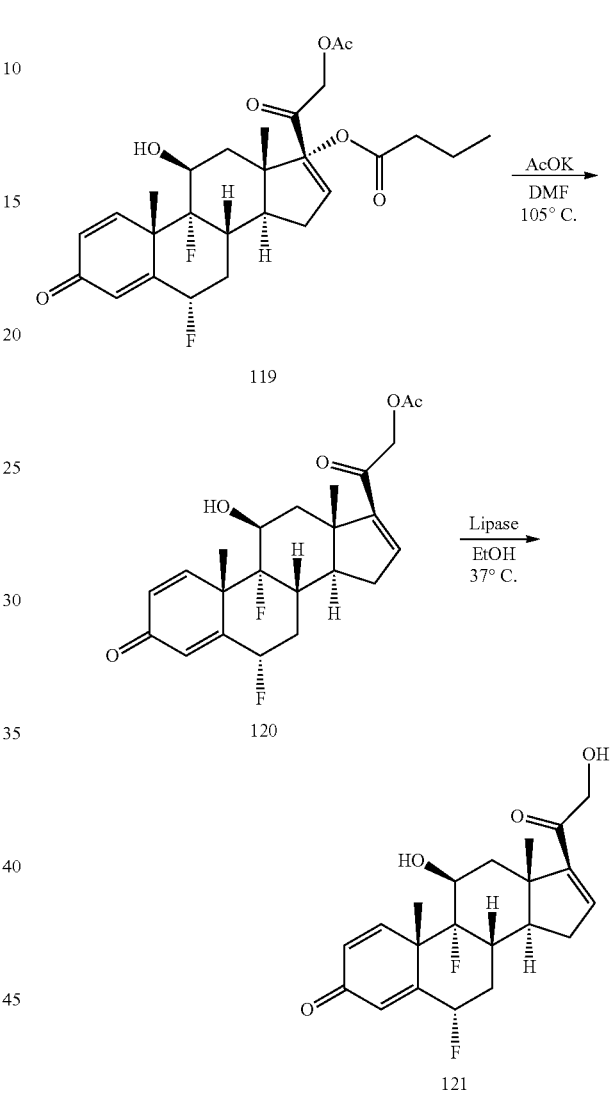

To a solution of butyric acid (9R,10S,11S,13S,17R)-17-(2-acetoxy-acetyl)-9-chloro-11-hydroxy-10,13-dimethyl-3-oxo-6,7,8,9,10,11,12,13,14,15,16,17-dodecahydro-3H-cyclopenta[a]phenanthren-17-yl ester (intermediate 119) (2.48 g, 4.88 mmol) in anhydrous DMF (60 ml), under nitrogen atmosphere, potassium acetate (3.83 g, 39.0 mmol) is added and the reaction mixture is stirred at 100° C. for 1.5 hours. The cooled reaction mixture is poured into ice and brine (200 ml), and the aqueous layer is extracted with AcOEt (3×150 ml). The combined organic extracts are washed with water and brine, dried over Na₂SO₄ and concentrated to afford 2.55 g of crude title compound which is used in the next step without further purification.

¹H NMR (300 MHz, DMSO-d₆): ppm 7.29 (dd, 1H), 6.99 (dd, 1H), 6.29 (dd, 1H), 5.98-6.15 (m, 1H), 5.68 (dddd, 1H), 5.56 (dd, 1H), 5.10 (d, 1H), 4.92 (d, 1H), 3.98-4.23 (m, 1H), 2.56-2.83 (m, 1H), 2.26-2.44 (m, 3H), 2.14-2.26 (m, 1H), 2.09 (s, 3H), 1.71-1.87 (m, 1H), 1.55-1.65 (m, 2H), 1.53 (s, 3H), 1.15 (s, 3H).
LC-MS (ESI POS): 421.97 (MH+)

Preparation of (6S,9R,10S,11S,13 S)-6,9-Difluoro-11-hydroxy-17-(2-hydroxy-acetyl)-10,13-dimethyl-6,7,8,9,10,11,12,13,14,15-decahydro-cyclopenta[a]phenanthren-3-one (intermediate 121)

To a solution of (intermediate 120) (2.55 g, 6.06 mmol) in ethanol (100 ml), Candida Antarctica Lipase (2 U/mg) (510 mg, 6.06 mmol) is added, and the reaction mixture is stirred at 37° C. overnight. The reaction mixture is filtered, washing with methanol, and the residue is purified by flash chromatography on silica gel, in gradient elution from DCM/AcOEt 90:10 to DCM/AcOEt 50:50, to afford 1.62 g of title compound (70.6% yield).
$^1$H NMR (300 MHz, DMSO-$d_6$): ppm 7.29 (dd, 1H), 6.87 (dd, 1H), 6.29 (dd, 1H), 6.09-6.17 (m, 1H), 5.67 (dddd, 1H), 5.53 (dd, 1H), 4.77 (t, 1H), 4.44 (dd, 1H), 4.26 (dd, 1H), 4.04-4.15 (m, 1H), 2.56-2.79 (m, 1H), 2.39 (dd, 1H), 2.25-2.35 (m, 2H), 2.09-2.25 (m, 1H), 1.76 (td, 1H), 1.55-1.66 (m, 2H), 1.53 (s, 3H), 1.17 (s, 3H).
LC-MS (ESI POS): 379.99 (MH+)

Example 15. Preparation of (4aS,4bR,5S,6aS,6bR,9aS,10aS,10bS,12S)-4b,12-Difluoro-5-hydroxy-6b-(2-hydroxy-acetyl)-4a,6a-dimethyl-8-phenyl-4a,4b,5,6,6a,6b,8,9,9a,10,10a,10b,11,12-tetradecahydro-7-oxa-8-aza-pentaleno[2,1-a]phenanthren-2-one (compound 122)

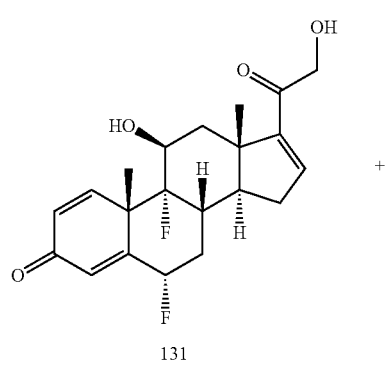

131

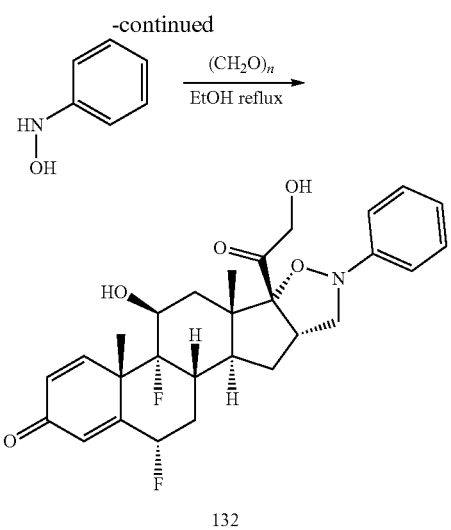

132

A mixture of 121, N-phenyl hydroxylamine (57.7 mg, 0.529 mmol) and paraformaldehyde (47.6 mg, 1.586 mmol) in Ethanol (6 ml) was stirred at 100° C. for 19 hours. The reaction was not complete. N-phenyl hydroxylamine (20 mg, 0.183 mmol) and paraformaldehyde (27 mg, 0.899 mmol) were added, and the mixture was heated at 100° C. for further 3 hours. The solvent was evaporated, and the residue was purified by silica gel flash chromatography in gradient elution from DCM to AcOEt/MeOH/DCM 9.8:0.2:90, to AcOEt/MeOH/DCM 29.8:0.2:70, affording 83 mg of pure compound (63% yield; Rf=0.24 in AcOEt/MeOH/DCM 29:1:70).
$^1$H NMR (300 MHz, DMSO-d6) ppm 7.19-7.36 (m, 3H), 6.90-7.04 (m, 3H), 6.28 (dd, 1H), 6.08 (s, 1H), 5.52-5.79 (m, 1H), 5.51 (dd, 1H), 4.92 (t, 1H), 4.51 (dd, 1H), 4.29 (dd, 1H), 4.17-4.24 (m, 1H), 4.13 (t, 1H), 3.50-3.66 (m, 1H), 2.61-2.71 (m, 1H), 2.57 (dd, 1H), 2.01-2.35 (m, 3H), 1.51-1.82 (m, 4H), 1.50 (s, 3H), 0.91 (s, 3H)
LC-MS (ESI POS): 500.17 MH+
$[\alpha]_D^{25}$=+71.09 (c 0.092; CHCl$_3$)

Compounds listed in Table 7 were prepared as previously described for compound 122, by cycloaddition of intermediate 121 with suitable hydroxylamine, hydroxylamine hydrochloride or protected hydroxylamine. In the last case, deprotection reaction was carried out on the final compound. Final compounds were purified by silica gel column chromatography or preparative HPLC.

TABLE 7

| Compound | Structure | Yield | Analytical |
|---|---|---|---|
| 123 | 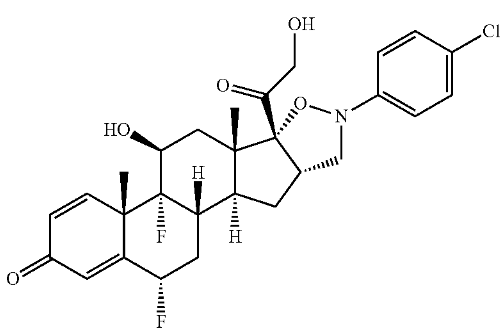 | 83% | LC-MS (ESI POS): 534.19 MH+<br>$[\alpha]_D^{25}$ = +72.74 (c 0.19;<br>CHCl$_3$) $^1$H NMR (300 MHz, DMSO-$d_6$) ppm 7.29-7.38 (m, 2 H), 7.25 (dd, 1 H), 6.93-7.05 (m, 2 H), 6.28 (dd, 1 H), 6.08 (s, 1 H), 5.52-5.77 (m, 1 H), 5.51 (d, 1 H), 4.94 (t, 1 H), 4.48 (dd, 1 H), 4.28 (dd, 1 H), 4.17-4.24 (m, 1 H), 4.13 (t, 1 H), 3.59 (q, 1 H), 2.60-2.69 (m, 1 H), 2.59 (dd, 1 H), 2.00-2.32 (m, 3 H), 1.51-1.83 (m, 4 H), 1.49 (s, 3 H), 0.90 (s, 3 H) |

TABLE 7-continued

| Compound | Structure | Yield | Analytical |
|---|---|---|---|
| 124 | 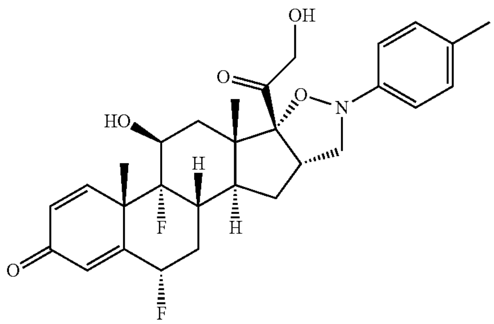 | 60% | LC-MS (ESI POS): 514.22 MH+<br>$[\alpha]_D^{25}$ = +81.8 (c 0.125, CHCl$_3$)<br>$^1$H NMR (300 MHz, DMSO-d$_6$) ppm 7.26 (d, 1 H), 7.09 (m, 2 H), 6.87 (m, 2 H), 6.28 (dd, 1 H), 6.08 (s, 1 H), 5.51-5.78 (m, 1 H), 5.31-5.52 (m, 1 H), 4.39-4.60 (m, 1 H), 4.14-4.36 (m, 2 H), 4.07 (t, 1 H), 3.57 (q, 1 H), 2.65 (m, 1 H), 2.23 (s, 3 H), 1.97-2.34 (m, 4 H), 1.59-1.85 (m, 2 H), 1.49 (s, 3 H), 1.39-1.59 (m, 3 H), 0.90 (s, 3 H) |
| 125 | 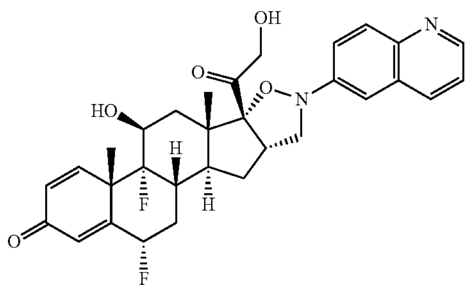 | 51% | LC-MS (ESI POS): 551.22 MH+<br>$[\alpha]_D^{25}$ = +57.3 (c 0.3, MeOH)<br>$^1$H NMR (300 MHz, DMSO-d$_6$) ppm 8.74 (dd, 1 H), 8.26 (dd, 1 H), 7.93 (d, 1 H), 7.50 (dd, 1 H), 7.46 (dd, 1 H), 7.40 (d, 1 H), 7.26 (dd, 1 H), 6.28 (dd, 1 H), 6.07 (s, 1 H), 5.53-5.78 (m, 1 H), 5.53 (dd, 1 H), 4.97 (t, 1 H), 4.58 (dd, 1 H), 4.35 (dd, 1 H), 4.28 (t, 1 H), 4.14-4.25 (m, 1 H), 3.57-3.77 (m, 1 H), 2.72-2.85 (m, 1 H), 2.56-2.70 (m, 1 H), 2.10-2.31 (m, 3 H), 1.54-1.90 (m, 4 H), 1.50 (s, 3 H), 0.94 (s, 3 H) |
| 126 | 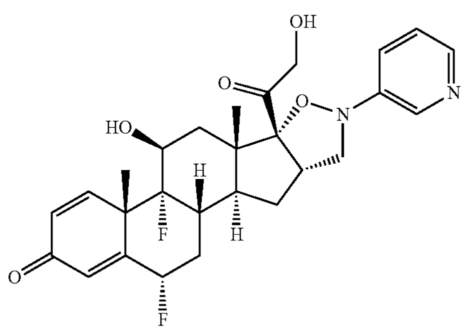 | 10% | LC-MS (ESI POS): 501.14 MH+<br>$[\alpha]_D^{25}$ = +78.05 (c 0.0925; CHCl$_3$)<br>$^1$H NMR (300 MHz, DMSO-d$_6$) ppm 8.29 (dd, 1 H), 8.21 (dd, 1 H), 7.38 (ddd, 1 H), 7.31 (ddd, 1 H), 7.26 (dd, 1 H), 6.28 (dd, 1 H), 6.08 (s, 1 H), 5.53-5.74 (m, 1 H), 5.51 (dd, 1 H), 4.95 (t, 1 H), 4.50 (dd, 1 H), 4.30 (dd, 1 H), 4.12-4.24 (m, 2 H), 3.53-3.71 (m, 1 H), 2.55-2.75 (m, 2 H), 1.98-2.33 (m, 3 H), 1.51-1.86 (m, 4 H), 1.49 (s, 3 H), 0.91 (s, 3 H) |
| 127 | 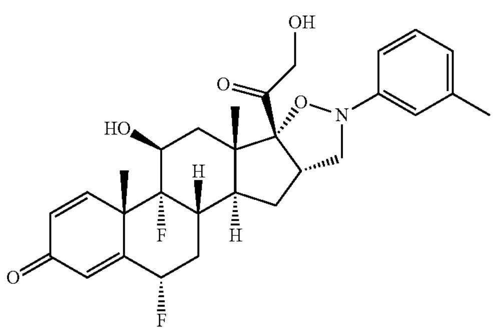 | 79% | LC-MS (ESI POS): 514.09 MH+<br>$[\alpha]_D^{25}$ = +70.69 (c 0.26, MeOH)<br>$^1$H NMR (300 MHz, DMSO-d$_6$) ppm 7.26 (d, 1 H), 7.15 (t, 1 H), 6.58-6.95 (m, 3 H), 6.28 (dd, 1 H), 6.08 (s, 1 H), 5.52-5.82 (m, 1 H), 5.50 (d, 1 H), 4.91 (t, 1 H), 4.50 (dd, 1 H), 4.28 (dd, 1 H), 4.16-4.28 (m, 1 H), 4.10 (t, 1 H), 3.58 (dd, 1 H), 2.54-2.68 (m, 2 H), 2.27 (s, 3 H), 2.03-2.34 (m, 3 H), 1.62-1.90 (m, 2 H), 1.49 (s, 3 H), 1.37-1.62 (m, 2 H), 0.90 (s, 3 H) |
| 128 | 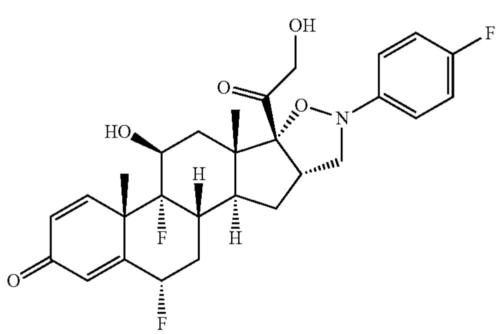 | 5% | LC-MS (ESI POS): 518.12 MH+<br>$[\alpha]_D^{25}$ = +87.67 (c 0.24, MeOH)<br>$^1$H NMR (300 MHz, DMSO-d$_6$) ppm 7.25 (dd, 1 H), 7.07-7.20 (m, 2 H), 6.91-7.07 (m, 2 H), 6.28 (dd, 1 H), 6.08 (s, 1 H), 5.52-5.76 (m, 1 H), 5.51 (dd, 1 H), 4.93 (t, 1 H), 4.49 (dd, 1 H), 4.27 (dd, 1 H), 4.16-4.27 (m, 1 H), 4.10 (t, 1 H), 3.59 (q, 1 H), 2.54-2.71 (m, 2 H), 2.10-2.33 (m, 2 H), 1.99-2.10 (m, 1 H), 1.49 (s, 3 H), 1.42-1.81 (m, 4 H), 0.90 (s, 3 H) |

TABLE 7-continued

| Compound | Structure | Yield | Analytical |
|---|---|---|---|
| 129 | 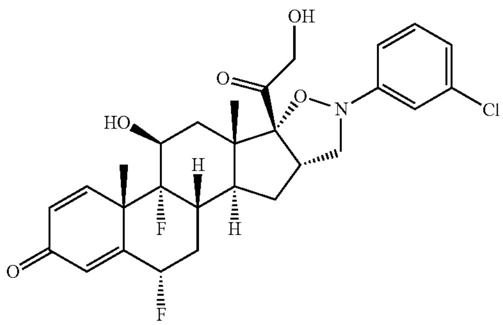 | 87% | LC-MS (ESI POS): 534.1 MH+<br>$[\alpha]_D^{25}$ = +69.70 (c 0.2 MeOH)<br>$^1$H NMR (300 MHz, DMSO-d$_6$) ppm<br>7.30 (t, 1 H), 7.26 (dd, 1 H), 6.98-7.06 (m, 2 H),<br>6.93 (ddd, 1 H), 6.28 (dd, 1 H), 6.08 (s, 1 H), 5.55-<br>5.81 (m, 1 H), 5.52 (dd, 1 H), 4.95 (t, 1 H), 4.47<br>(dd, 1 H), 4.29 (dd, 1 H), 4.18-4.25 (m, 1 H), 3.51-<br>3.69 (m, 1 H), 2.54-2.70 (m, 2 H), 2.02-2.34<br>(m, 3 H), 1.62-1.88 (m, 3 H), 1.51-1.62 (m, 2 H),<br>1.49 (s, 3 H), 0.90 (s, 3 H) |
| 130 | 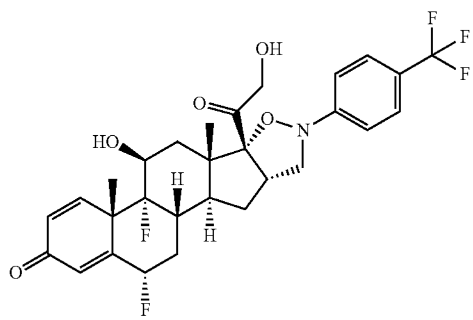 | 68% | LC-MS (ESI POS): 568.21 MH+<br>$[\alpha]_D^{25}$ = +49.5 (c 0.2 MeOH)<br>$^1$H NMR (300 MHz, DMSO-d$_6$) ppm 7.53-7.74<br>(m, 2 H), 7.26 (dd, 1 H), 7.03-7.20 (m, 2 H), 6.28<br>(dd, 1 H), 6.08 (s, 1 H), 5.55-5.85 (m, 1 H),<br>5.52 (dd, 1 H), 4.97 (t, 1 H), 4.47 (dd, 1 H),<br>4.30 (dd, 1 H), 4.16-4.25 (m, 2 H), 3.56-3.73<br>(m, 1 H), 2.55-2.71 (m, 2 H), 2.04-2.30 (m, 3 H),<br>1.64-1.86 (m, 2 H), 1.51-1.64 (m, 2 H),<br>1.50 (s, 3 H), 0.92 (s, 3 H) |
| 131 | 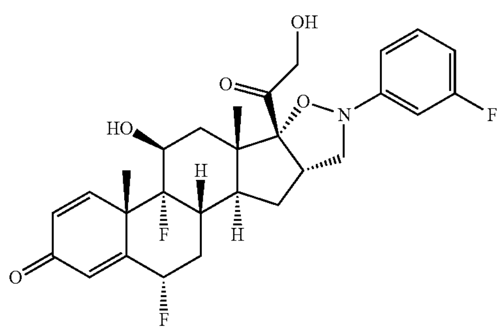 | 95% | LC-MS (ESI POS): 518.2 MH+<br>$[\alpha]_D^{25}$ = +69.15 (c = 0.26, MeOH)<br>$^1$H NMR (300 MHz, DMSO-d$_6$) ppm 7.28-7.40<br>(m, 1 H), 7.26 (dd, 1 H), 6.73-6.92 (m, 3 H),<br>6.28 (dd, 1 H), 6.08 (s, 1 H), 5.54-5.77 (m., 1<br>H), 5.51 (dd, 1 H), 4.94 (t, 1 H), 4.47 (dd, 1 H),<br>4.29 (dd, 1 H), 4.18-4.24 (m, 1 H), 4.16 (t, 1 H),<br>3.51-3.66 (m, 1 H), 2.63 (dd, 1 H), 2.55-2.70<br>(m, 1 H), 2.02-2.26 (m, 3 H), 1.63-1.86<br>(m, 2 H), 1.51-1.61 (m, 2 H), 1.49 (s, 3 H), 0.91<br>(s, 3 H) |
| 132 | 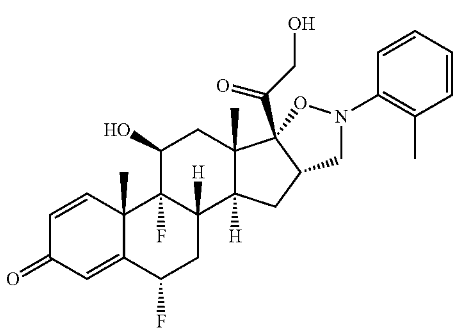 | 24% | LC-MS (ESI POS): 514.23 MH+<br>$[\alpha]_D^{25}$ = +54.83 (c 0.24, MeOH)<br>$^1$H NMR (300 MHz, DMSO-d$_6$) ppm 7.30<br>(dd, 1 H), 7.28 (dd, 1 H), 7.11-7.24 (m, 2 H), 7.05<br>(td, 1 H), 6.31 (dd, 1 H), 6.12 (s, 1 H), 5.53-<br>5.84 (m, 1 H), 5.50 (dd, 1 H), 4.88 (t, 1 H),<br>4.39 (dd, 1 H), 4.19-4.30 (m, 1 H), 4.14 (dd, 1 H),<br>3.85 (t, 1 H), 3.53-3.72 (m, 1 H), 2.58-2.70<br>(m, 1 H), 2.41 (dd, 1 H), 2.23-2.38 (m, 2 H),<br>2.15 (s, 3 H), 2.03-2.13 (m, 1 H), 1.70-1.84 (m, 1 H),<br>1.53-1.73 (m, 3 H), 1.51 (s, 3 H), 0.90 (s, 3 H) |

TABLE 7-continued

| Compound | Structure | Yield | Analytical |
|---|---|---|---|
| 133 | 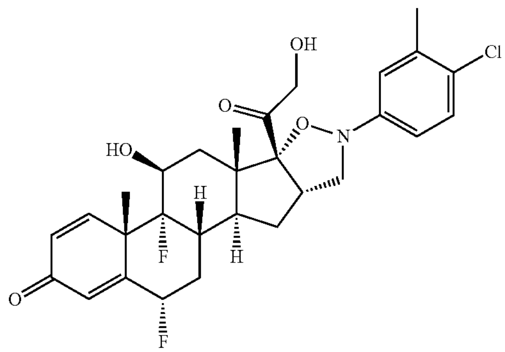 | 38% | LC-MS (ESI POS): 548.21 MH+ $[\alpha]_D^{25}$ = +54.96 (c 0.25, MeOH)<br>$^1$H NMR (300 MHz, DMSO-d$_6$) ppm 7.30 (d, 1 H), 7.26 (dd, 1 H), 6.96 (d, 1 H), 6.82 (dd, 1 H), 6.28 (dd, 1 H), 6.08 (s, 1 H), 5.52-5.78 (m, 1 H), 5.51 (d, 1 H), 4.93 (t, 1 H), 4.49 (dd, 1 H), 4.28 (dd, 1 H), 4.16-4.27 (m, 1 H), 4.11 (t, 1 H), 3.59 (q, 1 H), 2.54-2.69 (m, 2 H), 1.97-2.36 (m, 3 H), 2.29 (s, 3 H), 1.41-1.81 (m, 4 H), 1.49 (s, 3 H), 0.90 (s, 3 H) |
| 134 | 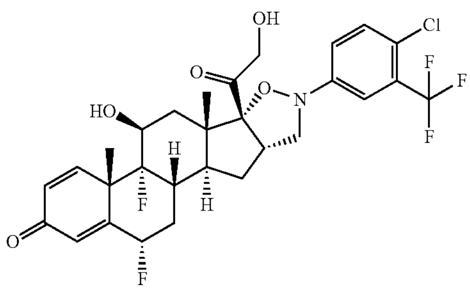 | 36% | LC-MS (ESI POS): 602.17 MH+<br>$[\alpha]_D^{25}$ = +48.8 (c 0.25, MeOH)<br>$^1$H NMR (300 MHz, DMSO-d$_6$) ppm 7.62 (d, 1 H), 7.11-7.40 (m, 3 H), 6.28 (dd, 1 H), 6.08 (s, 1 H), 5.55-5.76 (m, 1 H), 5.53 (dd, 1 H), 4.98 (t, 1 H), 4.46 (dd, 1 H), 4.30 (dd, 1 H), 4.14-4.28 (m, 2 H), 3.52-3.72 (m, 1 H), 2.73 (dd, 1 H), 2.56-2.67 (m, 1 H), 2.01-2.34 (m, 3 H), 1.63-1.87 (m, 2 H), 1.51-1.63 (m, 2 H), 1.49 (s, 3 H), 0.91 (s, 3 H) |
| 135 | 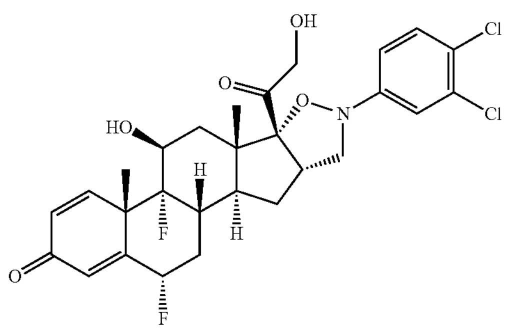 | 68% | LC-MS (ESI POS): 568.18 MH+<br>$[\alpha]_D^{25}$ = +53.21 (c 0.28, MeOH)<br>$^1$H NMR (300 MHz, DMSO-d$_6$) ppm 7.52 (d, 1 H), 7.26 (dd, 1 H), 7.20 (d, 1 H), 6.98 (dd, 1 H), 6.29 (dd, 1 H), 6.08 (s, 1 H), 5.54-5.74 (m, 1 H), 5.52 (d, 1 H), 4.96 (t, 1 H), 4.46 (dd, 1 H), 4.29 (dd, 1 H), 4.19-4.24 (m, 1 H), 4.18 (t, 1 H), 3.50-3.68 (m, 1 H), 2.65 (dd, 1 H), 2.54-2.61 (m, 1 H), 2.01-2.31 (m, 3 H), 1.62-1.84 (m, 2 H), 1.51-1.62 (m, 2 H), 1.49 (s, 3 H), 0.90 (s, 3 H) |
| 136 | 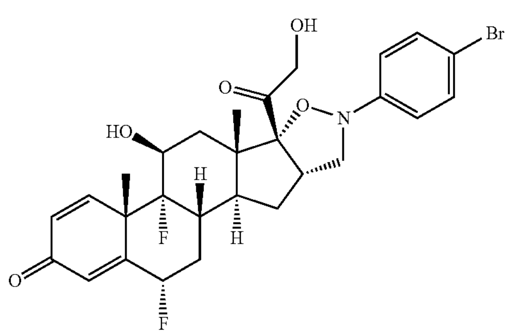 | 52% | LC-MS (ESI POS): 578.19 MH+<br>$[\alpha]_D^{25}$ = +56.2 (c 0.2, MeOH)<br>$^1$H NMR (300 MHz, DMSO-d$_6$) ppm 7.39-7.50 (m, 2 H), 7.25 (dd, 1 H), 6.86-7.02 (m, 2 H), 6.28 (dd, 1 H), 6.08 (s, 1 H), 5.53-5.77 (m, 1 H), 5.51 (dd, 1 H), 4.95 (t, 1 H), 4.47 (dd, 1 H), 4.27 (dd, 1 H), 4.17-4.23 (m, 1 H), 4.14 (t, 1 H), 3.59 (q, 1 H), 2.54-2.68 (m, 2 H), 2.01-2.25 (m, 3 H), 1.61-1.85 (m, 2 H), 1.50-1.61 (m, 2 H), 1.49 (s, 3 H), 0.90 (s, 3 H) |

TABLE 7-continued

| Compound | Structure | Yield | Analytical |
|---|---|---|---|
| 137 | 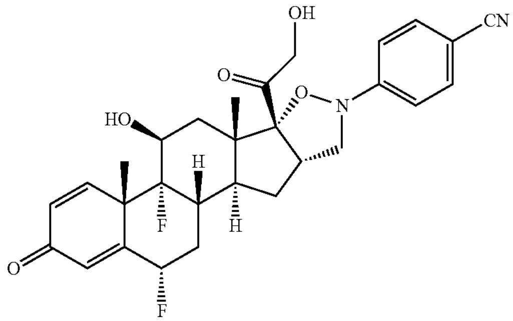 | 39% | LC-MS (ESI POS): 525.32 MH+<br>$[\alpha]_D^{25}$ = +19.35 (c 0.55, DMF)<br>$^1$H NMR (300 MHz, DMSO-$d_6$) ppm 7.59-7.86 (m, 2 H), 7.26 (dd, 1 H), 6.99-7.18 (m, 2 H), 6.28 (dd, 1 H), 6.08 (s, 1 H), 5.54 (dd, 1 H), 5.46-5.75 (m, 1 H), 4.99 (t, 1 H), 4.44 (dd, 1 H), 4.29 (dd, 1 H), 4.24 (t, 1 H), 4.13-4.23 (m, 1 H), 3.55-3.73 (m, 1 H), 2.77 (dd, 1 H), 2.54-2.71 (m, 1 H), 2.00-2.25 (m, 3 H), 1.65-1.90 (m, 2 H), 1.51-1.65 (m, 2 H), 1.49 (s, 3 H), 0.91 (s, 3 H) |
| 138 | 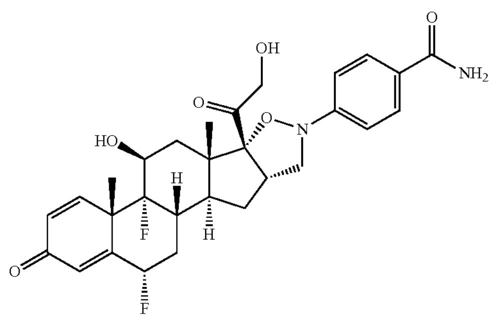 | 18% | LC-MS (ESI POS): 543.35 MH+<br>$[\alpha]_D^{25}$ = + 52.38 (c 0.21, MeOH)<br>$^1$H NMR (300 MHz, DMSO-$d_6$) ppm 7.78-7.89 (m, 2 H), 7.78 (br. s., 1 H), 7.26 (d, 1 H), 7.15 (br. s., 1 H), 6.89-7.04 (m, 2 H), 6.28 (dd, 1 H), 6.08 (s, 1 H), 5.54-5.77 (m, 1 H), 5.52 (d, 1 H), 4.95 (t, 1 H), 4.49 (dd, 1 H), 4.30 (dd, 1 H), 4.13-4.25 (m, 2 H), 3.50-3.72 (m, 1 H), 2.57-2.76 (m, 2 H), 1.98-2.39 (m, 3 H), 1.64-1.91 (m, 2 H), 1.52-1.64 (m, 2 H), 1.50 (s, 3 H), 0.91 (s, 3 H) |
| 139 | 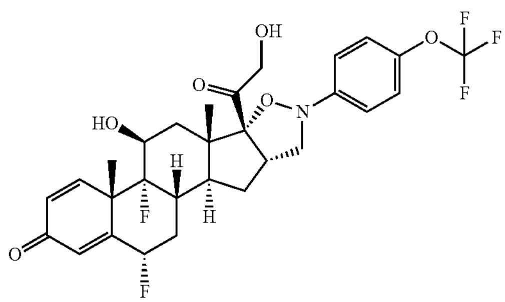 | 15% | LC-MS (ESI POS): 584.26 MH+<br>$[\alpha]_D^{25}$ = +63.04 (c 0.25, MeOH)<br>$^1$H NMR (300 MHz, DMSO-$d_6$) ppm 7.27 (m, 3 H), 7.07 (d, 2 H), 6.28 (dd, 1 H), 6.08 (s, 1 H), 5.49-5.78 (m, 1 H), 5.52 (dd, 1 H), 4.94 (t, 1 H), 4.49 (dd, 1 H), 4.28 (dd, 1 H), 4.11-4.23 (m, 1 H), 4.16 (t, 1 H), 3.48-3.75 (m, 1 H), 2.56-2.70 (m, 2 H), 1.99-2.25 (m, 3 H), 1.60-1.82 (m, 2 H), 1.49 (s, 3 H), 1.28-1.60 (m, 2 H), 0.91 (s, 3 H) |
| 140 | 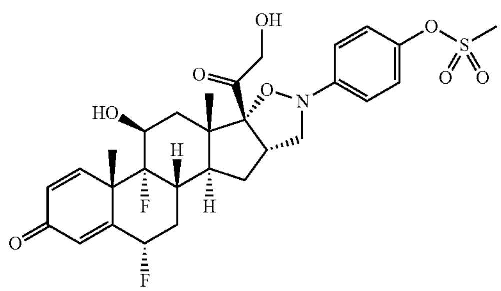 | 52% | LC-MS (ESI POS): 594.18 MH+<br>$[\alpha]_D^{25}$ = +50.7 (c 0.2 MeOH)<br>$^1$H NMR (300 MHz, DMSO-$d_6$) ppm 7.16-7.35 (m, 3 H), 6.93-7.11 (m, 2 H), 6.28 (dd, 1 H), 6.08 (s, 1 H), 5.54-5.87 (m, 1 H), 5.51 (dd, 1 H), 4.94 (t, 1 H), 4.49 (dd, 1 H), 4.29 (dd, 1 H), 4.17-4.23 (m, 1 H), 4.16 (t, 1 H), 3.50-3.69 (m, 1 H), 3.32 (s, 3 H), 2.56-2.71 (m, 2 H), 2.02-2.27 (m, 3 H), 1.63-1.86 (m, 2 H), 1.51-1.63 (m, 2 H), 1.50 (s, 3 H), 0.91 (s, 3 H) |
| 141 | 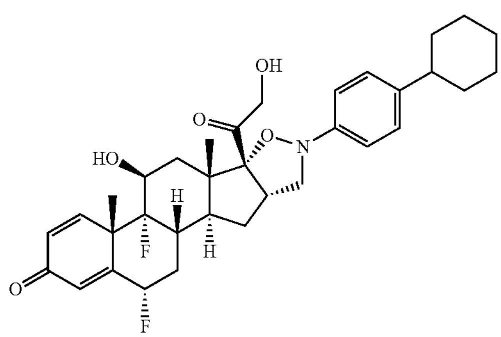 | 61% | LC-MS (ESI POS): 582.34 MH+<br>$[\alpha]_D^{25}$ = +64.4 (c 0.2, MeOH)<br>$^1$H NMR (300 MHz, DMSO-$d_6$) ppm 7.25 (dd, 1 H), 7.06-7.16 (m, 2 H), 6.81-6.93 (m, 2 H), 6.28 (dd, 1 H), 6.08 (s, 1 H), 5.52-5.83 (m, 1 H), 5.50 (dd, 1 H), 4.90 (t, 1 H), 4.51 (dd, 1 H), 4.27 (dd, 1 H), 4.15-4.23 (m, 1 H), 4.07 (t, 1 H), 3.50-3.64 (m, 1 H), 2.55-2.71 (m, 2 H), 2.33-2.45 (m, 1 H), 2.02-2.30 (m, 3 H), 1.51-1.88 (m, 8 H), 1.49 (s, 3 H), 1.12-1.44 (m, 6 H), 0.90 (s, 3 H) |

TABLE 7-continued

| Compound | Structure | Yield | Analytical |
|---|---|---|---|
| 142 | 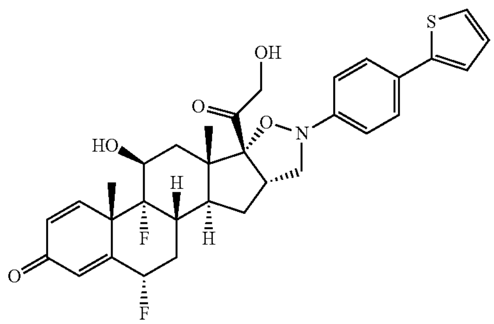 | 15% | LC-MS (ESI POS): 582.22 MH+<br>[α]$_D^{25}$ = +12.6 (c 0.4, CHCl$_3$)<br>$^1$H NMR (300 MHz, DMSO-d$_6$) ppm 7.52-7.62 (m, 2 H), 7.46 (dd, 1 H), 7.38 (dd, 1 H), 7.26 (dd, 1 H), 7.09 (dd, 1 H), 6.94-7.05 (m, 2 H), 6.28 (dd, 1 H), 6.08 (s, 1 H), 5.54-5.77 (m, 1 H), 5.52 (dd, .1 H), 4.95 (t, 1 H), 4.52 (dd, 1 H), 4.30 (dd, 1 H), 4.20-4.25 (m, 1 H), 4.16 (t, 1 H), 3.52-3.69 (m, 1 H), 2.55-2.71 (m, 2 H), 1.99-2.32 (m, 3 H), 1.62-1.89 (m, 2 H), 1.52-1.62 (m, 2 H), 1.50 (s, 3 H), 0.92 (s, 3 H) |
| 143 | 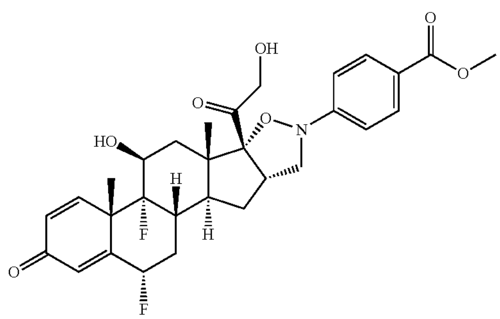 | 30% | LC-MS (ESI POS): 558.33 MH+<br>[α]$_D^{25}$ = +49.3 (c 0.2 MeOH)<br>$^1$H NMR (300 MHz, DMSO-d$_6$) ppm 7.73-7.96 (m, 2 H), 7.26 (dd, 1 H), 6.93-7.11 (m, 2 H), 6.28 (dd, 1 H), 6.08 (s, 1 H), 5.54-5.81 (m, 1 H), 5.52 (dd, 1 H), 4.98 (t, 1 H), 4.47 (dd, 1 H), 4.30 (dd, 1 H), 4.17-4.26 (m, 2 H), 3.81 (s, 3 H), 3.54-3.70 (m, 1 H), 2.55-2.85 (m, 2 H), 2.01-2.26 (m, 3 H), 1.64-1.87 (m, 2 H), 1.51-1.64 (m, 2 H), 1.49 (s, 3 H), 0.92 (s, 3 H) |
| 144 | 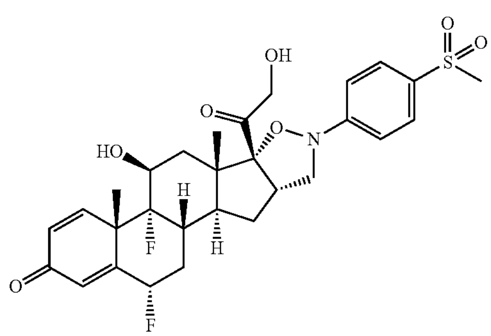 | 50% | LC-MS (ESI POS): 578.32 MH+<br>[α]$_D^{25}$ = +44.0 (c 0.2, MeOH)<br>$^1$H NMR (300 MHz, DMSO-d$_6$) ppm 7.72-7.87 (m, 2 H), 7.26 (dd, 1 H), 7.06-7.19 (m, 2 H), 6.29 (dd, 1 H), 6.08 (s, 1 H), 5.53 (dd, 1 H), 5.46-5.85 (m, 1 H), 4.91-5.05 (m, 1 H), 4.47 (dd, 1 H), 4.31 (dd, 1 H), 4.26 (t, 1 H), 4.15-4.24 (m, 1 H), 3.56-3.72 (m, 1 H), 3.12 (s, 3 H), 2.77 (dd, 1 H), 2.58-2.69 (m, 1 H), 2.02-2.32 (m, 3 H), 1.64-1.86 (m, 2 H), 1.52-1.64 (m, 2 H), 1.50 (s, 3 H), 0.92 (s, 3 H) |
| 145 | 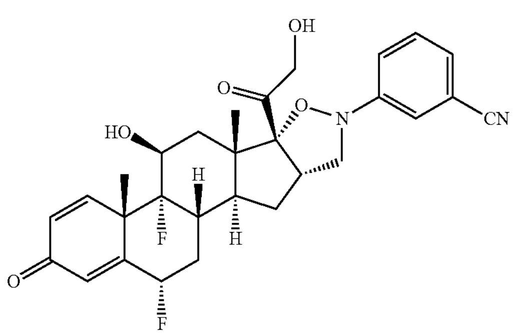 | 16% | LC-MS (ESI POS): 525.16 MH+<br>[α]$_D^{25}$ = +90.32 (c 0.25; DCM)<br>$^1$H NMR (300 MHz, DMSO-d$_6$) ppm 7.49 (t, 1 H), 7.37-7.45 (m, 2 H), 7.30 (ddd, 1 H), 7.26 (dd, 1 H), 6.28 (dd, 1 H), 6.08 (s, 1 H), 5.52-5.74 (m, 1 H), 5.52 (dd, 1 H), 4.95 (t, 1 H), 4.48 (dd, 1 H), 4.31 (dd, 1 H), 4.20-4.27 (m, 1 H), 4.21 (t, 1 H), 3.49-3.71 (m, 1 H), 2.67 (dd, 1 H), 2.56-2.63 (m, 1 H), 1.98-2.27 (m, 3 H), 1.63-1.88 (m, 2 H), 1.51-1.63 (m, 2 H), 1.50 (s, 3 H), 0.91 (s, 3 H) |

TABLE 7-continued

| Compound | Structure | Yield | Analytical |
|---|---|---|---|
| 146 | 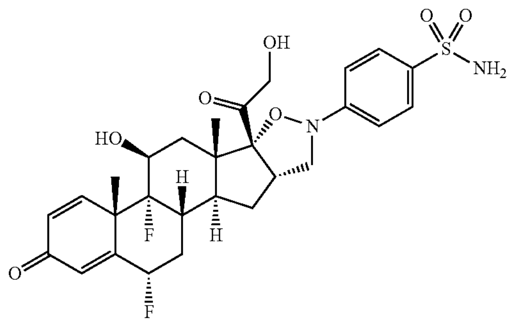 | 25% | LC-MS (ESI POS): 579.25 MH+<br>$[\alpha]_D^{25}$ = +45.41 (c 0.0925; MeOH)<br>$^1$H NMR (300 MHz, DMSO-d$_6$) ppm 7.60-7.79 (m, 2 H), 7.26 (dd, 1 H), 7.17 (s, 2 H), 7.01-7.12 (m, 2 H), 6.29 (dd, 1 H), 6.08 (s, 1 H), 5.52-5.80 (m, 1 H), 5.52 (dd, 1 H), 4.47 (d, 1 H), 4.30 (d, 1 H), 4.21 (t, 1 H), 4.12-4.23 (m, 1 H), 3.56-3.71 (m, 1 H), 2.67-2.78 (m, 1 H), 2.55-2.67 (m, 1 H), 2.01-2.33 (m, 3 H), 1.63-1.87 (m, 2 H), 1.51-1.63 (m, 2 H), 1.50 (s, 3 H), 0.92 (s, 3 H) |
| 147 | 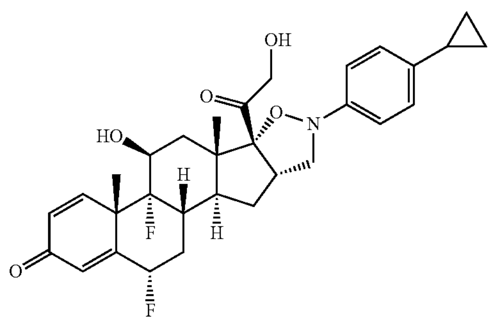 | 68% | LC-MS (ESI POS): 540.28 MH+<br>$[\alpha]_D^{25}$ = +78.53 (c 0.3; MeOH)<br>$^1$H NMR (300 MHz, DMSO-d$_6$) ppm 7.25 (dd, 1 H), 6.94-7.07 (m, 2 H), 6.76-6.93 (m, 2 H), 6.28 (dd, 1 H), 6.08 (s, 1 H), 5.52-5.79 (m, 1 H), 5.50 (d, 1 H), 4.90 (t, 1 H), 4.50 (dd, 1 H), 4.27 (dd, 1 H), 4.14-4.21 (m, 1 H), 4.06 (t, 1 H), 3.44-3.68 (m, 1 H), 2.53-2.70 (m, 2 H), 1.97-2.30 (m, 3 H), 1.79-1.92 (m, 1 H), 1.60-1.79 (m, 2 H), 1.51-1.60 (m, 1 H), 1.49 (s, 3 H), 1.42-1.49 (m, 1 H), 0.90 (s, 3 H), 0.78-0.88 (m, 2 H), 0.50-0.65 (m, 2 H) |
| 148 | 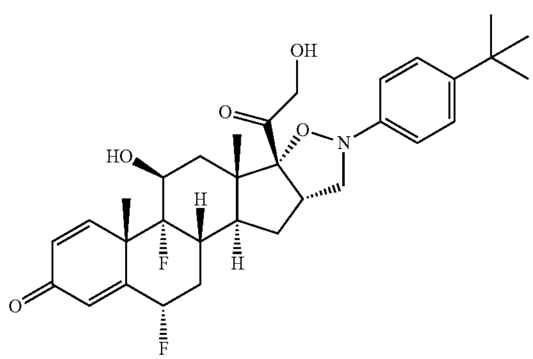 | 41% | LC-MS (ESI POS): 556.38 MH+<br>$[\alpha]_D^{25}$ = +71.25 (c 0.4, MeOH)<br>$^1$H NMR (300 MHz, DMSO-d$_6$) ppm 7.27-7.33 (m, 2 H), 7.26 (d, 1 H), 6.78-6.98 (m, 2 H), 6.28 (dd, 1 H), 6.08 (s, 1 H), 5.53-5.75 (m, 1 H), 5.51 (dd, 1 H), 4.90 (t, 1 H), 4.51 (dd, 1 H), 4.28 (dd, 1 H), 4.16-4.23 (m, 1 H), 4.08 (t, 1 H), 3.49-3.69 (m, 1 H), 2.55-2.70 (m, 2 H), 1.98-2.32 (m, 3 H), 1.61-1.84 (m, 2 H), 1.52-1.61 (m, 1 H), 1.49 (s, 3 H), 1.40-1.48 (m, 1 H), 1.24 (s, 9 H), 0.90 (s, 3 H) |
| 149 | 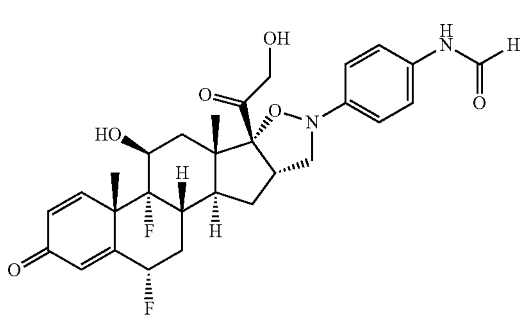 | 17% | LC-MS (ESI POS): 543.24 MH+<br>$[\alpha]_D^{25}$ = +32.5 (c 0.0415; MeOH)<br>$^1$H NMR (300 MHz, DMSO-d$_6$) ppm 10.04 (s, 1 H), 8.20 (d, 1 H), 7.50 (d, 2 H), 7.26 (d, 1 H), 6.78-7.02 (m, 2 H), 6.28 (dd, 1 H), 6.08 (s, 1 H), 5.51-5.79 (m, 1 H), 5.50 (d, 1 H), 4.92 (t, 1 H), 4.51 (dd, 1 H), 4.27 (dd, 1 H), 4.15-4.26 (m, 1 H), 4.07 (t, 1 H), 3.44-3.67 (m, 1 H), 2.60-2.71 (m, 2 H), 1.96-2.32 (m, 3 H), 1.60-1.81 (m, 2 H), 1.41-1.58 (m, 2 H), 1.49 (s, 3 H), 0.90 (s, 3 H) |

TABLE 7-continued

| Compound | Structure | Yield | Analytical |
|---|---|---|---|
| 150 | 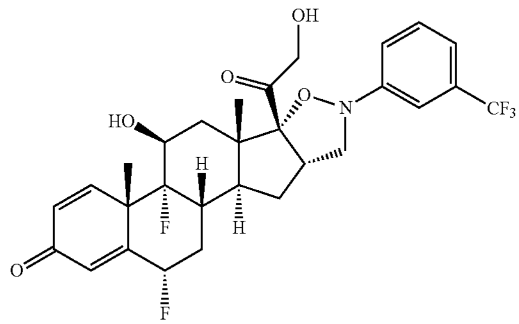 | 34% | LC-MS (ESI POS): 568.23 MH+<br>$[\alpha]_D^{25}$ = +57.8 (c 0.2, MeOH)<br>$^1$H NMR (300 MHz, DMSO-d$_6$) ppm 7.43-7.64 (m, 1 H), 7.12-7.39 (m, 4 H), 6.28 (dd, 1 H), 6.08 (s, 1 H), 5.44-5.79 (m, 1 H), 5.53 (d, 1 H), 4.96 (t, 1 H), 4.48 (dd, 1 H), 4.31 (dd, 1 H), 4.15-4.31 (m, 2 H), 3.62 (q, 1 H), 2.55-2.79 (m, 3 H), 1.96-2.25 (m, 2 H), 1.63-1.93 (m, 2 H), 1.50 (s, 3 H), 1.27-1.63 (m, 2 H), 0.92 (s, 3 H) |
| 151 | 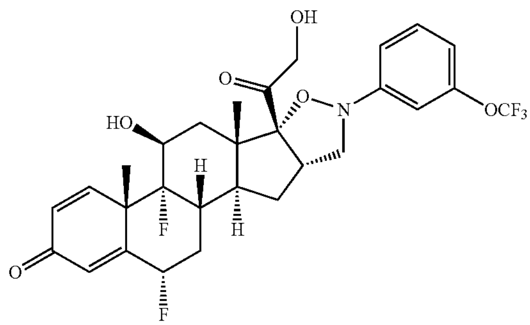 | 15% | LC-MS (ESI POS): 584.2 MH+<br>$[\alpha]_D^{25}$ = +76.6 (c 0.22, DCM)<br>$^1$H NMR (300 MHz, DMSO-d$_6$) ppm 7.41 (t, 1H), 7.26 (dd, 1 H), 6.90-7.02 (m, 3 H), 6.28 (dd, 1 H), 6.08 (s, 1 H), 5.50-5.77 (m, 1 H), 5.50-5.54 (m, 1 H), 4.92-4.98 (m, 1 H), 4.46 (dd, 1 H), 4.29 (dd, 1 H), 4.20 (t, 1 H), 4.07-4.24 (m, 1 H), 3.61 (q, 1 H), 2.67 (dd, 2 H), 2.04-2.28 (m, 3 H), 1.65-1.82 (m, 2 H), 1.50 (s, 3 H), 1.55 (dd, 2 H), 0.91 (s, 3 H) |
| 152 | 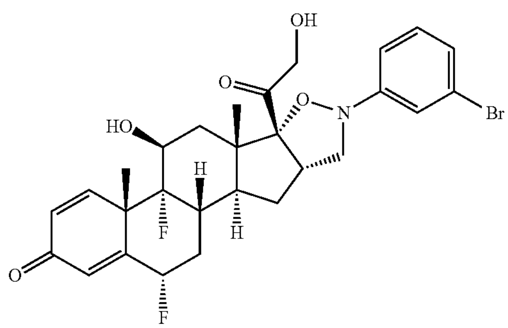 | 71% | LC-MS (ESI POS): 578.04 MH+<br>$[\alpha]_D^{25}$ = +65.8 (c 0.0900, MeOH)<br>$^1$H NMR (300 MHz, DMSO-d$_6$) ppm 7.19-7.33 (m, 2 H), 7.10-7.19 (m, 2 H), 6.97 (ddd, 1 H), 6.28 (dd, 1 H), 6.08 (s, 1 H), 5.53-5.78 (m, 1 H), 5.52 (dd, 1 H), 4.95 (t, 1 H), 4.46 (dd, 1 H), 4.29 (dd, 1 H), 4.18-4.26 (m, 1 H), 4.17 (t, 1 H), 3.47-3.75 (m, 1 H), 2.63 (dd, 1 H), 2.55-2.70 (m, 1 H), 1.98-2.37 (m, 3 H), 1.60-1.88 (m, 2 H), 1.51-1.60 (m, 2 H), 1.49 (s, 3 H), 0.90 (s, 3 H) |
| 153 | 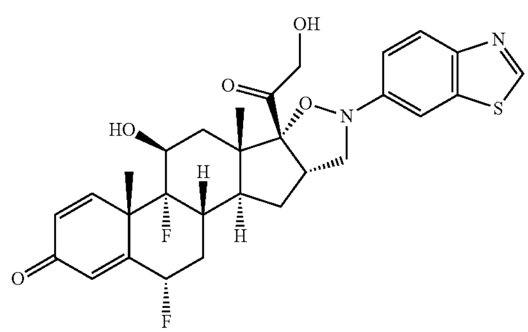 | 46% | LC-MS (ESI POS): 557.1 MH+<br>$[\alpha]_D^{25}$ = +71.16 (c 0.6, MeOH)<br>$^1$H NMR (300 MHz, DMSO-d$_6$) ppm 9.21 (s, 1 H), 7.98 (d, 1 H), 7.75 (d, 1 H), 7.26 (dd, 1 H), 7.21 (dd, 1 H), 6.28 (dd, 1 H), 6.07 (s, 1 H), 5.54-5.77 (m, 1 H), 5.52 (dd, 1 H), 4.95 (t, 1 H), 4.55 (dd, 1 H), 4.33 (dd, 1 H), 4.20-4.27 (m, 1 H), 4.22 (t, 1 H), 3.51-3.79 (m, 1 H), 2.69 (dd, 1 H), 2.54-2.65 (m, 1 H), 2.02-2.31 (m, 3 H), 1.64-1.89 (m, 2 H), 1.52-1.63 (m, 2 H), 1.50 (s, 3 H), 0.92 (s, 3 H) |
| 154 | 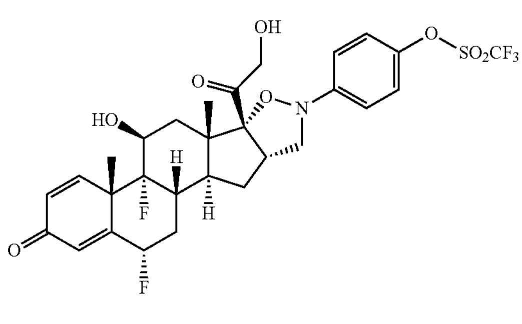 | 82% | LC-MS (ESI POS): 647.97 MH+<br>$[\alpha]_D^{25}$ = +56.0 (c 0.24, MeOH)<br>$^1$H NMR (300 MHz, DMSO-d$_6$) ppm 7.31-7.52 (m, 2H), 7.26 (dd, 1 H), 6.95-7.18 (m, 2 H), 6.28 (dd, 1 H), 6.08 (s, 1 H), 5.44-5.77 (m, 1 H), 5.52 (dd, 1 H), 4.95 (t, 1 H), 4.48 (dd, 1 H), 4.29 (dd, 1 H), 4.11-4.24 (m, 1 H), 4.18 (t, 1 H), 3.62 (q, 1 H), 2.55-2.72 (m, 2 H), 1.98-2.30 (m, 3 H), 1.44-1.83 (m, 4 H), 1.49 (s, 3 H), 0.91 (s, 3 H) |

TABLE 7-continued

| Compound | Structure | Yield | Analytical |
|---|---|---|---|
| 155 | 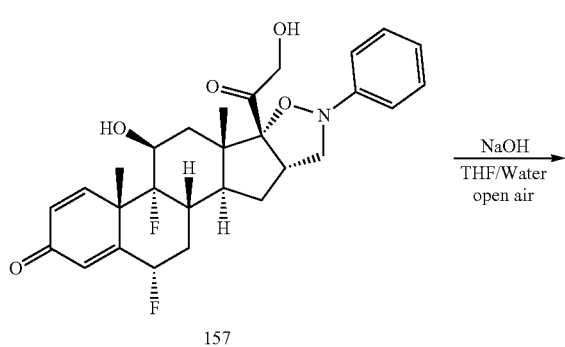 | 19% | LC-MS (ESI POS): 540.1 MH+<br>$[\alpha]_D^{25}$ = +43.6 (c 0.3; MeOH)<br>$^1$H NMR (300 MHz, DMSO-d$_6$) ppm 7.26 (dd, 1 H), 7.14 (t, 1 H), 6.75 (ddd, 1 H), 6.55-6.70 (m, 2 H), 6.28 (dd, 1 H), 6.08 (s, 1 H), 5.54-5.79 (m, 1 H), 5.51 (dd, 1 H), 4.91 (t, 1 H), 4.50 (dd, 1 H), 4.28 (dd, 1 H), 4.17-4.23 (m, 1 H), 4.11 (t, 1 H), 3.49-3.66 (m, 1 H), 2.60-2.69 (m, 1 H), 2.56 (dd, 1 H), 2.00-2.25 (m, 3 H), 1.88 (tt, 1 H), 1.61-1.81 (m, 2 H), 1.51-1.59 (m, 2 H), 1.50 (s, 3 H), 0.91-0.97 (m, 2 H), 0.90 (s, 3 H), 0.49-0.71 (m, 2 H) |
| 156 | 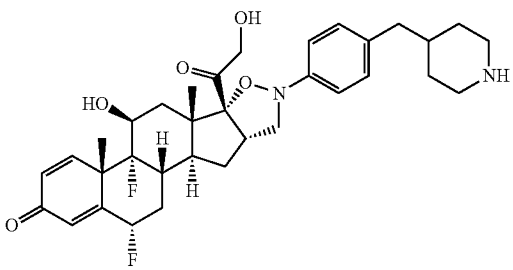 | 21% | LC-MS (ESI POS): 597.16 MH+<br>$[\alpha]_D^{25}$ = +54.6 (c 0.29 MeOH)<br>$^1$H NMR (300 MHz, DMSO-d$_6$) ppm 7.26 (d, 1 H), 7.05 (m, 2 H), 6.88 (m, 2 H), 6.28 (dd, 1 H), 6.08 (s, 1 H), 5.37-5.82 (m, 1 H), 5.51 (br. s., 1 H), 4.74-5.03 (m, 1 H), 4.51 (dd, 1 H), 4.21 (m, 1 H), 4.27 (dd, 1 H), 4.07 (t, 1 H), 3.57 (q, 1 H), 2.77-2.98 (m, 2 H), 2.56-2.70 (m, 2 H), 2.13-2.43 (m, 7 H), 2.03-2.12 (m, 1 H), 1.59-1.87 (m, 2 H), 1.38-1.59 (m, 5 H), 1.49 (s, 3 H), 0.80-1.08 (m, 2 H), 0.90 (s, 3 H) |

Example 16. Preparation of (4aS,4bR,5S,6aS,6bR,9aS,10aS,10bS,12S)-4b,12-Difluoro-5-hydroxy-4a,6a-dimethyl-2-oxo-8-phenyl-2,4a,4b,5,6,6a,8,9,9a,10,10a,10b,11,12-tetradecahydro-7-oxa-8-azapentaleno[2,1-a]phenanthrene-6b-carboxylic acid (compound 158)

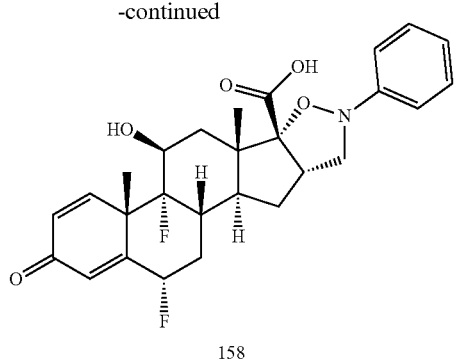

157 →(NaOH, THF/Water, open air)→ 158

To a solution of 157 (733 mg, 1.461 mmol) in tetrahydrofuran (12 ml), at 0° C., air was bubbled for 15 minutes; then, 6 N sodium hydroxide (0.974 ml, 5.85 mmol) was slowly dropped, and air was bubbled for further 5 minutes at 0° C. The reaction mixture was left to warm up to RT and it was stirred at RT overnight. The reaction mixture was acidified to pH 1 and tetrahydrofuran was evaporated. The aqueous layer was extracted with AcOEt (100 ml×3). The combined organic extracts were washed with brine, dried (Na$_2$SO$_4$) and concentrated. The crude was purified by silica gel flash chromatography in DCM/AcOEt/HCO2H 39.5:0.5:50, affording 396 mg of the title compound (56%).

LC-MS (ESI POS): 486.1 (MH+)

Compounds in Table 8 were prepared as previously described for compound 58 158:

TABLE 8

| Compound | Structure | Yield | Analytical |
|---|---|---|---|
| 159 | 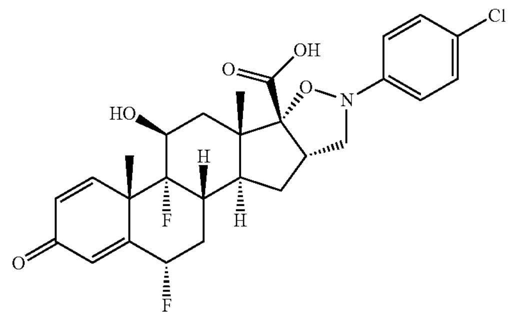 | 90% | LC_MS (ESI POS): 519.9 (MH+) |
| 160 | 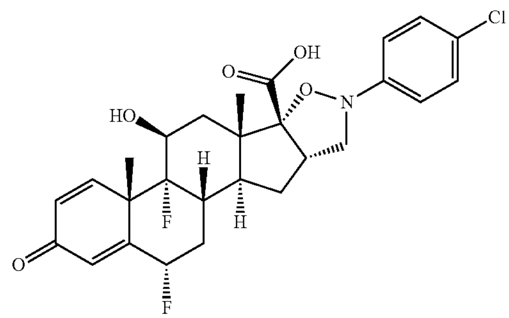 | 60% | LC_MS (ESI POS): 520.0 (MH+) |
| 161 | 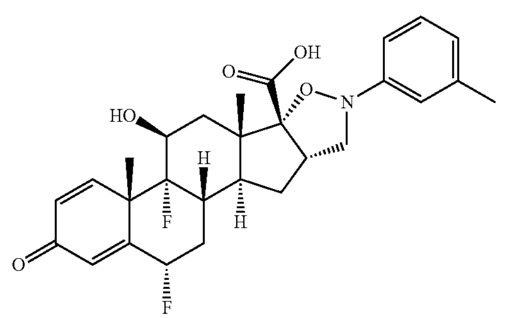 | 53% | LC_MS (ESI POS): 500.1 (MH+) |
| 162 | 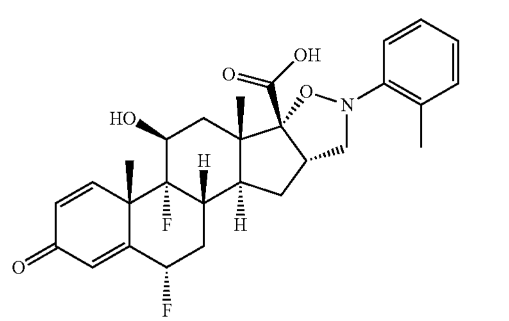 | 97% | LC_MS (ESI POS): 500.1 (MH+) |

TABLE 8-continued

| Compound | Structure | Yield | Analytical |
|---|---|---|---|
| 163 | 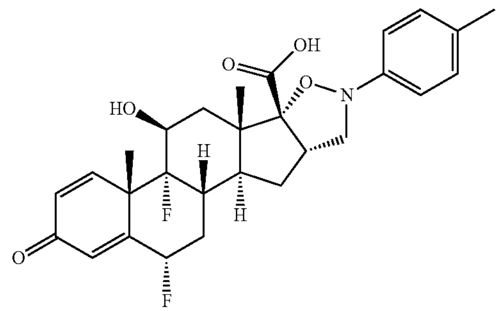 | 16% | LC_MS (ESI POS): 500.2 (MH+) |
| 164 | 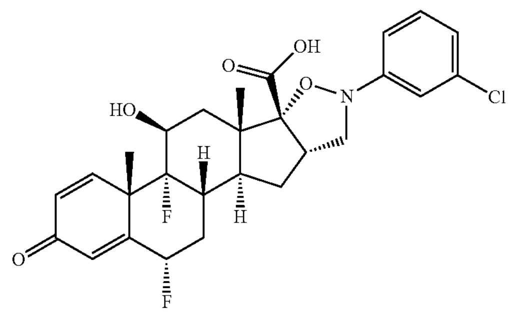 | 84% | LC_MS (ESI POS): 520.0 (MH+) |
| 165 | 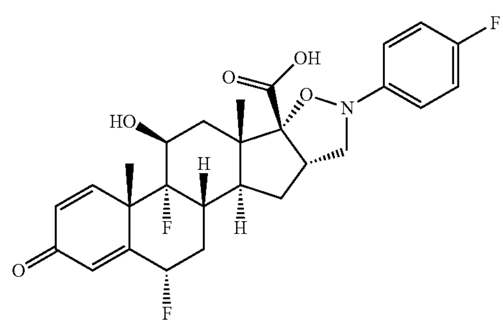 | 93% | LC_MS (ESI POS): 504.1 (MH+) |
| 166 | 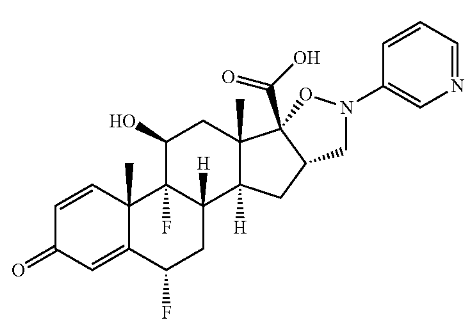 | Used as crude | LC_MS (ESI POS): 487.0 (MH+) |

TABLE 8-continued

| Compound | Structure | Yield | Analytical |
|---|---|---|---|
| 167 | 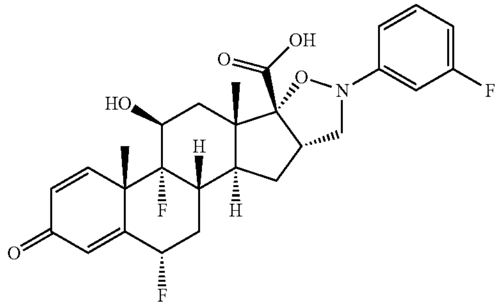 | 93% | LC_MS (ESI POS): 504.1 (MH+) |
| 168 | 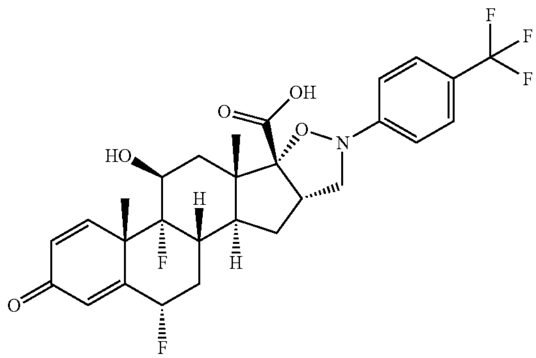 | 46% | LC_MS (ESI POS): 534.1 (MH+) |

Example 17. Preparation of (4aS,4bR,5S,6aS,6bR,9aS,10aS,10bS,12S)-4b,12-Difluoro-5-hydroxy-4a,6a-dimethyl-2-oxo-8-phenyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester (compound 169)

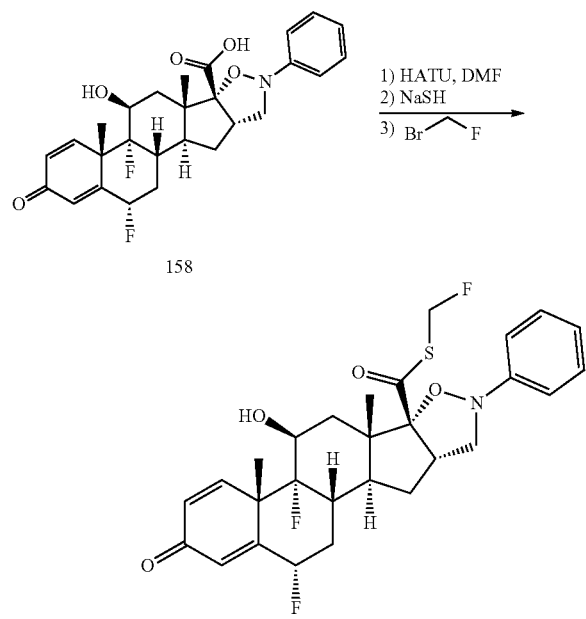

A mixture of compound 158 (396 mg, 0.816 mmol), HATU (341 mg, 0.897 mmol) and N-methylmorpholine (90 µl, 0.816 mmol) in thy DMF (5 ml) was stirred under nitrogen atmosphere at 70° C. for 4 hours, and LC-MS showed the formation of the desired activated ester. The solution was cooled to RT, and anhydrous sodium hydrogen sulfide (137 mg, 2.447 mmol) was added. The mixture was stirred at RT for 25 minutes, then 2 M solution of bromofluoromethane (1.223 ml, 2.447 mmol) in DMF was added and the mixture was stirred at RT for 2 hours overnight. Water (20 ml) was added to the reaction mixture, and the formed precipitate was filtered. The collected precipitate was purified by flash chromatography on silica gel in gradient elution from AcOEt/DCM 5:95 to AcOEt/DCM 10:90 and then preparative HPLC to afford 39 mg of the title compound (9% yield).

$^1$H NMR (300 MHz, DMSO-$d_6$) ppm 7.27-7.36 (m, 2H), 7.24 (dd, 1H), 6.93-7.09 (m, 3H), 6.28 (dd, 1H), 6.08 (s, 1H), 5.92 (dd, 1H), 5.84 (dd, 1H), 5.56 (dd, 1H), 5.47-5.74 (m, 1H), 4.22 (t, 1H), 4.14-4.23 (m, 1H), 3.59 (q, 1H), 2.64 (dd, 1H), 2.54-2.71 (m, 1H), 2.07-2.33 (m, 2H), 1.94-2.07 (m, 1H), 1.84 (d, 1H), 1.68-1.80 (m, 1H), 1.52-1.66 (m, 2H), 1.50 (s, 3H), 0.98 (s, 3H)

LC-MS (ESI POS): 534.17 (MH+)

$[\alpha]_D^{25}$=+87.4 (c 0.114; CHCl$_3$)

Compounds in Table 9 were prepared as previously described for compound 169, starting from the suitable acid derivative:

TABLE 9

| Compound | Structure | Yield | Analytical |
|---|---|---|---|
| 170 | 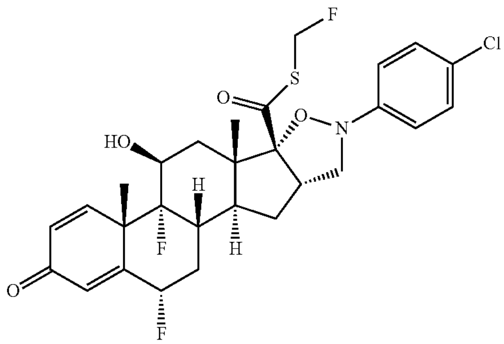 | 42% | LC-MS (ESI POS): 568.09 MH+<br>$[\alpha]_D^{25}$ = +55.80 (c 0.157; CHCl$_3$)<br>$^1$H NMR (300 MHz, DMSO-d$_6$) ppm 7.29-7.43 (m, 2 H), 7.24 (dd, 1 H), 6.89-7.11 m, 2 H), 6.28 (dd, 1 H), 6.09 (s, 1 H), 5.92 (dd, 1 H), 5.84 (dd, 1 H), 5.54-5.62 (m, 1 H), 5.47-5.74 (m, 1 H), 4.04-4.34 (m, 2 H), 3.50-3.68 (m, 1 H), 2.65 (t, 2 H), 2.05-2.31 (m, 2 H), 1.92-2.05 (m, 1 H), 1.68-1.89 (m, 2 H), 1.52-1.66 (m, 2 H), 1.49 (s, 3 H), 0.98 (s, 3 H) |
| 171 | 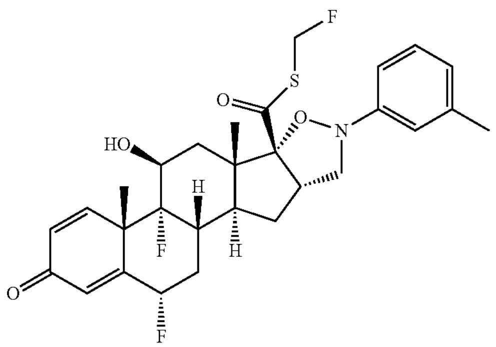 | 50% | LC-MS (ESI POS): 548.23 MH+<br>$[\alpha]_D^{25}$ = +64.0 (c 0.24, CHCl$_3$)<br>$^1$H NMR (300 MHz, DMSO-d$_6$) ppm 7.24 (dd, 1 H), 7.17 (t, 1 H), 6.74-6.89 (m, 3 H), 6.28 (dd, 1 H), 6.08 (s, 1 H), 5.92 (dd, 1 H), 5.84 (dd, 1 H), 5.56 (dd, 1 H), 5.46-5.74 (m, 1 H) 4.17-4.29 (m, 1 H), 4.19 (t, 1 H), 3.58 (q, 1 H), 2.55-2.67 (m, 2 H), 2.27 (s, 3 H), 1.95-2.25 (m, 3 H), 1.83 (d, 1 H), 1.68-1.79 (m, 1 H), 1.52-1.66 (m, 2 H), 1.49 (s, 3 H), 0.98 (s, 3 H) |
| 172 | 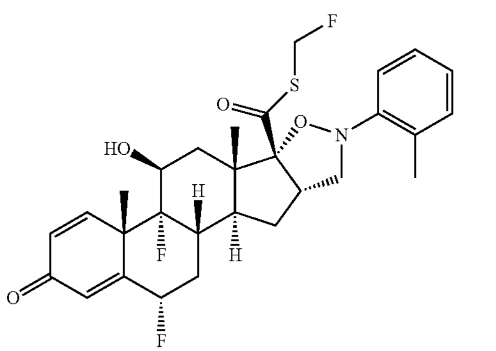 | 37% | LC-MS (ESI POS): 547.91 MH+<br>$[\alpha]_D^{25}$ = +77.1 (c 0.2 dmso)<br>$^1$H NMR (300 MHz, DMSO-d$_6$) ppm 7.35 (dd, 1 H) 7.27 (dd, 1 H), 7.17-7.24 (m, 1 H), 7.12-7.17 (m, 1 H), 7.07 (td, 1 H), 6.31 (dd, 1 H), 6.09-6.19 (m, 1 H), 5.90 (dd, 1 H), 5.81 (dd, 1 H), 5.57-5.79 (m, 1 H), 5.56 (dd, 1 H), 4.15-4.35 (m, 1 H), 3.92 (t, 1 H), 3.54-3.66 (m, 1 H), 2.22-2.47 (m, 4 H), 2.16 (s, 3 H), 1.95-2.10 (m, 1 H), 1.55-1.87 (m, 4 H), 1.51 (s, 3 H), 0.98 (s, 3 H) |
| 173 | 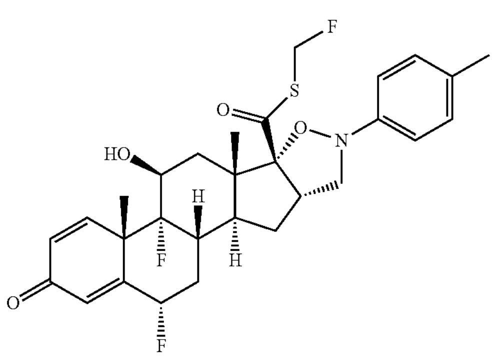 | 14% | LC-MS (ESI POS): 548.11 MH+<br>$[\alpha]_D^{25}$ = +66.4 (c 0.103, CHCl$_3$)<br>$^1$H NMR (300 MHz, DMSO-d$_6$) ppm 7.24 (dd, 1 H), 7.04-7.16 (m, 2 H), 6.82-7.02 (m, 2 H), 6.28 (dd, 1 H), 6.08 (s, 1 H), 5.92 (dd, 1 H), 5.84 (dd, 1 H), 5.55 (dd, 1 H), 5.49-5.73 (m, 1 H), 4.17-4.29 (m, 1 H), 4.16 (t, 1 H), 3.58 (q, 1 H), 2.62-2.79 (m, 1 H), 2.53-2.62 (m, 1 H), 2.23 (s, 3 H), 1.93-2.22 (m, 3 H), 1.67-1.88 (m, 2 H), 1.50-1.66 (m, 2 H), 1.49 (s, 3 H), 0.97 (s, 3 H) |

TABLE 9-continued

| Compound | Structure | Yield | Analytical |
|---|---|---|---|
| 174 | 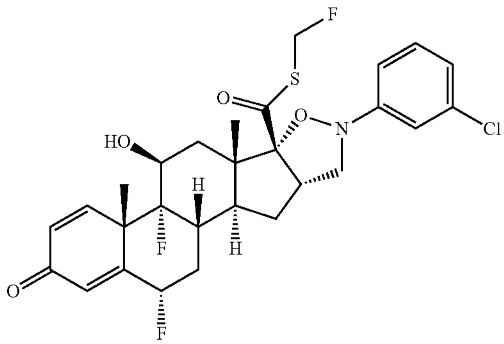 | 29% | LC-MS (ESI POS): 568.07 MH+<br>$[\alpha]_D^{25}$ = +55.0 (c 0.2, CHCl$_3$)<br>$^1$H NMR (300 MHz, DMSO-d$_6$) ppm 7.33 (t, 1 H), 7.24 (dd, 1 H), 7.01-7.09 (m, 2 H), 6.97 (ddd, 1 H), 6.28 (dd, 1 H), 6.07-6.12 (m, 1 H), 5.92 (dd, 1 H), 5.85 (dd, 1 H), 5.57 (dd, 1 H), 5.48-5.72 (m, 1 H), 4.27 (t, 1 H), 4.14-4.25 (m, 1 H), 3.48-3.68 (m, 1 H), 2.56-2.71 (m, 2 H), 1.94-2.24 (m, 4 H), 1.52-1.93 (m, 3 H), 1.49 (s, 3 H), 0.98 (s, 3 H) |
| 175 | 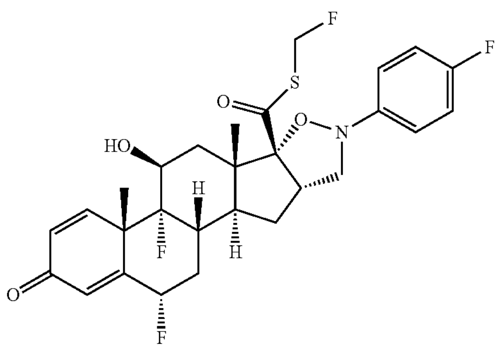 | 24% | LC-MS (ESI POS): 552.15 MH+<br>$[\alpha]_D^{25}$ = +76.56 (c 0.25, MeOH)<br>$^1$H NMR (300 MHz, DMSO-d$_6$) ppm 7.24 (dd, 1 H), 7.10-7.20 (m, 2 H), 7.00-7.10 (m, 2 H), 6.28 (dd, 1 H), 6.08 (s, 1 H), 5.93 (dd, 1 H), 5.85 (dd, 1 H), 5.56 (dd, 1 H), 5.41-5.73 (m, 1 H), 4.11-4.31 (m, 2 H), 3.52-3.69 (m, 1 H), 2.57-2.72 (m, 2 H), 2.06-2.34 (m, 2 H), 1.93-2.05 (m, 1 H), 1.67-1.89 (m, 2 H), 1.52-1.67 (m, 2 H), 1.49 (s, 3 H), 0.98 (s, 3 H) |
| 176 | 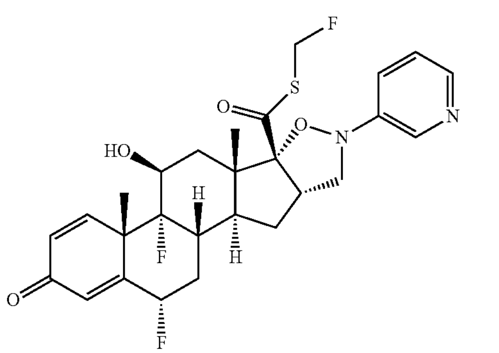 | 12% | LC-MS (ESI POS): 535.1 MH+<br>$[\alpha]_D^{25}$ = +29.84 (c 0.0925; MeOH)<br>$^1$H NMR (300 MHz, DMSO-d$_6$) ppm 8.33 (d, 1 H), 8.24 (dd, 1 H), 7.42 (ddd, 1 H), 7.35 (dd, 1 H), 7.24 (dd, 1 H), 6.28 (dd, 1 H), 6.08 (s, 1 H), 5.93 (dd, 1 H), 5.85 (dd, 1 H), 5.55-5.60 (m, 1 H), 5.47-5.75 (m, 1 H), 4.30 (t, 1 H), 4.10-4.25 (m, 1 H), 3.55-3.71 (m, 1 H), 2.66-2.78 (m, 1 H), 2.59-2.66 (m, 1 H), 2.02-2.35 (m, 3 H), 1.52-1.90 (m, 4 H), 1.50 (s, 3 H), 0.99 (s, 3 H) |
| 177 | 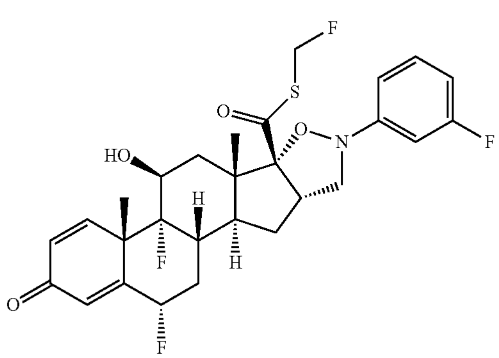 | 24% | LC-MS (ESI POS): 552.11 MH+<br>$[\alpha]_D^{25}$ = +68.31 (c 0.26, DCM)<br>$^1$H NMR (300 MHz, DMSO-d$_6$) ppm 7.29-7.49 (m, 1 H), 7.24 (dd, 1 H), 6.69-6.91 (m, 3 H), 6.28 (dd, 1 H), 6.09 (s, 1 H), 5.92 (dd, 1 H), 5.85 (dd, 1 H), 5.57 (dd, 1 H), 5.49-5.74 (m, 1 H), 4.25 (t, 1 H), 4.14-4.22 (m, 1 H), 3.50-3.67 (m, 1 H), 2.57-2.81 (m, 2 H), 2.07-2.34 (m, 2 H), 1.95-2.07 (m, 1 H), 1.68-1.92 (m, 2 H), 1.53-1.68 (m, 2 H), 1.50 (s, 3 H), 0.98 (s, 3 H) |

TABLE 9-continued

| Compound | Structure | Yield | Analytical |
|---|---|---|---|
| 178 | 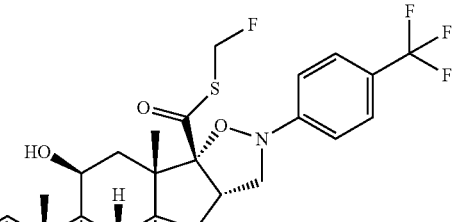 | 35% | LC-MS (ESI POS): 602.21 MH+<br>$[\alpha]_D^{25}$ = +42.6 (c 0.2, MeOH)<br>$^1$H NMR (300 MHz, DMSO-$d_6$) ppm 7.53-7.84 (m, 2 H), 7.24 (dd, 1 H), 7.08-7.21 (m, 2 H), 6.28 (dd, 1 H), 6.08 (s, 1 H), 5.92 (dd, 1 H), 5.85 (dd, 1 H), 5.58 (dd, 1 H), 5.42-5.74 (m, 1 H), 4.35 (t, 1 H), 4.07-4.29 (m, 1 H), 3.50-3.76 (m, 1 H), 2.59-2.86 (m, 2 H), 1.96-2.35 (m, 3 H), 1.69-1.94 (m, 2 H), 1.53-1.69 (m, 2 H), 1.50 (s, 3 H), 1.00 (s, 3 H) |

Example 18. Preparation of (4aS,4bR,5S,6aS,6bR,9aS,10aS,10bS,12S)-4b,12-Difluoro-6b-(2-fluoroacetyl)-5-hydroxy-4a,6a-dimethyl-8-phenyl-4a,4b,5,6,6a,6b,8,9,9a,10,10a,10b,11,12-tetradecahydro-7-oxa-8-aza-pentaleno[2,1-a]phenanthren-2-one (compound 179)

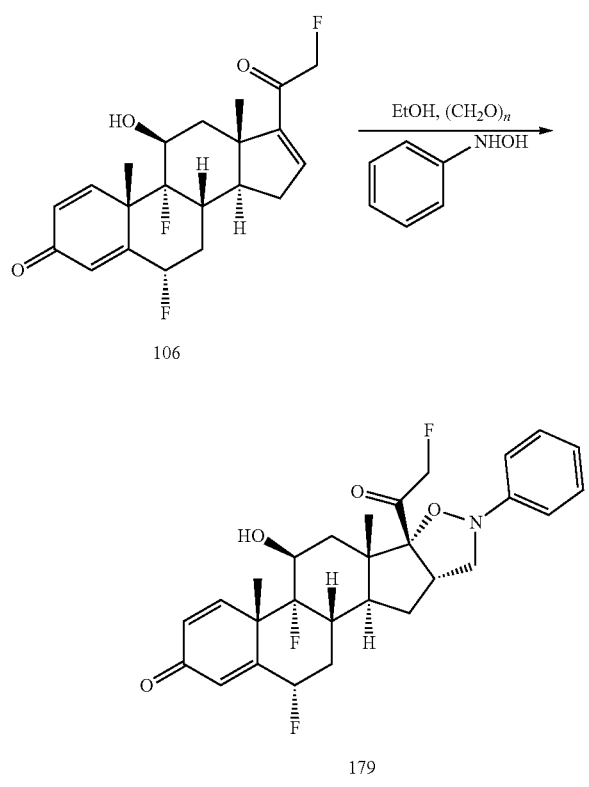

A mixture of 106 (150 mg, 0.394 mmol), N-phenyl hydroxylamine (86 mg, 0.789 mmol), and paraformaldehyde (71.0 mg, 2.366 mmol) in ethanol (13 ml) was stirred at 100° C. for 20 hours. N-phenyl hydroxylamine (47.3 mg, 0.434 mmol) and paraformaldehyde (52.1 mg, 1.735 mmol) were further added, and the mixture was heated at 100° C. for 3 hours. The solvent was evaporated, and the residue was purified by silica gel flash chromatography in gradient elution from AcOEt/MeOH/DCM 4.8:0.2:95, to AcOEt/MeOH/DCM 9.8:0.2:90, affording 144 mg of desired compound (Rf=0.22 in AcOEt/MeOH/DCM 9.8:0.2:90). The compound was further purified by silica gel flash chromatography in gradient elution from DCM, to DCM/AcOEt 87:13 to afford 122 mg of the title compound (62% yield).

$^1$H NMR (300 MHz, DMSO-$d_6$) ppm 7.27-7.34 (m, 2H), 7.27 (dd, 1H), 6.93-7.07 (m, 3H), 6.28 (dd, 1H), 6.08 (s, 1H), 5.52 (d, 1H), 5.49-5.74 (m, 1H), 5.37 (dd, 1H), 5.30 (dd, 1H), 4.17-4.27 (m, 1H), 4.19 (t, 1H), 3.56 (q, 1H), 2.60-2.71 (m, 1H), 2.59 (dd, 1H), 2.11-2.32 (m, 2H), 2.07 (ddd, 1H), 1.80 (d, 1H), 1.63-1.77 (m, 1H), 1.51-1.62 (m, 2H), 1.50 (s, 3H), 0.95 (s, 3H)

LC-MS (ESI POS): 502.15 MH+
$[\alpha]_D^{25}$=+68.72 (c 0.094; CHCl$_3$)

The compounds listed in Table 10 were prepared as previously described for compound 179, by cycloaddition of intermediate 106 with suitable hydroxylamine or hydroxylamine hydrochloride.

TABLE 10

| Compound | Structure | Yield | Analytical |
|---|---|---|---|
| 180 | 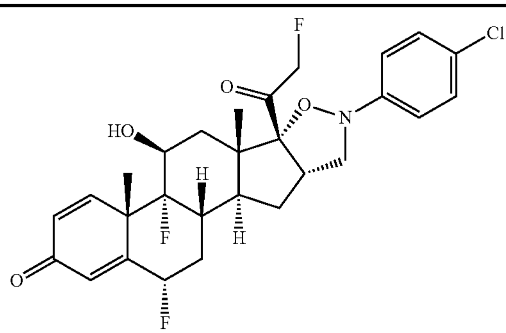 | 65% | LC-MS (ESI POS): 536.07 MH+<br>$[\alpha]_D^{25}$ = +50.85 (c 0.0885; CHCl$_3$)<br>$^1$H NMR (300 MHz, DMSO-d$_6$) ppm 7.30-7.43 (m, 2 H), 7.26 (dd, 1 H), 6.93 - 7.08 (m, 2 H), 6.28 (dd, 1 H), 6.08 (s, 1 H), 5.52 (d, 1 H) 5.47-5.80 (m, 1 H), 5.36 (dd, 1 H), 5.29 (dd, 1 H), 4.14-4.25 (m, 1 H), 4.19 (t, 1 H), 3.44-3.65 (m, 1 H), 2.58-2.73 (m, 1 H), 2.60 (dd, 1 H), 1.97-2.30 (m, 3 H), 1.63-1.87 (m, 2 H), 1.51-1.61 (m, 2 H), 1.49 (s, 3 H), 0.94 (s, 3 H) |

Example 20. Preparation of Methanesulfonic acid 2-[(4aS,4bR,5S,6aS,6bR,9aS,10aS,10b S,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester (compound 181)

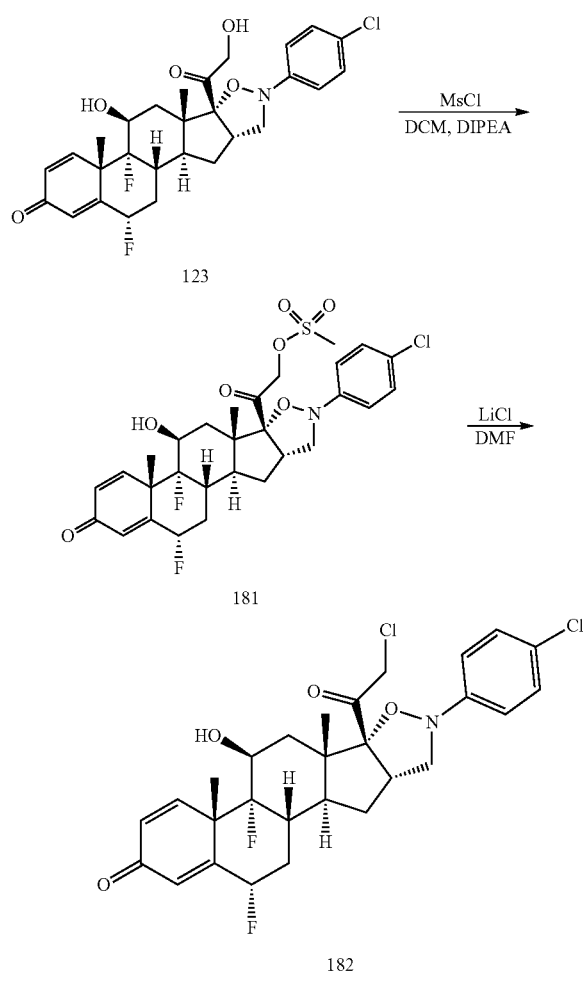

Methanesulfonyl chloride (79 µL, 1.011 mmol) was added at 0° C. under nitrogen atmosphere to a solution of 123 (450 mg, 0.843 mmol) and DIPEA (221 µL, 1.264 mmol) in DCM (dried over CaCl$_2$, 20 ml). The mixture was stirred at RT for 2 hours. The mixture was diluted with DCM, and washed with 2.5% aqueous NaHCO$_3$. The aqueous phase was extracted with DCM, and the combined organics were washed with brine, dried over Na$_2$SO$_4$ and filtered. The solvent was evaporated.

LC-MS (ESI POS): 612.2 (MH+)

Preparation of (4aS,4bR,5S,6aS,6bR,9aS,10aS,10bS,12S)-6b-(2-Chloro-acetyl)-8-(4-chloro-phenyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one (compound 182)

A mixture of compound 181 (195 mg, 0.319 mmol) and lithium chloride (162 mg, 3.82 mmol) in dry DMF (6 ml) was stirred under nitrogen at 70° C. for 2 hours. The mixture was partitioned between AcOEt and brine, and then the aqueous phase was extracted with AcOEt. The combined organics were washed with brine, dried over Na$_2$SO$_4$ and filtered. The solvent was evaporated and the crude was purified by silica gel flash chromatography (eluent:DCM:MeOH 99:1). A solid was obtained, which was triturated with Et$_2$O/EtOH (95:5) to give the title compound (33% yield).

$^1$H NMR (300 MHz, DMSO-d$_6$) ppm 7.30-7.41 (m, 2H), 7.27 (dd, 1H), 6.95-7.12 (m, 2H), 6.29 (dd, 1H), 6.08 (s, 1H), 5.33-5.80 (m, 1H), 5.52 (d, 1H), 4.70 (s, 2H), 3.96-4.33 (m, 2H), 3.60 (q, 1H), 2.55-2.70 (m, 2H), 2.00-2.36 (m, 3H), 1.83 (d, 1H), 1.63-1.78 (m, 1H), 1.28-1.63 (m, 2H), 1.49 (s, 3H), 0.92 (s, 3H)

LC-MS (ESI POS): 552.21 (MH+)

$[\alpha]_D^{25}$=+81.85 (c 0.26, CHCl$_3$)

Example 21. Preparation of (4aS,4bR,5S,6aS,6bR, 9aS,10aS,10bS,12S)-8-(4-Chloro-phenyl)-4b,12-difluoro-5-hydroxy-4a,6a-dimethyl-6b-(2-methylsulfanyl-acetyl)-4a,4b,5,6,6a,6b,8,9,9a,10,10a,10b,11,12-tetradecahydro-7-oxa-8-aza-pentaleno[2,1-a]phenanthren-2-one (compound 183)

Example 22. Preparation of (4aS,4bR,5S,6aS,6bR, 9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid chloromethyl thioester (compound 184)

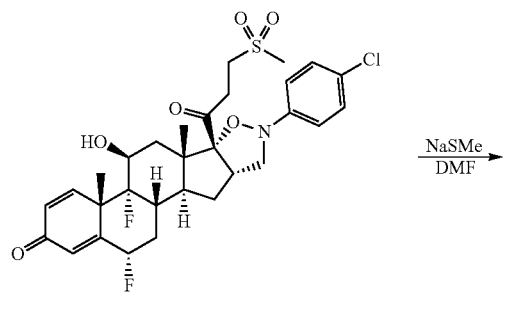

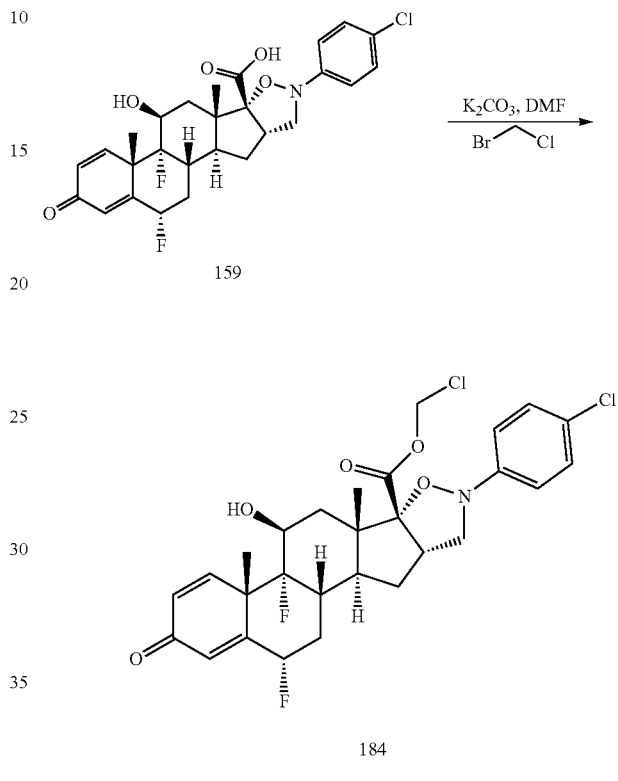

A mixture of compound 181 (175 mg, 0.286 mmol) and sodium methanethiolate (24.05 mg, 0.343 mmol) in DMF dry (4 ml) was stirred at RT under nitrogen atmosphere for 3 hours. The mixture was partitioned between AcOEt and brine, and the aqueous phase was extracted with AcOEt. The combined organics were washed with brine, dried over $Na_2SO_4$ and filtered. The solvent was evaporated, and the residue was triturated with acetonitrile. The obtained crude was purified by silica gel flash chromatography (DCM:MeOH 99:1) and then it was triturated with $Et_2O$ to afford the desired compound (16% yield).

$^1$H NMR (300 MHz, DMSO-$d_6$) ppm 7.29-7.48 (m, 2H), 7.26 (dd, 1H), 6.89-7.10 (m, 2H), 6.29 (dd, 1H), 6.08 (s, 1H), 5.53-5.78 (m, 1H), 5.51 (dd, 1H), 4.17-4.30 (m, 1H), 4.13 (t, 1H), 3.70 (d, 1H), 3.62 (d, 1H), 3.54-3.63 (m, 1H), 2.61 (dd, 1H), 2.55-2.71 (m, 1H), 2.06-2.25 (m, 3H), 2.04 (s, 3H), 1.88 (d, 1H), 1.63-1.81 (m, 1H), 1.51-1.62 (m, 2H), 1.50 (s, 3H), 0.93 (s, 3H)

LC-MS (ESI POS): 564.24 (MH+)

$[\alpha]_D^{25}$=+85.92 (c 0.24, $CHCl_3$)

Compound 159 was dissolved in DMF (4 ml) under a nitrogen atmosphere; potassium carbonate (106 mg, 0.769 mmol) and bromochloromethane (0.125 ml, 1.923 mmol) were added, and the mixture was stirred at room temperature for 4 hours. The reaction mixture was partitioned between water and AcOEt. The organic phase was separated, and the solvent was removed. The crude was purified by silica gel flash chromatography (eluent DCM/AcOEt 95/5 to 9/1) affording a solid that was further triturated in $Et_2O$, affording the title compound (23% yield).

$^1$H NMR (300 MHz, DMSO-$d_6$) ppm 7.28-7.35 (m, 2H), 7.25 (dd, 1H), 6.83-7.04 (m, 2H), 6.29 (dd, 1H), 6.09 (s, 1H), 5.95 (d, 1H), 5.93 (d, 1H), 5.61 (dd, 1H), 5.47-5.78 (m, 1H), 4.20-4.35 (m, 1H), 4.16 (t, 1H), 3.63-3.81 (m, 1H), 2.77 (dd, 1H), 2.61-2.72 (m, 1H), 1.96-2.26 (m, 3H), 1.68-1.93 (m, 2H), 1.52-1.62 (m, 2H), 1.50 (s, 3H), 1.02 (s, 3H)

LC-MS (ESI POS): 568.17 (MH+)

$[\alpha]_D^{25}$=+56.2 (c 0.3, MeOH)

The compounds in Table 12 were prepared as previously described for compound 184, starting from acid 159, the suitable alkylating agent and a base such as $Na_2CO_3$, $K_2CO_3$ or triethylamine with the suitable solvent:

TABLE 12

| Compound | Structure | Yield | Analytical |
|---|---|---|---|
| 185 | 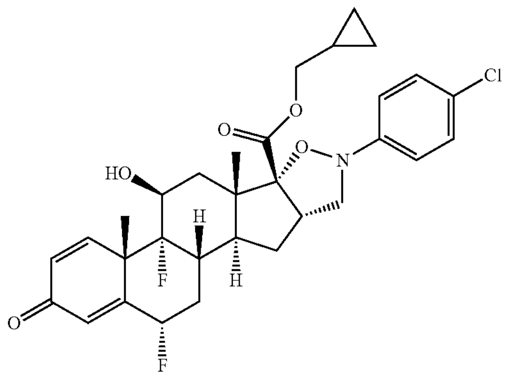 | 33% | LC-MS (ESI POS): 574.3 MH+<br>$[\alpha]_D^{25}$ = +59.5 (c 0.2, MeOH)<br>$^1$H NMR (300 MHz, DMSO-d$_6$) ppm 7.26-7.33 (m, 2 H), 7.26 (dd, 1 H), 6.89-7.01 (m, 2 H), 6.29 (dd, 1 H), 6.09 (s, 1 H), 5.55 (d, 1 H), 5.48-5.77 (m, 1 H), 4.16-4.34 (m, 1 H), 4.11 (t, 1 H), 3.95 (dd, 1 H), 3.87 (dd, 1 H), 3.60-3.75 (m, 1 H), 2.81 (dd, 1 H), 2.55-2.71 (m, 1 H), 1.95-2.31 (m, 3 H), 1.82-1.94 (m, 1 H), 1.66-1.82 (m, 1 H), 1.52-1.61 (m, 2 H), 1.50 (s, 3 H), 1.04-1.22 (m, 1 H), 1.00 (s, 3 H), 0.43-0.60 (m, 2 H), 0.20-0.37 (m, 2 H) |
| 186 | 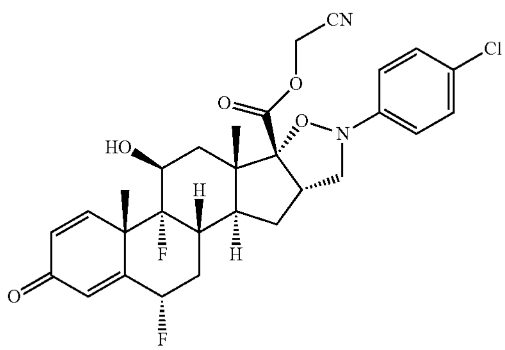 | 25% | LC-MS (ESI POS): 559.14 MH+<br>$[\alpha]_D^{25}$ = +78.96 (c 0.25, DCM)<br>$^1$H NMR (300 MHz, DMSO-d$_6$) ppm 7.28-7.36 (m, 2 H), 7.26 (dd, 1 H), 6.87-7.03 (m, 2 H), 6.29 (dd, 1 H), 6.09 (s, 1 H), 5.61 (dd, 1 H), 5.43-5.78 (m, 1 H), 5.11 (d, 1 H), 5.05 (d, 1 H), 4.19-4.38 (m, 1 H), 4.18 (t, 1 H), 3.66-3.81 (m, 1 H), 2.78 (dd, 1 H), 2.56-2.70 (m, 1 H), 1.96-2.26 (m, 3 H), 1.66-1.88 (m, 2 H), 1.52-1.64 (m, 2 H), 1.50 (s, 3 H), 1.01 (s, 3 H) |
| 187 | 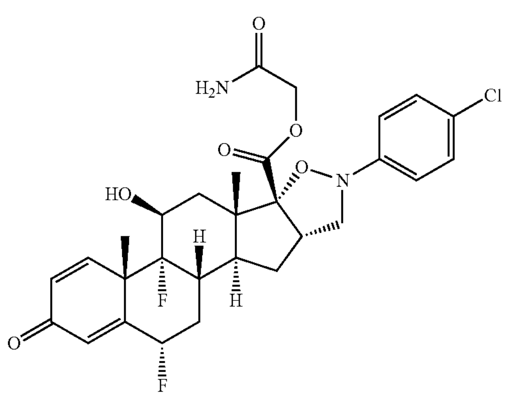 | 24% | LC-MS (ESI POS): 577.13 MH+<br>$[\alpha]_D^{25}$ = +51.0 (c 0.3, MeOH)<br>$^1$H NMR (300 MHz, DMSO-d$_6$) ppm 7.25-7.40 (m, 2 H), 7.23-7.29 (m, 1 H), 7.14-7.23 (m, 2 H), 6.85-7.07 (m, 2 H), 6.29 (dd, 1 H), 6.09 (s, 1 H), 5.47-5.80 (m, 1 H), 5.56 (d, 1 H), 4.46 (s, 2 H), 4.16-4.26 (m, 1 H), 4.11 (t, 1 H), 3.60-3.82 (m, 1 H), 2.82 (dd, 1 H), 2.56-2.69 (m, 1 H), 1.86-2.25 (m, 4 H), 1.65-1.86 (m, 1 H), 1.50 (s, 3 H), 1.33-1.63 (m, 2 H), 1.06 (s, 3 H) |

TABLE 12-continued

| Compound | Structure | Yield | Analytical |
|---|---|---|---|
| 188 | 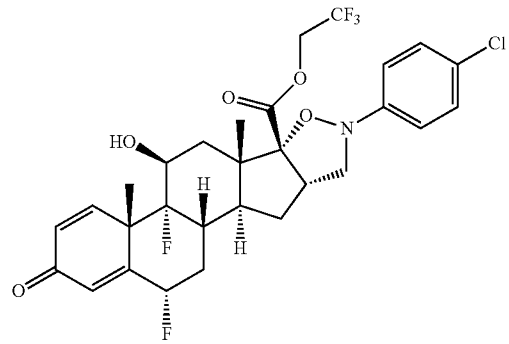 | 20% | LC-MS (ESI POS): 602.26 MH+<br>$[\alpha]_D^{25}$ = +57.6 (c 0.3, MeOH)<br>$^1$H NMR (300 MHz, DMSO-d$_6$) ppm 7.29-7.37 (m, 2 H), 7.26 (dd, 1 H), 6.90-7.03 (m, 2 H), 6.29 (dd, 1 H), 6.09 (s, 1 H), 5.64 (d, 1 H), 5.46-5.81 (m, 1 H), 4.71-4.96 (m, 2 H), 4.18-4.26 (m, 1 H), 4.16 (t, 1 H), 3.50-3.81 (m, 1 H), 2.79 (dd, 1 H), 2.59-2.68 (m, 1 H), 1.94-2.25 (m, 3 H), 1.66-1.85 (m, 2 H), 1.52-1.63 (m, 2 H), 1.50 (s, 3 H), 1.00 (s, 3 H) |
| 189 | 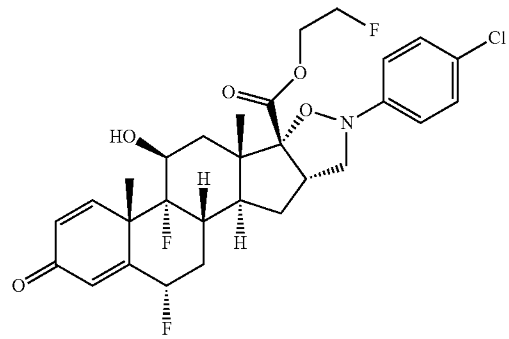 | 38% | LC-MS (ESI POS): 566.18 MH+<br>$[\alpha]_D^{25}$ = +55 (c 0.21, MeOH)<br>$^1$H NMR (300 MHz, DMSO-d$_6$) ppm 7.19-7.37 (m, 3 H), 6.86-7.04 (m, 2 H), 6.29 (dd, 1 H), 6.09 (s, 1 H), 5.56 (dd, 1 H), 5.43-5.81 (m, 1 H), 4.63 (dt, 2 H), 4.02-4.49 (m, 4 H), 3.55-3.76 (m, 1 H), 2.82 (dd, 1 H), 2.55-2.68 (m, 1 H), 1.96-2.35 (m, 3 H), 1.86 (d, 1 H), 1.68-1.81 (m, 1 H), 1.51-1.64 (m, 2 H), 1.50 (s, 3 H), 0.99 (s, 3 H) |

Example 23. Preparation of (4aS,4bR,5S,6aS,6bR,9aS,10aS,10bS,12S)-8-(4-Chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-cyanomethyl ester (compound 190)

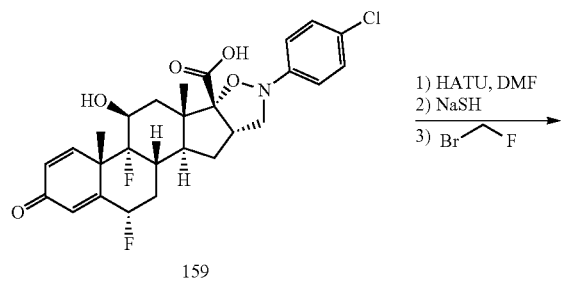

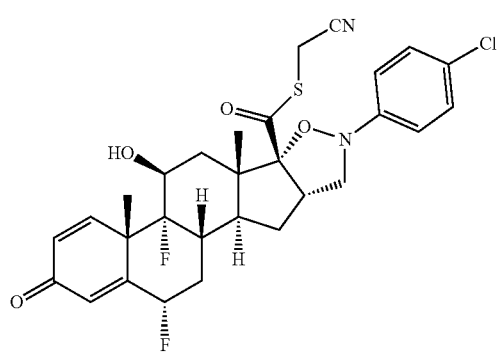

Compound 159 (218 mg, 0.419 mmol) was dissolved in DMF (5 ml) under a nitrogen atmosphere; HATU (175 mg, 0.461 mmol) and 4-methylmorpholine (50.9 mg, 0.503 mmol) were added, and the mixture was stirred at room temperature for 1 hour. Then sodium hydrogensulfide (47.0 mg, 0.839 mmol) was added, and the mixture turned into dark green. The resulting mixture was stirred at RT for 1 hour, 2-bromoacetonitrile (0.117 ml, 1.677 mmol) was added, and the solution was stirred in closed vessel at RT overnight. The reaction mixture was diluted with AcOEt, and the organic layer was washed with water and brine, dried (Na$_2$SO$_4$) and concentrated. The crude was purified by silica gel flash chromatography (eluent DCM/AcOEt 95/5 to 9/1) affording a solid that was further triturated with Et2O, to yield the desired compound (22% yield).

$^1$H NMR (300 MHz, DMSO-d$_6$) ppm 7.32-7.45 (m, 2H), 7.24 (dd, 1H), 6.93-7.10 (m, 2H), 6.28 (dd, 1H), 6.09 (s, 1H), 5.62 (dd, 1H), 5.40-5.79 (m, 1H), 4.24 (t, 1H), 4.15-4.21 (m, 1H), 4.00 (d, 1H), 3.92 (d, 1H), 3.50-3.69 (m, 1H), 2.56-2.71 (m, 2H), 2.04-2.25 (m, 2H), 1.94-2.04 (m, 1H), 1.77-1.87 (m, 1H), 1.69-1.77 (m, 1H), 1.52-1.66 (m, 2H), 1.50 (s, 3H), 1.00 (s, 3H)

LC-MS (ESI POS): 575.21 (MH+)

$[\alpha]_D^{25}$=+31.76 (c 0.25, MeOH)

The compounds in Table 13 were prepared as previously described for compound 190, starting from acid 159 and the suitable alkylating:

TABLE 13

| Compound | Structure | Yield | Analytical |
|---|---|---|---|
| 191 | 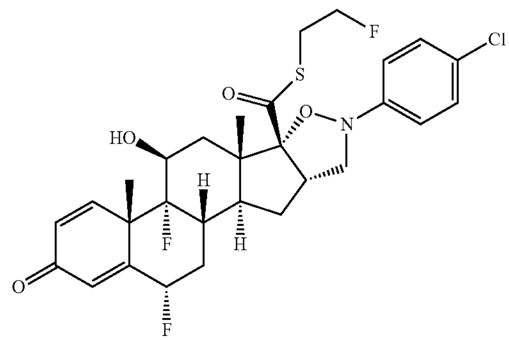 | 18% | LC-MS (ESI POS): 582.25 MH+<br>$[\alpha]_D^{25}$ = +40.00 (c 0.2, MeOH)<br>$^1$H NMR (300 MHz, DMSO-d$_6$) ppm 7.30-7.42 (m, 2 H), 7.24 (dd, 1 H), 6.90-7.12 (m, 2 H), 6.28 (dd, 1 H), 6.00-6.15 (m, 1 H), 5.56 (dd, 1 H), 5.40-5.86 (m, 1 H), 4.49 (m, 2 H), 4.18-4.29 (m, 1 H), 4.20 (t, 1 H), 3.49-3.71 (m, 1 H), 2.97-3.25 (m, 2 H), 2.55-2.70 (m, 2 H), 1.92-2.31 (m, 3 H), 1.80-1.92 (m, 1 H), 1.65-1.80 (m, 1 H), 1.51-1.65 (m, 2H), 1.49 (s, 3H), 0.96 (s, 3H) |
| 192 | 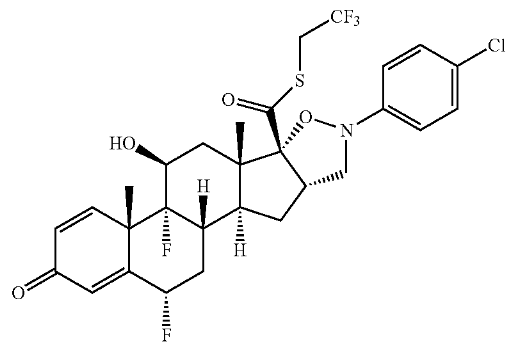 | 29% | LC-MS (ESI POS): 618.18 MH+<br>$[\alpha]_D^{25}$ = +46.50 (c 0.2, MeOH)<br>$^1$H NMR (300 MHz, DMSO-d$_6$) ppm 7.30-7.48 (m, 2 H), 7.23 (dd, 1 H), 6.80-7.12 (m, 2 H), 6.29 (dd, 1 H), 6.08 (s, 1 H), 5.63 (dd, 1 H), 5.46-5.77 (m, 1 H), 4.23 (t, 1 H), 4.12-4.32 (m, 1 H), 3.88 (d, 1 H), 3.81 (d, 1 H), 3.58 (q, 1 H), 2.60-2.71 (m, 2 H), 1.93-2.30 (m, 3 H), 1.67-1.89 (m, 2 H), 1.49 (s, 3 H), 1.33-1.67 (m, 2 H), 0.96 (s, 3 H) |
| 193 | 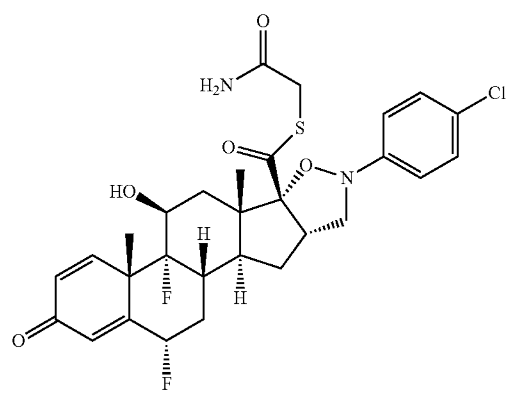 | 15% | LC-MS (ESI POS): 593.3 MH+<br>$[\alpha]_D^{25}$ = +45.10 (c 0.2, DCM)<br>$^1$H NMR (300 MHz, DMSO-d$_6$) ppm 7.48 (br. s., 1 H), 7.35 (d, 2 H), 7.25 (d, 1 H), 7.02 (d, 2 H), 6.90-7.15 (m, 1 H), 6.28 (dd, 1 H), 6.08 (s, 1 H), 5.37-5.79 (m, 0 H), 5.58 (d, 1 H), 4.03-4.34 (m, 2 H), 3.47-3.63 (m, 4 H), 2.63 (d, 3 H), 2.22 (d, 1 H), 2.05-2.16 (m, 1 H), 1.94 (d, 1 H), 1.64-1.84 (m, 1 H), 1.49 (s, 3 H), 1.31-1.64 (m, 2 H), 0.96 (s, 3 H) |
| 194 | 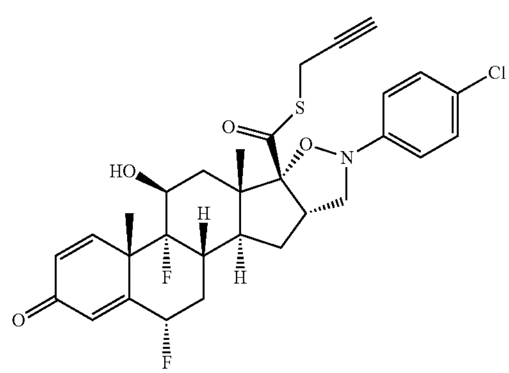 | 28% | LC-MS (ESI POS): 574.2 MH+<br>$[\alpha]_D^{25}$ = +56.7 (c 0.5, MeOH)<br>$^1$H NMR (300 MHz, DMSO-d$_6$) ppm 7.30-7.44 (m, 2 H), 7.24 (dd, 1 H) 6.93-7.07 (m, 2 H), 6.28 (dd, 1 H), 6.08 (s, 1 H), 5.58 (dd, 1 H), 5.40-5.75 (m, 1 H), 4.21 (t, 1 H), 4.11-4.27 (m, 1 H), 3.60-3.71 (m, 2 H), 3.50-3.62 (m, 2 H), 3.09 (t, 1 H), 2.55-2.69 (m, 2 H), 2.17-2.31 (m, 1 H), 2.03-2.17 (m, 1 H), 1.92-2.03 (m, 1 H), 1.80-1.90 (m, 1 H), 1.67-1.81 (m, 1H), 1.51-1.65 (m, 2 H), 1.49 (s, 3 H), 0.97 (s, 3 H) |

TABLE 13-continued

| Compound | Structure | Yield | Analytical |
|---|---|---|---|
| 195 | 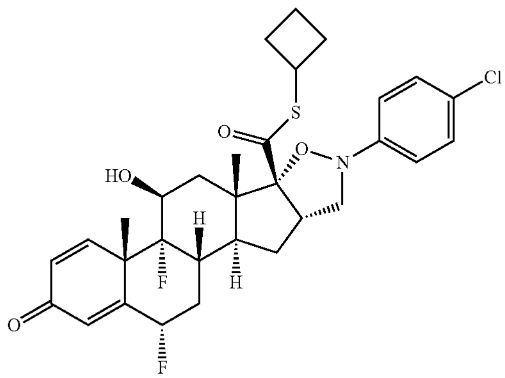 | 8% | LC-MS (ESI POS): 622.19 MH+<br>[α]$_D^{25}$ = +65 (c 0.3, MeOH)<br>$^1$H NMR (300 MHz, DMSO-d$_6$) ppm 7.37 (m, 2 H), 7.24 (d, 1 H), 7.07 (m, 2 H), 6.29 (dd, 1 H), 6.09 (s, 1 H), 5.59 (d, 1 H), 5.46-5.79 (m, 1 H), 4.23 (t, 1 H), 4.02-4.35 (m, 1 H), 3.61 (dq, 2 H), 2.55-2.72 (m, 2 H), 2.04-2.29 (m, 5H), 1.67-2.04 (m, 5H), 1.50 (s, 3 H), 1.37-1.67 (m, 2 H), 0.97 (s, 3 H) |
| 196 | 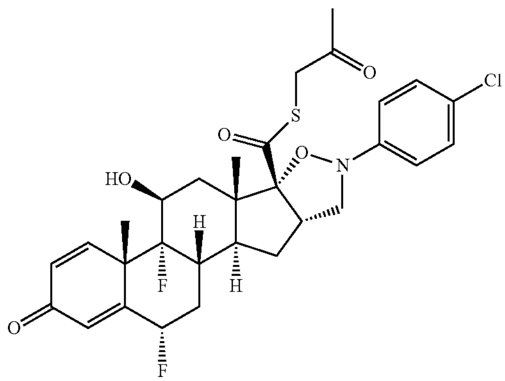 | 49% | LC-MS (ESI POS): 592.19 MH+<br>[α]$_D^{25}$ = +31.4 (c 0.21, MeOH)<br>$^1$H NMR (300 MHz, DMSO-d$_6$) ppm 7.30-745 (m, 2 H), 7.25 (dd, 1 H) 6.91-7.08 (m, 2 H), 6.29 (dd, 1 H), 6.08 (s, 1 H), 5.61 (dd, 1 H), 5.43-5.80 (m, 1 H), 4.19-4.29 (m, 1 H), 4.18 (t, 1 H), 3.87 (d, 1 H), 3.79 (d, 1 H), 3.54 (q, 1 H), 2.55-2.71 (m, 2 H), 2.22-2.31 (m, 1 H), 2.20 (s, 3 H), 2.02-2.16 (m, 1 H), 1.85-2.00 (m, 2 H), 1.64-1.80 (m, 1 H), 1.51-1.64 (m, 2 H), 1.50 (s, 3 H), 0.95 (s, 3H) |

Example 24. Preparation of (4aS,4bR,5S,6aS,6bR, 9aS,10aS,10bS,12S)-8-(4-Chloro-phenyl)-4b,12-difluoro-5-hydroxy-4a,6a-dimethyl-2-oxo-2,4a,4b,5, 6,6a,8,9,9a,10,10a,10b,11,12-tetradecahydro-7-oxa-8-aza-pentaleno[2,1-a]phenanthrene-6b-carboxylic acid methyl ester (compound 197)

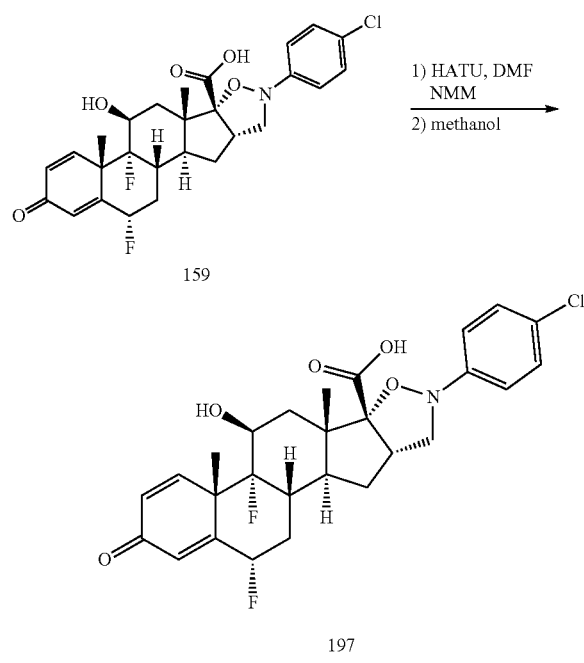

In a nitrogen atmosphere 159 (290 mg, 0.558 mmol) was dissolved in dry DMF, N-methylmorpholine (73.6 μL, 0.669 mmol) and HATU (233 mg, 0.614 mmol) were added, and the mixture was stirred at room temperature for 1 hour. Methanol (250 μL, 6.18 mmol) was added, and the mixture was heated at 60° C. for 3 hours and at room temperature overnight. Further methanol (400 μL, 9.86 mmol) was added, and the mixture was stirred at 60° C. for 4 hours. The reaction mixture was diluted with water, and the formed solid was recovered by filtration. The obtained solid was triturated in acetonitrile, then it was purified by preparative HPLC (acetonitrile/water without TFA) affording the title compound (55 mg, 18.5% yield).

$^1$H NMR (300 MHz, DMSO-d$_6$) ppm 7.26-7.33 (m, 2H), 7.26 (dd, 1H), 6.87-7.04 (m, 2H), 6.29 (dd, 1H), 6.09 (s, 1H), 5.52-5.78 (m, 1H), 5.51 (dd, 1H), 4.16-4.25 (m, 1H), 4.12 (t, 1H), 3.69 (t, 1H), 3.65 (s, 3H), 2.80 (dd, 1H), 2.55-2.68 (m, 1H), 2.18-2.26 (m, 1H), 2.05-2.18 (m, 1H), 1.94-2.05 (m, 1H), 1.78-1.92 (m, 1H), 1.66-1.79 (m, 1H), 1.52-1.64 (m, 2H), 1.50 (s, 3H), 0.96 (s, 3H)

LC-MS (ESI POS): 534.11 (MH+)

[α]$_D^{25}$=+35 (c 0.34; MeOH)

The compounds listed in Table 14 were prepared as previously described for compound 197, starting from acid 159 and the suitable nucleophile, such as alcohol, amine or amine salt, or metal thiolates:

TABLE 14

| Compound | Structure | Yield | Analytical |
|---|---|---|---|
| 198 | 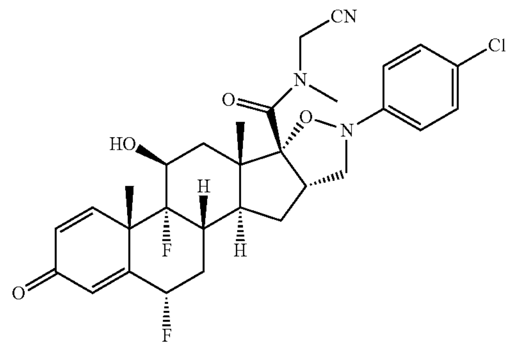 | 13% | LC-MS (ESI POS): 572.28 MH+<br>[α]$_D^{25}$ = +7.3 (c 0.3, MeOH)<br>$^1$H NMR (300 MHz, DMSO-d$_6$) ppm 7.31 (d, 2 H), 7.26 (d, 1 H), 7.00 (d, 2 H), 6.29 (dd, 1 H), 6.09 (s, 1 H), 5.56-5.65 (m, 1 H), 5.45-5.80 (m, 1 H), 4.45 (d, 1 H), 4.28 (d, 1 H), 4.18-4.27 (m, 1 H), 4.08 (dd, 1 H), 4.02 (q, 1 H), 3.38 (s, 3 H), 2.64 (dd, 2 H), 2.05-2.30 (m, 3 H), 1.62-1.94 (m, 2 H), 1.50 (s, 3 H), 1.34-1.61 (m, 2 H), 0.99 (s, 3 H) |
| 199 | 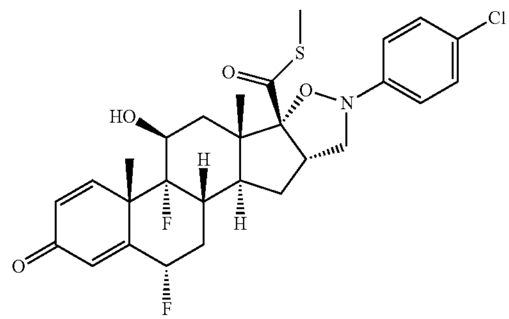 | 30% | LC-MS (ESI POS): 550.26 MH+<br>[α]$_D^{25}$ = +66.2 (c 0.2, DCM)<br>$^1$H NMR (300 MHz, DMSO-d$_6$) ppm 7.29-7.46 (m, 2 H), 7.24 (dd, 1 H), 6.88-7.08 (m, 2 H), 6.28 (dd, 1 H), 6.08 (s, 1 H), 5.52-5.82 (m, 1 H), 5.50 (dd, 1 H), 4.16-4.26 (m, 1 H), 4.17 (t, 1 H), 3.52-3.65 (m, 1 H), 2.55-2.67 (m, 2 H), 2.22 (s, 3 H), 1.92-2.19 (m, 3 H), 1.81-1.91 (m, 1 H), 1.65-1.81 (m, 1 H), 1.51-1.65 (m, 2 H), 1.49 (s, 3 H), 0.95 (s, 3 H) |

Example 25. Preparation of (4aS,4bR,5S,6aS,6bR,9aS,10aS,10bS,12S)-6b-(2-Bromo-acetyl)-8-(4-chloro-phenyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one (compound 200)

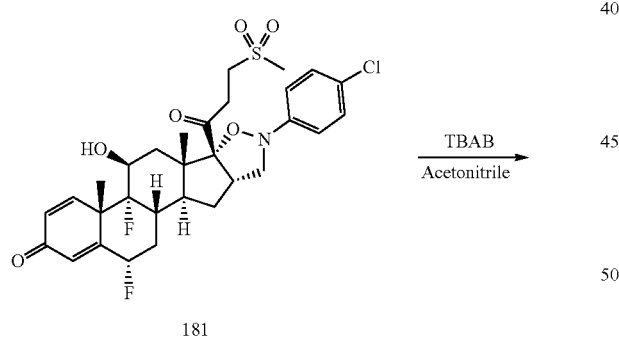

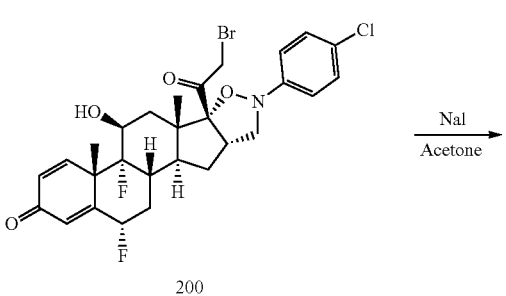

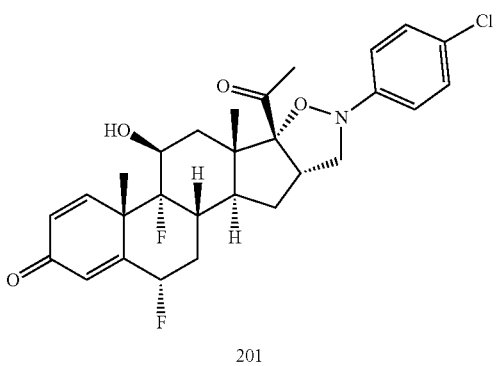

Methanesulfonic acid 181 (653 mg, 1.067 mmol) was dissolved in acetonitrile (20 ml), tetrabutylammonium bromide (344 mg, 1.067 mmol) was added, and the mixture was heated at 80° C. for 6 hours, then at room temperature overnight. Further tetrabutylammonium bromide (344 mg, 1.067 mmol) was added, and the mixture was heated at 80° C. for further 2 hours. The reaction mixture was partitioned between water and AcOEt. The organic layer was separated, dried over Na$_2$SO$_4$ and concentrated. The crude was purified by silica gel flash chromatography (eluent DCM/AcOEt from 8/2 to 7/3) to yield the title compound (630 mg, 1.055 mmol, 99% yield).

LC-MS (ESI POS): 596.0 (MH+)

Preparation of (4aS,4bR,5S,6aS,6bR,9aS,10aS, 10bS,12S)-6b-Acetyl-8-(4-chloro-phenyl)-4b,12-difluoro-5-hydroxy-4a,6a-dimethyl-4a,4b,5,6,6a,6b, 8,9,9a,10,10a,10b,11,12-tetradecahydro-7-oxa-8-aza-pentaleno[2,1-a]phenanthren-2-one (compound 201)

A mixture of 190 (373 mg, 0.625 mmol) and sodium iodide (937 mg, 6.25 mmol) in acetone (17 ml) was heated under microwave irradiation at 110° C. for 3 hours. More sodium iodide (468 mg, 3.12 mmol) was added, and the mixture was heated under microwave irradiation for further 3 hours. The reaction mixture was partitioned between AcOEt and a saturated solution of $NaS_2O_3$. The organic layer was washed with water, dried over $Na_2SO_4$ and concentrated. The crude was purified by silica gel flash chromatography (eluent DCM/MeOH=99/1), then by preparative HPLC ($CH_3CN/H_2O$ without TFA) to give the title compound (31 mg, 0.060 mmol, 10% yield).

$^1$H NMR (300 MHz, DMSO-$d_6$) ppm 7.29-7.43 (m, 2H), 7.27 (dd, 1H), 6.94-7.08 (m, 2H), 6.29 (dd, 1H), 6.09 (s, 1H), 5.52-5.75 (m, 1H), 5.51 (d, 1H), 4.16-4.30 (m, 1H), 4.09 (t, 1H), 3.51-3.64 (m, 1H), 2.62-2.70 (m, 1H), 2.61 (dd, 2H), 2.20 (s, 3H), 2.04-2.19 (m, 2H), 1.82 (d, 1H), 1.59-1.74 (m, 1H), 1.51-1.59 (m, 2H), 1.50 (s, 3H), 0.89 (s, 3H)

LC-MS (ESI POS): 518.2 (MH+)

$[\alpha]_D^{25}$=+65.2 (0.072, $CHCl_3$)

Example 26. Preparation of (4aS,4bR,5S,6aS,6bR, 9aS,10aS,10bS,12S)-8-(4-Chloro-phenyl)-4b,12-difluoro-5-hydroxy-4a,6a-dimethyl-2-oxo-2,4a,4b,5, 6,6a,8,9,9a,10,10a,10b,11,12-tetradecahydro-7-oxa-8-aza-pentaleno[2,1-a]phenanthrene-6b-carboxylic acid 1,1-dimethyl-prop-2-ynyl ester (compound 202)

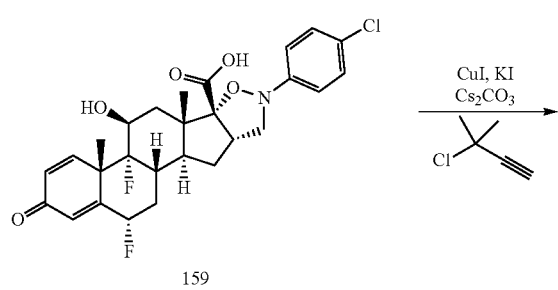

159

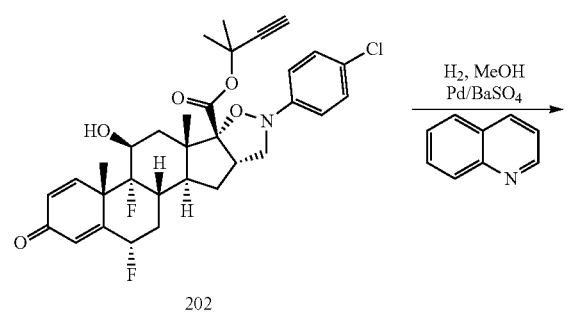

202

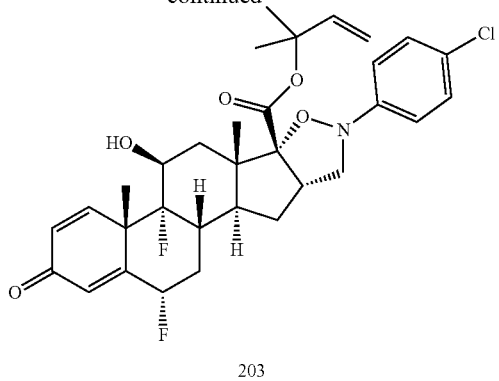

203

To a mixture of 159 (450 mg, 0.865 mmol), $Cs_2CO_3$ (282 mg, 0.865 mmol), copper(I) iodide (16.48 mg, 0.087 mmol) and KI (230 mg, 1.385 mmol), in dry DMF (4 ml), 3-chloro-3-methylbut-1-yne (178 mg, 1.731 mmol) was added, and the reaction mixture was stirred at RT overnight. Ethyl acetate was added, and the formed solid was removed by filtration; water was added, and the organic phase was washed with brine, dried over $Na_2SO_4$ and concentrated. The residue was purified by silica gel flash chromatography (eluent: DCM/MeOH, 98/2) and, after evaporation of the solvent, the obtained solid was triturated with $Et_2O$, filtered and dried under vacuum, to give the title compound (200 mg, 0.341 mmol, 39.4% yield).

$^1$H NMR (300 MHz, DMSO-$d_6$) ppm 7.22-7.35 (m, 2H), 7.25 (dd, 1H), 6.75-7.07 (m, 2H), 6.28 (dd, 1H), 6.09 (s, 1H), 5.53-5.78 (m, 1H), 5.51 (d, 1H), 4.19 (d, 1H), 4.07 (t, 1H), 3.55-3.80 (m, 1H), 3.50 (s, 1H), 2.83 (dd, 1H), 2.54-2.61 (m, 1H), 2.19-2.33 (m, 1H), 1.82-2.18 (m, 3H), 1.67-1.82 (m, 1H), 1.63 (s, 3H), 1.58 (s, 3H), 1.55 (m, 2H), 1.51 (s, 3H), 1.03 (s, 3H)

LC-MS (ESI POS): 586.15 (MH+)

$[\alpha]_D^{25}$=+40.6 (c 0.2, DCM)

Preparation of (4aS,4bR,5S,6aS,6bR,9aS,10aS, 10bS,12S)-8-(4-Chloro-phenyl)-4b,12-difluoro-5-hydroxy-4a,6a-dimethyl-2-oxo-2,4a,4b,5,6,6a,8,9,9a, 10,10a,10b,11,12-tetradecahydro-7-oxa-8-aza-pentaleno[2,1-a]phenanthrene-6b-carboxylic acid 1,1-dimethyl-allyl ester (compound 203)

A mixture of 202 (150 mg, 0.256 mmol), quinoline (9.10 μL, 0.077 mmol) and 5% Pd/$BaSO_4$ (15 mg, 0.00 mol) was hydrogenated for 5 hours at 15 psi. The catalyst was removed by filtration, and the solvent evaporated. The residue was purified by silica gel flash chromatography (eluent: DCM/MeOH, 98/2) then by preparative HPLC ($CH_3CN/H_2O$ without TFA), to afford the title compound (37 mg, 0.063 mmol, 25% yield).

$^1$H NMR (300 MHz, DMSO-$d_6$) ppm 7.27-7.32 (m, 2H), 7.25 (dd, 1H), 6.89-7.01 (m, 2H), 6.28 (dd, 1H), 6.09 (s, 1H), 5.99 (dd, 1H), 5.50-5.77 (m, 1H), 5.48 (dd, 1H), 5.20 (dd, 1H), 5.04 (dd, 1H), 4.12-4.26 (m, 1H), 4.05 (t, 1H), 3.62 (td, 1H), 2.82 (dd, 1H), 2.55-2.69 (m, 1H), 2.18-2.26 (m, 1H), 2.04-2.18 (m, 1H), 1.84-2.04 (m, 2H), 1.63-1.80 (m, 1H), 1.51-1.61 (m, 2H), 1.51 (s, 3H), 1.48 (s, 3H), 1.46 (s, 3H), 1.01 (s, 3H)

LC-MS (ESI POS): 588.23 (MH+)

$[\alpha]_D^{25}$=+48.4 (c 0.2, DCM)

Legend
*NMR
s=singlet
d=doublet
t=triplet
q=quartet
dd=doublet of doublets
m=multiplet
br=broad
ESI-POS=electrospray positive ionization
LC-MS=liquid chromatography-mass spectrometry
Pharmacological Activity of the Compounds of the Invention
In Vivo Studies Example 27. Lipopolysaccharide (LPS)-induced Lung Neutrophilia The potency and duration of action of the compounds described in the present invention were evaluated in vivo in an acute model of lung inflammation following a method described in *Am. J. Respir. Crit. Care Med.*, Vol 162. pp 1455-1461, 2000 (which is incorporated herein by reference in its entirety), with minor modifications. The tests were performed on Sprague-Dawley male rats (200 g).

Intratracheal instillation of LPS resulted in a statistically significant increase in neutrophil concentration in BALF, a hallmark of acute ongoing pulmonary inflammation. For the dose of glucocorticoid producing a 75% inhibition (ED75 dose) assessment test, compounds (0.01-1 µmoles/Kg of body weight) were administered intratracheally as suspension (0.2% Tween 80 in NaCl 0.9%) 1 hour before LPS challenge.

A dose-response curve of the inhibitory effect of the test compounds on LPS-induced lung neutrophilia was performed, and the ED50 dose of glucocorticoid was taken as a measure of potency in this bioassay. The ED50 dose values for some representative compounds of the present invention were comprised between 0.05 and 0.16 µmoles/Kg of body weight.

In a second series of experiments, aimed at the evaluation of the duration of action, the compounds were administered as suspension intratracheally, at the ED75 dose, administered 24 hours before LPS challenge. The most interesting compounds were active (percent of inhibition higher than 50%) when administered 24 hours before LPS challenge.

In Vitro Studies

Example 28. Glucocorticoid Receptor (GR) Translocation Assay Protocol

A quantitative measurement of GR nuclear translocation of the compounds of the present invention was performed according to ASSAY Drug Devel. Technol., 4(3), 263-272, 2006 (which is incorporated herein by reference in its entirety), through a novel cell-based GR-translocation assay in Enzyme Fragment Complementation (EFC) format developed by DiscoveRx (Fremont, Calif.). In the absence of the glucocorticoid, the glucocorticoid receptor (GR) resides in the cytosol complexed with a variety of proteins including heat shock proteins. When a glucocorticoid diffuses through the cell membrane into the cytoplasm and binds to the glucocorticoid receptor (GR), it results in release of the heat shock proteins and the translocation into the nucleus where it modulates gene transcription.

The DiscoveRx assay uses EFC of b-galactosidase (b-gal) as an indicator of GR-translocation in engineered CHO-K1 biosensor cells. The enzyme acceptor (EA) fragment of b-gal resides in the nucleus, as designed through the use of a proprietary set of sequence additions and modifications. The small peptide enzyme donor (ED) fragment of b-gal was fused directly to the C-terminus of GR, and was localized in the cytoplasm in the absence of receptor signaling. Upon binding to a GR ligand, the complex translocates to the nucleus, where intact enzyme activity was restored by complementation and b-gal activity was detected.

CHO-K1 cells stably expressing NLS-enzyme acceptor fragment (EA) of b-gal and GR-enzyme donor (ED) fragment of b-gal were maintained in F12 medium (Invitrogen, Carlsbad, Calif.) at 37° C. under a humidified atmosphere containing 5% $CO_2$ and 95% air. The medium contained 10% FBS,2 mM L-glutamine, 50 U/ml penicillin 50 µg/ml streptomycin, and 250 µg/ml hygromycin and 500n/ml G418 (Invitrogen). GR-translocation was measured using the PathHunter Detection Kit containing cell membrane permeabilizing reagent and beta-gal substrate (DiscoveRx, Fremont, Calif.). All compounds were screened using varying concentrations ranging from $10^{-11}$ to $10^{-6}$ M. The assay was performed in 48-wells (105 cells/well). Incubation with screened compounds was performed at 37° C. for two hours. Detection was made by adding the detection buffer from the kit supplied by DiscoveRx and incubating at room temperature for one hour. Luminescence was detected by using a CENTRO LB 960 microplate reader (Berthold Technologies).

Statistical analysis and determinations of EC50s were performed by using Prism-version 3.0 Graphpad Software (San Diego, Calif.).

Some representative compounds of the invention assayed with the GR translocation displayed a EC50 comprised between 0.35 nM and 10 nM.

Example 29. Inhibition of LPS-Induced Nitric Oxide Production in RAW 264.7 Macrophages An in vitro model based on macrophagic murine cell line RAW 264.7 was used for testing the anti-inflammatory effects of the corticosteroids of the present invention. During the inflammatory process, large amounts of nitric oxide (NO) were generated by the inducible isoforms of NO synthase (iNOS). Bacterial lipopolysaccharide (LPS) was commonly used in experimental settings to stimulate inflammatory responses in macrophages.

Cells were grown in a culture medium (RPMI supplemented with heat-inactivated 10% fetal calf serum, 2 mM glutamine, 100 U/ml penicillin and 0.1 mg/ml streptomycin) without phenol red. Cell stimulation was elicited by incubating cells for 24 hours with LPS to final concentrations ranging from 100 ng/ml. Treatments with the compounds of the invention were carried out by adding such compounds vehicled in DMSO (0.1% final concentration) to the final desired concentrations 15 minutes before LPS exposure. As an index of nitric oxide production, the concentration of nitrite was measured in the conditioned media by using the Griess colorimetric reaction (*J. Neuroimmunol.*, 150, 29-36, 2004, which is incorporated herein by reference in its entirety).

Statistical analysis and determinations of IC50s were performed by using Prism-version 3.0 Graphpad Software (San Diego, Calif.). The IC50 values tested on some representative compounds of the invention were comprised between 0.06 and 5.3 nM.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

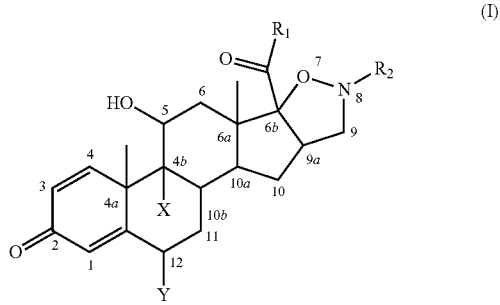

wherein
$R_1$ is —$(CH_2)_n$—Z—$(CH_2)_{n'}$—$R_3$ wherein n and n' are each independently 0, 1 or 2;
Z is a single bond, —S—, —O—, or —OC($R_4R_5$)—;
$R_3$ is selected from the group consisting of:
H, halogen, —CN, —OH, —CONH$_2$, ($C_1$-$C_6$)alkyl, ($C_2$-$C_4$)alkenyl, ($C_1$-$C_6$)haloalkyl, ($C_2$-$C_4$)alkynyl, ($C_1$-$C_6$)alkylsulfonyl; and ($C_1$-$C_6$)alkylcarbonyl;
—$NR_4R_5$, wherein $R_4$ and $R_5$ are independently selected from the group consisting of ($C_1$-$C_6$)alkyl and ($C_1$-$C_6$)alkoxy;
($C_3$-$C_8$)cycloalkyl, ($C_3$-$C_8$)heterocycloalkyl, aryl, and heteroaryl, each of which is optionally substituted by one or more halogen atoms or oxo groups or —CN groups; and
$R_2$ is:
a group selected from the group consisting of linear or branched ($C_1$-$C_6$)alkoxy and ($C_1$-$C_6$)haloalkyl, optionally substituted by one or more CN groups or halogen atoms; or
—$(CH_2)_mR_6$, wherein:
(1) $R_6$ is selected from the group consisting of ($C_3$-$C_8$)heterocycloalkyl, aryloxy, and arylthio, each of which is optionally substituted by one or more substituents selected from the group consisting of oxo, —OH, halogen, —CN, —NH$_2$, —CONH$_2$, —NO$_2$, —NHC(O)H, linear or branched ($C_1$-$C_6$)alkyl, linear or branched ($C_1$-$C_6$)haloalkyl, linear or branched ($C_1$-$C_6$)alkoxy, linear or branched ($C_1$-$C_6$)haloalkoxy, ($C_1$-$C_6$)hydroxyalkoxy, ($C_1$-$C_6$)alkoxycarbonyl, ($C_1$-$C_6$)alkylcarboxyl, ($C_1$-$C_6$)alkylsulfonyl, ($C_1$-$C_6$)alkylsulfanyl, ($C_1$-$C_6$)alkyloxysulfonyl, ($C_1$-$C_6$)haloalkylsulfonyloxy, aminosulfonyl, ($C_3$-$C_8$)cycloalkyl, ($C_3$-$C_6$)heterocycloalkyl, and heteroaryl, wherein m is 0; or (2) $R_6$ is aryl substituted by one or more ($C_1$-$C_6$) alkylsulfanyl groups, wherein m is 0; or
(3) $R_6$ is selected from the group consisting of ($C_3$-$C_8$)cycloalkyl, aryl, and heteroaryl, each of which is optionally substituted by one or more substituents selected from the group consisting of oxo, —OH, halogen, —CN, —NH2, —CONH$_2$, —NO$_2$, —NHC(O)H, linear or branched ($C_1$-$C_6$)alkyl, linear or branched ($C_1$-$C_6$)haloalkyl, linear or branched ($C_1$-$C_6$)alkoxy, linear or branched ($C_1$-$C_6$)haloalkoxy, ($C_1$-$C_6$)hydroxyalkoxy, ($C_1$-$C_6$)alkoxycarbonyl, ($C_1$-$C_6$)alkylcarboxyl, ($C_1$-$C_6$)alkylsulfonyl, ($C_1$-$C_6$)alkylsulfanyl, ($C_1$-$C_6$)alkyloxysulfonyl, ($C_1$-$C_6$)haloalkylsulfonyloxy, aminosulfonyl, ($C_3$-$C_8$)cycloalkyl, ($C_3$-$C_6$)heterocycloalkyl and heteroaryl, wherein m is 0 and
X and Y are both fluorine,
or a pharmaceutically acceptable salt thereof.

2. A compound according to claim 1, having formula (I'') or a pharmaceutically acceptable salt thereof:

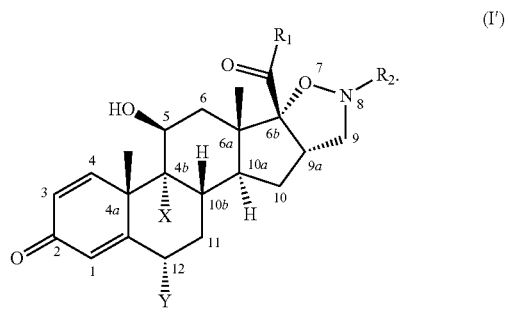

3. A compound according to claim 1, having formula (IF):

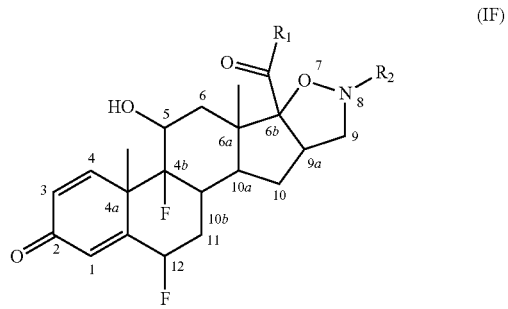

wherein
$R_1$ is —$(CH_2)_n$—Z—$(CH_2)_{n'}$—$R_3$ wherein n is 1 and n' is zero;
Z is a single bond;
$R_3$ is a fluorine atom;
$R_2$ is:
group selected from the group consisting of linear or branched ($C_1$-$C_6$)alkoxy and ($C_1$-$C_6$)haloalkyl, optionally substituted by one or more CN groups; or
—$(CH_2)_mR_6$, wherein:
$R_6$ is selected from the group consisting of ($C_3$-$C_8$)heterocycloalkyl and arylthio, each of which is optionally substituted by one or more substituents selected from the group consisting of oxo, —OH, halogen, —CN, —NH₂, —NO₂, linear or branched (C₁-C₆)alkyl, (C₁-C₆)alkoxy, aryl, (c1-C6)hydroxyalkoxy, (C₁-C₆)haloalkoxy, straight or branched (C₁-C₆)alkoxycarbonyl, (C₁-C₆)alkylcarboxyl, arylthio, and (C₁-C₆)alkylsulfanyl, wherein m is 0;
or a pharmaceutically acceptable salt thereof.

4. A compound according to claim 1, having formula (IH):

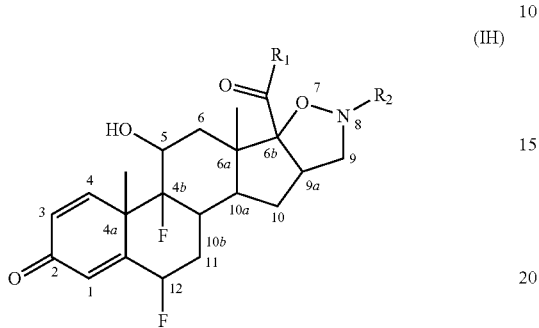

(IH)

wherein
R₁ is —(CH₂)ₙ—Z—(CH₂)ₙ'—R₃ wherein n is zero and n' is 1;
Z is —S—;
R₃ is a fluorine atom;
R₂ is:
  a group selected from the group consisting of linear or branched (C₁-C₆)alkoxy and (C₁-C₆)haloalkyl, optionally substituted by one or more —CN groups or halogen atoms; or
  —(CH₂)ₘR₆, wherein:
    R₆ is selected from the group consisting of (C₃-C₈) heterocycloalkyl, aryloxy, and arylthio, each of which optionally substituted by one or more substituents selected from the group consisting of oxo, —OH, halogen, —CN, —NH₂, —NO₂, linear or branched (C₁-C₆)alkyl, linear or branched (C₁-C₆)haloalkyl, linear or branched (C₁-C₆)alkoxy, aryl, (C₁-C₆)hydroxyalkoxy, (C₁-C₆)haloalkoxy, (C₁-C₆)alkoxycarbonyl, (C₁-C₆)alkylcarboxyl, arylthio, and (C₁-C₆)alkylsulfanyl, wherein m is 0;
or a pharmaceutically acceptable salt thereof.

5. A compound according to claim 1, having formula (IM):

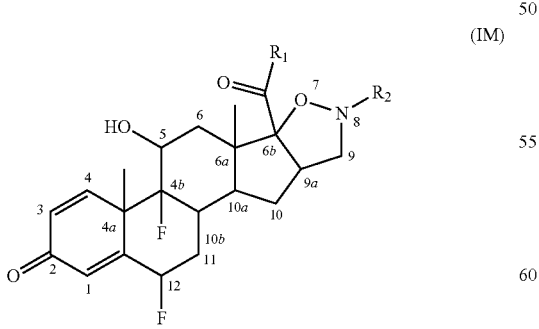

(IM)

wherein
R₁ is —(CH₂)ₙ—Z—(CH₂)ₙ'-R₃ wherein n is zero and n' is 1;
Z is a single bond;

R₃ is —OH;
R₂ is —(CH₂)ₘR₆, wherein:
  R₆ is (C₃-C₈)cycloalkyl, wherein m is 0;
or a pharmaceutically acceptable salt thereof.

6. A compound according to claim 1, having formula (IN):

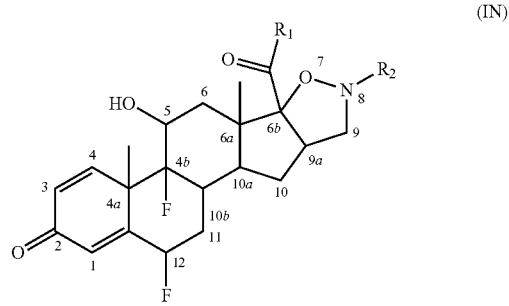

(IN)

wherein
R₁ is —(CH₂)ₙ—Z—(CH₂)ₙ'—R₃ wherein n is zero and n' is 1;
Z is a single bond;
R₃ is-OH;
R₂ is —(CH₂)ₘR₆, wherein R₆ is aryl optionally substituted by one or more substituents selected from the group consisting of halogen, —CN, —CONH₂, —NHC(O)H, linear or branched (C₁-C₆)alkyl, (C₁-C₆)alkylsulfonyl, linear or branched (C₁-C₆)haloalkyl, linear or branched (C₁-C₆)haloalkoxy, (C₁-C₆)alkoxycarbonyl, (C₁-C₆)alkoxysulfonyl, (C₁-C₆) haloalkylsulfonyloxy, (C₃-C₈)cycloalkyl, (C₃-C₆) heterocycloalkyl, aminosulfonyl, and heteroaryl, and m is 0,
or a pharmaceutically acceptable salt thereof.

7. A compound selected from the group consisting of:
(4aS,4bR,5S,6aS,6bR,9aS,10aS,10bS,12S)-4b,12-difluoro-5-hydroxy-6b-(2-hydroxy-acetyl)-4a,6a-dimethyl-8-phenyl-4a,4b,5,6,6a,6b,8,9,9a,10,10a,10b,11,12-tetradecahydro-7-oxa-8-aza-pentaleno[2,1-a]phenanthren-2-one;
(4aS,4bR,5S,6aS,6bR,9aS,10aS,10bS,12S)-8-(4-chlorophenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;
(4aS,4bR,5S,6aS,6bR,9aS,10aS,10bS,12S)-4b,12-difluoro-5-hydroxy-6b-(2-hydroxy-acetyl)-4a,6a-dimethyl-8-p-tolyl-4a,4b,5,6,6a,6b,8,9,9a,10,10a,10b,11,12-tetradecahydro-7-oxa-8-aza-pentaleno[2,1-a]phenanthren-2-one;
(4aS,4bR,5S,6aS,6bR,9aS,10aS,10bS,12S)-4b,12-difluoro-5-hydroxy-6b-(2-hydroxy-acetyl)-4a,6a-dimethyl-8-quinolin-6-yl-4a,4b,5,6,6a,6b,8,9,9a,10,10a,10b,11,12-tetradecahydro-7-oxa-8-aza-pentaleno[2,1-a]phenanthren-2-one;
(4aS,4bR,5S,6aS,6bR,9aS,10aS,10bS,12S)-4b,12-difluoro-5-hydroxy-6b-(2-hydroxy-acetyl)-4a,6a-dimethyl-8-pyridin-3-yl-4a,4b,5,6,6a,6b,8,9,9a,10,10a,10b,11,12-tetradecahydro-7-oxa-8-aza-pentaleno[2,1-a]phenanthren-2-one;
(4aS,4bR,5S,6aS,6bR,9aS,10aS,10bS,12S)-4b,12-difluoro-5-hydroxy-6b-(2-hydroxy-acetyl)-4a,6a-dimethyl-8-m-tolyl-4a,4b,5,6,6a,6b,8,9,9a,10,10a,10b,11,12-tetradecahydro-7-oxa-8-aza-pentaleno[2,1-aphenanthren-2-one;

(4aS,4bR,5S,6bR,9aS,10aS,10bS,12S)-4b,12-difluoro-8-(4-fluorophenyl)-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(3-chlorophenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-(4-trifluoromethylphenyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6bR,9aS,10aS,10bS,12S)-4b,12-difluoro-8-(3-fluoro-phenyl)-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-o-tolyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6bR,9aS,10aS,10bS,12S)-8-(4-chloro-3-methyl-phenyl)-4b,12-difluoro-5-hydroxy-6b-((S)-2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-chloro-3-trifluoromethyl-phenyl)-4b,12-difluoro-5-hydroxy-6b-(2-hydroxyacetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(3,4-dichlorophenyl)-4b,12-difluoro-5-hydroxy-6b-(2-hydroxyacetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-bromophenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

4-[(4aS,4bR,5 S,6aS,6bR,9aS,10aS,10bS)-4b-fluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzonitrile;

4-[(4aS,4bR,5S,6aS,6bR,9aS,10aS,10bS,12S)-4b,12-difluoro-5-hydroxy-6b-(2-hydroxyacetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzamide;

(4aS,4bR,5S,6aS,6bR,9aS,10aS,10bS,12S)-4b,12-difluoro-5-hydroxy-6b-(2-hydroxy-acetyl)-4a,6a-dimethyl-8-(4-trifluoromethoxy-phenyl)-4a,4b,5,6,6a,6b,8,9,9a,10,10a,10b,11,12-tetradecahydro-7-oxa-8-aza-pentaleno[2,1-a]phenanthren-2-one;

methanesulfonic acid 4-[(4aS,4bR,5S,6aS,6bR,9aS,10aS,10bS,12S)-4b,12-difluoro-5-hydroxy-6b-(2-hydroxy-acetyl)-4a,6a-dimethyl-2-oxo-2,4-a,4b,5,6,6a,6b,9,9a,10,10a,10b,11,12-tetradecahydro-7-oxa-8-aza-pentaleno[2,1-a]phenanthren-8-yl]-phenyl ester;

(4aS,4bR,5S,6aS,6bR,9aS,10aS,10bS,12S)-8-(4-cyclohexyl-phenyl)-4b,12-difluoro-5-hydroxy-6b-(2-hydroxyacetyl)-4-a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-(4-thiophen-2-yl-phenyl)-4a,4b,5,6,6a,6b,8,9,9a,10,10a,10b,11,12-tetradecahydro-7-oxa-8-aza-pentaleno[2,1-a]phenanthren-2-one;

4-[(4aS,4bR,5S,6aS,6bR,9aS,10aS,10bS,12S)-4b,12-difluoro-5-hydroxy-6b-(2-hydroxyacetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzoic acid methyl ester;

(4aS,4bR,5S,6aS,6bR,9aS,10aS,10bS,12S)-4b,12-difluoro-5-hydroxy-6b-(2-hydroxy-acetyl)-8-(4-methanesulfonyl-phenyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

3-[(4aS,4bR,5S,6aS,6bR,9aS,10aS,10bS,12S)-4b,12-difluoro-5-hydroxy-6b-(2-hydroxyacetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzonitrile;

4-[(4aS,4bR,5S,6aS,6bR,9aS,10aS,10bS,12S)-4b,12-difluoro-5-hydroxy-6b-(2-hydroxyacetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-benzene sulfonamide;

(4aS,4bR,5S,6aS,6bR,9aS,10aS,10bS,12S)-8-(4-cyclopropylphenyl)-4b,12-difluoro-5-hydroxy-6b-(2-hydroxyacetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-tert-butyl-phenyl)-4b,12-difluoro-5-hydroxy-6b-(2-hydroxyacetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

N-{4-[(4aS,4bR,5S,6aS,6bR,9aS,10aS,10bS,12S)-4b,12-difluoro-5-hydroxy-6b-(2-hydroxyacetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-yl]-phenyl}-formamide;

(4aS,4bR,5S,6aS,6bR,9aS,10aS,10bS,12S)-4b,12-difluoro-5-hydroxy-6b-(2-hydroxy-acetyl)-4a,6a-dimethyl-8-(3-trifluoromethyl-phenyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-(3-trifluoromethoxy-phenyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(3-bromo-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-benzothiazol-6-yl-4b,12-difluoro-5-hydroxy-6b-(2-hydroxy-acetyl)-4a,6a-dimethyl-4a,4b,5,6,6a,6b,8,9,-9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-8-(4-hydroxyphenyltrifluoromethansulfonate)-4a,6a-dimethyl-4a, 4b,5,6,6a,6b,8,9,9a,10,10a,10b,11,12-tetradecahydro-7-oxa-8-az-a-pentaleno[2,1-a]phenanthren-2-one;

(4aS,4bR,5S,6aS,6bR,9aS,10aS,10bS,12S)-8-(3-cyclopropyl-phenyl)-4b,12-difluoro-5-hydroxy-6b-(2-hydroxyacetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5 S,6aS,6bR,9aS,10aS,10bS,12S)-4b,12-difluoro-5-hydroxy-6b-(2-hydroxy-acetyl)-4a,6a-dimethyl-8-(4-piperidin-4-ylmethyl-phenyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-4a,6a-dimethyl-2-oxo-8-phenyl-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,-1,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-difluoro-5-hydroxy-4a,6a-dimethyl-2-oxo-8-m-tolyl-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-difluoro-5-hydroxy-4a,6a-dimethyl-2-oxo-8-o-tolyl-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-difluoro-5-hydroxy-4a,6a-dimethyl-2-oxo-8-p-tolyl-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-8-(3-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-difluoro-8-(4-fluorophenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-difluoro-5-hydroxy-4a,6a-dimethyl-2-oxo-8-pyridin-3-yl-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-difluoro-8-(3-fluorophenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-difluoro-5-hydroxy-4a,6a-dimethyl-2-oxo-8-(4-trifluoromethyl-phenyl)-2,4a,4b,5,6,6a,8,9,9a,10,10a,10b,11,12-tetradecahydro-7-oxa-8-aza-pentaleno[2,1-a] phenanthrene-6b-carboxylic acid;

(4aS,4bR,5S,6aS,6bR,9aS,10aS,10bS,12S)-4b,12-difluoro-5-hydroxy-4a,6a-dimethyl-2-oxo-8-phenyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-m-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-o-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-p-tolyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(3-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6bR,9aS,10aS,10bS,12S)-4b,12-difluoro-8-(4-fluorophenyl)-5-hydroxy-4-a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S—((S)-fluoromethyl)ester;

(4aS,4bR,5S,6aS,6bR,9aS,10aS,10bS,12S)-4b,12-difluoro-5-hydroxy-4a,6a-dimethyl-2-oxo-8-pyridin-3-yl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6bR,9aS,10aS,10bS,12S)-4b,12-difluoro-8-(3-fluoro-phenyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S—((S)-fluoromethyl)ester;

(4aS,4bR,5S,6aS,6bR,9aS,10aS,10bS,12S)-4b,12-difluoro-5-hydroxy-4a,6a-dimethyl-2-oxo-8-(4-trifluoromethyl-phenyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-6b-(2-fluoro-acetyl)-5-hydroxy-4a,6a-dimethyl-8-phenyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-chlorophenyl)-4b,12-difluoro-6b-(2-fluoroacetyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

methanesulfonic acid 2-[(4aS,4bR,5S,6aS,6bR,9aS,10aS,10bS,12S)-8-(4-chloro-phenyl)-4b,12-difluoro-5-hydroxy-4-a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester;

(4aS,4bR,5S,6aS,6bR,9aS,10aS,10bS,12S)-6b-(2-chloro-acetyl)-8-(4-chlorophenyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

4aS,4bR,5S,6aS,6bR,9aS,10aS,10bS,12S)-8-(4-chlorohenyl)-4b,12-difluoro-5-hydroxy-4a,6a-dimethyl-6b-(2-methylsulfanyl-acetyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid chloromethyl thioester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyclopropylmethyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid carbamoylmethyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid 2,2,2-trifluoro-ethyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid 2-fluoro-ethyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-cyanomethyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-fluoro-ethyl)ester;

4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2,2,2-trifluoro-ethyl)ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2, -a,4b,5,6,6a,8,9,9a,10,10a,10b,11,12-tetradecahydro-7-oxa-8-aza-pentaleno[2,1-a]phenanthrene-6b-carbothioic acid S-carbamoylmethyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-prop-2-ynyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12 tetradecahydro-7-oxa-8-aza-pentaleno[2,1-a]phenanthrene-6b-carbothioic acid S-cyclobutyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothoic acid S-(2-oxo-propyl)ester;

4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid methyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl-methyl-amide;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-methyl ester;

(4aS,4bR,5S,6aS,6bR,9aS,10aS,10S,12S)-6b-acetyl-8-(4-chlorophenyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid 1,1-dimethyl-prop-2-ynyl ester;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid 1,1-dimethyl-allyl ester;

(4aS,4bR,5S,6aS,6bR,9aS,10aS,10bS,12S)-4b,12-difluoro-8-(4-fluorobenzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthr-hren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-thiophen-2-ylmethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-8-furan-2-yl-methyl-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-phenyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-chlorophenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-4a,6a-dimethyl-2-oxo-8-phenyl-2,4a, 4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid; and (4aS,4bR,5S,6aS,6bR,9aS,10aS,10bS,12S)-4b,12-difluoro-5-hydroxy-4a,6a-dimethyl-2-oxo-8-phenyl-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester; or a pharmaceutically acceptable salt of said compound.

8. A compound according to claim 1, wherein $R_1$ is —CH$_2$OH.

9. A compound of formula (I):

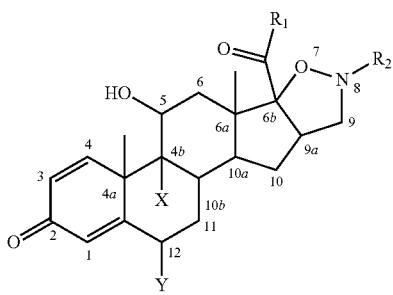

(I)

wherein $R_1$ is —(CH$_2$)$_n$—Z—(CH$_2$)$_n$'-R$_3$ wherein n and n' are each independently 0, 1 or 2;

Z is a single bond, —S—, —O—, or —OC(R$_4$R$_5$)—;

$R_3$ is selected from the group consisting of:
H, halogen, —CN, —OH, —CONH$_2$, (C$_1$-C$_6$)alkyl, (C$_2$-C$_4$)alkenyl, (C$_1$-C$_6$)haloalkyl, (C$_2$-C$_4$)alkynyl, and (C$_1$-C$_6$)alkylsulfonyl;
—NR$_4$R$_5$, wherein R$_4$ and R$_5$ are independently selected from the group consisting of (C$_1$-C$_6$)alkyl and (C$_1$-C$_6$)alkoxy;
(C$_3$-C$_8$)cycloalkyl, (C$_3$-C$_8$)heterocycloalkyl, aryl, and heteroaryl, each of which is optionally substituted by one or more halogen atoms or oxo groups or —CN groups; and $R_2$ is substituted aryl; and X and Y are both fluorine, or a pharmaceutically acceptable salt thereof.

10. A compound of formula (I):

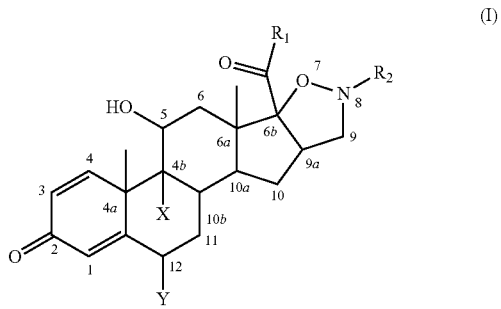

(I)

wherein $R_1$ is —CH$_2$—OH;

$R_2$ is substituted aryl: and

X and Y are both fluorine, or a pharmaceutically acceptable salt thereof.

* * * * *